United States Patent
Nakamura et al.

(10) Patent No.: US 12,263,159 B2
(45) Date of Patent: *Apr. 1, 2025

(54) FUSED RING COMPOUND HAVING UREA STRUCTURE

(71) Applicant: Sanford Burnham Prebys Medical Discovery Institute, La Jolla, CA (US)

(72) Inventors: Tsuyoshi Nakamura, Tokyo (JP); Mayuko Akiu, Tokyo (JP); Takashi Tsuji, Tokyo (JP); Jun Tanaka, Tokyo (JP); Koji Terayama, Tokyo (JP); Mika Yokoyama, Tokyo (JP); Anthony B. Pinkerton, Rancho Santa Fe, CA (US); Edward Hampton Sessions, Orlando, FL (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/420,446

(22) Filed: Jan. 23, 2024

(65) Prior Publication Data

US 2024/0285597 A1 Aug. 29, 2024

Related U.S. Application Data

(63) Continuation of application No. 17/257,262, filed as application No. PCT/US2019/040595 on Jul. 3, 2019, now Pat. No. 11,918,568.

(Continued)

(51) Int. Cl.
| | | |
|---|---|---|
| *A61K 31/4439* | (2006.01) | |
| *A61K 31/422* | (2006.01) | |
| *A61K 31/423* | (2006.01) | |
| *A61K 31/437* | (2006.01) | |
| *A61K 31/443* | (2006.01) | |
| *A61K 31/444* | (2006.01) | |
| *A61K 31/519* | (2006.01) | |

(Continued)

(52) U.S. Cl.
CPC ........ *A61K 31/4439* (2013.01); *A61K 31/422* (2013.01); *A61K 31/423* (2013.01); *A61K 31/437* (2013.01); *A61K 31/443* (2013.01); *A61K 31/444* (2013.01); *A61K 31/519* (2013.01); *A61K 31/538* (2013.01); *A61K 31/55* (2013.01); *A61K 31/553* (2013.01); *A61P 3/04* (2018.01); *A61P 25/28* (2018.01); *A61P 27/02* (2018.01); *C07D 401/12* (2013.01); *C07D 401/14* (2013.01); *C07D 405/12* (2013.01); *C07D 405/14* (2013.01); *C07D 413/12* (2013.01); *C07D 413/14* (2013.01); *C07D 471/04* (2013.01); *C07D 487/04* (2013.01); *C07D 498/08* (2013.01)

(58) Field of Classification Search
CPC .............. A61K 31/4439; A61K 31/422; A61K 31/423; A61K 31/437; A61K 31/443; A61K 31/444; A61K 31/519; A61K 31/538; A61K 31/55; A61K 31/553; A61P 3/04; A61P 25/28; A61P 27/02; A61P 3/00; A61P 9/00; A61P 25/00; C07D 401/12; C07D 401/14; C07D 405/12; C07D 405/14; C07D 413/12; C07D 413/14; C07D 471/04; C07D 487/04; C07D 498/08
See application file for complete search history.

(56) References Cited

U.S. PATENT DOCUMENTS

| | | |
|---|---|---|
| 3,128,280 A | 4/1964 | Rorig |
| 4,001,256 A | 1/1977 | Callahan et al. |

(Continued)

FOREIGN PATENT DOCUMENTS

| | | |
|---|---|---|
| CN | 102670625 A | 9/2012 |
| EP | 1630165 A1 | 3/2006 |

(Continued)

OTHER PUBLICATIONS

Alisky. Niacin improved rigidity and bradykinesia in a Parkinson's disease patient but also caused unacceptable nightmares and skin rash—a case report. Nutr Neurosci 8:327-9 (2005).

(Continued)

*Primary Examiner* — Alicia L Otton
*Assistant Examiner* — David M Shim
(74) *Attorney, Agent, or Firm* — WILSON SONSINI GOODRICH & ROSATI

(57) ABSTRACT

The present invention relates to a novel fused ring compound having urea structure that exhibits excellent NAMPT activating effect, and a method using the same for treating/preventing metabolic disorder, cardiovascular and kidney disease, mitochondrial disease, neurodegenerative disease, ocular disease, and muscle wasting disorder.

The present invention provides a compound represented by following formula (I) or a pharmacologically acceptable salt:

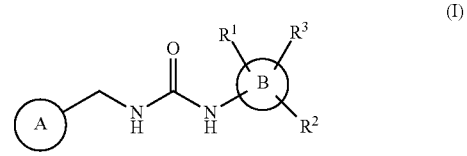

(I)

wherein A, B, R$^1$, R$^2$ and R$^3$ represent the same meanings as in the claims.

19 Claims, 7 Drawing Sheets

Related U.S. Application Data

(60) Provisional application No. 62/694,373, filed on Jul. 5, 2018.

(51) Int. Cl.

| | |
|---|---|
| *A61K 31/538* | (2006.01) |
| *A61K 31/55* | (2006.01) |
| *A61K 31/553* | (2006.01) |
| *A61P 3/04* | (2006.01) |
| *A61P 25/28* | (2006.01) |
| *A61P 27/02* | (2006.01) |
| *C07D 401/12* | (2006.01) |
| *C07D 401/14* | (2006.01) |
| *C07D 405/12* | (2006.01) |
| *C07D 405/14* | (2006.01) |
| *C07D 413/12* | (2006.01) |
| *C07D 413/14* | (2006.01) |
| *C07D 471/04* | (2006.01) |
| *C07D 487/04* | (2006.01) |
| *C07D 498/08* | (2006.01) |

(56) References Cited

U.S. PATENT DOCUMENTS

| | | | |
|---|---|---|---|
| 11,452,717 | B2 | 9/2022 | Gardell et al. |
| 11,806,337 | B2 | 11/2023 | Gardell et al. |
| 11,918,568 | B2 * | 3/2024 | Nakamura ......... A61K 31/4439 |
| 2013/0317027 | A1 | 11/2013 | Willardsen et al. |
| 2016/0108039 | A1 | 4/2016 | Allerheiligen et al. |

FOREIGN PATENT DOCUMENTS

| | | | |
|---|---|---|---|
| EP | 1961745 A1 | 8/2008 | |
| EP | 1630165 B1 | 3/2010 | |
| EP | 2277881 A1 | 1/2011 | |
| EP | 2444403 A1 | 4/2012 | |
| EP | 2727920 A1 | 5/2014 | |
| EP | 2762476 A1 | 8/2014 | |
| EP | 2727920 B1 | 11/2016 | |
| TW | 201216963 A | 5/2012 | |
| TW | 201217359 A | 5/2012 | |
| TW | 201245152 A | 11/2012 | |
| WO | WO-9724343 A1 | 7/1997 | |
| WO | WO-2004108729 A1 | 12/2004 | |
| WO | WO-2007086584 A1 | 8/2007 | |
| WO | WO 2008/100463 A1 * | 8/2008 | ......... A61K 31/4985 |
| WO | WO-2009128520 A1 | 10/2009 | |
| WO | WO-2011109441 A1 | 9/2011 | |
| WO | WO-2012031196 A1 | 3/2012 | |
| WO | WO-2012031199 A1 | 3/2012 | |
| WO | WO-2012150952 A1 | 11/2012 | |
| WO | WO-2013018733 A1 | 2/2013 | |
| WO | WO-2013063214 A1 | 5/2013 | |
| WO | WO-2014111871 A1 | 7/2014 | |
| WO | WO-2016198698 A2 | 12/2016 | |
| WO | WO-2018132372 A1 | 7/2018 | |
| WO | WO-2020010252 A1 | 1/2020 | |

OTHER PUBLICATIONS

Araki, et al. Increased nuclear NAD biosynthesis and SIRT1 activation prevent axonal degeneration. Science305.5686 (2004): 1010-1013.
CAS Registration No. 1503328-38-8, Registry [STN] Dec. 25, 2013.
Chemical Abstract compounds, STN express. RN 1178624-49-1 (Entered STN: Sep. 1, 2009).
Chemical Abstract compounds, STN express. RN 1183437-25-3 (Entered STN: Sep. 13, 2009).
Chemical Abstract compounds, STN express. RN 1271453-69-0 (Entered STN: Mar. 28, 2011).
Chemical Abstract compounds, STN express. RN 1271453-76-9 (Entered STN: Mar. 28, 2011).
Chemical Abstract compounds, STN express. RN 1272140-38-1 (Entered STN: Mar. 30, 2011).
Chemical Abstract compounds, STN express. RN 1273721-48-4 (Entered STN: Apr. 3, 2011).
Chemical Abstract compounds, STN express. RN 1273762-09-6 (Entered STN: Apr. 3, 2011).
Chemical Abstract compounds, STN express. RN 1274550-75-2 (Entered STN: Apr. 4, 2011).
Chemical Abstract compounds, STN express. RN 1275953-27-9 (Entered STN: Apr. 6, 2011).
Chemical Abstract compounds, STN express. RN 1293152-85-8 (Entered STN: May 11, 2011).
Chemical Abstract compounds, STN express. RN 1304288-66-1 (Entered STN: Jun. 2, 2011).
Chemical Abstract compounds, STN express. RN 1305713-75-0 (Entered STN: Jun. 5, 2011).
Chemical Abstract compounds, STN express. RN 1308075-89-9 (Entered STN: Jun. 9, 2011).
Chemical Abstract compounds, STN express. RN 1308605-94-8 (Entered STN: Jun. 10, 2011).
Chemical Abstract compounds, STN express. RN 1406753-89-6 (Entered STN: Nov. 26, 2012).
Chemical Abstract compounds, STN express. RN 1479013-07-4 (Entered STN: Nov. 22, 2013).
Chemical Abstract compounds, STN express. RN 1492549-76-4 (Entered STN: Dec. 11, 2013).
Chemical Abstract compounds, STN express. RN 1493376-67-2 (Entered STN: Dec. 12, 2013).
Chemical Abstract compounds, STN express. RN 1553431-46-1 (Entered STN: Feb. 24, 2014).
Cho. Recent Advances in Oral Prodrug Discovery. Annual Reports in Medicinal Chemistry 41:395-407 (2006).
Conze et al. Safety assessment of nicotinamide riboside, a form of vitamin B3. Hum Exp Toxicol. 35 (11):1149-1160 (2016).
Costford et al. Skeletal muscle overexpression of nicotinamide phosphoribosyl transferase in mice coupled with voluntary exercise augments exercise endurance. Mol Metab 7:1-11 (2018).
Dragovich et al. Identification of 2,3-dihydro-1H-pyrrolo[3,4-c]pyridine-derived ureas as potent inhibitors of human nicotinamide phosphoribosyltransferase (NAMPT). Bioorg Med Chem Lett 23(17):4875-4885 (2013).
Galli et al. Medicinal Chemistry of Nicotinamide Phosphoribosyltransferase (NAMPT) Inhibitors. J Med Chem 56(16):6279-6296 (2013).
Gardell et al. Boosting NAD + with a small molecule that activates NAMPT. Nat Commun 10(1):3241 (2019).
Gerpe et al. Indazole N-oxide derivatives as antiprotozoal agents: synthesis, biological evaluation and mechanism of action studies. Bioorg. Med. Chem. 14:3467-3480 (2006).
Gleen et al. Urea compounds that increase the biosynthesis of prostaglandins in vivo-in vitro. Agents and actions 7(5-6):517-528 (1977).
Gomes, et al. Declining NAD+ induces a pseudohypoxic state disrupting nuclear-mitochondrial communication during aging. Cell155.7 (2013): 1624-1638.
Gong et al. Nicotinamide riboside restores cognition through an upregulation of proliferator-activated receptor-γ coactivator 1α regulated β-secretase 1 degradation and mitochondrial gene expression in Alzheimer's mouse models. Neurobiol Aging 34:1581-8 (2013).
Hershberger et al. Role of NAD + and mitochondrial sirtuins in cardiac and renal diseases. Nat Rev Nephrol. 13(4):213-225 (2017).
Ichihara et al. Development of Self-Indicating Resin. Comb Chem High Throughput Screen 10(4):261-267 (2007).
Jia et al. High doses of nicotinamide prevent oxidative mitochondrial dysfunction in a cellular model and improve motor deficit in a *Drosophila* model of Parkinson's disease. J Neurosci Res 86:2083-90 (2008).
Khan et al. Effective treatment of mitochondrial myopathy by nicotinamide riboside, a vitamin B3. EMBO Mol Med. 6(6):721-31 (2014).

(56) References Cited

OTHER PUBLICATIONS

Koenekoop et al. Mutations in NMNAT1 cause Leber congenital amaurosis and identify a new disease pathway for retinal degeneration. Nature Genetics 44:1035-9 (2012).
Lee et al. Normalization of NAD+ Redox Balance as a Therapy for Heart Failure. Circulation 134:883-894 (2016).
Lin et al. NAMPT-Mediated NAD(+) Biosynthesis Is Essential for Vision In Mice. Cell Reports 17:69-85 (2016).
Liu et al. Exploiting an Allosteric Binding Site of PRMT3 Yields Potent and Selective Inhibitors. J Med Chem 56(5):2110-2124 (2013).
Massey et al. Preliminary evidence for the interaction of the oxytocin receptor gene (oxtr) and face processing in differentiating prenatal smoking patterns. Neuroscience Lett 259:21-4 (1999).
Nishigaya et al. Discovery of novel pyrazolo[1,5-a]pyridine-based EP1 receptor antagonists by scaffold hopping: Design, synthesis, and structure-activity relationships. Bioorg Med Chem Lett 27:4044-4050 (2017).
Nogrady. Chapter 4: Pro Drugs and Soft Drugs. In: Medicinal Chemistry: A Biochemical approach. New York: Oxford University Press, p. 388-392 (1985).
PCT/US2019/040595 International Search Report and Written Opinion dated Aug. 29, 2019.
Rajman et al. Therapeutic Potential of NAD-Boosting Molecules: The In Vivo Evidence. Cell Metab. 27(3):529-547 (2018).
Ren et al. Potent and selective pyrazolo[1,5-a]pyrimidine based inhibitors of B-RafV600E kinase with favorable physicochemical and pharmacokinetic properties. Bioorg med Chem Lett 22(2):1165-1168 (2012).
Rooseboom et al. Enzyme-catalyzed activation of anticancer prodrugs. Pharmacological Reviews 56:53-102 (2004).
Silverman. Chapter 8: Prodrugs and Drug Delivery Systems. The Organic Chemistry of Drug Design and Drug Action, Academic Press, Inc., San Diego (pp. 352-401) (1992).
Swamy et al. Mitsunobu and related reactions: advances and applications. Chemical Reviews 109(6):2551-2651 (2009).
Tran et al. PGC1α drives NAD biosynthesis linking oxidative metabolism to renal protection. Nature 531:528-532 (2016).
U.S. Appl. No. 16/475,635 Office Action dated Jan. 7, 2022.
U.S. Appl. No. 17/875,216 Office Action dated Mar. 10, 2023.
U.S. Appl. No. 17/257,262 Office Action dated Feb. 23, 2023.
Vo et al. Total Synthesis of Viniferifuran, Resveratrol-Piceatannol Hybrid, Anigopreissin A and Analogues—Investigation of Demethylation Strategies. Adv Synth Catal 358(24):4085-4092 (2016).
Wang et al. P7C3 Neuroprotective Chemicals Function by Activating the Rate-Limiting Enzyme in NAD Salvage. Cell 158(6):1324-1334 (2014).
Wei et al. NAD replenishment with nicotinamide mononucleotide protects blood-brain barrier integrity and attenuates delayed tissue plasminogen activator-induced haemorrhagic transformation after cerebral ischaemia. Br J Pharmacol 174:3823-36 (2017).
Williams et al. Vitamin B3 modulates mitochondrial vulnerability and prevents glaucoma in aged mice. Science 355:756-60 (2017).
Yoshino et al. NAD + Intermediates: The Biology and Therapeutic Potential of NMN and NR. Cell Metab. 27(3):513-528 (2018).
Yoshino et al. Nicotinamide mononucleotide, a key NAD(+) intermediate, treats the pathophysiology of diet- and age-induced diabetes in mice. Cell Metab. 14:528-536 (2011).
Zhang et al. NAD$^+$ repletion improves mitochondrial and stem cell function and enhances life span in mice. Science 352:1436-43 (2016).
Zheng et al. Structure-Based Discovery of Novel Amide-Containing Nicotinamide Phosphoribosyltransferase (Nampt) Inhibitors. J Med Chem 56(16):6413-6433 (2013).

\* cited by examiner

FUSED RING COMPOUND HAVING UREA STRUCTURE

CROSS-REFERENCE TO RELATED APPLICATION

This application is a continuation of U.S. application Ser. No. 17/257,262, filed Dec. 30, 2020, which is a U.S. National Phase Application of International Application No. PCT/US2019/040595, filed Jul. 3, 2019; and claims the benefit of U.S. Application No. 62/694,373, filed Jul. 5, 2018, all of which are expressly incorporated herein by reference in their entirety.

STATEMENT OF JOINT RESEARCH AGREEMENT

The subject matter of the claimed invention was made as a result of activities undertaken within the scope of a joint research agreement, within the meaning of 35 U.S.C. § 102(c), by, or on behalf of, Daiichi Sankyo Company, Limited and Sanford Burnham Prebys Medical Discovery Institute that was in effect on or before the effective filing date of the claimed invention.

TECHNICAL FIELD

The present invention relates to a novel fused ring compound having a urea structure, or a pharmacologically acceptable salt thereof.

BACKGROUND ART

Nicotinamide phosphoribosyltransferase (NAMPT) is an essential intracellular enzyme involved in mammalian biosynthetic pathway of nicotinamide adenine dinucleotide (NAD$^+$), a coenzyme participating in adenosine triphosphate (ATP) production and redox metabolism. The pathway includes the first rate-limiting step of the NAMPT-catalyzed synthesis of nicotinamide mononucleotide (NMN) from nicotinamide (NAM), and the second step which is a subsequent conversion of nicotinamide mononucleotide to NAD$^+$ catalyzed by nicotinamide mononucleotide adenyltransferase (NMNAT). It was established that NAD$^+$ depletion in tissues inevitably suppresses ATP generation, which in turn disrupts intracellular energy homeostasis and eventually leads to cell death and to organ injuries. Upregulation of NAMPT has been shown as a response to the decreased NAD$^+$ level in several ischemic stroke models, including several clinical studies.

In addition to its role in intracellular energy production, NAMPT also works as a co-substrate for NAD$^+$-dependent enzymes such as sirtuin (SIRT) and poly (ADP-ribose) polymerase (PARP). The SIRT signaling is a key endogenous defense element against various stresses, cell metabolic homeostasis, survival, and aging. A family of PARP proteins is involved in a number of cellular processes such as DNA repair, genomic stability, and programmed cell death. PARP1, the most abundant PARP member, senses DNA damage and consumes NAD$^+$ to synthesize poly (ADP-ribose) in order to recruit DNA repair proteins and perform other functions.

It is known that NAMPT expression and activity can be regulated by various stimuli, including circadian rhythms, diet, caloric intake restriction, stress, aging, and disease (Non Patent Literature 1, Non Patent Literature 2).

CITATION LIST

Non Patent Literature

NPL 1: Yoshino, J., et al. Cell Metab. 2018; 27(3):513-528
NPL 2: Rajman, L., et al. Cell Metab. 2018; 27(3):529-547

SUMMARY OF THE INVENTION

Technical Problem

The present inventors have conducted diligent studies on compounds having NAMPT activating effect and consequently completed the present invention by finding that fused ring compounds having a specific urea structure have excellent NAMPT activating effect.

Solution to Problem

Specifically, the present invention provides:
A compound of formula (I), or a pharmaceutically acceptable salt thereof:

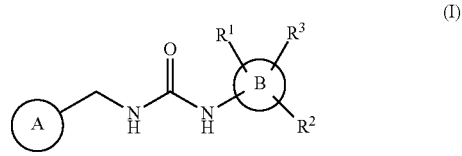

wherein:

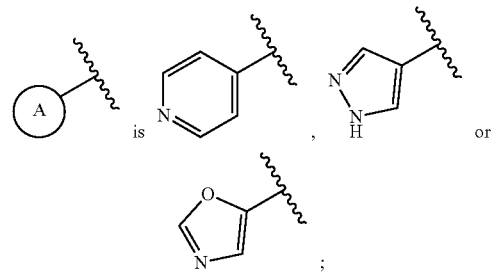

ring B represents a bicyclic ring containing one or more heteroatoms in the ring;
R$^1$ represents a hydrogen atom or a halogen atom;
R$^2$ represents a hydrogen atom, a phenyl group or a heteroaryl group each optionally substituted with one or more groups selected from the following group Y, and a C$_1$-C$_6$ alkyl group optionally substituted with a C$_3$-C$_6$ cycloalkyl group, or is absent;
R$^3$ represents a hydrogen atom; a cyano group; a phenyl group or a heteroaryl group each optionally substituted with one or more groups selected from the following group Y; a C$_1$-C$_4$ alkylcarbonyl group or a C$_1$-C$_4$ alkyl group, optionally substituted with one or more groups selected from the following group Z; and a carbonyl group substituted with a group selected from the following group Z; or is absent;
group Y consists of a C$_1$-C$_6$ alkyl group, a C$_1$-C$_6$ alkoxy group, a phenyl group, a C$_1$-C$_3$ alkylsulfonyl group, a C$_1$-C$_3$ haloalkyl group, a halogen group, and a C$_1$-C$_3$ alkyl group or a C$_1$-C$_3$ alkoxy group each substituted with a C$_1$-C$_3$ alkoxy group;

group Z consists of a $C_1$-$C_3$ alkoxy group, a dioxanyl group, an 8-oxa-3-azabicyclo[3.2.1]octyl group, a $C_1$-$C_4$ alkoxycarbonyl group, and an amino group or a $C_3$-$C_6$ cycloalkylamino group each optionally substituted with one or more groups selected from the following group W; and group W consists of a phenyl group, a heteroaryl group, a $C_1$-$C_3$ alkyl group, a $C_1$-$C_3$ alkyl group substituted with phenyl, and a $C_1$-$C_3$ alkyl group substituted with a heteroaryl group.

The compound of formula (I) of [1], or a pharmaceutically acceptable salt thereof, wherein A is

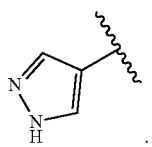

The compound of formula (I) of [1], or a pharmaceutically acceptable salt thereof, wherein A is

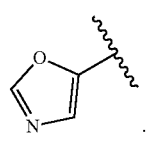

The compound of formula (I) of [1], or a pharmaceutically acceptable salt thereof, wherein A is

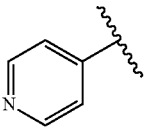

The compound of any one of [1]-[4], or a pharmaceutically acceptable salt thereof, wherein B is any one of the following formulas:

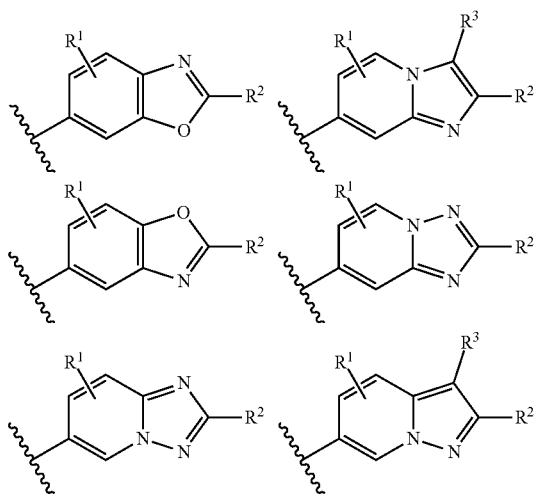

-continued

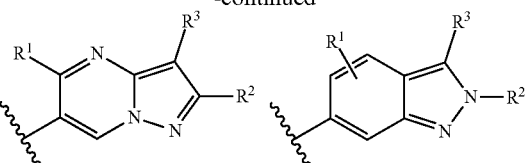

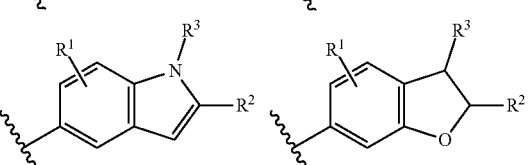

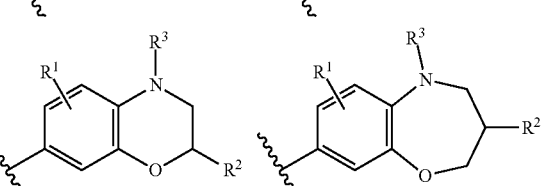

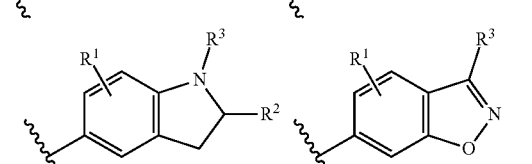

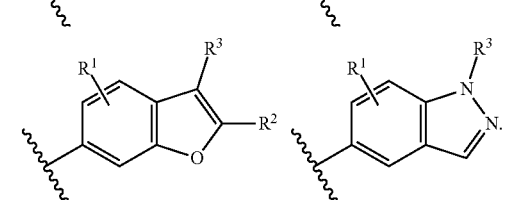

The compound of any one of [1]-[5], or a pharmaceutically acceptable salt thereof, wherein $R^1$ is a hydrogen atom or a fluorine atom.

The compound of any one of [1]-[6], or a pharmaceutically acceptable salt thereof, wherein $R^2$ is a hydrogen atom; a phenyl group, a pyrazolyl group, a pyridinyl group, or a pyrrole group optionally monosubstituted with a group selected from the following group Y; a $C_1$-$C_3$ alkyl group optionally substituted with a $C_3$-$C_6$ cycloalkyl group; or is absent; and group Y consists of a phenyl group, a halogen atom, a $C_1$-$C_4$ alkyl group, a $C_1$-$C_3$ haloalkyl group, a $C_1$-$C_3$ alkylsulfonyl group, a $C_1$-$C_3$ alkoxy group, and a $C_1$-$C_3$ alkyl group or a $C_1$-$C_3$ alkoxy group substituted with a $C_1$-$C_3$ alkoxy group.

The compound of any one of [1]-[6], or a pharmaceutically acceptable salt thereof, wherein $R^2$ is a hydrogen atom; a phenyl group, a pyrazolyl group, or a pyridinyl group each optionally monosubstituted with a group selected from the following group Y; a $C_1$-$C_3$ alkyl group; 1-methyl-cyclopropyl; or is absent; and group Y consists of a $C_1$-$C_4$ alkyl group, a methanesulfonyl group, an ethanesulfonyl group, a methoxy group, an ethoxy group, a 2-methoxyethoxy group, a phenyl group, a trifluoromethyl group, a difluoromethyl group, a 2-methoxyethyl group, and a chlorine atom.

The compound of any one of [1]-[8], or a pharmaceutically acceptable salt thereof, wherein $R^3$ is a hydrogen atom; a cyano group; a $C_1$-$C_4$ alkyl group; a phenyl group or a heteroaryl group each optionally substituted with one or more groups selected from the following group Y; a methylcarbonyl group or a methyl group each optionally substituted with one or more groups selected from the following group Z; and a carbonyl group substituted with a group selected from the following group Z; or is absent;
  group Y consists of a $C_1$-$C_3$ alkyl group, a $C_1$-$C_3$ alkoxy group, a phenyl group, a $C_1$-$C_3$ alkylsulfonyl group, a $C_1$-$C_3$ haloalkyl group, a halogen atom, and a $C_1$-$C_3$ alkyl group or a $C_1$-$C_3$ alkoxy group each substituted with a $C_1$-$C_3$ alkoxy group;
  group Z consists of a $C_1$-$C_2$ alkoxy group, a dioxanyl group, an 8-oxa-3-azabicyclo[3.2.1]octyl group, and an amino group or a $C_3$-$C_6$ cycloalkylamino group each optionally substituted with one or more groups selected from the following group W; and
  group W consists of a phenyl group, a heteroaryl group, a $C_1$-$C_3$ alkyl group, a $C_1$-$C_3$ alkyl group substituted with phenyl, and a $C_1$-$C_3$ alkyl group substituted with a heteroaryl group.

The compound of any one of [1]-[8], or a pharmaceutically acceptable salt thereof, wherein $R^3$ is a hydrogen atom, a cyano group, a N-methylpyrazolyl group, a phenyl group, a methyl group, a 2-methoxyethyl group, a dioxanylmethyl group, or a carbonyl group optionally substituted with one or more groups selected from the following group Z;
  group Z consists of an amino group optionally substituted with one or more groups selected from the following group W, and an 8-oxa-3-azabicyclo[3.2.1]octyl group; and group W consists of a $C_1$-$C_3$ alkyl group, a methylphenyl group, and a $C_1$-$C_3$ alkyl group substituted with a heteroaryl group.

The compound of [1], or a pharmaceutically acceptable salt thereof, wherein the compound is selected from the group consisting of:
N-(2-phenyl-1,3-benzoxazol-5-yl)-N'-[(pyridin-4-yl) methyl]urea,
N-(2-phenyl-1,3-benzoxazol-6-yl)-N'-[(pyridin-4-yl) methyl]urea,
N-[2-(2-methylphenyl)-1,3-benzoxazol-6-yl]-N'-[(pyridin-4-yl)methyl]urea,
N-[(1,3-oxazol-5-yl)methyl]-N'-(2-phenyl-1,3-benzoxazol-6-yl)urea,
N-[2-(1-methyl-1H-pyrazol-4-yl)-1,3-benzoxazol-6-yl]-N'-[(pyridin-4-yl)methyl]urea,
N-[2-(1-methylcyclopropyl)-1,3-benzoxazol-6-yl]-N'-[(pyridin-4-yl)methyl]urea,
N-(5-fluoro-2-phenyl-1,3-benzoxazol-6-yl)-N'-[(pyridin-4-yl) methyl]urea,
N-(2-phenylimidazo[1,2-a]pyridin-7-yl)-N'-[(pyridin-4-yl) methyl]urea,
N-(2-phenyl-1H-indol-5-yl)-N'-[(pyridin-4-yl)methyl]urea,
methyl [2-phenyl-5-({[(pyridin-4-yl)methyl]carbamoyl}amino)-1H-indol-1-yl]acetate,
N-{2-[3-(methanesulfonyl)phenyl]-1-methyl-1H-indol-5-yl}-N'-[(pyridin-4-yl)methyl]urea,
N-{2-[3-(2-methoxyethoxy)phenyl]-1-methyl-1H-indol-5-yl}-N'-[(pyridin-4-yl)methyl]urea,
N-[1-(2-methoxyethyl)-2-phenyl-1H-indol-5-yl]-N'-[(pyridin-4-yl)methyl]urea,
N-[1-methyl-2-(pyridin-2-yl)-1H-indol-5-yl]-N'-[(pyridin-4-yl)methyl]urea,
N-(1-methyl-2-phenyl-1H-indol-5-yl)-N'-[(pyridin-4-yl) methyl]urea,
N-{1-[(1,4-dioxan-2-yl)methyl]-2-phenyl-1H-indol-5-yl}-N'-[(pyridin-4-yl)methyl]urea,
N,N-dimethyl-2-phenyl-5-({[(pyridin-4-yl)methyl]carbamoyl}amino)-1H-indole-1-carboxamide,
N-[1-(2-methylpropyl)-1H-indazol-5-yl]-N'-[(pyridin-4-yl) methyl]urea,
N-(2-phenyl[1,2,4]triazolo[1,5-a]pyridin-6-yl)-N'-[(pyridin-4-yl)methyl]urea,
N-[(1,3-oxazol-5-yl)methyl]-N'-(2-phenyl[1,2,4]triazolo[1,5-a]pyridin-6-yl)urea,
N-(2-phenyl[1,2,4]triazolo[1,5-a]pyridin-6-yl)-N'-[(1H-pyrazol-4-yl)methyl]urea,
N-[2-(2-butylphenyl) [1,2,4]triazolo[1,5-a]pyridin-6-yl]-N'-[(pyridin-4-yl)methyl]urea,
N-[2-(1-phenyl-1H-pyrrol-2-yl) [1,2,4]triazolo[1,5-a]pyridin-6-yl]-N'-[(pyridin-4-yl)methyl]urea,
N-[2-(1-methyl-1H-pyrazol-5-yl) [1,2,4]triazolo[1,5-a]pyridin-6-yl]-N'-[(pyridin-4-yl)methyl]urea,
N-[(pyridin-4-yl)methyl]-N'-{2-[2-(trifluoromethyl)phenyl] [1,2,4]triazolo[1,5-a]pyridin-6-yl}urea,
N-(2-phenyl[1,2,4]triazolo[1,5-a]pyridin-7-yl)-N'-[(pyridin-4-yl)methyl]urea,
N-(2-phenylpyrazolo[1,5-a]pyridin-6-yl)-N'-[(pyridin-4-yl) methyl]urea,
N-(2-phenylpyrazolo[1,5-a]pyrimidin-6-yl)-N'-[(pyridin-4-yl) methyl]urea,
N-(3-methyl-2-phenylpyrazolo[1,5-a]pyridin-6-yl)-N'-[(pyridin-4-yl)methyl]urea,
N-(3-cyano-2-phenylpyrazolo[1,5-a]pyridin-6-yl)-N'-[(pyridin-4-yl)methyl]urea,
N-[2-(3-methoxyphenyl)pyrazolo[1,5-a]pyridin-6-yl]-N'-[(pyridin-4-yl)methyl]urea,
N,N-dimethyl-2-phenyl-6-({[(pyridin-4-yl)methyl]carbamoyl}amino)pyrazolo[1,5-a]pyridine-3-carboxamide,
N-[3-(1-methyl-1H-pyrazol-5-yl)-2-phenylpyrazolo[1,5-a]pyridin-6-yl]-N'-[(pyridin-4-yl)methyl]urea,
4-fluoro-N,N-dimethyl-2-phenyl-6-({[(pyridin-4-yl)methyl]carbamoyl}amino)pyrazolo[1,5-a]pyridine-3-carboxamide,
N-(2-phenyl-2H-indazol-6-yl)-N'-[(pyridin-4-yl) methyl] urea,
N-[(1,3-oxazol-5-yl)methyl]-N'-(2-phenyl-2H-indazol-6-yl) urea,
N-[2-(3-methoxyphenyl)-2H-indazol-6-yl]-N'-[(pyridin-4-yl) methyl]urea,
N-{2-[2-(2-methoxyethoxy)phenyl]-2H-indazol-6-yl}-N'-[(pyridin-4-yl)methyl]urea,
N-(3-methyl-2-phenyl-2H-indazol-6-yl)-N'-[(pyridin-4-yl) methyl]urea,
N-{2-[3-(methanesulfonyl)phenyl]-2H-indazol-6-yl}-N'-[(pyridin-4-yl)methyl]urea,
N-(3-cyano-2-phenyl-2H-indazol-6-yl)-N'-[(pyridin-4-yl) methyl]urea,
N,N-diethyl-2-phenyl-6-({[(pyridin-4-yl)methyl]carbamoyl}amino)-2H-indazole-3-carboxamide,
N-[2-phenyl-3-(pyrrolidine-1-carbonyl)-2H-indazol-6-yl]-N'-[(pyridin-4-yl)methyl]urea,
N-[3-cyano-2-(2-methoxypyridin-4-yl)-2H-indazol-6-yl]-N'-[(pyridin-4-yl)methyl]urea,
N-[2-(2-chlorophenyl)-3,4-dihydro-2H-1,4-benzoxazin-7-yl]-N'-[(pyridin-4-yl)methyl]urea,
N-[4-(2-methoxyethyl)-2-phenyl-3,4-dihydro-2H-1,4-benzoxazin-7-yl]-N'-[(pyridin-4-yl)methyl]urea, 2-(2-chlorophenyl)-N-ethyl-7-({[(pyridin-4-yl)methyl]carbamoyl}amino)-2,3-dihydro-4H-1,4-benzoxazine-4-carboxamide,
N-(2-phenyl-3,4-dihydro-2H-1,4-benzoxazin-7-yl)-N'-[(pyridin-4-yl)methyl]urea,
N-(3-phenyl-5-propanoyl-2,3,4,5-tetrahydro-1,5-benzoxazepin-8-yl)-N'-[(pyridin-4-yl)methyl]urea,
N-(1-acetyl-2-phenyl-2,3-dihydro-1H-indol-5-yl)-N'-[(pyridin-4-yl)methyl]urea, N,N-diethyl-6-({[(pyridin-4-yl)methyl]carbamoyl}amino)-1,2-benzoxazole-3-carboxamide, N-(2-phenyl-2,3-dihydro-1-benzofuran-6-yl)-N'-[(pyridin-4-yl)methyl]urea, N-[2-(3-methoxyphenyl)-2,3-dihydro-1-benzofuran-6-yl]-N'-[(pyridin-4-yl)methyl]urea, N-[(2S,3S)-2-(3-methoxyphenyl)-3-methyl-2,3-dihydro-1-benzofuran-6-yl]-N'-[(pyridin-4-yl)methyl]urea, N-(3-phenyl-2,3-dihydro-1-benzofuran-6-yl)-N'-[(pyridin-4-yl)methyl]urea, N,N-diethyl-6-({[(pyridin-4-yl)methyl]carbamoyl}amino)-1-benzofuran-3-carboxamide, N-{2-[3-(difluoromethoxy)phenyl]-2H-indazol-6-yl}-N'-[(pyridin-4-yl)methyl]ureaN-benzyl-N-ethyl-6-({[(pyridin-4-yl)methyl]carbamoyl}amino)-1,2-benzoxazole-3-carboxamide, and N-[3-(8-oxa-3-azabicyclo[3.2.1]octane-3-carbonyl)-1,2-benzoxazol-6-yl]-N'-[(pyridin-4-yl)methyl]urea.

A pharmaceutical composition comprising a compound of any one of [1]-[11], or a pharmaceutically acceptable salt thereof, and at least one pharmaceutically acceptable excipient.

The pharmaceutical composition of [12], wherein the pharmaceutical composition is formulated for oral administration, intravenous injection, subcutaneous injection, inhalation, nasal administration, dermal administration, or ophthalmic administration.

The pharmaceutical composition of [12], wherein the pharmaceutical composition is a tablet, a pill, a capsule, a liquid, an inhalant, a nasal spray solution, a suppository, a suspension, a gel, a colloid, a dispersion, a solution, an emulsion, an ointment, a lotion, an eye drop or ear drop.

The pharmaceutical composition of [12], further comprising another therapeutic agent.

A method of treating a disease or condition mediated by nicotinamide phosphoribosyltransferase (NAMPT) activity in a mammal comprising administering a compound of any one of [1]-[12], or a pharmaceutically acceptable salt thereof, to the mammal.

The method of [16], wherein the disease or condition is a metabolic disorder.

The method of [16], wherein the disease or condition is cardiovascular disease.

The method of [16], wherein the disease or condition is kidney disease.

The method of [16], wherein the disease or condition is mitochondrial disease.

The method of [16], wherein the disease or condition is a neurodegenerative disease.

The method of [16], wherein the disease or condition is an ocular disease.

The method of [16], wherein the disease or condition is a muscle wasting disorder.

Use of a compound of any one of [1]-[12], or a pharmaceutically acceptable salt thereof, in the manufacture of a medicament for the treatment or prevention of a disease or condition mediated by NAMPT activity.

In the present invention, the $C_1$-$C_6$ alkyl group refers to a straight or branched hydrocarbon chain radical, having from 1 to 6 carbon atoms, and which is attached to the rest of the molecule by a single bond. Likewise, an alkyl group comprising up to 3 carbon atoms is a $C_1$-$C_3$ alkyl group, and an alkyl group comprising up to 4 carbon atoms is a $C_1$-$C_4$ alkyl group.

Examples thereof include methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl.

The $C_1$-$C_3$ alkyl group may be optionally substituted with a $C_1$-$C_3$ alkoxy group. Examples thereof include methoxyethyl, methoxypropyl, methoxyisopropyl, ethoxyethyl, ethoxypropyl, ethoxyisopropyl, propoxyethyl, propoxypropyl, and propoxyisopropyl.

The $C_1$-$C_6$ alkyl group may be optionally substituted with a $C_3$-$C_6$ cycloalkyl group. Examples thereof include 1-methylcyclopropyl, 1-methylcyclobutyl, and 1-methylcyclohexyl.

In the present invention, the $C_1$-$C_6$ alkoxy group refers to a radical of the formula —OR where R is a $C_1$-$C_6$ alkyl group as defined. Likewise, an alkoxy group comprising up to 3 carbon atoms is a $C_1$-$C_3$ alkoxy group. Examples thereof include methoxy, ethoxy, n-propoxy, isopropoxy, n-butoxy, isobutoxy, s-butoxy, tert-butoxy, n-pentoxy, isopentoxy, 2-methylbutoxy, neopentoxy, 1-ethylpropoxy, n-hexyloxy, isohexyloxy, 4-methylpentoxy, 3-methylpentoxy, 2-methylpentoxy, 1-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, and 2-ethylbutoxy.

The $C_1$-$C_3$ alkoxy group may be optionally substituted with a $C_1$-$C_3$ alkoxy group. Examples thereof include methoxymethoxy, methoxyethoxy, methoxypropoxy, methoxyisopropoxy, ethoxymethoxy, ethoxyethoxy, ethoxypropoxy, ethoxyisopropoxy, propoxymethoxy, propoxyethoxy, propoxypropoxy, and propoxyisopropoxy.

In the present invention, the "$C_3$-$C_6$ cycloalkylamino group" is, for example, azacyclobutyl, pyrrolidino, piperidino, or hexamethylenimino.

In the present invention, the $C_3$-$C_6$ cycloalkyl group refers to a monocyclic non-aromatic radical having from 3 to 6 ring atoms, wherein each of the atoms forming the ring (i.e. skeletal atoms) is a carbon atom. Examples thereof include cyclopropyl, cyclobutyl, cyclopentyl, and cyclohexyl.

In the present invention, the halogen atom refers to fluorine atom, a chlorine atom, a bromine atom, or iodine atom.

In the present invention, the $C_1$-$C_3$ haloalkyl group refers to a $C_1$-$C_3$ alkyl radical, as defined above that is substituted with one or more halo radicals, as defined above. Examples thereof include trifluoromethyl, difluoromethyl, fluoromethyl, trichloromethyl, 2,2,2-trifluoroethyl, 1,2-difluoroethyl, 3-bromo-2-fluoropropyl, and 1,2-dibromoethyl.

In the present invention, the heteroaryl group refers to a monocyclic aryl group that includes one or more ring heteroatoms selected from nitrogen, oxygen and sulfur. Examples thereof include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazyl.

In the present invention, the $C_1$-$C_4$ alkylcarbonyl group refers to a carbonyl radical that is substituted by $C_1$-$C_4$ alkyl radical, as defined above. Examples thereof include methylcarbonyl, ethylcarbonyl, n-propylcarbonyl, isopropylcarbonyl, butylcarbonyl, and tert-butylcarbonyl.

In the present invention, the $C_1$-$C_3$ alkylsulfonyl group refers to a sulfonyl radical that is substituted by $C_1$-$C_3$ alkyl radical, as defined above. Examples thereof include methanesulfonyl, ethanesulfonyl, n-propanesulfonyl, and isopropanesulfonyl.

In the present invention, the $C_1$-$C_4$ alkoxycarbonyl group refers to a carbonyl radical that is substituted by $C_1$-$C_4$ alkoxy radical, as defined above. Examples thereof include methoxycarbonyl, ethoxycarbonyl, n-propoxycarbonyl, isopropoxycarbonyl, butoxycarbonyl, and tert-butoxycarbonyl.

In the present invention, the bicyclic ring containing one or more heteroatoms in the ring refers to a bicyclic ring containing one or more heteroatoms selected from nitrogen, oxygen, and sulfur in the ring. The bicyclic ring may be an aromatic heterocyclic ring or may be a non-aromatic heterocyclic ring. The aromatic heterocyclic ring may be partially saturated. The bicyclic ring contains one or more heteroatoms selected from nitrogen, oxygen, and sulfur in the ring and includes a fused ring of a 6-membered ring and a 5-membered ring, a fused ring of a 6-membered ring and a 6-membered ring, or a fused ring of a 6-membered ring and a 7-membered ring. Examples thereof include indolizinyl, isoindolyl, indolyl, indolinyl, octahydroindolyl, pyrazolopyridine, benzimidazolyl, 1H-pyrrolo[2,3-b]pyridyl, imidazo[1,2-a]pyridyl, benzopyrazolyl, 1H-indazolyl, 2H-indazolyl, triazolopyridine, pyrazolopyrimidine, benzofuranyl, 2,3-dihydrobenzofuranyl, octahydrobenzofuranyl, isobenzofuranyl, 1,3-dihydroisobenzofuranyl, hydroxybenzofuranyl, 1,3-benzodioxolanyl, 1,2-benzoxazolyl, benzisoxazolyl, benzothienyl, octahydrobenzothienyl, benzothiazolyl, chromenyl, quinolyl, decahydroquinolyl, isoquinolyl, decahydroisoquinolyl, 1,2,3,4-tetrahydroisoquinolyl, quinoxalyl, quinazolinyl, benzomorpholinyl, 3,4-dihydro-2H-1,4-benzoxazine, and 2,3,4,5-tetrahydro-1,5-benzoxazepine.

The compound of the present invention or a pharmacologically acceptable salt thereof is a compound represented by formula (I):

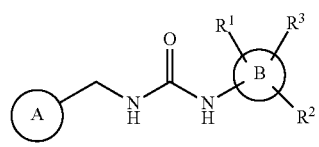

(I)

or a pharmacologically acceptable salt thereof.
In formula (I), ring A is

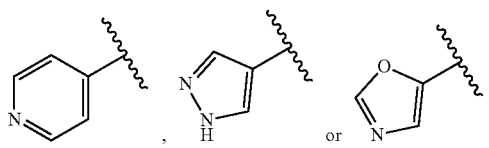

Ring B is a bicyclic ring containing one or more heteroatoms in the ring. The heteroatoms are selected from a nitrogen atom, an oxygen atom, and a sulfur atom. The bicyclic ring is preferably a bicyclic ring containing one or more heteroatoms selected from a nitrogen atom, an oxygen atom, and a sulfur atom in the ring and having a 6-membered ring fused with a 5-membered ring, a 6-membered ring fused with a 6-membered ring, or a 6-membered ring fused with a 7-membered ring. The bicyclic ring is more preferably a bicyclic ring containing one or more heteroatoms selected from a nitrogen atom and an oxygen atom in the ring and having a 6-membered ring fused with a 5-membered ring, a 6-membered ring fused with a 6-membered ring, or a 6-membered ring fused with a 7-membered ring. Preferred specific examples thereof include bicyclic rings represented by the following chemical structural formulas:

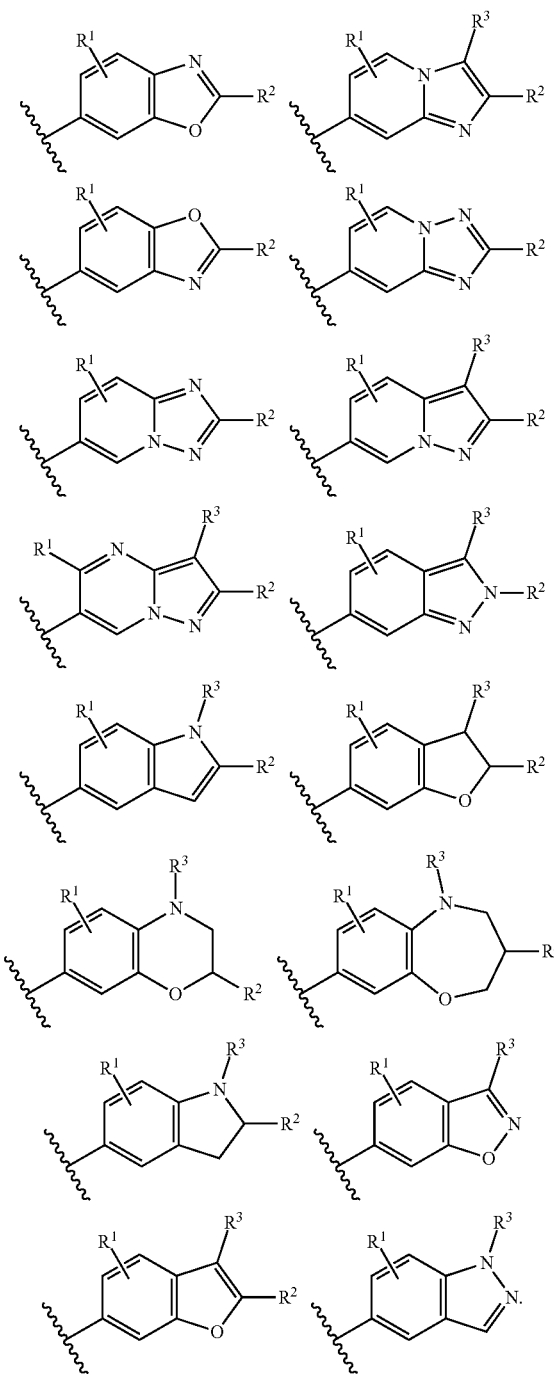

In the formulas, $R^1$, $R^2$, and R have the same meanings as those of $R^3$, $R^2$, and $R^3$ mentioned later.

$R^1$ is a hydrogen atom or a halogen atom. $R^1$ is preferably a hydrogen atom or a fluorine atom, more preferably a hydrogen atom.

$R^2$ is a hydrogen atom, a phenyl group or a heteroaryl group optionally substituted with one or more groups selected from group Y, as defined in [1], a $C_1$-$C_6$ alkyl group optionally substituted with a $C_3$-$C_6$ cycloalkyl group, or is absent.

$R^2$ is preferably a hydrogen atom; a phenyl group, a pyrazolyl group, a pyridinyl group, or a pyrrole group each optionally monosubstituted with a group selected from substituents of the following group Y; a $C_1$-$C_6$ alkyl group optionally substituted with one or more $C_3$-$C_6$ cycloalkyl groups; or is absent.

Group Y: a phenyl group, a halogen group, a $C_1$-$C_4$ alkyl group, a $C_1$-$C_3$ haloalkyl group, a $C_1$-$C_3$ alkylsulfonyl group, a $C_1$-$C_3$ alkoxy group, or a $C_1$-$C_3$ alkyl group or a $C_1$-$C_3$ alkoxy group each substituted with a $C_1$-$C_3$ alkoxy group.

$R^2$ is more preferably a hydrogen atom; a phenyl group, a pyrazolyl group, or a pyridinyl group each optionally monosubstituted with a group selected from substituents of the following group Y; a $C_1$-$C_3$ alkyl group; 1-methyl-cyclopropyl; or is absent.

Group Y: a $C_1$-$C_4$ alkyl group, a methanesulfonyl group, an ethanesulfonyl group, a methoxy group, an ethoxy group, a 2-methoxyethoxy group, a phenyl group, a trifluoromethyl group, a difluoromethyl group, a 2-methoxyethyl group, and a chlorine atom.

Among the more preferred $R^2$, examples of the phenyl group, pyrazolyl group, or pyridinyl group optionally monosubstituted with a group selected from substituents of group Y, as defined above, include 2-methylphenyl, 2-ethylphenyl, 2-(n-propyl)phenyl, 2-(n-butyl)phenyl, 3-methanesulfonylphenyl, 3-ethanesulfonylphenyl, 3-methoxyphenyl, 3-ethoxyphenyl, 3-(2-methoxyethoxy)phenyl, 2-trifluoromethylphenyl, 2-difluoromethylphenyl, 2-chlorophenyl, 1-methylpyrazol-4-yl, 1-methylpyrazol-5-yl, 1-ethylpyrazol-4-yl, 1-ethylpyrazol-5-yl, 1-(n-propyl)pyrazol-4-yl, 1-(n-propyl)pyrazol-5-yl, 1-butylpyrazol-4-yl, 1-butylpyrazol-5-yl, 1-ethanesulfonylpyrazol-5-yl, 5-methoxypyrazol-1-yl, 5-ethoxypyrazol-1-yl, 5-(2-methoxyethoxy)pyrazol-1-yl, 1-phenylpyrazol-5-yl, 1-(2-methoxyethyl)pyrazol-5-yl, 4-chloropyrazol-5-yl, 4-methylpyridin-2-yl, 3-ethylpyridin-4-yl, 3-propylpyridin-4-yl, 4-butylpyridin-2-yl, 3-methoxypyridin-4-yl, 4-(2-methoxyethoxy)pyridin-2-yl, 3-phenylpyridin-4-yl, 4-trifluoromethylpyridin-2-yl, and 3-chloropyridin-4-yl.

$R^2$ is particularly preferably a hydrogen atom, 2-methylphenyl, 2-(n-butyl)phenyl, 3-methanephenyl, 3-methoxyphenyl, 3-(2-methoxyethoxy)phenyl, 2-trifluoromethylphenyl, 2-chlorophenyl, 1-methylpyrazol-4-yl, 1-(2-methoxyethyl)pyrazol-5-yl, 1-methylpyrazol-5-yl, 1-butylpyrazol-4-yl, 1-butylpyrazol-5-yl, 5-methoxypyridin-4-yl, 1-methyl-cyclopropyl, or is absent.

$R^3$ is a hydrogen atom, a cyano group, a phenyl group or a heteroaryl group each optionally substituted with one or more groups selected from group Y, as defined in [1], a $C_1$-$C_4$ alkylcarbonyl group or a $C_1$-$C_4$ alkyl group each optionally substituted with one or more groups selected from group Z, as defined in [1], a carbonyl group substituted with a group selected from group Z, as defined in [1] or is absent.

$R^3$ is preferably a hydrogen atom; a cyano group; a $C_1$-$C_4$ alkyl group; a phenyl group or a heteroaryl group each optionally substituted with one or more groups selected from substituents of the following group Y; a methylcarbonyl group or a methyl group each optionally substituted with one or more groups selected from substituents of the following group Z; a carbonyl group substituted with a group selected from substituents of the following group Z; or is absent.

Group Y: a $C_1$-$C_3$ alkyl group, a $C_1$-$C_3$ alkoxy group, a phenyl group, a $C_1$-$C_3$ alkylsulfonyl group, a $C_1$-$C_3$ haloalkyl group, a halogen atom, and a $C_1$-$C_3$ alkyl group or a $C_1$-$C_3$ alkoxy each group substituted with a $C_1$-$C_3$ alkoxy group.

Group Z: a $C_1$-$C_2$ alkoxy group, a dioxanyl group, an 8-oxa-3-azabicyclo[3.2.1]octyl group, and an amino group or a $C_3$-$C_6$ cycloalkylamino group each optionally substituted with one or more groups selected from the following group W.

Group W: a phenyl group, a heteroaryl group, a $C_1$-$C_3$ alkyl group, a $C_1$-$C_3$ alkyl group substituted with phenyl, and a $C_1$-$C_3$ alkyl group substituted with a heteroaryl group.

$R^3$ is more preferably a hydrogen atom, a cyano group, a N-methylpyrazolyl group, a phenyl group, a methyl group, a 2-methoxyethyl group, a dioxanylmethyl group, and a carbonyl group substituted with a group selected from substituents of the following group Z.

Group Z: an 8-oxa-3-azabicyclo[3.2.1]octyl group, and an amino group optionally substituted with one or more groups selected from substituents of the following group W.

Group W: a $C_1$-$C_3$ alkyl group, a methylphenyl group, and a $C_1$-$C_3$ alkyl group substituted with a heteroaryl group.

Among the more preferred $R^3$, examples of the carbonyl group optionally substituted with a group selected from substituents of group Z, as defined above, include methylaminocarbonyl, ethylaminocarbonyl, dimethylaminocarbonyl, diethylaminocarbonyl, N-benzyl-N-ethylaminocarbonyl, and N-ethyl-N-phenylcarbonyl.

Particularly preferred examples of $R^3$ include a hydrogen atom, a cyano group, a N-methylpyrazolyl group, a phenyl group, a methyl group, a 2-methoxyethyl group, a dioxanylmethyl group, an 8-oxa-3-azabicyclo[3.2.1]octylcarbonyl group, a diethylaminocarbonyl group, and a N-benzyl-N-ethylaminocarbonyl group.

Examples of the compound represented by formula (I) of the present invention can include the following compounds, though the present invention is not limited by these compounds:

N-(2-phenyl-1,3-benzoxazol-5-yl)-N'-[(pyridin-4-yl)methyl]urea,

N-(2-phenyl-1,3-benzoxazol-6-yl)-N'-[(pyridin-4-yl)methyl]urea,

N-[2-(2-methylphenyl)-1,3-benzoxazol-6-yl]-N'-[(pyridin-4-yl)methyl]urea,

N-[(1,3-oxazol-5-yl)methyl]-N'-(2-phenyl-1,3-benzoxazol-6-yl)urea,

N-[2-(1-methyl-1H-pyrazol-4-yl)-1,3-benzoxazol-6-yl]-N'-[(pyridin-4-yl)methyl]urea, N-[2-(1-methylcyclopropyl)-1,3-benzoxazol-6-yl]-N'-[(pyridin-4-yl)methyl]urea, N-(5-fluoro-2-phenyl-1,3-benzoxazol-6-yl)-N'-[(pyridin-4-yl)methyl]urea, N-(2-phenylimidazo[1,2-a]pyridin-7-yl)-N'-[(pyridin-4-yl)methyl]urea, N-(2-phenyl-1H-indol-5-yl)-N'-[(pyridin-4-yl)methyl]urea, methyl [2-phenyl-5-({[(pyridin-4-yl)methyl]carbamoyl}amino)-1H-indol-1-yl]acetate, N-{2-[3-(methanesulfonyl)phenyl]-1-methyl-1H-indol-5-yl}-N'-[(pyridin-4-yl)methyl]urea, N-{2-[3-(2-methoxyethoxy)phenyl]-1-methyl-1H-indol-5-yl}-N'-[(pyridin-4-yl)methyl]urea, N-[1-(2-methoxyethyl)-2-phenyl-1H-indol-5-yl]-N'-[(pyridin-4-yl)methyl]urea, N-[1-methyl-2-(pyridin-2-yl)-1H-indol-5-yl]-N'-[(pyridin-4-yl)methyl]urea, N-(1-methyl-2-phenyl-1H-indol-5-yl)-N'-[(pyridin-4-yl)methyl]urea, N-{1-[(1,4-dioxan-2-yl)methyl]-2-phenyl-1H-indol-5-yl}-N'-[(pyridin-4-yl)methyl]urea, N,N-dimethyl-2-phenyl-5-({[(pyridin-4-yl)methyl]carbamoyl}amino)-1H-indole-1-carboxamide, N-[1-(2-methylpropyl)-1H-indazol-5-yl]-N'-[(pyridin-4-yl)methyl]urea, N-(2-phenyl[1,2,4]triazolo[1,5-a]pyridin-6-yl)-N'-[(pyridin-4-yl)methyl]urea,
N-[(1,3-oxazol-5-yl)methyl]-N'-(2-phenyl[1,2,4]triazolo[1,5-a]pyridin-6-yl)urea,
N-(2-phenyl[1,2,4]triazolo[1,5-a]pyridin-6-yl)-N'-[(1H-pyrazol-4-yl)methyl]urea,
N-[2-(2-butylphenyl) [1,2,4]triazolo[1,5-a]pyridin-6-yl]-N'-[(pyridin-4-yl)methyl]urea,
N-[2-(1-phenyl-1H-pyrrol-2-yl) [1,2,4]triazolo[1,5-a]pyridin-6-yl]-N'-[(pyridin-4-yl)methyl]urea,
N-[2-(1-methyl-1H-pyrazol-5-yl) [1,2,4]triazolo[1,5-a]pyridin-6-yl]-N'-[(pyridin-4-yl)methyl]urea,
N-[(pyridin-4-yl)methyl]-N'-{2-[2-(trifluoromethyl)phenyl][1,2,4]triazolo[1,5-a]pyridin-6-yl}urea,
N-(2-phenyl[1,2,4]triazolo[1,5-a]pyridin-7-yl)-N'-[(pyridin-4-yl)methyl]urea,
N-(2-phenylpyrazolo[1,5-a]pyridin-6-yl)-N'-[(pyridin-4-yl)methyl]urea,
N-(2-phenylpyrazolo[1,5-a]pyrimidin-6-yl)-N'-[(pyridin-4-yl) methyl]urea,
N-(3-methyl-2-phenylpyrazolo[1,5-a]pyridin-6-yl)-N'-[(pyridin-4-yl)methyl]urea,
N-(3-cyano-2-phenylpyrazolo[1,5-a]pyridin-6-yl)-N'-[(pyridin-4-yl)methyl]urea,
N-[2-(3-methoxyphenyl)pyrazolo[1,5-a]pyridin-6-yl]-N'-[(pyridin-4-yl)methyl]urea,
N,N-dimethyl-2-phenyl-6-({[(pyridin-4-yl)methyl]carbamoyl}amino)pyrazolo[1,5-a]pyridine-3-carboxamide,
N-[3-(1-methyl-1H-pyrazol-5-yl)-2-phenylpyrazolo[1,5-a]pyridin-6-yl]-N'-[(pyridin-4-yl)methyl]urea, 4-fluoro-N,N-dimethyl-2-phenyl-6-({[(pyridin-4-yl)methyl]carbamoyl}amino)pyrazolo[1,5-a]pyridine-3-carboxamide,
N-(2-phenyl-2H-indazol-6-yl)-N'-[(pyridin-4-yl) methyl]urea,
N-[(1,3-oxazol-5-yl)methyl]-N'-(2-phenyl-2H-indazol-6-yl)urea,
N-[2-(3-methoxyphenyl)-2H-indazol-6-yl]-N'-[(pyridin-4-yl) methyl]urea,
N-{2-[2-(2-methoxyethoxy)phenyl]-2H-indazol-6-yl}-N'-[(pyridin-4-yl)methyl]urea,
N-(3-methyl-2-phenyl-2H-indazol-6-yl)-N'-[(pyridin-4-yl)methyl]urea,
N-{2-[3-(methanesulfonyl)phenyl]-2H-indazol-6-yl}-N'-[(pyridin-4-yl)methyl]urea,
N-(3-cyano-2-phenyl-2H-indazol-6-yl)-N'-[(pyridin-4-yl)methyl]urea,
N,N-diethyl-2-phenyl-6-({[(pyridin-4-yl)methyl]carbamoyl}amino)-2H-indazole-3-carboxamide,
N-[2-phenyl-3-(pyrrolidine-1-carbonyl)-2H-indazol-6-yl]-N'-[(pyridin-4-yl)methyl]urea,
N-[3-cyano-2-(2-methoxypyridin-4-yl)-2H-indazol-6-yl]-N'-[(pyridin-4-yl)methyl]urea,
N-[2-(2-chlorophenyl)-3,4-dihydro-2H-1,4-benzoxazin-7-yl]-N'-[(pyridin-4-yl)methyl]urea,
N-[4-(2-methoxyethyl)-2-phenyl-3,4-dihydro-2H-1,4-benzoxazin-7-yl]-N'-[(pyridin-4-yl)methyl]urea, 2-(2-chlorophenyl)-N-ethyl-7-({[(pyridin-4-yl)methyl]carbamoyl}amino)-2,3-dihydro-4H-1,4-benzoxazine-4-carboxamide,
N-(2-phenyl-3,4-dihydro-2H-1,4-benzoxazin-7-yl)-N'-[(pyridin-4-yl)methyl]urea,
N-(3-phenyl-5-propanoyl-2,3,4,5-tetrahydro-1,5-benzoxazepin-8-yl)-N'-[(pyridin-4-yl)methyl]urea,
N-(1-acetyl-2-phenyl-2,3-dihydro-1H-indol-5-yl)-N'-[(pyridin-4-yl)methyl]urea,
N,N-diethyl-6-({[(pyridin-4-yl)methyl]carbamoyl}amino)-1,2-benzoxazole-3-carboxamide,
N-(2-phenyl-2,3-dihydro-1-benzofuran-6-yl)-N'-[(pyridin-4-yl)methyl]urea,
N-[2-(3-methoxyphenyl)-2,3-dihydro-1-benzofuran-6-yl]-N'-[(pyridin-4-yl)methyl]urea,
N-[(2S,3S)-2-(3-methoxyphenyl)-3-methyl-2,3-dihydro-1-benzofuran-6-yl]-N'-[(pyridin-4-yl)methyl]urea,
N-(3-phenyl-2,3-dihydro-1-benzofuran-6-yl)-N'-[(pyridin-4-yl)methyl]urea, and
N,N-diethyl-6-({[(pyridin-4-yl)methyl]carbamoyl}amino)-1-benzofuran-3-carboxamide.

As for the pharmacologically acceptable salt of the compound represented by formula (I) of the present invention, examples of acid addition salts formed with acids can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornithine salts, glutamate, and aspartate.

Examples of the base addition salts formed with bases can include: alkali metal salts such as sodium salt, potassium salt, and lithium salt; alkaline earth metal salts such as calcium salt and magnesium salt; inorganic salts such as ammonium salt; organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N,N'-dibenzylethylenediamine salt, diethanolamine salt, N-benzyl-N-(2-phenylethoxy)amine salt, piperazine salt, tetramethyl ammonium salt, and tris(hydroxymethyl)aminomethane salt; and amino acid salts such as arginine salt.

When the compound represented by formula (I) of the present invention or the pharmacologically acceptable salt thereof has at least one chiral center, carbon-carbon double bond, axial chiral, tautomerism, or the like, optical isomers including enantiomers and diastereomers, geometric isomers, rotational isomers, and tautomers may exist. The present invention encompasses each of these isomers and mixtures thereof at arbitrary ratios. Mixture can include racemates thereof at arbitrary ratios. Mixture thereof can be isolated by well-known isolation means.

The compound represented by formula (I) of the present invention or the pharmacologically acceptable salt thereof can form an isotopic compound by the replacement of one or more atoms constituting the compound or the salt with isotopes at nonnatural ratios. The isotopes can be radioactive or nonradioactive. Examples thereof include deuterium ($^2H$; D), tritium ($^3H$; T), carbon-14 ($^{14}C$), and iodine-125 ($^{125}I$). The radioactive or nonradioactive isotopic compound can be used as a pharmaceutical drug for the treatment or prevention of a disease, a reagent for research (e.g., a reagent for assay), a diagnostic agent (e.g., a diagnostic imaging agent), or the like. The present invention encompasses these radioactive or nonradioactive isotopic compounds.

The compound represented by formula (I) of the present invention or the pharmacologically acceptable salt thereof may be present as a solvate. Such a solvent is also included in the compound represented by formula (I) of the present invention or the pharmacologically acceptable salt thereof.

The solvate is not particularly limited as long as the solvate is pharmacologically acceptable. Examples thereof include hydrate and ethanol solvate.

When the compound represented by formula (I) of the present invention or a pharmacologically acceptable salt thereof has a substituent such as a carboxy group, this compound or salt can be converted to a pharmaceutically acceptable prodrug. The present invention also encompasses such a pharmaceutically acceptable prodrug.

The "pharmacologically acceptable prodrug" refers to a compound that is converted to the compound represented by formula (I) of the present invention (hereinafter, also referred to as the present compound (I)) through reaction with an enzyme, gastric juice, or the like under physiological conditions in vivo, i.e., a compound that is converted to the present compound (I) by enzymatic oxidation, reduction, hydrolysis, etc., or a compound that is converted to the present compound (I) by hydrolysis, etc. by gastric juice or the like.

Examples of such a prodrug include present compound (I) with its carboxy group esterfied or amidated (e.g., compounds with its carboxy group ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolan-4-yl)methyl-esterified, cyclohexyloxycarbonylethyl-esterified, sulfuric acid-esterified, glucuronidated, glycosidated, galactosidated, or methylamidated).

The pharmacologically acceptable prodrug of the present compound (I) can be easily manufactured from the present compound (I) by a known method. The prodrug of the compound of the present invention also includes compounds that are converted to the present compound (I) under physiological conditions, as described in "Iyakuhin no Kaihatsu", Vol. 7, Molecular Design, p. 163-198, Hirokawa-Shoten Ltd. (1990).

The compound represented by formula (I) of the present invention or the pharmacologically acceptable salt thereof is a potent NAMPT activator and is useful as a pharmaceutical drug for use as a therapeutic agent and/or a prophylactic agent for various human diseases including metabolic disorders, cardiovascular diseases, kidney diseases, mitochondrial disease, neurodegenerative diseases, ocular diseases and muscle wasting disorders, etc., or a pharmaceutical drug for use in a method of treating and/or preventing these diseases. Hereinafter, the compound represented by formula (I) of the present invention or the pharmacologically acceptable salt thereof is also referred to as a NAMPT activator.

Metabolic Disorders

Metabolic disorders including obesity, diabetes mellitus and so on are involved in energy imbalance between energy intake and expenditure. Although proper dietary restriction and exercise are the best means to improve the metabolic disorders, weight maintenance interventions are usually of limited duration and long-term adherence to exercise is often problematic. The drug intervention can help to achieve the goal of clinical treatments. Thus, modulation of energy expenditure is a promising approach to correct the energy imbalance in the metabolic disorders.

$NAD^+$ is an essential coenzyme in all cells and involved cellular metabolism. Recent report suggests that supplementation of nicotinamide mononucleotide (NMN), a product of the NAMPT reaction, is beneficial in treatment of diabetes and obesity (Yoshino, J., et al. 2011; Cell Metab. 14, 528-536). The $NAD^+$ salvage pathway supplements such as NAM, nicotinic acid, NMN or nicotinamide riboside can increase $NAD^+$ and may be beneficial in treatment of metabolic disorders. However, these supplements has limitation to use because of their side-effects (Conze, D. B., et al. Hum Exp Toxicol. 2016; (11), 1149-1160) and poor pharmacokinetics such as short half-life. Based on the importance of $NAD^+$ level in the regulation of energy metabolism, NAMPT activation is expected to modulate processes involved in metabolic disorders including obesity and diabetes.

In some embodiments, administration of a NAMPT activator to a subject with diabetes treats, prevents, or ameliorates the symptoms of hyperglycemia and insulin resistance.

In some embodiments, administration of a NAMPT activator to a subject with obesity and/or diabetes induces the increase of energy expenditure which leads to weight loss by the increase of $NAD^+$.

In some embodiment, a NAMPT activator in this invention may be administered as a combination therapy for treating or preventing a metabolic disorder. For example, a pharmaceutical composition of the invention may be administered in combination with one or more anti-diabetic agents including insulin (including orally bioavailable insulin preparations), an insulin mimetic, metformin, acarbose, a peroxisome proliferator-activated receptor-y (PPAR-y) ligand, a sulfonylurea, a glucosidase inhibitor, a glucagon-like peptide-1 agonist, a dipeptidyl peptidase IV inhibitor, a sodium-glucose co-transporter 2 inhibitor, an aldose reductase inhibitor, a glycogen phosphorylase inhibitor, a sorbitol dehydrogenase inhibitor, a protein tyrosine phosphatase IB inhibitor, a dipeptidyl protease inhibitor and so on.

In some embodiment, a NAMPT activator in this invention may be administered as a combination therapy for treating or preventing a metabolic disorder. For example, a pharmaceutical composition of the invention may be administered in combination with one or more anti-obesity agents including a pancreatic lipase inhibitor, a combination of appetite-suppressant sympathomimetic amine and anticonvulsant such as Qsymia® (Phentermine/Topiramate ER) or Contrave® (Naltrexone SR/Bupropion SR), a serotonin 2c receptor agonist, a glucagon-like peptide-1 agonist, a sodium-glucose co-transporter 2 inhibitor and so on.

Cardiovascular and Kidney Disease

ATP is the most important energy for the cell functions in human body. Some organs in body including heart and kidney require the greatest amounts of ATP to sustain their functions. $NAD^+$ is involved in ATP generation and the level of $NAD^+$ is critical for heart and kidney function and recovery from injury (Hershberger K. A. et al. Nat Rev Nephrol. 2017; 13(4): 213-225). $NAD^+$ level is a key factor for responses to pathological stress in the heart and kidney. Based on the importance of NAMPT in the regulation of $NAD^+$ level, NAMPT has a critical role in protecting the heart against pathological stress, whereas in the kidneys, in cell growth and survival.

$NAD^+$ supplementation has a beneficial effect on cardiac function. In a model of pressure-overload induced left ventricle hypertrophy, supplementation with NMN or genetic manipulation of enzymes in the $NAD^+$ salvage pathways increased $NAD^+$ levels and improved cardiac function (Lee, C. F. et al., 2016; Circulation 134, 883-894). Similarly, in kidneys subjected to ischemia, nicotinamide supplementation increased $NAD^+$ levels and decreased the levels of toxic fatty acids that have a critical role in the pathological progression of AKI (Tran M T, et al., Nature 2016; 531:528-532.)

In some embodiment, the invention provides a method for treating and/or preventing a cardiovascular disease including acute/chronic heart failure, cardiac hypertrophy, cardiomyopathy or myocarditis, such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries.

In some embodiment, a NAMPT activator in this invention may be administered as a combination therapy for treating or preventing cardiovascular and/or kidney disease For example, a pharmaceutical composition of the invention may be administered in combination with one or more anti-hypertensive agents including an angiotensin converting enzyme inhibitor, a calcium channel blocker, an angiotensin-receptor blockers, a beta-blocker, a diuretic, a mineralocorticoid receptor blocker and so on.

In some embodiment, a NAMPT activator in this invention may be administered as a combination therapy for treating or preventing cardiovascular and/or kidney disease. For example, a pharmaceutical composition of the invention may be administered in combination with one or more drugs for heart failure treatment including an angiotensin converting enzyme inhibitor, a calcium channel blocker, an angiotensin-receptor blockers, a beta-blocker, a diuretic, a mineralocorticoid receptor blocker, an angiotensin receptor/neprilysin inhibitor, an $I_f$ channel blocker, an aldosterone antagonist, a digoxin, a combination drug such as hydralazine and isosorbide dinitrate BiDil, an anti-coagulant, a cholesterol lowering drug such as statins and so on.

Mitochondrial Disease Mitochondria are responsible for generating most of the energy needed by the body to sustain life and support organ function. Mitochondria generate ATP which is the most important energy for the cell functions in human body. Some organs in body including brain, heart, and skeletal muscles, require the greatest amounts of ATP to sustain their functions.

Mitochondrial diseases are caused by dysfunction of mitochondria in the cells. Mitochondrial dysfunctions in the diseases are caused by mutations in genes in the mitochondrial DNA and nuclear DNA that encode the proteins involved into mitochondrial structures and functions. Mitochondrial respiratory chain activity is insufficient in mitochondrial diseases and the organs that need much ATP to keep their functions are the most affected by the dysfunction of mitochondria.

The symptoms of mitochondrial disease are various and mitochondrial disease should be suspected when three or more organ systems are involved. The severity of mitochondrial disease is different from person to person. The most common symptoms are metabolic and neurological disorders including poor growth, weakness of skeletal muscle, vision and/or hearing loss, problems with heart, lungs, brain or other organs, learning disabilities, neurological problems and so on.

Recent paper mentions the importance to increase $NAD^+$ level for treating a mitochondrial disease (Khan N. A. et al., EMBO Mol Med. 2014; 6(6):721-31). Based on importance of NAMPT in regulation of $NAD^+$ and ATP levels, NAMPT activator in this invention may be useful for treating and/or preventing a mitochondrial disease by increasing the level of $NAD^+$ in the cells. Suitable mitochondrial diseases include Leber's hereditary optic neuropathy (LHON), mitochondrial encephalomyopathy lactic acidosis and stroke-like episodes (MELAS), myoclonic epilepsy and ragged-red fiber disease (MERRF), and Leigh syndrome (LS), Charcot-Marie-Tooth disease, Type 2A2, Barth Syndrome, fatty acid oxidation disorders, inherited forms of deafness and blindness, metabolic abnormalities induced by toxic chemicals and/or drugs such as cisplatin induced deafness, gentamycin induced deafness, and as otherwise described herein.

In some embodiment, a NAMPT activator in this invention may be administered as a combination therapy for treating or preventing mitochondrial disease. For example, a pharmaceutical composition of the invention may be administered in combination with one or more drugs/supplementations for mitochondrial disease treatment including vitamins and/or amino acids.

Neurodegeneration

Neurodegeneration is a progressive deterioration of neuronal structures and functions ultimately leading to impaired motor function, cognitive disability and/or dementia. Recently, accumulating data suggest that neurodegenerative diseases are associated with mitochondrial dysfunction. The brain is one of the most energy-consuming organs. Mitochondria are involved in energy production and plays an important role in maintaining nerve functions.

The slow Wallerian degeneration mutant ($Wld^s$) mice show the delayed Wallerian degeneration. The $Wld^s$ mice overexpress a chimeric Ube4b/Nmnat1 gene. NMNAT1 is an enzyme responsible for the final process of $NAD^+$ synthesis in the salvage pathway. Araki et al. showed that the increased Nmnat activity was responsible for the axon-sparing activity of the $Wld^s$ protein, which suggests increasing the supply of $NAD^+$ may be effective for treatment of diseases (Araki et al. Science (2004) 305, 1010-3).

The beneficial effects of increasing $NAD^+$ on neurodegeneration have also been confirmed by some experiments using intermediates of $NAD^+$ synthesis.

For example, it has been reported that NAM, a substrate of $NAD^+$ biosynthesis, reduces the infarct size in rat models of cerebral ischemia (Ayoub A I et al., Neuroscience Lett (1999) 259, 21-4). Similar results were also reported using NMN (Wei C C et al., Br J Pharmacol (2017) 174, 3823-36). In Alzheimer's disease, the supplementation of nicotinamide riboside (NR) which is converted by nicotinamide riboside kinases to NMN ameliorates the cognitive functions and suppresses their pathological progression in mouse models for Alzheimer's disease (Gong B et al., Neurobiol Aging (2013) 34, 1581-8). It has also been reported that the administration of niacin ameliorates the physical functions of patients with Parkinson's disease (Alisky J M Nutr Neurosci (2005) 8, 327-9). In addition, it has been reported that: NAM suppresses mitochondrial dysfunction and inhibits cell death in a cellular model cells of Parkinson's disease; NAM protected the monitor functions of Parkinson's disease in *drosophila* models (Jia H et al., J Neurosci Res (2008) 86, 2083-90).

These results suggest that reduced $NAD^+$ levels are largely involved in neurodegeneration, and the intervention of medicaments such as NAMPT activators may increase $NAD^+$ supply and suppress the onset and/or progression of neurodegenerative diseases including, for example, Alzheimer's disease, Parkinson's disease, amyotrophic lateral sclerosis (ALS), traumatic brain injury, depression, Down syndrome, neonatal brain injury, ischemic stroke, carpal tunnel syndrome, Guillain-Barre syndrome, and nerve injury and spinal cord injury caused by trauma, diabetes mellitus, alcohol, polio, or the like so that nerve functions can be maintained.

The NAMPT activator of the present invention may be used in combination with various medicaments for use in the prevention of onset or treatment of neurodegenerative diseases. For example, combined use with donepezil hydrochloride, galantamine, rivastigmine, memantine, L-dopa, a dopamine agonist, a catechol-O-methyltransferase (COMT) inhibitor, a monoamine oxidase B (MAO-B) inhibitor, zonisamide, an adenosine A2A receptor antagonist, droxidopa, amantadine, an anticholinergic drug, SSRI, SNRI, NaSSA, a tricyclic or tetracyclic antidepressant, an antiplatelet drug, an anticoagulant, or an anti-arrhythmic drug is possible.

Retinal Degeneration

In recent years, it has been pointed out that reduced $NAD^+$ levels are involved in retinal degeneration. Koenekoop et al. have found that NMNAT1 is one of the causative genes of LCA (Leber congenital amaurosis), the most common cause of blindness in children, and $NAD^+$ may play an important role in maintaining retinal functions (Koenekoop R K et al., Nature Genetics (2012) 44, 1035-9). Lin et al. have reported that: intraretinal $NAD^+$ contents are decreased prior to retinal degeneration in various retinal degeneration mouse models; retinal degeneration is caused by NAMPT deficiency in photoreceptor cells in the retina (Lin J B et al., Cell Reports (2016) 17, 69-85). Williams et al. have reported that: the administration of NAM to DBA/2J (D2) mice, which develop glaucoma by aging, increases intraretinal $NAD^+$ contents and accordingly suppresses the onset/progression of glaucoma; the onset/progression of glaucoma can also be suppressed by the overexpression of the NMNAT1 gene using AAV vectors in the eyes of the mice (Williams P A et al., Science (2017) 355, 756-60). These facts suggest that intraretinal $NAD^+$ levels are deeply involved in the onset and progression of retinal degeneration, and the intervention of medicaments such as NAMPT activators can be expected to suppress the onset and/or progression of retinal degeneration including, for example, age-related macular degeneration, retinal pigmentary degeneration, diabetic retinopathy, retinal vein occlusion, glaucoma, and macular dystrophy.

The NAMPT activator of the present invention may be used in combination with medicaments for use in the prevention of onset or treatment of retinal degenerative diseases or medicaments that are often used in combination with remedies for these diseases. For example, combined use with a prostaglandin-related drug, a sympatholytic drug, a carbonate dehydratase inhibitor, an α2 receptor agonist, a calpain inhibitor, or an angiogenesis inhibitor such as an anti-VEGF antibody is possible.

Muscle Wasting Disorder

There are many causes for the muscle wasting and atrophy. For example, there are two major forms of muscle wasting; disuse atrophy in which the muscles waste away due to lack of exercise, neurogenic atrophy which is muscle deterioration due to disease or injury. Malnutrition associated with insufficient energy intakes and/or physiological change such as cancer cachexia and sarcopenia with aging also can cause muscle atrophy. The skeletal muscle occupies approximately 40% of the body weight. The skeletal system is an important body system to keep critical functions for the human body such as the body support, movement and protection of internal organs. The skeletal muscle is also responsible for regulating amino acid and carbohydrate metabolism. Thus, the maintenance of skeletal muscle mass and functions is important to keep the physical functions and prevent metabolic syndrome. The prevention of skeletal muscle wasting is an important public health challenge in the super-aging society.

Accumulating data suggest that mitochondrial dysfunction as well as imbalance between protein synthesis and degradation is responsible for skeletal muscle wasting. Gomes et al. have found that the administration of NMN to old mice restores mitochondrial functions and ATP production, which are reduced with aging, in the skeletal muscle, and switches gastrocnemius muscle to a more oxidative fiber type (Gomes A P et al., Cell (2013) 155, 1624-38). Zhang et al. have reported that the administration of NR to old mice ameliorates mitochondrial functions in the skeletal muscle and improves muscle stem cells to promote muscle regeneration (Zhang H et al., Science (2016) 352, 1436-43). Cosford et al. have developed skeletal muscle-specific NAMPT-overexpressing transgenic mice and found that these mice significantly increase $NAD^+$ contents in the skeletal muscle and significantly increase running endurance in a treadmill test (Cosford S R et al., Mol Metab (2018) 7, 1-11). These facts suggest that the decreased $NAD^+$ level is involved in disuse muscle atrophy or muscle wasting with aging, and the administration of NAMPT activators can restore mitochondrial functions in the skeletal muscle and restore or maintain skeletal muscle mass decreased due to disuse muscle atrophy, muscle wasting ascribable to decreased energy intakes, cancer cachexia, sarcopenia, muscular dystrophy, congenital myopathy, inflammatory and metabolic myopathy, mitochondrial encephalomyopathy, spinal muscular atrophy, amyotrophic lateral sclerosis, spinal and bulbar atrophy, Guillain-Barre syndrome, or chronic inflammatory demyelinating polyradiculoneuritis.

The NAMPT activator of the present invention may be used in combination with various medicaments for use in the prevention or treatment of various diseases associated with skeletal muscle wasting. For example, combined use with steroid, an immunosuppressant, riluzole, edaravone, or perampanel is possible.

Advantageous Effects of Invention

The compounds of the present invention represented by the formula (I) or pharmaceutically acceptable salt thereof are potent NAMPT activators and can be beneficial in the treatment and/or prevention of various human diseases including metabolic disorders, cardiovascular diseases, kidney diseases, mitochondrial disease, neurodegenerative diseases, ocular diseases and muscle wasting disorders.

BRIEF DESCRIPTION OF DRAWINGS

FIG. 1 is a graph showing that the administration of a compound of Example 2(Compound 2) increases $NAD^+$ levels in various tissues of normal mice, wherein the ordinate depicts the $NAD^+$ concentrations [nmol/g] in various tissues of mice after the oral administration of the compound of Example 2 (30, 100 mg/kg), and the abscissa depicts names of various tissues. The Compound 2-treated groups were compared to the vehicle control group by Dunnet's test; *$P<0.05$(Mean±SEM, n=4).

FIG. 2 is a graph showing that the oral administration of the compound of Example 2(Compound 2, 30, 100 mg/kg) increases $NAD^+$ levels in various tissues of diet-induced obese (DIO) mice, wherein the ordinate depicts the $NAD^+$ concentrations [nmol/g] in various tissues of the mice after the administration of the compound of Example 2, and the abscissa depicts names of various tissues. The compound 2-treated groups were compared to the vehicle control group by Dunnet's test; *$P<0.05$, **$P<0.01$ (Mean±SEM, n=4).

FIG. 3 is a graph showing that the oral administration of the compound of Example 2(Compound 2, 100 mg/kg) increases oxygen consumption, wherein the ordinate depicts the oxygen consumptions (VO2 [mL/kg]) of DIO mice given the compound of Example 2 and DIO mice given vehicle (0.5% methylcellulose), and the abscissa depicts time [hour] after the start of administration. The graph shows representative data of oxygen consumption (Mean, n=4).

FIG. 4 is a graph showing that the oral administration of the compound of Example 2(Compound 2, 30 mg/kg) decreases body weights as compared to a vehicle group, wherein the ordinate depicts the weight changes [%] of DIO mice freely fed a purified high-fat diet and also given the compound of Example 2, and DIO mice given vehicle (0.5% methylcellulose), and the abscissa depicts the number of days [day] after the start of administration. The Compound 2-treated group was compared to the vehicle control group by student's t-test; *$P<0.05$, $P<0.01$, *$P<0.001$ (Mean±SEM, n=6).

FIG. 5 is a graph showing that high-fat loading decreases or makes no change in $NAD^+$ levels in various tissues, whereas the oral administration of the compound of Example 2(Compound 2, 30 mg/kg) increases $NAD^+$ levels, wherein the ordinate depicts the $NAD^+$ concentrations [nmol/g tissue] in various tissues (WAT, lung, heart, kidney, spleen) of DIO mice given or not given the compound of Example 2 after induction of an obese condition, and the abscissa depicts mice fed a normal diet and given vehicle, DIO mice given vehicle, and DIO mice given the compound of Example 2 in this order. P values were calculated by student's t-test; +++$P<0.001$ (DIO-vehicle control group vs Normal-vehicle control group); $P<0.01$, *$P<0.001$ (DIO-Compound 2-treaded group vs DIO-vehicle control group). The data represents Mean±SEM (n=4).

FIG. 6 is a graph showing that the oral administration of the compound of Example 2(Compound 2, 30 mg/kg) increases $NAD^+$ levels in a retinal tissue, wherein the ordinate depicts the $NAD^+$ concentrations [nmol/g tissue] in the retinal tissue, and the abscissa depicts a vehicle group and mice given the compound of Example 2 in this order. The data represents Mean±SEM (n=3).

FIG. 7 is a graph showing that the administration of the compound 2 shortened the immobility time in the FST of WKY rats, reflecting the anti-depressant-like effect. Ketamine group was compared to vehicle control by t-test (Mean±SEM, n=16).

DESCRIPTION OF EMBODIMENTS

Figure 1:
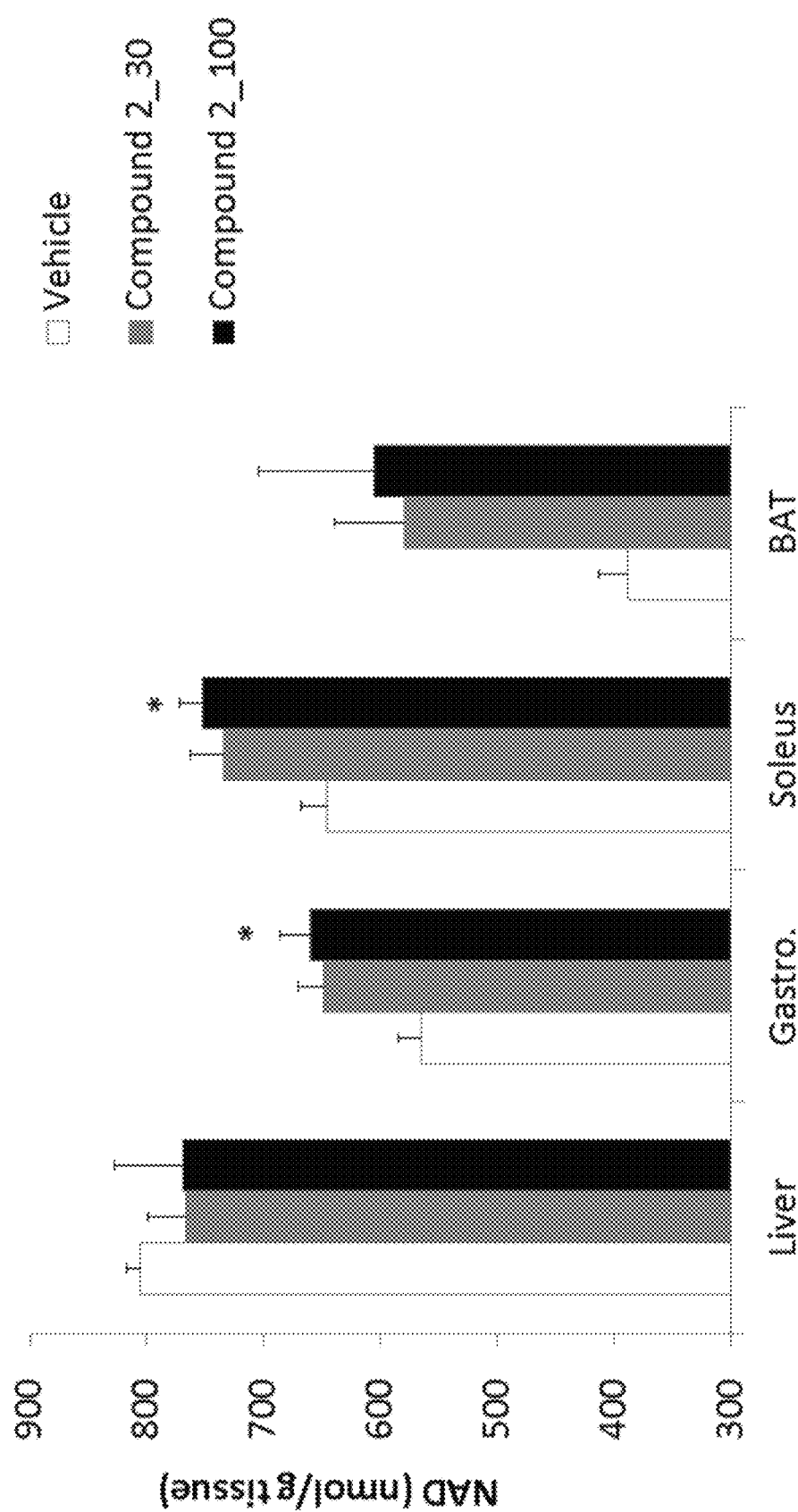
FIG. 1 Effect of NAMPT activator on tissue $NAD^+$ levels in normal mice

Hereinafter, typical methods for manufacturing the compound represented by formula (I) of the present invention will be described.

The solvent for use in the reaction of each step of manufacturing methods given below is not particularly limited as long as the solvent partially dissolves a starting material without inhibiting the reaction. The solvent is selected from the following solvent group: aliphatic hydrocarbons such as hexane, pentane, heptane, petroleum ether, and cyclohexane; aromatic hydrocarbons such as toluene, benzene, and xylene; halogenated hydrocarbons such as methylene chloride, chloroform, carbon tetrachloride, dichloroethane, chlorobenzene, and dichlorobenzene; ethers such as diethyl ether, diisopropyl ether, cyclopentyl methyl ether, t-butyl methyl ether, tetrahydrofuran, 1,4-dioxane, dimethoxyethane, and diethylene glycol dimethyl ether; ketones such as acetone, methyl ethyl ketone, methyl isobutyl ketone, and cyclohexanone; esters such as methyl acetate, ethyl acetate, propyl acetate, butyl acetate, and diethyl carbonate; nitriles such as acetonitrile, propionitrile, butyronitrile, and isobutyronitrile; organic acids such as formic acid, acetic acid, propionic acid, trifluoroacetic acid, and pentafluoropropionic acid; alcohols such as methanol, ethanol, 1-propanol, 2-propanol, 1-butanol, 2-butanol, 2-methyl-1-propanol, and 2-methyl-2-propanol; amides such as formamide, N,N-dimethylformamide, N,N-dimethylacetamide, N-methylpyrrolidone, N,N'-dimethylpropyleneurea, and hexamethylphosphorotriamide; sulfoxides such as dimethyl sulfoxide and sulfolane; water; and mixtures thereof.

The acid for use in the reaction of each step of manufacturing methods given below is not particularly limited as long as the acid does not inhibit the reaction. The acid is selected from the following acid group: inorganic acids such as hydrochloric acid, hydrobromic acid, hydroiodic acid, phosphoric acid, sulfuric acid, and oxalic acid; organic acids such as formic acid, acetic acid, propionic acid, trifluoroacetic acid, and pentafluoropropionic acid; and organic sulfonic acids such as methanesulfonic acid, trifluoromethanesulfonic acid, p-toluenesulfonic acid, and camphorsulfonic acid.

The base for use in the reaction of each step of manufacturing methods given below is not particularly limited as long as the base does not inhibit the reaction. The base is selected from the following base group: alkali metal carbonates such as lithium carbonate, sodium carbonate, potassium carbonate, and cesium carbonate; alkali metal bicarbonates such as lithium bicarbonate, sodium bicarbonate, and potassium bicarbonate; alkali metal hydroxides such as lithium hydroxide, sodium hydroxide, and potassium hydroxide; alkaline earth metal hydroxides such as calcium hydroxide and barium hydroxide; alkali metal phosphates such as sodium phosphate and potassium phosphate; alkali metal hydrides such as lithium hydride, sodium hydride, and potassium hydride; alkali metal amides such as lithium amide, sodium amide, and potassium amide; metal alkoxides such as lithium methoxide, sodium methoxide, sodium ethoxide, sodium-tert-butoxide, and potassium-tert-butoxide; lithium amides such as lithium diisopropylamide (LDA), lithium cyclohexylisopropylamide, and lithium tetramethylpiperazide; alkali metal silylamides such as lithium bistrimethylsilylamide, sodium bistrimethylsilylamide, and potassium bistrimethylsilylamide; alkyllithiums such as methyllithium, n-butyllithium, sec-butyllithium, and tert-butyllithium; alkyl magnesium halides such as methyl magnesium chloride, methyl magnesium bromide, methyl magnesium iodide, ethyl magnesium chloride, ethyl magnesium bromide, isopropyl magnesium chloride, isopropyl magnesium bromide, and isobutyl magnesium chloride; and organic amines such as triethylamine, tributylamine, diisopropylethylamine, diethylamine, diisopropylamine, N-methylpiperidine, N-methylmorpholine, N-ethylmorpholine, pyridine, picoline, 2,6-lutidine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO), and 1,8-diazabicyclo[5,4,0]-7-undecene (DBU).

The reaction temperature in the reaction of each step of manufacturing methods given below differs depending on a solvent, a starting material, a reagent, etc. The reaction time differs depending on a solvent, a starting material, a reagent, etc.

After completion of the reaction of each step of manufacturing methods given below, the target compound of each step is isolated from the reaction mixture according to a routine method. The target compound is obtained, for example, by (i) filtering off insoluble matter such as a catalyst, if necessary, (ii) adding water and a water-miscible solvent (e.g., methylene chloride, chloroform, diethyl ether, ethyl acetate, and toluene) to the reaction mixture to extract the target compound, (iii) washing the organic phase with water, followed by drying using a desiccant such as anhydrous sodium sulfate or anhydrous magnesium sulfate, and (iv) distilling off the solvent. The obtained target compound can be further purified, if necessary, by a routine method, for example, recrystallization, reprecipitation, or silica gel column chromatography. Alternatively, the target compound of each step may be used directly in the next reaction without purification.

[Manufacturing method 1] is a method of synthesizing the compound represented by formula (I) of the present invention.

[Manufacturing Method 1]

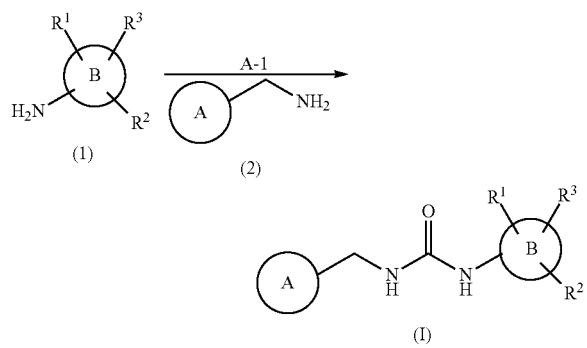

In the structural formulas of the compounds in [Manufacturing method 1] shown above, $R^1$, $R^2$, $R^3$, A, and B represent the same meanings as in formula (I).

The A-1 step is a step of synthesizing the present compound (I) by reacting compound (1) with compound (2) using a condensing agent. Compound (1) is commercially available, or can be prepared from a known compound by a manufacturing method given below. Compound (2) is commercially available, or can be easily prepared from a known compound. This step proceeds by converting either compound (1) or compound (2) to a carbamic acid ester compound, which is then subsequently reacted with the remaining compound (1) or compound (2). A more preferable method is converting compound (2) to the corresponding carbamic acid ester compound, followed by reaction with compound (1). If necessary, the carbamic acid ester compound produced in this step may be isolated, for use.

Thus, the A-1 step consists of:
(A-1a step): a step of converting compound (2) to a carbamic acid ester compound; and
(A-1b step): a step of reacting the compound obtained in the A-1a step with compound (1).

(A-1A Step)

Examples of the reactant used include substituted or unsubstituted phenyl chloroformate and substituted or unsubstituted bisphenyl carbonate. Bis(4-nitrophenyl) carbonate is preferred.

The base used is preferably an organic amine, more preferably pyridine.

Examples of the solvent used include aliphatic hydrocarbons, aromatic hydrocarbons, halogenated hydrocarbons, ethers, ketones, esters, and nitriles. Dichloroethane is preferred.

The reaction temperature is preferably from 0° C. to room temperature, more preferably 0° C.

The reaction time is preferably from 1 h to 5 h, more preferably 2 h.

(A-1b Step)

The base used is preferably an organic amine, more preferably triethylamine or diisopropylethylamine.

Examples of the solvent used include aliphatic hydrocarbons, aromatic hydrocarbons, halogenated hydrocarbons, ethers, ketones, esters, nitriles, amides, and sulfoxides. 1,4-Dioxane is preferred.

The reaction temperature is preferably from room temperature to 90° C., more preferably 70° C.

The reaction time is preferably from 1 h to 12 h, more preferably 7 h.

[Manufacturing method 2] is a method of synthesizing the compound represented by formula (I) of the present invention and is different from [Manufacturing method 1].

[Manufacturing Method 2]

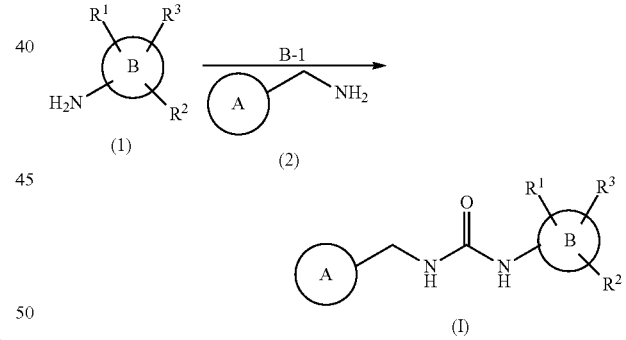

In the structural formulas of the compounds in [Manufacturing method 2] shown above, $R^1$, $R^2$, $R^3$, A, and B represent the same meanings as in [Manufacturing method 1].

The B-1 step is a step of synthesizing the present compound (I) by reacting compound (1) with compound (2) using a condensing agent. This step proceeds by converting either compound (1) or compound (2) to an isocyanate, which is then subsequently reacted with the remaining compound (1) or compound (2). A more preferable method is converting compound (1) to the corresponding isocyanate compound, followed by reaction with compound (2).

Thus, the B-1 step consists of:
(B-1a step): a step of converting compound (1) to an isocyanate compound; and (B-1b step): a step of reacting the compound obtained in the B-1a step with compound (2).

(B-1A Step)

The method of converting compound (1) to an isocyanate is not particularly limited as long as the method does not influence the other moieties of the compound. This method can be performed in accordance with a method well known in the technology of organic synthetic chemistry, for example, methods described in The fourth series of experimental chemistry (1992, The Chemical Society of Japan, pp. 473-483).

Examples of the reactant used preferably include phosgene, triphosgene, and oxalyl chloride, more preferably triphosgene.

The base used is preferably an organic amine, more preferably triethylamine or diisopropylethylamine.

Examples of the solvent used include aliphatic hydrocarbons, aromatic hydrocarbons, halogenated hydrocarbons, ethers, ketones, esters, and nitriles. Dichloroethane is preferred.

The reaction temperature is preferably from 0° C. to room temperature, more preferably 0° C.

The reaction time is preferably from 10 min to 1 h, more preferably 30 min.

(B-1b Step)

This step is a method of synthesizing the compound represented by formula (I) of the present invention by reacting the isocyanate compound converted from compound (1) with compound (2) under basic conditions. This step can also be performed by directly reacting the isocyanate produced in the B-1a step with compound (2), in the same pot without isolation of the isocyanate.

The base used is preferably an organic amine, more preferably triethylamine or diisopropylethylamine.

Examples of the solvent used include aliphatic hydrocarbons, aromatic hydrocarbons, halogenated hydrocarbons, ethers, ketones, esters, nitriles, amides, and sulfoxides. Dichloromethane is preferred.

The reaction temperature is preferably from room temperature to 60° C., more preferably room temperature.

The reaction time is preferably from 1 h to 12 h, more preferably 3 h.

[Manufacturing method 3] is a method of synthesizing the compound represented by formula (I) of the present invention and is different from [Manufacturing method 1] and [Manufacturing method 2].

[Manufacturing method 3]

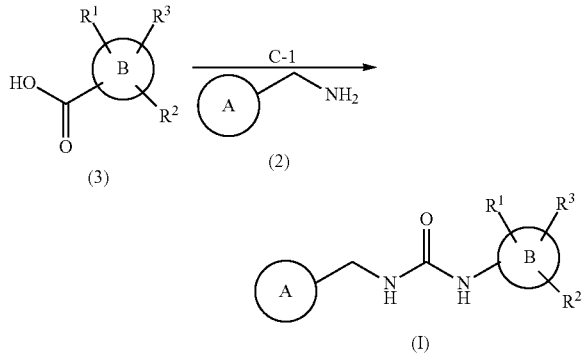

In the structural formulas of the compounds in [Manufacturing method 3] shown above, $R^1$, $R^2$, $R^3$, A, and B represent the same meanings as in formula (I).

The C-1 step involves reaction to synthesize the present compound (I) using compound (3) and compound (2). Compound (3) is commercially available, or can be easily prepared from a known compound. This step proceeds by converting compound (3) to an isocyanate through rearrangement reaction, followed by reaction with compound (2).

Thus, the C-1 step consists of:
(C-1a step): a step of converting compound (3) to an isocyanate compound; and
(C-1b step): a step of reacting the isocyanate compound obtained in the C-1a step with compound (2).

(C-1A Step)

This step is a method of synthesizing an isocyanate compound by performing the rearrangement reaction of carboxylic acid compound (3) using an azide compound under basic conditions.

The base used is preferably an organic amine, more preferably triethylamine or diisopropylethylamine.

The azide compound used is not particularly limited as long as the azide compound is a reagent that forms an acid azide through reaction with a carboxylic acid. For example, azide compounds described in Eric F. V. Scriven et al., Chem. Rev., 1988, 88 (2), pp. 297-368 may be used, and diphenylphosphonic acid azide is preferred.

Examples of the solvent used include aliphatic hydrocarbons, aromatic hydrocarbons, and halogenated hydrocarbons. Toluene is preferred.

The reaction temperature is preferably from room temperature to 120° C.

The reaction time is from 1 h to 12 h, preferably from 1 h to 3 h.

(C-1b Step)

This step is a method of synthesizing the compound represented by formula (I) of the present invention by adding compound (2) to the isocyanate compound produced in the C-1a step. This reaction can be carried out in the same system as in the isocyanate compound produced in the C-1a step, without isolation.

Examples of the solvent used include aliphatic hydrocarbons, aromatic hydrocarbons, and halogenated hydrocarbons. Toluene is preferred.

The reaction temperature is preferably from room temperature to 120° C.

The reaction time is from 1 h to 12 h, preferably from 2 h to 6 h.

[Manufacturing method 4] is a method of synthesizing compound (8) when ring B represents the following compound (4), and $R^3$ is a hydrogen atom, in formula (I).

[Manufacturing Method 4]

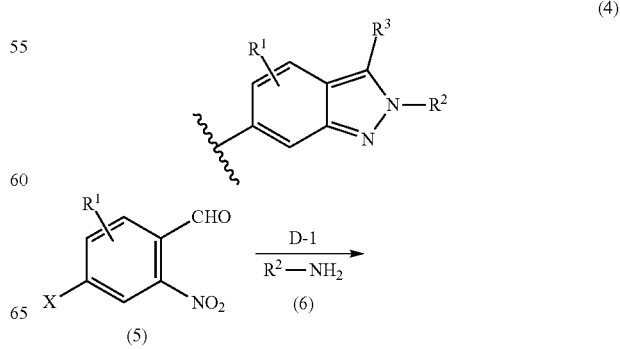

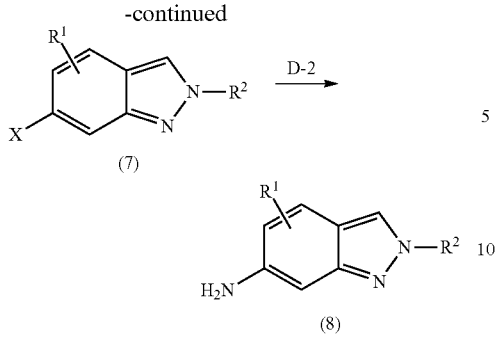

In the structural formulas of the compounds in [Manufacturing method 4] shown above, $R^1$ and $R^2$ represent the same meanings as in formula (I). X represents a substituent that can generally be converted to an amino group by a method well known in the technology of organic synthetic chemistry, for example, methods described in The fifth series of experimental chemistry, 2005, The Chemical Society of Japan. For example, X is an ester group, a halogen atom, or a nitro group, preferably a halogen atom.

The D-1 step is a method of synthesizing compound (7) by forming an imine from compound (5) and compound (6) and then performing intramolecular cyclization reaction in the presence of a reducing agent. The reaction can be carried out in accordance with, for example, a method described in Nathan E. Genung, Liuqing Wei, and Gary E. Aspnes, Org. Lett. 2014, 16, 3114-3117. Compound (5) and compound (6) are commercially available or can each be easily prepared from a known compound.

The reducing agent used is preferably a phosphine compound, more preferably tributylphosphine.

Examples of the solvent used include aliphatic hydrocarbons, aromatic hydrocarbons, halogenated hydrocarbons, ethers, and alcohols. Isopropyl alcohol is preferred.

The reaction temperature is preferably from room temperature to 100° C., more preferably 80° C.

The reaction time is preferably from 1 h to 12 h, more preferably 8 h.

The D-2 step is a step of converting substituent X of the compound (7) obtained in the D-1 step to an amino group, and can be performed by, for example, a method described in Palladium Reagents and Catalysts (2004, John Wiley & Sons Ltd.). Substituent X is preferably a bromo group, which can be converted to a protected amide followed by deprotection to give compound (8).

Thus, the D-2 step consists of:
(D-2a step): a step of converting compound (7) to a protected amine form; and
(D-2b step): a step of deprotecting the compound obtained in the D-2a step.

(D-2A Step)

This step is not particularly limited as long as the step does not influence the other moieties of the compound. This step can generally be performed by a method well known in the technology of organic synthetic chemistry, for example, methods described in Palladium Reagents and Catalysts (2004, John Wiley & Sons Ltd.).

The amine used is preferably benzophenone imine.

The metal catalyst used is preferably palladium(II) acetate.

The base used is preferably an alkali metal carbonate, an alkali metal phosphate, or an alkali metal alkoxide, more preferably cesium carbonate.

The solvent used is preferably an ether, more preferably 1,4-dioxane.

The reaction temperature is preferably from room temperature to 120° C., more preferably 100° C.

The reaction time is preferably from 30 min to 5 h, more preferably 3 h.

(D-2b Step) The reaction conditions of the deprotection reaction of the amino group in this step differ depending on the type of the protective group. The deprotection reaction can be performed according to a routine method, for example, methods described in T. W. Greene, P. G. M. Wuts, Protective Groups in Organic Synthesis. Fourth Edition, 2007, John Wiley & Sons, Inc. Preferably, the protected amino group is benzophenone imine, and examples of the acid for use in the deprotection thereof include hydrochloric acid and trifluoroacetic acid.

The solvent used is preferably an ether or an alcohol, more preferably tetrahydrofuran.

The reaction temperature is preferably from 0° C. to room temperature, more preferably room temperature.

The reaction time is preferably from 10 min to 3 h, more preferably 1 h.

[Manufacturing method 5] is a method of synthesizing compound (12) when ring B represents compound (4), and $R^3$ is a cyano group, in formula (I).

[Manufacturing Method 5]

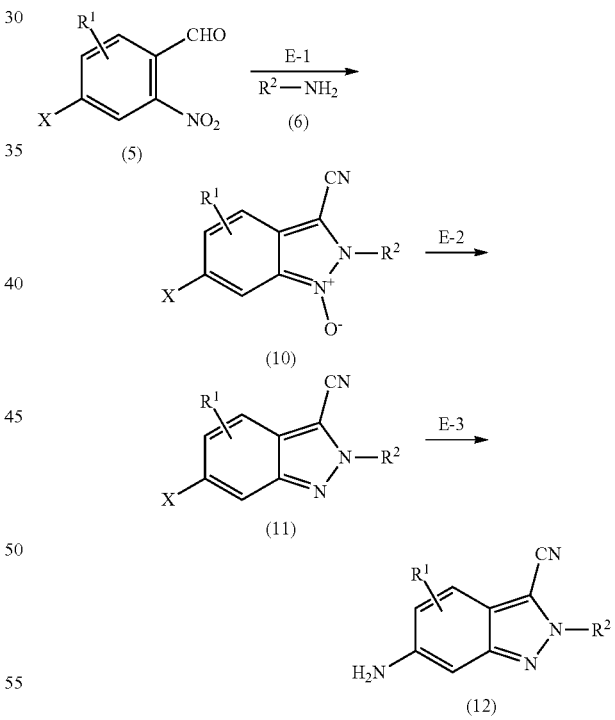

In the structural formulas of the compounds in [Manufacturing method 5] shown above, $R^1$, $R^2$, and X represent the same meanings as in formula (I) and [Manufacturing method 4]. X is preferably a nitro group.

The E-1 step is a method of synthesizing compound (10) by performing intramolecular cyclization reaction using compound (5) and compound (6) in the presence of a cyanating agent, and can be carried out in accordance with a method described in A. Gerpe et al., Bioorg. Med. Chem.

2006, vol. 14, p. 3467-3480, or Behr et al., Journal of Organic Chemistry, 1962, vol. 27, p. 65-66.

The cyanating agent used is preferably a metal cyanate compound, more preferably potassium cyanate.

The solvent used is preferably an organic acid, more preferably acetic acid.

The reaction temperature is preferably from 0° C. to room temperature, more preferably room temperature.

The reaction time is preferably from 2 h to 24 h.

The E-2 step is a method of synthesizing compound (11) by reducing the compound (10) obtained in the E-1 step in the presence of a reducing agent.

The reducing agent used is preferably an organophosphorus compound, more preferably triphenylphosphine or phosphorus trichloride.

The solvent used is an aliphatic hydrocarbon, an aromatic hydrocarbon, a halogenated hydrocarbon, an ester, an ether, or an alcohol, more preferably chloroform or ethanol.

The reaction temperature is preferably from room temperature to 100° C., more preferably 80° C.

The reaction time is preferably from 1 h to 7 h.

The E-3 step is a method of converting substituent X of the compound (11) obtained in the E-2 step to an amino group, and can generally be performed according to a method well known in the technology of organic synthetic chemistry. Preferably, X is a nitro group, and the reaction is performed through catalytic reduction reaction in the presence of a metal catalyst to afford compound (12).

Examples of the hydrogen source used include hydrogen and ammonium chloride. Ammonium chloride is preferred.

The metal catalyst used is preferably palladium/carbon, iron, or the like, more preferably iron.

The solvent used is an aliphatic hydrocarbon, an aromatic hydrocarbon, an ester, an ether, an alcohol, or water, more preferably a mixed solvent of ethanol and water.

The reaction temperature is preferably from room temperature to 100° C., more preferably 80° C.

The reaction time is from 1 h to 5 h, preferably 3 h.

[Manufacturing method 6] is a method of synthesizing compound (17) when ring B represents the following compound (13), in formula (I).

[Manufacturing Method 6]

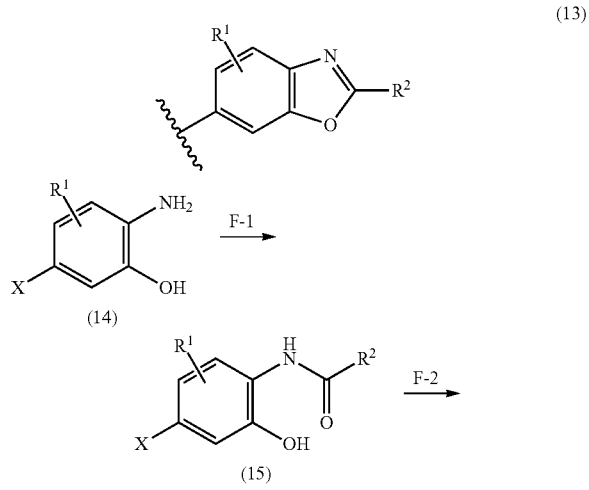

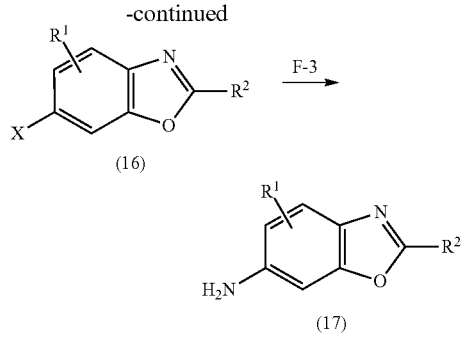

In the structural formulas of the compounds in [Manufacturing method 6] shown above, $R^1$, $R^2$, and X represent the same meanings as in formula (I) and [Manufacturing method 4]. X is preferably a nitro group.

The F-1 step is a method of synthesizing compound (15) by reacting the amino group of compound (14) with a carboxylic acid or an acid chloride. Compound (14) is commercially available, or can be easily prepared from a known compound. This step can generally be carried out by a method well known in the technology of organic synthetic chemistry, for example, methods described in The fifth series of experimental chemistry, 2005, The Chemical Society of Japan. For example, F-1 step is a method of condensing compound (14) with a carboxylic acid using a condensing agent, or a method of reacting compound (14) with an acid chloride. A preferable method is to condense a carboxylic acid with the amino group of compound (14) using a condensing agent.

The condensing agent used is preferably 1-ethyl-3-(3-dimethylaminopropyl)carbodiimide hydrochloride.

The base used is preferably an organic amine, more preferably triethylamine or diisopropylethylamine.

Examples of the solvent used include aliphatic hydrocarbons, aromatic hydrocarbons, halogenated hydrocarbons, and ethers. Dichloromethane is preferred.

The reaction temperature is from 0° C. to room temperature, preferably room temperature.

The reaction time is from 1 h to 24 h, preferably from 6 h to 12 h.

The F-2 step is a method of synthesizing compound (16) by performing the intramolecular cyclization reaction of the compound (15) obtained in the F-1 step in the presence of an acid catalyst. This step can generally be performed according to a method well known in the technology of organic synthetic chemistry, for example, methods described in Shinpen Heterokan Kagobutsu Oyo-hen, p. 64-81, Kodansha Ltd.

The acid catalyst used is an inorganic acid, an organic acid, or an organic sulfonic acid, preferably p-toluenesulfonic acid.

Examples of the solvent used include aliphatic hydrocarbons, aromatic hydrocarbons, halogenated hydrocarbons, and ethers. Toluene is preferred.

The reaction temperature is from room temperature to 150° C., preferably 100° C.

The reaction time is from 30 min to 4 h, preferably 2 h.

The F-3 step is a method of converting substituent X of the compound (16) obtained in the F-2 step to an amino group. When X is, for example, a nitro group, this step can be performed in the same way as in the E-3 step of [Manufacturing method 5].

[Manufacturing method 7] is a method of synthesizing compound (17) when ring B represents compound (13), in formula (I), and is different from [Manufacturing method 6].
[Manufacturing Method 7]

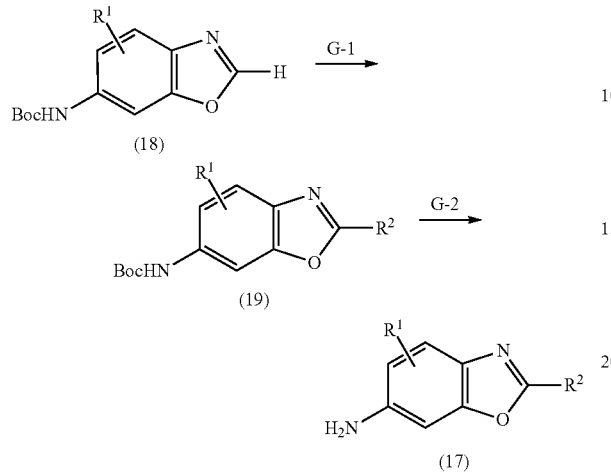

In the structural formulas of the compounds in [Manufacturing method 7] shown above, $R^1$ and $R^2$ represent the same meanings as in formula (I).

The G-1 step is a step of manufacturing compound (19) by performing the coupling reaction of compound (18) with an aryl halide in the presence of a transition metal catalyst. Compound (18) is commercially available, or can be easily prepared from a known compound. This step is not particularly limited as long as the step does not influence the other moieties of the compound. This step can generally be performed by a method well known in the technology of organic synthetic chemistry, for example, methods described in Palladium Reagents and Catalysts (2004, John Wiley & Sons Ltd.).

The metal catalyst used is preferably palladium(II) acetate, tetrakis(triphenylphosphine)palladium, [1,1'-bis(diphenylphosphino)ferrocene]dichloropalladium(II), or a dichloromethane complex, preferably palladium(II) acetate.

The ligand used is preferably 4,6-bis(diphenylphosphino) phenoxazine.

The base used is a metal alkoxide or an alkali metal silylamide, preferably sodium tert-butoxide.

Examples of the solvent used include aliphatic hydrocarbons, aromatic hydrocarbons, halogenated hydrocarbons, and ethers. 1,2-Dimethoxyethane is preferred.

The reaction temperature is from 0° C. to room temperature, preferably room temperature.

The reaction time is from 2 h to 24 h, preferably 12 h.

The G-2 step involves reaction to synthesize compound (17) by deprotecting the BOC group of the compound (19) obtained in the G-1 step under acidic conditions.

The deprotection reaction of this step is not particularly limited as long as the reaction does not influence the other moieties of the compound. This reaction can be performed according to, for example, methods described in T. W. Greene, P. G. M. Wuts, Protective Groups in Organic Synthesis. Fourth Edition, 2007, John Wiley & Sons, Inc.

[Manufacturing method 8] is a method of synthesizing compound (24) when ring B represents the following compound (20), in formula (I). [Manufacturing method 8]

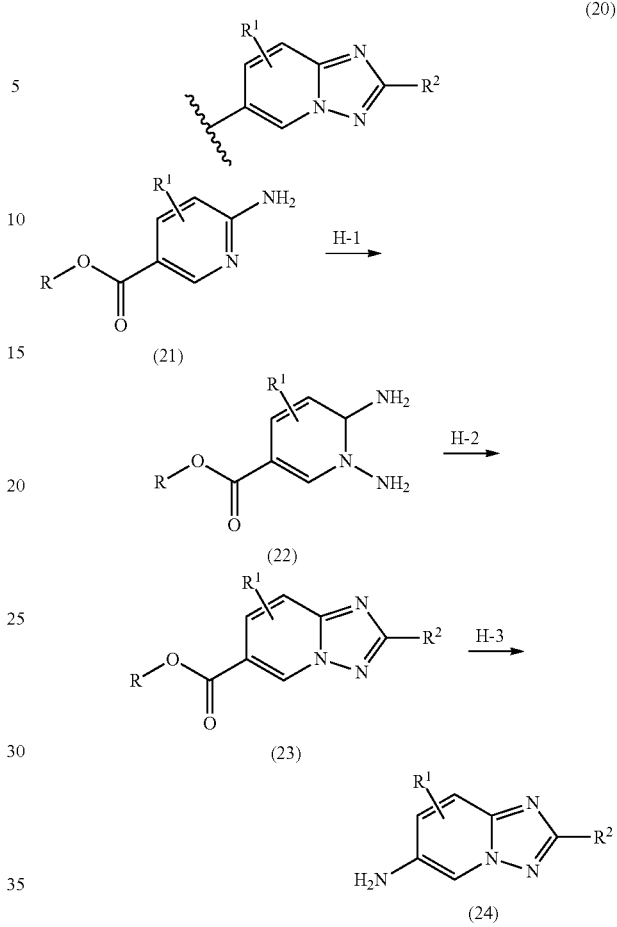

In the structural formulas of the compounds in [Manufacturing method 8] shown above, $R^1$ and $R^2$ represent the same meanings as in formula (I), and R represents an alkyl group.

The H-1 step is a method of converting nitrogen-containing aromatic compound (21) to hydrazine compound (22) in the presence of a nitrating agent. Compound (21) is commercially available, or can be easily prepared from a known compound. This step can be performed in accordance with a method described in Y. Tamura, J, Minamikawa, M. Ikeda, SYNTHESIS, 1977, 1-17.

The H-2 step involves reaction to give compound (23) by condensing the compound (22) obtained in the H-1 step with a carboxylic acid and then performing intramolecular cyclization reaction. The condensation reaction of compound (22) with a carboxylic acid can generally be carried out by a method well known in the technology of organic synthetic chemistry, for example, methods described in The Fifth Series of Experimental Chemistry, 2005, The Chemical Society of Japan.

Examples of the solvent for use in the cyclization reaction preferably include aliphatic hydrocarbons, aromatic hydrocarbons, halogenated hydrocarbons, and the absence of the solvent, more preferably dichloromethane or the absence of the solvent.

The base used is an organic amine, preferably pyridine.

The reaction temperature is from room temperature to 100° C., preferably 80° C.

The reaction time is from 30 min to 4 h, preferably 2 h.

The H-3 step involves reaction to give compound (24) by converting the ester group of the compound (23) obtained in the H-2 step to an amino group. This step is a method of obtaining compound (24) by producing a carboxylic acid through the hydrolysis of the ester group and converting the carboxylic acid to a protected amino group through rearrangement reaction, followed by the deprotection of the protective group.

The conversion reaction from the carboxylic acid to an amino group can be performed in accordance with, for example, a method described in Scriven, E. F.; Turnbull, K. Chem. Rev. 1988, 88, 297. The subsequent deprotection reaction differs depending on the protective group and can be performed according to, for example, methods described in T. W. Greene, P. G. M. Wuts, Protective Groups in Organic Synthesis. Fourth Edition, 2007, John Wiley & Sons, Inc.

[Manufacturing method 9] is a method of synthesizing compound (23) when ring B represents compound (20), in formula (I), and is different from [Manufacturing method 8].

[Manufacturing method 9]

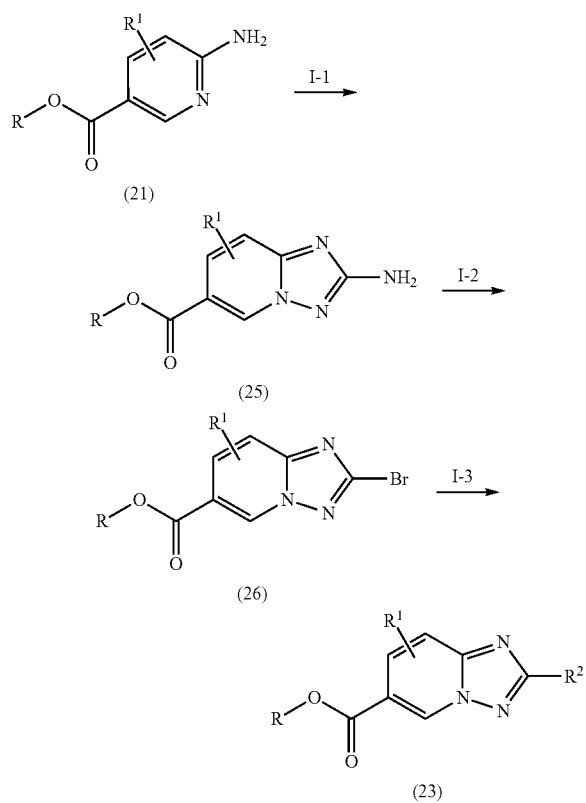

In the structural formulas of the compounds in [Manufacturing method 9] shown above, $R^1$, $R^2$, and R represent the same meanings as in formula (I) and [Manufacturing method 8].

The I-1 step is a method of synthesizing compound (25) by cyclizing compound (21). Compound (21) is commercially available, or can be easily prepared from a known compound. This step can generally be carried out in accordance with a method well known in the technology of organic synthetic chemistry, for example, a method described in BAYER PHARMA AKTIENGESELL-SCHAFT US2016/108039, 2016, A1.

The I-2 step involves reaction to synthesize compound (26) by converting the amino group of the compound (25) obtained in the I-1 step to a bromo group. This step can generally be carried out by a method well known in the technology of organic synthetic chemistry, for example, a method described in The fifth series of experimental chemistry, 2005, The Chemical Society of Japan.

The I-3 step involves reaction to synthesize compound (23) by performing the coupling reaction of the compound (26) obtained in the I-2 step with an aryl halide in the presence of a transition metal catalyst. This step is not particularly limited as long as the step does not influence the other moieties of the compound. This step can generally be performed by a method well known in the technology of organic synthetic chemistry, for example, a method described in Palladium Reagents and Catalysts (2004, John Wiley & Sons Ltd.).

The metal catalyst used is preferably tetrakis(triphenylphosphine)palladium, [1,1'-bis(diphenylphosphino)ferrocene]dichloropalladium(II), or a dichloromethane complex, more preferably [1,1'-bis(diphenylphosphino)ferrocene]dichloropalladium(II) or a dichloromethane complex.

The base used is an alkali metal carbonate, an alkali metal bicarbonate, or an alkali metal phosphate, preferably potassium carbonate, sodium carbonate, or potassium phosphate.

Examples of the solvent used include aliphatic hydrocarbons, aromatic hydrocarbons, halogenated hydrocarbons, ethers, and water. A mixed solvent of 1,2-dimethoxyethane and water is preferred.

The reaction temperature is from room temperature to 80° C., preferably from 60° C. to 80° C.

The reaction time is from 2 h to 24 h, preferably 12 h.

[Manufacturing method 10] is a method of synthesizing compound (32) when ring B represents the following compound (27), in formula (I).

[Manufacturing method 10]

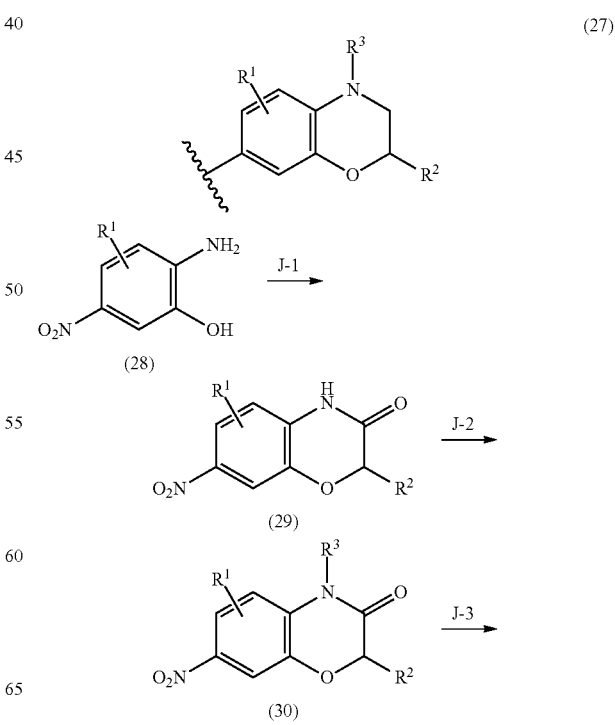

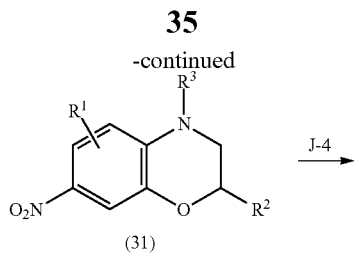

(31)

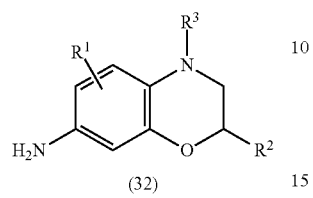

(32)

In the structural formulas of the compounds in [Manufacturing method 10] shown above, $R^1$, $R^2$, and $R^3$ represent the same meanings as in formula (I).

The J-1 step is a method of synthesizing compound (29) by performing the cyclization reaction of compound (28) using alpha haloacetic acid ester under basic conditions. Compound (28) is commercially available, or can be easily prepared from a known compound.

The base used is an alkali metal carbonate, an alkali metal bicarbonate, or an alkali metal phosphate, preferably potassium carbonate or sodium carbonate.

The solvent used is an aliphatic hydrocarbon, an aromatic hydrocarbon, a halogenated hydrocarbon, an amide, or a sulfoxide, preferably N,N-dimethylformamide.

The reaction temperature is from room temperature to 120° C., preferably 80° C.

The reaction time is from 1 h to 4 h, preferably 2 h.

The J-2 step involves reaction to introduce substituent $R^3$ to the compound (29) obtained in the J-1 step under basic conditions. The reaction conditions of this step differ depending on the substituent to be introduced. This step can generally be carried out by a method well known in the technology of organic synthetic chemistry, for example, methods described in The fifth series of experimental chemistry, 2005, The Chemical Society of Japan.

The J-3 step involves reaction to synthesize compound (31) by removing the carbonyl group from the compound (30) obtained in the J-2 step using a reducing agent. This step can generally be carried out by a method well known in the technology of organic synthetic chemistry, for example, methods described in The fifth series of experimental chemistry, 2005, The Chemical Society of Japan.

The reducing agent used is preferably lithium aluminum hydride or a borane-THF complex.

The solvent used is preferably an ether, more preferably tetrahydrofuran or diethyl ether.

The reaction temperature is from 0° C. to room temperature, preferably room temperature.

The reaction time is from 2 h to 12 h, preferably 10 h.

The J-4 step involves reaction to synthesize compound (32) by reducing the nitro group of the compound (31) obtained in the J-3 step.

Examples of the hydrogen source used include hydrogen and ammonium chloride. Ammonium chloride is preferred.

The reducing agent used is preferably palladium/carbon, iron, zinc, or the like. Zinc is more preferred.

The solvent used is an aliphatic hydrocarbon, an aromatic hydrocarbon, an ester, an ether, an alcohol, or water, more preferably a mixed solvent of THF and water.

The reaction temperature is preferably from room temperature to 100° C., more preferably 90° C.

The reaction time is from 1 h to 5 h, preferably 2 h.

[Manufacturing method 11] is a method of synthesizing compound (36) when ring B represents the following compound (33), in formula (I).

[Manufacturing Method 11]

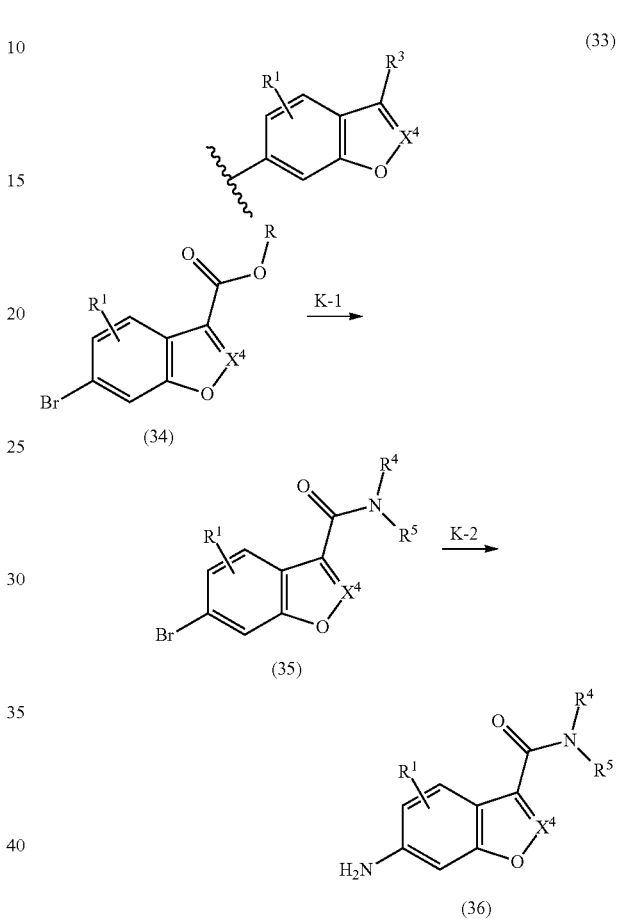

In the structural formulas of the compounds in [Manufacturing method 11] shown above, $R^1$, $R^3$, and R represent the same meanings as in formula (I) and [Manufacturing method 9]. $X^4$ represents a nitrogen atom or a carbon atom, and $R^4$ and $R^5$ each represent a substituent group conforming to group Z, as defined in [1].

The K-1 step is a method of synthesizing compound (35) by hydrolyzing the ester group of compound (34) into a carboxylic acid, followed by condensation with an amine compound. Compound (34) is commercially available, or can be easily prepared from a known compound. In this step, the hydrolysis reaction and the amide condensation reaction can generally be carried out by methods well known in the technology of organic synthetic chemistry, for example, methods described in The Fifth Series of Experimental Chemistry, 2005, The Chemical Society of Japan.

The K-2 step is a method of synthesizing compound (36) by converting the bromo group of the compound (35) obtained in the K-1 step to an amino group. This step can be performed in the same way as in the D-2 step of [Manufacturing method 4].

[Manufacturing method 12] is a method of synthesizing compound (39) which is included in the compound repre-

[Manufacturing Method 12]

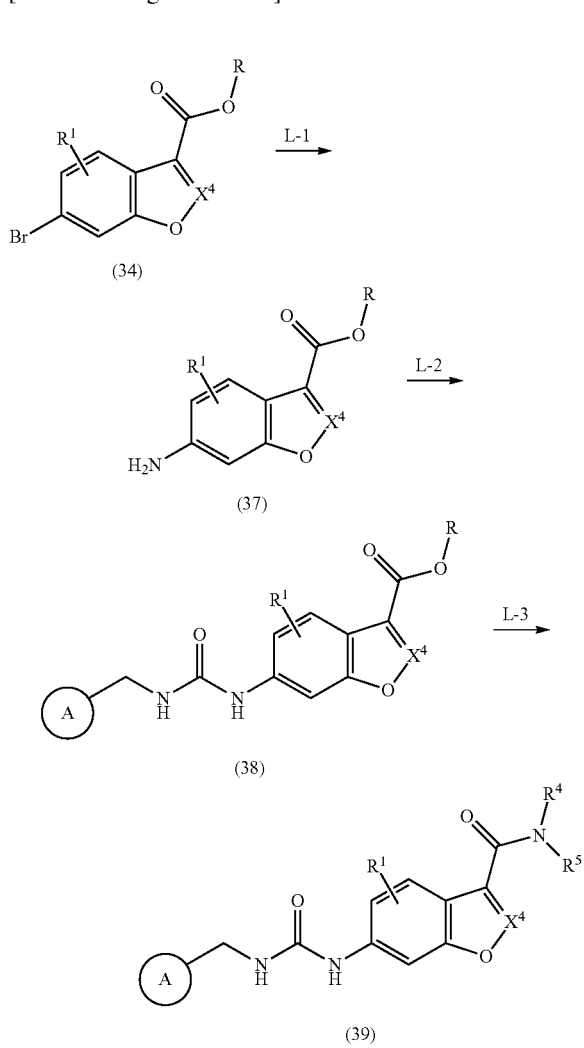

[Manufacturing Method 13]

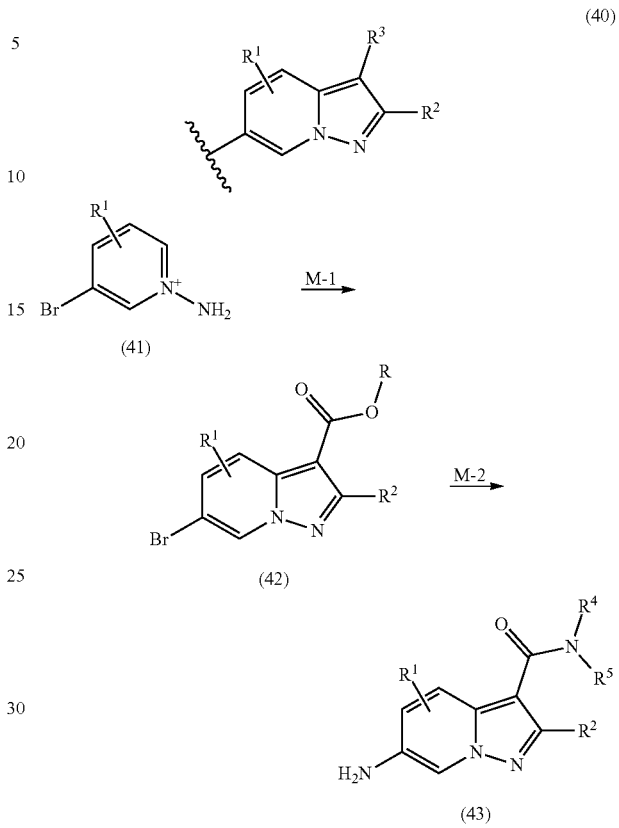

In the structural formulas of the compounds in [Manufacturing method 12] shown above, $R^1$, $R^4$, $R^5$, R, $X^4$, and A represent the same meanings as in formula (I) and [Manufacturing method 11].

The L-1 step is a method of synthesizing compound (37) by converting the bromo group of compound (34) to an amino group. This step can be performed in the same way as in the D-2 step of [Manufacturing method 4].

The L-2 step is a method of synthesizing compound (38) by constructing a urea structure having ring A in the compound (37) obtained in the L-1 step. This step can be performed in the same way as in [Manufacturing method 1] or [Manufacturing method 2].

The L-3 step is a method of synthesizing compound (39) by converting the ester group of the compound (38) obtained in the L-2 step to an amide group. This step can be performed in the same way as in the K-1 step of [Manufacturing method 11].

[Manufacturing method 13] is a method of synthesizing compound (43) when ring B represents the following compound (40), in formula (I).

In the structural formulas of the compounds in [Manufacturing method 13] shown above, $R^1$, $R^2$, $R^3$, $R^4$, $R^5$, and R represent the same meanings as in formula (I) and [Manufacturing method 11].

The M-1 step is a method of synthesizing compound (42) by performing the cyclization reaction of compound (41). Compound (41) is commercially available, or can be easily prepared from a known compound. This step can be carried out in accordance with a method described in M. Cheung et al. Bioorg. Med. Chem. Lett. 18 (2008) 5428-5430.

The M-2 step is a method of synthesizing compound (43) by converting the bromo group of the compound (42) obtained in the M-1 step to an amino group. This step can be performed in the same way as in the D-2 step of [Manufacturing method 4].

[Manufacturing method 14] is a method of synthesizing compound (48) when ring B represents compound (40), and $R^3$ is a methyl group, a cyano group, a heteroaryl group, an aryl group, or the like, in formula (I), and is different from [Manufacturing method 13].

[Manufacturing Method 14]

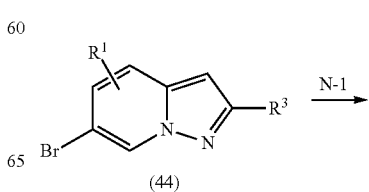

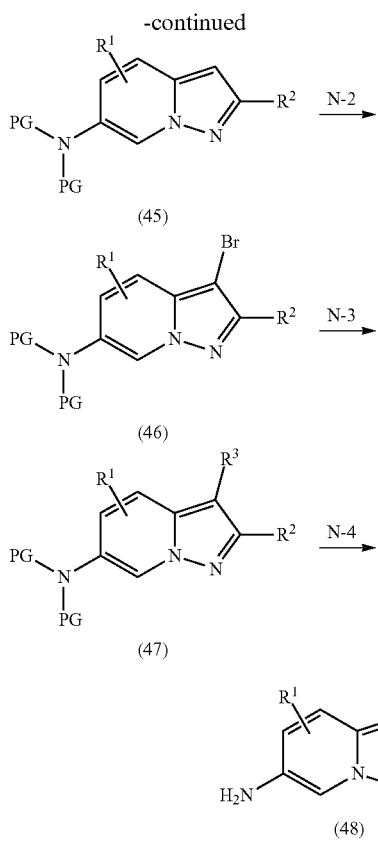

In the structural formulas of the compounds in [Manufacturing method 14] shown above, $R^1$, $R^2$, and $R^3$ represent the same meanings as in formula (I), and PG represents a substituent that generally functions as a protective group for an amino group described in the technology of organic synthetic chemistry, for example, T. W. Greene, P. G. M. Wuts, Protective Groups in Organic Synthesis. Fourth Edition, 2007, John Wiley & Sons, Inc.

The N-1 step involves reaction to synthesize compound (45) by converting the bromo group of compound (44) to a protected amino group. Compound (44) is commercially available, or can be easily prepared from a known compound. This step is not particularly limited as long as the step does not influence the other moieties of the compound. This step can generally be performed by a method well known in the technology of organic synthetic chemistry, for example, a method described in Palladium Reagents and Catalysts (2004, John Wiley & Sons Ltd.).

The metal catalyst used is preferably 9,9-dimethyl-4,5-bis(diphenylphosphino)xanthene, tetrakis(triphenylphosphine)palladium, [1,1'-bis(diphenylphosphino)ferrocene]dichloropalladium(II), or a dichloromethane complex, preferably 9,9-dimethyl-4,5-bis(diphenylphosphino)xanthene.

The base used is an alkali metal carbonate, an alkali metal bicarbonate, or an alkali metal phosphate, preferably potassium carbonate, sodium carbonate, or potassium phosphate.

Examples of the solvent used include aliphatic hydrocarbons, aromatic hydrocarbons, halogenated hydrocarbons, ethers, and water. Toluene is preferred.

The reaction temperature is from room temperature to 120° C., preferably 100° C.

The reaction time is from 2 h to 24 h, preferably 12 h.

The N-2 step is a method of synthesizing compound (46) by brominating the compound (45) obtained in the N-1 step, and can be carried out in accordance with a method described in ONO Pharmaceutical Co., Ltd. EP1961745 A1 2008.

The N-3 step is a method of synthesizing compound (47) by performing various coupling reactions of the compound (46) obtained in the N-2 step in the presence of a transition metal catalyst. This step is not particularly limited as long as the step does not influence the other moieties of the compound. This step can generally be performed by a method well known in the technology of organic synthetic chemistry, for example, a method described in Palladium Reagents and Catalysts (2004, John Wiley & Sons Ltd.).

The N-4 step is a method of synthesizing compound (48) by deprotecting the protected amino group of the compound (47) obtained in the N-3 step. The reaction conditions differ depending on the type of the protective group. This step can be performed in accordance with methods described in T. W. Greene, P. G. M. Wuts, Protective Groups in Organic Synthesis. Fourth Edition, 2007, John Wiley & Sons, Inc.

[Manufacturing method 15] is a method of synthesizing compound (48) when ring B represents compound (40), in formula (I), and is different from [Manufacturing method 12] and [Manufacturing method 13].

[Manufacturing Method 15]

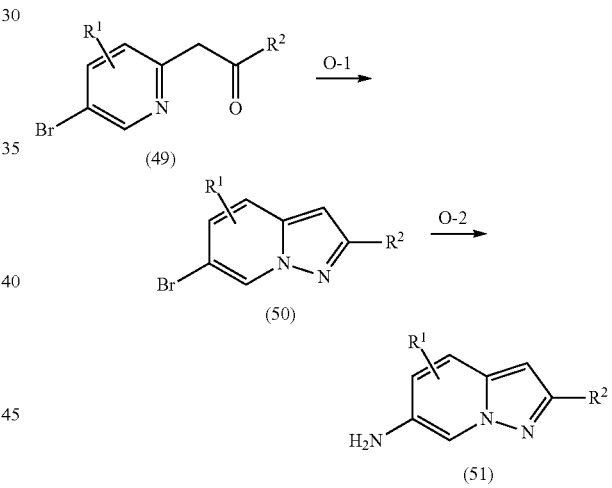

In the structural formulas of the compounds in [Manufacturing method 15] shown above, $R^1$ and $R^2$ represent the same meanings as in formula (I).

The O-1 step is a method of synthesizing compound (50) from compound (49) via an azirine intermediate by reacting compound (49) with hydroxylamine. Compound (49) is commercially available, or can be easily prepared from a known compound. This step can be carried out in accordance with a method described in Kirk L. Stevens, et al., Org. Lett., Vol. 7, No. 21, 2005.

The O-2 step is a method of converting the bromo group of the compound (50) obtained in the O-1 step to an amino group. This step can be performed in the same way as in the D-2 step of [Manufacturing method 4].

[Manufacturing method 16] is a method of synthesizing compound (55) when ring B represents compound (52), in formula (I).

[Manufacturing Method 16]

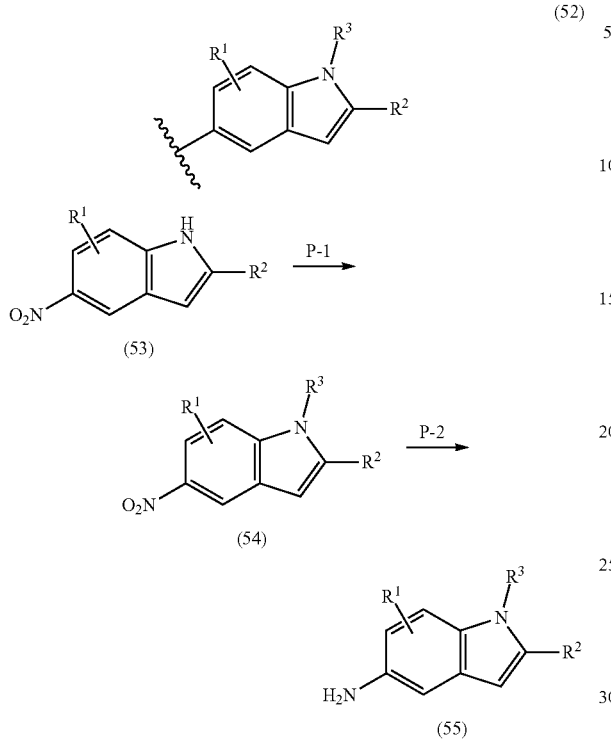

In the structural formulas of the compounds in [Manufacturing method 16] shown above, $R^1$, $R^2$, and $R^3$ represent the same meanings as in formula (I).

The P-1 step is a method of synthesizing compound (54) by alkylating or amidating compound (53). Compound (53) is commercially available, or can be easily prepared from a known compound. This step can generally be carried out by a method well known in the technology of organic synthetic chemistry, for example, methods described in The fifth series of experimental chemistry, 2005, The Chemical Society of Japan.

The P-2 step is a method of synthesizing compound (55) by reducing the nitro group of the compound (54) obtained in the P-1 step through catalytic reduction reaction in the presence of a transition metal catalyst.

Examples of the hydrogen source used include hydrogen and ammonium chloride. Hydrogen is preferred and performing the reaction under pressure may accelerate the reaction.

The reducing agent used is preferably palladium/carbon, iron, or the like, more preferably palladium/carbon.

The solvent used is an aliphatic hydrocarbon, an aromatic hydrocarbon, an ester, an ether, an alcohol, or water, more preferably a mixed solvent of ethyl acetate and ethanol.

The reaction temperature is preferably from room temperature to 60° C., more preferably room temperature.

The reaction time is from 1 h to 5 h, preferably 3 h.

[Manufacturing method 17] is a method of synthesizing compound (61) when ring B represents compound (56), in formula (I).

[Manufacturing method 17]

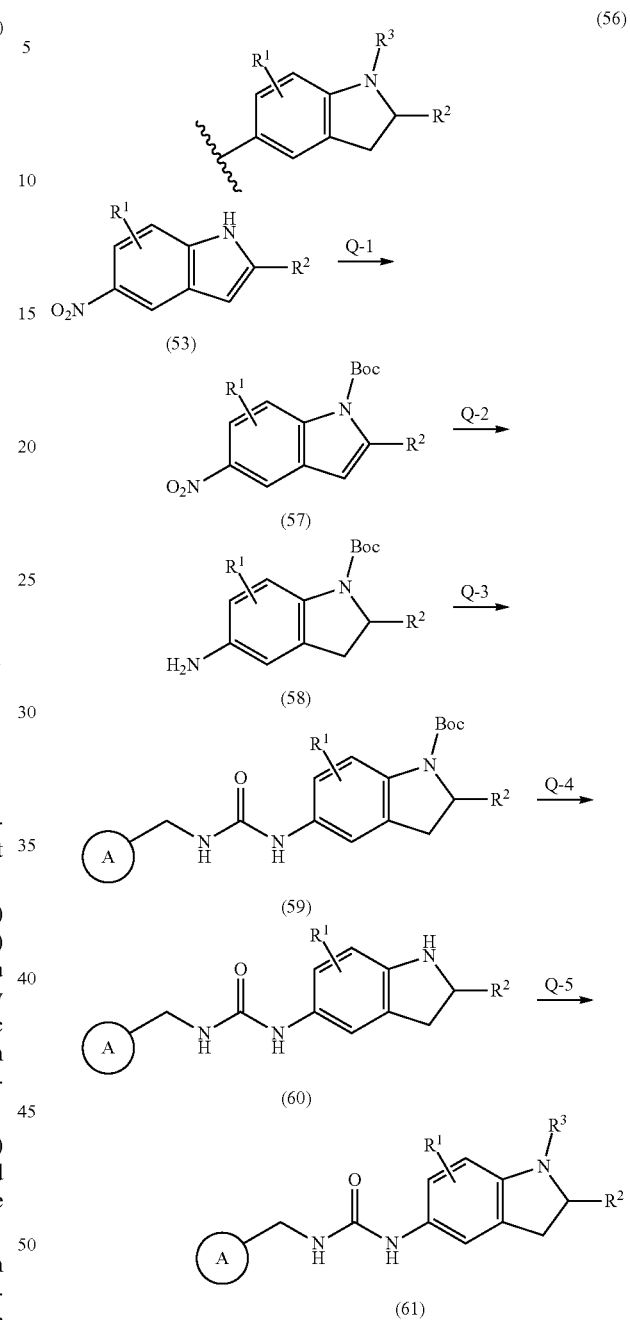

In the structural formulas of the compounds in [Manufacturing method 17] shown above, A, $R^1$, $R^2$, and $R^3$ represent the same meanings as in formula (I).

The Q-1 step involves reaction to protect the nitrogen atom in the indole ring with a BOC group and can be performed in accordance with methods described in T. W. Greene, P. G. M. Wuts, Protective Groups in Organic Synthesis. Fourth Edition, 2007, John Wiley & Sons, Inc.

The Q-2 step is a method of synthesizing iodoline compound (58) by reducing the indole ring of the compound (57) obtained in the Q-1 step. This step can be performed in the same way as in the P-2 step of [Manufacturing method 16]. Desirably, the reaction is performed under pressure.

The Q-3 step is a method of synthesizing compound (59) by constructing a urea structure in accordance with the method described in [Manufacturing method 1] or [Manufacturing method 2] using the compound (58) obtained in the Q-2 step.

The Q-4 step is a method of synthesizing compound (60) by deprotecting the Boc group of the compound (59) obtained in the Q-3 step. This step can be performed in the same way as in the G-2 step of [Manufacturing method 7].

The Q-5 step is a method of introducing the $R^3$ group onto the nitrogen atom of the indoline ring of the compound (60) obtained in the Q-4 step. The reactant and the conditions used in this step differ depending on the $R^3$ group to be introduced. This step can generally be carried out by a method well known in the technology of organic synthetic chemistry, for example, methods described in The fifth series of experimental chemistry, 2005, The Chemical Society of Japan.

[Manufacturing method 18] is a method of synthesizing compound (65) when ring B represents compound (62), in formula (I).

[Manufacturing method 18]

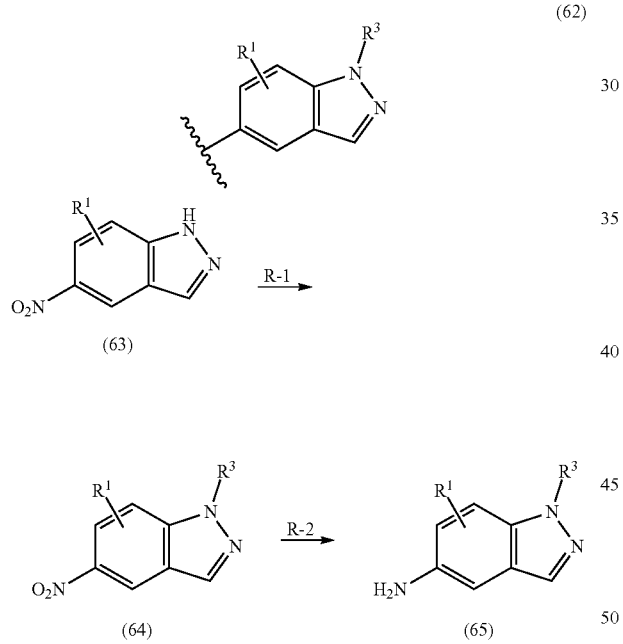

In the structural formulas of the compounds in [Manufacturing method 18] shown above, $R^1$ and $R^3$ represent the same meanings as in formula (I).

The R-1 step is a method of introducing the $R^3$ group to compound (63). Compound (63) is commercially available, or can be easily prepared from a known compound. This step can be performed in the same way as in the Q-5 step of [Manufacturing method 17].

The R-2 step is a method of synthesizing compound (65) by reducing the nitro group of the compound (64) obtained in the R-1 step. This step can be performed in the same way as in the P-2 step of [Manufacturing method 16]. [Manufacturing method 19] is a method of synthesizing compound (72) when ring B represents compound (66), in formula (I).

[Manufacturing Method 19]

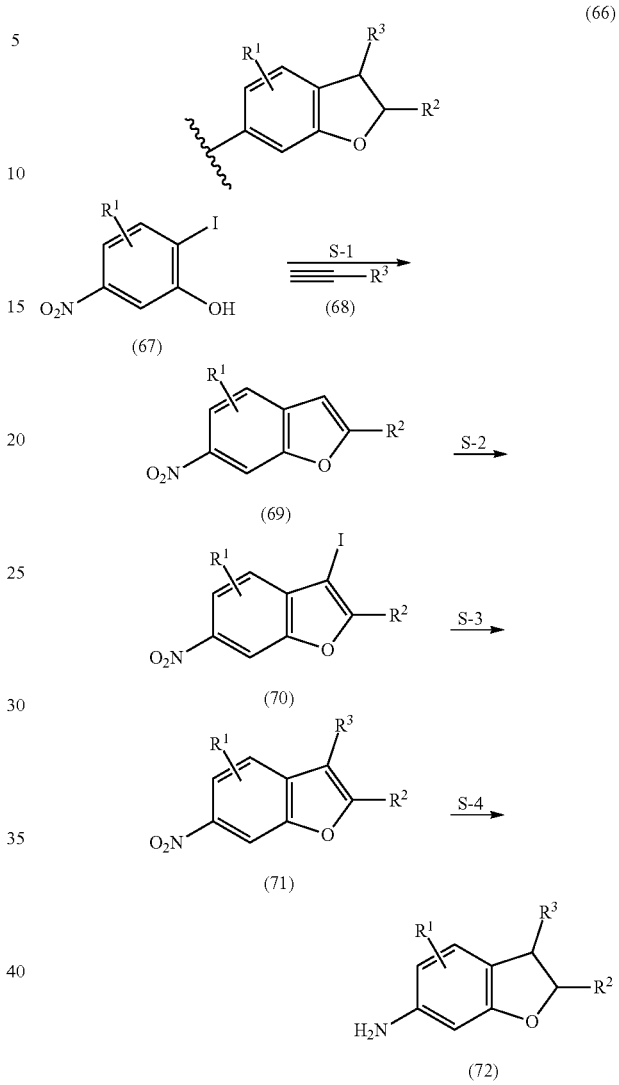

In the structural formulas of the compounds in [Manufacturing method 19] shown above, $R^1$, $R^2$, and $R^3$ represent the same meanings as in formula (I).

The S-1 step is a step of synthesizing compound (69) by coupling compound (67) to compound (68) in the presence of a metal catalyst. Compound (67) and compound (68) are commercially available, or can each be easily prepared from a known compound. This step can generally be performed in accordance with a method well known in the technology of organic synthetic chemistry, for example, a method described in Rafael Chinchilla et al., Chem. Soc. Rev., 2011, 40, p. 5084-5121.

The S-2 step is a method of synthesizing compound (70) by iodinating the compound (69) obtained in the S-1 step using an iodinating agent, and can be performed in accordance with a method described in Vo, Duc Duy, Elofsson, Mikael, Advanced Synthesis and Catalysis, 2016, vol. 358, #24, p. 4085-4092.

The S-3 step involves reaction to synthesize compound (71) by performing the coupling reaction of the compound (70) obtained in the S-2 step in the presence of a transition metal catalyst. This step can generally be performed by a method well known in the technology of organic synthetic chemistry, for example, a method described in Palladium Reagents and Catalysts (2004, John Wiley & Sons Ltd.).

The S-4 step is a method of synthesizing compound (72) by reducing the nitro group of the compound (71) obtained in the S-3 step. This step can be performed in the same way as in the P-2 step of [Manufacturing method 16]. Desirably, the reaction is performed under pressure.

[Manufacturing method 20] is a method of synthesizing compound (72) when ring B represents compound (66), in formula (I), and is different from [Manufacturing method 19].

[Manufacturing method 20]

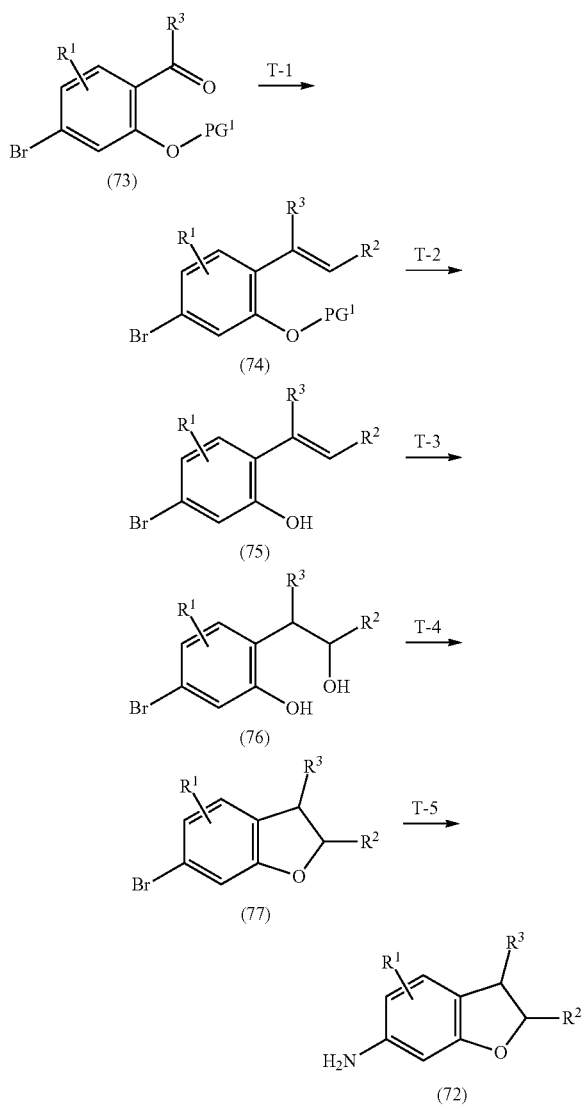

In the structural formulas of the compounds in [Manufacturing method 10] shown above, $R^1$, $R^2$, and $R^3$ represent the same meanings as in formula (I). $PG^1$ represents a protective group for a phenolic hydroxy group described in, for example, T. W. Greene, P. G. M. Wuts, Protective Groups in Organic Synthesis. Fourth Edition, 2007, John Wiley & Sons, Inc.

The T-1 step involves reaction to synthesize alkene compound (74) by reacting phosphoric acid ester to the carbonyl group of compound (73) under basic conditions. Compound (73) is commercially available, or can be easily prepared from a known compound. This step can generally be performed by a method well known in the technology of organic synthetic chemistry, for example, a method described in Murphy, P. J.; Brennan, J. Chem. Soc. Rev. 1988, 17, 1.

The T-2 step involves reaction to synthesize compound (75) by deprotecting the protective group on the hydroxy group of the compound (74) obtained in the T-1 step. The reaction conditions of this step differ depending on the protective group used. This step can be performed according to, for example, methods described in T. W. Greene, P. G. M. Wuts, Protective Groups in Organic Synthesis. Fourth Edition, 2007, John Wiley & Sons, Inc.

The T-3 step involves reaction to synthesize compound (76) by performing the hydroboration reaction of the compound (75) obtained in the T-2 step and then replacing the boron to a hydroxy group under basic conditions. This step can be performed according to, for example, a method described in Burgess, K.; Ohlmeyer, M. J. Chem. Rev. 1991, 91, 1179.

The T-4 step is a method of synthesizing compound (77) by performing the intramolecular cyclization reaction of the compound (76) obtained in the T-3 step. This step can be performed according to, for example, a method described in Swamy, K. C. K.; Kumar, N. N. B.; Balaraman, E.; Kumar, K. V. P. P. Chem. Rev. 2009, 109, 2551.

The T-5 step is a method of synthesizing compound (72) by converting the bromo group of the compound (77) obtained in the T-4 step to an amino group. This step can be performed in the same way as in the D-2 step of [Manufacturing method 4].

The compounds manufactured by these methods can be isolated or purified by a known method, for example, extraction, precipitation, distillation, chromatography, fractional crystallization, or recrystallization.

When each compound or an intermediate of manufacture has an asymmetric carbon, optical isomers are present. These optical isomers can each be isolated or purified by a routine method such as fractional crystallization for recrystallization with a suitable salt (salt resolution) or column chromatography. Examples of references for methods of resolving racemates to optical isomers can include J. Jacques et al., Enantiomers, Racemates and Resolution, John Wiley & Sons, Inc.

The compound represented by formula (I) of the present invention or the pharmacologically acceptable salt thereof has an excellent NAMPT activating effect, as mentioned above, and is useful as a therapeutic agent and/or a prophylactic agent for metabolic disorders, cardiovascular diseases, kidney diseases, mitochondrial disease, neurodegenerative diseases, ocular diseases, and muscle wasting disorders.

When the compound of formula (I) or a pharmacologically acceptable salt thereof according to the present invention is used as the above-described remedy or preventive agent, it can be administered as it is or, if necessary, after being mixed with a pharmacologically acceptable excipient, diluent or the like, orally as tablets, capsules, granules, powders or syrups or parenterally as injections or suppositories.

The above pharmaceutical formulations can be prepared in a known manner by using additives. Examples of the additives include an excipient (e.g. organic excipients, for example, sugar derivatives such as lactose, sucrose, dextrose, mannitol and sorbitol; starch derivatives such as corn starch, potato starch, α-starch and dextrin; and cellulose derivatives such as crystalline cellulose, gum arabic, dextran, and pullulan; and inorganic excipients, for example, silicate derivatives such as soft silicic anhydride, synthetic aluminum silicate, calcium silicate and magnesium aluminate metasilicate; phosphate derivatives such as calcium hydrogenphosphate; carbonate derivatives such as calcium carbonate; and sulfates such as calcium sulfate), a lubricant (e.g. stearic acid, metal salts of stearic acid such as calcium stearate and magnesium stearate; talc; colloidal silica; wax such as bee gum or spermaceti; boric acid; adipic acid; sulfates such as sodium sulfate; glycol; fumaric acid; sodium benzoate; DL leucine; fatty acid sodium salts; lauryl sulfates such as sodium lauryl sulfate or magnesium lauryl sulfate; silicic acids such as silicic anhydride or silicic hydrate; and the above-exemplified starch derivatives), a binder (e.g. hydroxypropylcellulose, hydroxypropyl methylcellulose, polyvinyl pyrrolidine, Macrogol and compounds similar to those described in the above excipient), a disintegrator (e.g. cellulose derivatives such as low degree substituted hydroxypropyl cellulose, carboxymethyl cellulose, carboxymethyl cellulose calcium and internally crosslinked carboxymethyl cellulose sodium, and chemically-modified starch cellulose such as carboxymethyl starch, carboxymethyl starch sodium and crosslinked polyvinyl pyrrolidone), a stabilizer (e.g. a paraoxybenzoate such as methyl paraben and propyl paraben; an alcohol such as chlorobutanol, benzyl alcohol or phenylethyl alcohol; benzalkonium chloride; phenol and phenol derivatives such as cresol; thimerosal; dehydroacetic acid; and sorbic acid), a corrigent (e.g. an ordinarily-employed sweetener, acidifier or flavor), and diluent.

The dose of the compound of the invention will vary depending upon the condition and age of the patient, weight of the patient, administration method and the like. Orally, it is administered in an amount of 0.001 mg/kg of body weight (preferably 0.01 mg/kg weight) in one to several doses per day as a lower limit and 500 mg/kg of body weight (preferably 50 mg/kg weight) in one to several doses per day depending upon the conditions of the patient as an upper limit, while intravenously, it is administered in an amount of 0.005 mg/kg weight (preferably, 0.05 mg/kg weight) in one to several doses per day as a lower limit and 50 mg/kg weight (preferably, 5 mg/kg weight) in one to several doses per day depending upon the conditions of the patient as an upper limit.

The compound represented by formula (I) of the present invention or the pharmacologically acceptable salt thereof may be used in combination with any of various therapeutic agents or prophylactic agents for the aforementioned diseases for which the present invention is considered effective. These preparations may be concurrently administered or may be separately administered either continuously or at a desired time interval. The preparations to be concurrently administered may be a combination drug or may be separately formulated.

Abbreviation List

The abbreviations in Examples are as follows:
ACN acetonitrile
AcOH acetic acid
BINAP 2,2'-bis(diphenylphosphino)-1,1'-binaphthyl
BoC$_2$O Di-tert-butyl dicarbonate
DCM dichloromethane
DEA Diethylamine
DIPEA N,N-diisopropylethylamine
DMAP N,N-dimethyl-4-aminopyridine
DMF N,N-dimethylformamide
DMT-MM 4-(4,6-Dimethoxy-1,3,5-triazin-2-yl)-4-methylmorpholinium Chloride
DPPA Diphenylphosphoryl Azide
Dppf 1,1'-Bis(diphenylphosphino)ferrocene
EA ethyl acetate
HATU 1-[Bis(dimethylamino)methylene]-1H-1,2,3-triazolo[4,5-b]pyridinium 3-Oxide Hexafluorophosphate
HEIP Hexafluoro-2-propanol
LiHMDS Lithium Hexamethyldisilazide
PE petroleum ether
PIFA phenyliodine (III) bis (trifluoroacetate)
TEA triethylamine
TFA trifluoroacetic acid
TFAA Trifluoroacetic Anhydride
THF tetrahydrofuran

EXAMPLES

Hereinafter, the present invention will be described in more detail with reference to Examples, Reference Examples and Test Examples. However, the scope of the present invention is not limited by these examples.

Example 1

N-[2-(2-Methylphenyl)-1,3-benzoxazol-6-yl]-N'-[(pyridin-4-yl)methyl]urea

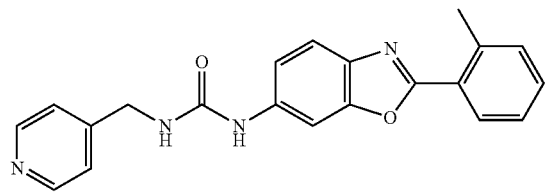 [SMILES: Cc1ccccc1-c1nc2ccc(NC(=O)NCc3ccncc3)cc2o1]

(Example 1-a) (2-Amino-5-nitrophenyl) 2-methylbenzoate

2-Amino-5-nitrophenol (0.62 g, 4.0 mmol) and o-toluoic acid (0.55 g, 4.0 mmol) were dissolved in dichloromethane (10 mL). To the solution were added triethylamine (1.1 mL, 8.1 mmol) and 1-ethyl-3-(3-dimethylaminopropyl)carbodiimide hydrochloride (0.85 g, 4.4 mmol). The mixture was stirred at room temperature for 12 h. The reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (ethyl acetate:hexane=10:90 to 50:50) to give the title compound (0.13 g, 12%) as a solid.
$^1$H NMR (400 MHz, CDCl$_3$) δ (ppm) 2.69 (s, 3H), 4.16-4.73 (m, 2H), 6.83 (d, J=9.0 Hz, 1H), 7.32-7.41 (m, 2H), 7.50-7.59 (m, 1H), 8.02-8.12 (m, 2H) 8.18-8.24 (m, 1H).

(Example 1-b) 6-Nitro-2-(2-methylphenyl)-1,3-benzoxazole (2-Amino-5-nitrophenyl) 2-methylbenzoate (0.13 g, 0.48 mmol) obtained in (Example 1-a) and p-toluenesulfonic acid monohydrate (18 mg, 0.096 mmol) were dissolved in toluene (10 mL) and then stirred at 100° C. for 2 h. The reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (ethyl acetate:hexane=10:90 to 50:50) to give the title compound (74 mg, 61%) as a solid.

$^1$H NMR (400 MHz, CDCl$_3$) δ (ppm) 2.84 (s, 3H), 7.37-7.44 (m, 2H), 7.47-7.53 (m, 1H), 7.88 (d, J=9.0 Hz, 1H), 8.22-8.26 (m, 1H), 8.32-8.36 (m, 1H), 8.51 (d, J=2.35 Hz, 1H).

(Example 1-c) 2-(2-Methylphenyl)-1,3-benzoxazol-6-amine

6-Nitro-2-(2-methylphenyl)-1,3-benzoxazole (74 mg, 0.29 mmol) obtained in (Example 1-b) was dissolved in ethanol (5 mL) and ethyl acetate (5 mL). To the solution was added 10% Pd/C (50% wet) (20 mg). After purging of the reaction container with hydrogen, the mixture was stirred at room temperature for 1 h. The reaction solution was filtered through celite. Then, the filtrate was concentrated under reduced pressure to give the crude title compound. The crude product was purified by silica gel column chromatography (ethyl acetate:hexane=10:9 to 50:50) to give the title compound (66 mg, 100%) as a solid.

$^1$H NMR (400 MHz, CDCl$_3$) δ (ppm) 2.76-2.80 (m, 3H), 3.85 (br s, 2H), 6.71 (dd, J=8.4, 2.2 Hz, 1H), 6.88 (d, J=2.4 Hz, 1H), 7.28-7.40 (m, 3H), 7.55 (d, J=8.6 Hz, 1H), 8.08-8.12 (m, 1H).

(Example 1-d) N-[2-(2-Methylphenyl)-1,3-benzoxazol-6-yl]-N'-[(pyridin-4-yl)methyl]urea 2-(2-Methylphenyl)-1,3-benzoxazol-6-amine (67 mg, 0.30 mmol) obtained in (Example 1-c) and triethylamine (0.13 mL, 0.90 mmol) were dissolved in dichloromethane (3 mL) and cooled to 0° C. To the solution was added triphosgene (31 mg, 0.11 mmol). The mixture was stirred for 10 min. 4-Picolylamine (0.033 mL, 0.33 mmol) was added thereto, and the mixture was stirred for 1 h. The reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (methanol:dichloromethane=1:99 to 10:90) to give the title compound (43 mg, 40%) as a solid.

$^1$H NMR (400 MHz, DMSO-d$_6$) δ (ppm) 2.74 (s, 3H), 4.37 (d, J=5.9 Hz, 2H), 6.85 (t, J=5.9 Hz, 1H), 7.23 (dd, J=8.6, 2.0 Hz, 1H), 7.31-7.33 (m, 2H), 7.38-7.51 (m, 3H), 7.68 (d, J=8.6 Hz, 1H), 8.08-8.11 (m, 2H), 8.49-8.55 (m, 2H), 9.08 (s, 1 H).

LCMS (ES): m/z 359 [M+H]$^+$.

Example 2

N-(2-Phenyl-1,3-benzoxazol-6-yl)-N'-[(pyridin-4-yl)methyl]urea

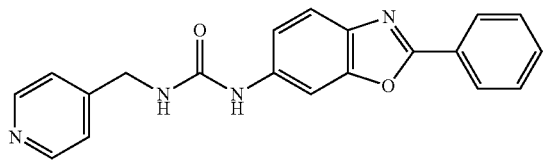 [SMILES: O=C(NCc1ccncc1)Nc1ccc2nc(-c3ccccc3)oc2c1]

2-Phenyl-1,3-benzoxazol-6-ylamine (64 mg, 0.30 mmol) and (4-nitrophenyl)-N-(4-pyridylmethyl)carbamate (92 mg, 0.33 mmol) obtained in (Reference Example 1) were suspended in 1,4-dioxane (2 mL). To the suspension was added N,N-diisopropylamine (0.058 mL, 0.33 mmol). The mixture was stirred at 50° C. for 2 h. After cooling to room temperature, the precipitated solid was collected by filtration and washed with diethyl ether to give the title compound (32 mg, 31%) as a solid.

$^1$H NMR (400 MHz, CDCl$_3$) δ (ppm) 3.10-3.20 (m, 2H), 3.97-4.09 (m, 2H), 6.96 (d, J=7.4 Hz, 1H), 7.19-7.29 (m, 4H), 7.36-7.44 (m, 1H), 7.50 (s, 1 H), 7.61-7.75 (m, 4H), 7.79-8.00 (m, 1H).

LCMS (ES): m/z 345 [M+H]$^+$.

Example 3

N-[2-(1-Methylcyclopropyl)-1,3-benzoxazol-6-yl]-N'-[(pyridin-4-yl)methyl]urea

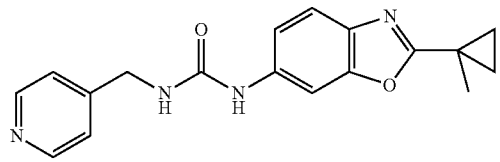 [SMILES: CC1(c2nc3ccc(NC(=O)NCc4ccncc4)cc3o2)CC1]

(Example 3-a) 2-(1-Methylcyclopropyl)-6-nitro-1,3-benzoxazole

2-Amino-5-nitrophenol (200 mg, 1.30 mmol), 1-methylcyclopropane-1-carboxylic acid (156 mg, 1.56 mmol), 3H-1,2,3-triazolo[4,5-b]pyridin-3-ol (212 mg, 1.56 mmol), and triethylamine (0.432 mL, 3.11 mmol) were dissolved in dichloromethane (5 mL). To the solution was added 1-ethyl-3-(3-dimethylaminopropyl)carbodiimide hydrochloride (299 mg, 1.56 mmol). The mixture was stirred at room temperature for 92 h. Then, water (20 mL) was added to the reaction solution, followed by partition operation using ethyl acetate. The organic phase was washed with brine, then dried over magnesium sulfate, and filtered. Then, the solvent was distilled off under reduced pressure to give the crude compound. The residue was purified by silica gel column chromatography (silica gel, ethyl acetate:hexane=0:100 to 30:70) to give N-(2-hydroxy-4-nitrophenyl)-1-methylcyclopropane-1-carboxamide (246 mg, <80%) as a crude product.

The obtained crude product (246 mg, <1.04 mmol) and p-toluenesulfonic acid monohydrate (20 mg, 0.104 mmol) were dissolved in toluene (25 mL) and then stirred at 120°

C. for 5 h. Water (40 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 30:70) to give the title compound (201 mg, two steps 74%) as a solid.

$^1$H NMR (CDCl$_3$) δ (ppm) 1.06-1.17 (m, 2H), 1.50-1.59 (m, 2H), 1.66 (s, 3H), 7.69 (dd, J=8.8, 1.3 Hz, 1H), 8.26 (dt, J=8.8, 2.2 Hz, 1H), 8.31-8.36 (m, 1H).

(Example 3-b) 2-(1-Methylcyclopropyl)-1,3-benzoxazol-6-amine 2-(1-Methylcyclopropyl)-6-nitro-1,3-benzoxazole (201 mg, 0.921 mmol) obtained in (Example 3-a) was dissolved in ethanol (10 mL). To the solution was added 10% Pd/C (50% wet) (20 mg). After purging of the reaction container with hydrogen, the mixture was stirred at room temperature for 7 h. The reaction solution was filtered through celite. Then, the filtrate was concentrated under reduced pressure to give the crude title compound. The residue was purified by silica gel column chromatography (silica gel, ethyl acetate: hexane=0:100 to 30:70) to give the title compound (136 mg, 78%) as a solid.

$^1$H NMR (CDCl$_3$) δ (ppm): 0.87-0.95 (m, 2H), 1.34-1.43 (m, 2H), 1.59 (s, 3H), 3.75 (br s, 2H), 6.61 (dd, J=8.4, 2.0 Hz, 1H), 6.72 (d, J=2.0 Hz, 1H), 7.38 (d, J=8.4 Hz, 1H).

(Example 3-c)N-[2-(1-Methylcyclopropyl)-1,3-benzoxazol-6-yl]-N'-[(pyridin-4-yl)methyl]urea The title compound (82 mg, 75%) was obtained as a solid from 2-(1-methylcyclopropyl)-1,3-benzoxazol-6-amine (64 mg, 0.340 mmol) in the same way as in (Example 2).

$^1$H NMR (DMSO-d$_6$) δ (ppm): 0.99 (dd, J=6.7, 4.1 Hz, 2H), 1.30 (dd, J=6.7, 4.1 Hz, 2H), 1.52 (s, 3H), 4.34 (d, J=6.0 Hz, 2H), 6.77 (t, J=6.0 Hz, 1H), 7.13 (dd, J=8.5, 2.0 Hz, 1H,) 7.27-7.33 (m, 2H), 7.46 (d, J=8.4 Hz, 1H), 7.87 (d, J=2.0 Hz, 1H) 8.47-8.54 (m, 2H), 8.91 (s, 1H).

LCMS (ES): m/z 323.2 [M+H]$^+$.

Example 4

N-[2-(1-Methyl-1H-pyrazol-4-yl)-1,3-benzoxazol-6-yl]-N'-[(pyridin-4-yl)methyl]urea

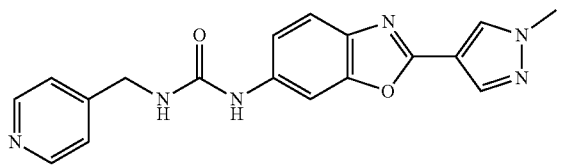 [SMILES: Cn1cc(-c2nc3ccc(NC(=O)NCc4ccncc4)cc3o2)cn1]

(Example 4-a) 2-(1-Methyl-1H-pyrazol-4-yl)-6-nitro-1,3-benzoxazole

The title compound (34 mg, two steps 28%) was obtained as a solid from 2-amino-5-nitrophenol (77 mg, 0.501 mmol) in the same way as in (Example 3-a).

$^1$H NMR (CDCl$_3$) δ (ppm): 4.04 (s, 3H), 7.75 (d, J=8.7 Hz, 1H), 8.15 (s, 1H), 8.20 (s, 1H), 8.31 (ddd, J=8.7, 2.2, 0.6 Hz, 1H), 8.43 (d, J=2.2 Hz, 1H).

(Example 4-b)N-[2-(1-Methyl-1H-pyrazol-4-yl)-1,3-benzoxazol-6-yl]-N'-[(pyridin-4-yl)methyl]urea The title compound (29 mg, two steps 59%) was obtained as a solid from 2-(1-methyl-1H-pyrazol-4-yl)-6-nitro-1,3-benzoxazole (34 mg, 0.139 mmol) obtained in (Example 4-a) in the same way as in (Example 3-b) and (Example 2).

$^1$H NMR (CD$_3$OD) δ (ppm): 3.98 (s, 3H), 4.48 (s, 2H),7.16 (dd, J=8.5, 2.1 Hz, 1H), 7.38-7.43 (m, 2H), 7.50 (dd, J=8.6, 0.4 Hz, 1H), 7.92-7.97 (m, 1H), 8.08 (d, J=0.8 Hz, 1H), 8.29-8.36 (m, 1H), 8.40-8.55 (m, 2H).

LCMS (ES): m/z 349.3 [M+H]$^+$.

Example 5

N-[(1,3-Oxazol-5-yl)methyl]-N'-(2-phenyl-1,3-benzoxazol-6-yl)urea

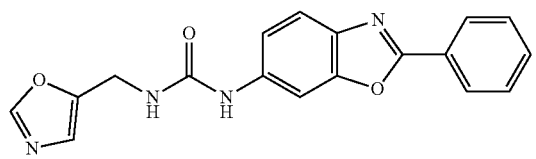 [SMILES: O=C(NCc1cnco1)Nc1ccc2nc(-c3ccccc3)oc2c1]

The title compound (39 mg, 66%) was obtained as a solid from 2-phenyl-benzoxazol-6-ylamine (37 mg, 0.176 mmol) in the same way as in (Example 1-d).

$^1$H NMR (CD$_3$OD) δ (ppm): 4.50 (s, 2H), 7.06 (s, 1H), 7.18 (dd, J=8.6, 2.0 Hz, 1H), 7.53-7.61 (m, 4H), 8.03 (d, J=2.0 Hz, 1H), 8.16 (s, 1H), 8.17-8.22 (m, 2H).

LCMS (ES): m/z 335.2 [M+H]$^+$.

Example 6

N-(5-Fluoro-2-phenyl-1,3-benzoxazol-6-yl)-N'-[(pyridin-4-yl)methyl]urea

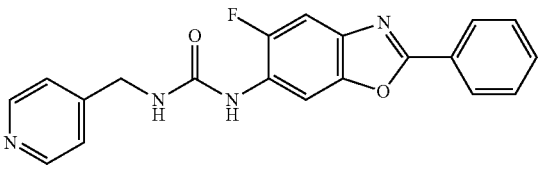 [SMILES: O=C(NCc1ccncc1)Nc1cc2oc(-c3ccccc3)nc2cc1F]

(Example 6-a) 5-Fluoro-6-nitro-2-phenyl-1,3-benzoxazole

5-Fluoro-2-phenyl-1,3-benzoxazole (0.34 g, 1.6 mmol) was dissolved in concentrated sulfuric acid (2 mL) and then cooled to 0° C. To the solution was added nitric acid (1.42) (0.20 mL, 5.0 mmol). The mixture was stirred at 0° C. for 20 min. The reaction solution was poured into ice water (20 mL), followed by partition operation using dichloromethane. The organic phase was washed with a saturated aqueous solution of sodium bicarbonate and brine, then dried over magnesium sulfate, and filtered. Then, the solvent was distilled off under reduced pressure to give the crude title compound. The crude product was purified by silica gel column chromatography (ethyl acetate:hexane=3:97 to 35:65) to give the title compound (0.20 g, 49%) as a solid.

$^1$H NMR (400 MHz, CDCl$_3$) δ (ppm) 7.55-7.68 (m, 5H), 8.26-8.31 (m, 1H), 8.36 (d, J=6.1 Hz, 1H).

(Example 6-b)
5-Fluoro-2-phenyl-1,3-benzoxazol-6-amine

5-Fluoro-6-nitro-2-phenyl-1,3-benzoxazole (0.20 g, 0.77 mmol) obtained in Example 6-a) was dissolved in ethanol (4 mL) and ethyl acetate (6 mL). To the solution was added 10% Pd/C (50% wet) (70 mg). After purging of the reaction container with hydrogen, the mixture was stirred at 60° C. for 2 h. The reaction solution was filtered through celite. Then, the filtrate was concentrated under reduced pressure to give the crude title compound. A small amount of ethyl acetate/dichloromethane (1:1) was added thereto. Then, the precipitated solid was collected by filtration to give the title compound (0.13 g, 71%) as a solid.

$^1$H NMR (400 MHz, DMSO-d$_6$) δ (ppm) 5.51 (br s, 2H), 7.05 (d, J=7.6 Hz, 1H), 7.49 (d, J=11.0 Hz, 1H), 7.54-7.60 (m, 3H), 8.06-8.12 (m, 2H).

(Example 6-c)N-(5-Fluoro-2-phenyl-1,3-benzoxazol-6-yl)-N'-[(pyridin-4-yl)methyl]urea 5-Fluoro-2-phenyl-1,3-benzoxazol-6-amine (36 mg, 0.16 mmol) obtained in (Example 6-b) and N,N-diisopropylethylamine (0.082 mL, 0.47 mmol) were dissolved in dichloromethane (2 mL) and cooled to 0° C. To the solution was added triphosgene (16 mg, 0.055 mmol). The mixture was stirred for 10 min. 4-Picolylamine (0.019 mL, 0.19 mmol) was added thereto, and the mixture was stirred for 1 h. The reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. A small amount of dichloromethane was added thereto. Then, the precipitated solid was collected by filtration and washed with diethyl ether to give the title compound (43 mg, 74%) as a solid.

$^1$H NMR (500 MHz, DMSO-d$_6$) δ (ppm) 4.40 (d, J=5.9 Hz, 2 H), 7.29-7.34 (m, 3H), 7.58-7.64 (m, 3H), 7.75 (d, J=11.0 Hz, 1H), 8.14-8.17 (m, 2H), 8.50-8.54 (m, 3H), 8.79 (d, J=2.9 Hz, 1H).

LCMS (ES): m/z 363 [M+H]$^+$.

Example 7

N-(2-Phenyl-1,3-benzoxazol-5-yl)-N'-[(pyridin-4-yl)methyl]urea

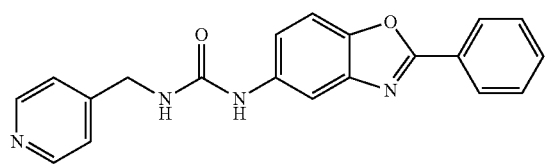 [SMILES: O=C(NCc1ccncc1)Nc1ccc2oc(-c3ccccc3)nc2c1]

2-Phenyl-1,3-benzoxazol-5-ylamine (70 mg, 0.33 mmol) and (4-nitrophenyl)-N-(4-pyridylmethyl)carbamate (0.10 g, 0.37 mmol) obtained in (Reference Example 1) were suspended in 1,4-dioxane. To the suspension was added triethylamine (0.051 mL, 0.37 mmol). The mixture was stirred at 60° C. for 2 h. After cooling to room temperature, the precipitated solid was collected by filtration and washed with diethyl ether to give the title compound (74 mg, 65%) as a solid.

$^1$H NMR (400 MHz, DMSO-d$_6$) δ (ppm) 4.36 (d, J=6.3 Hz, 2 H), 6.80 (t, J=5.9 Hz, 1H), 7.30-7.37 (m, 3H), 7.57-7.69 (m, 4H), 7.96 (d, J=2.0 Hz, 1H), 8.14-8.23 (m, 2H), 8.50-8.55 (m, 2H), 8.92 (s, 1H).

LCMS (ES): m/z 345 [M+H]$^+$.

Example 8

N-(2-Phenyl[1,2,4]triazolo[1,5-a]pyridin-6-yl)-N'-[(pyridin-4-yl)methyl]urea

(Example 8-a) 2-Phenyl-[1,2,4]triazolo[1,5-a]pyridine-6-carboxylic acid

Methyl 2-phenyl-[1,2,4]triazolo[1,5-a]pyridine-6-carboxylate (0.15 g, 0.59 mmol) was dissolved in THF (3 mL) and MeOH (1 mL). To the solution was added a 2 M aqueous sodium hydroxide solution (0.59 mL, 1.2 mmol). The mixture was stirred at room temperature for 18 h. The reaction solution was neutralized by the addition of a 2 M aqueous hydrochloric acid solution (0.59 mL, 1.2 mmol). Then, the solvent was distilled off under reduced pressure. The obtained white solid was suspended in a small amount of water, then collected by filtration, and washed with a small amount of ethanol and diethyl ether to give the title compound (0.13 g, 88%) as a solid.

$^1$H NMR (400 MHz, DMSO-d$_6$) δ (ppm) 7.52-7.61 (m, 3H), 7.92 (d, J=9.2 Hz, 1H), 8.06 (dd, J=9.6, 2.0 Hz, 1H), 8.20-8.27 (m, 2H), 9.43 (m, J=0.8 Hz, 1H), 13.62 (br s, 1H).

(Example 8-b)N-(2-Phenyl[1,2,4]triazolo[1,5-a]pyridin-6-yl)-N'-[(pyridin-4-yl)methyl]urea 2-Phenyl-[1,2,4]triazolo[1,5-a]pyridine-6-carboxylic acid (57 mg, 0.24 mmol) obtained in (Example 8-a) was suspended in 1,4-dioxane (2 mL). To the suspension were added triethylamine (0.040 mL, 0.29 mmol) and diphenylphosphoryl azide (0.062 mL, 0.29 mmol). The mixture was stirred at 90° C. for 1 h. After cooling of the reaction solution to room temperature, 4-picolylamine (0.029 mL, 0.29 mmol) was added thereto, and the mixture was stirred at room temperature for 1 h. The reaction solution was concentrated under reduced pressure to give the crude title compound. The crude product was purified by silica gel column chromatography (NH silica gel, MeOH:CH$_2$Cl$_2$=1:99 to 10:90) to give the title compound (26 mg, 31%) as a solid.

$^1$H NMR (400 MHz, DMSO-d$_6$) δ (ppm) 4.37 (d, J=6.1 Hz, 2 H), 7.05 (t, J=6.3 Hz, 1H), 7.29-7.34 (m, 2H), 7.44-7.56 (m, 4H), 7.81 (dd, J=9.6, 2.0 Hz, 1H), 8.13-8.20 (m, 2H), 8.49-8.55 (m, 2H), 9.12 (s, 1 H), 9.21-9.25 (m, 1H).

LCMS (ES): m/z 345 [M+H]$^+$.

Example 9

N-(2-Phenyl[1,2,4]triazolo[1,5-a]pyridin-6-yl)-N'-[(1H-pyrazol-4-yl)methyl]urea

(Example 9-a) 2-Phenyl[1,2,4]triazolo[1,5-a]pyridin-6-amine

2-Phenyl[1,2,4]triazolo[1,5-a]pyridine-6-carboxylic acid (262 mg, 1.095 mmol) was dissolved in DMF (15 mL). To the solution were added triethylamine (0.182 mL, 1.31 mmol) and DPPA (0.283 mL, 1.31 mmol). The mixture was stirred at room temperature for 30 min. Water (3 mL) was added to the reaction solution. The mixture was stirred at 80° C. for 3.5 h. A saturated aqueous solution of sodium bicarbonate (30 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (NH silica gel, ethyl acetate:hexane=0:100 to 100:0) to give the title compound (130 mg, 56%) as a solid.

$^1$H NMR (DMSO-d$_6$) δ (ppm): 3.68 (br s, 2H), 7.06 (dd, J=9.4, 2.2 Hz, 1H), 7.40-7.50 (m, 3H), 7.56 (dd, J=9.2, 0.7 Hz, 1H), 8.04 (dd, J=2.2, 0.7 Hz, 1H), 8.17-8.29 (m, 2H).

(Example 9-b) N-(2-Phenyl[1,2,4]triazolo[1,5-a]pyridin-6-yl)-N'-[(1H-pyrazol-4-yl)methyl]urea 2-Phenyl[1,2,4]triazolo[1,5-a]pyridin-6-amine (61 mg, 0.290 mmol) obtained in (Example 9-a) and 4-nitrophenyl chloroformate (70 mg, 0.348 mmol) were dissolved in toluene (2 mL) and then stirred at 90° C. for 7.5 h. The solvent was distilled off under reduced pressure. Then, the residue was dissolved in methanol (5 mL). The reaction solution was cooled to 0° C. N,N-Diisopropylethylamine (0.202 mL, 1.16 mmol) and 1H-pyrazol-4-ylmethylamine dihydrochloride (99 mg, 0.580 mmol) were added to the reaction solution. Then, the mixture was stirred at room temperature for 2 h. The solvent was distilled off under reduced pressure. Then, the residue was purified by silica gel column chromatography (NH silica gel+silica gel, methanol:dichloromethane=0:100 to 10:90) to give the title compound (22 mg, 22%) as a solid.

$^1$H NMR (DMSO-d$_6$) δ (ppm): 4.19 (d, J=5.5 Hz, 2H), 6.61 (t, J=5.5 Hz, 1H), 7.44-7.55 (m, 5H), 7.65-7.68 (m, 1H), 7.76 (dd, J=9.6, 0.8 Hz, 1H), 8.15-8.19 (m, 2H), 8.80 (s, 1H), 9.24-9.27 (m, 1H), 12.68 (br s, 1H).

LCMS (ES): m/z 334 [M+H]$^+$.

Example 10

N-[(1,3-Oxazol-5-yl)methyl]-N'-(2-phenyl[1,2,4]triazolo[1,5-a]pyridin-6-yl)urea

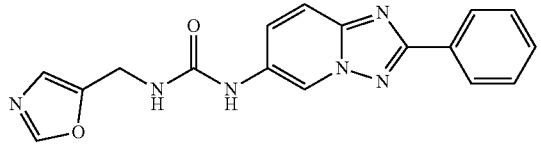 [SMILES: O=C(NCc1cnco1)Nc1ccc2nc(-c3ccccc3)nn2c1]

2-Phenyl[1,2,4]triazolo[1,5-a]pyridin-6-amine (58 mg, 0.276 mmol) obtained in (Example 9-a) was dissolved in dichloromethane (3 mL). Then, the reaction solution was cooled to 0° C. N,N-Diisopropylethylamine (0.336 mL, 1.93 mmol) and triphosgene (32 mg, 0.110 mmol) were added to the reaction solution. Then, the mixture was stirred at 0° C. for 30 min. Oxazol-5-yl-methylamine (81 mg, 0.828 mmol) was added to the reaction solution. Then, the mixture was stirred at room temperature for 27 h. Water (10 mL) was added to the reaction solution, followed by partition operation using dichloromethane. The organic phase was washed with brine, then dried over magnesium sulfate, and filtered. Then, the solvent was distilled off under reduced pressure to give the crude title compound. The residue was purified by silica gel column chromatography (NH silica gel+silica gel, methanol:dichloromethane=0:100 to 10:90) to give the title compound (26 mg, 28%) as a solid.

$^1$H NMR (DMSO-d$_6$) δ (ppm): 4.41 (d, J=5.8 Hz, 2H), 6.92 (t, J=5.8 Hz, 1H), 7.05 (s, 1H), 7.46-7.56 (m, 4H), 7.78 (dd, J=9.4, 0.8 Hz, 1H), 8.15-8.19 (m, 2H), 8.31 (s, 1H), 8.98 (s, 1H), 9.23 (dd, J=2.2, 0.8 Hz, 1H).

LCMS (ES): m/z 335 [M+H]$^+$.

Example 11

N-[2-(2-Butylphenyl) [1,2,4]triazolo[1,5-a]pyridin-6-yl]-N'-[(pyridin-4-yl)methyl]urea

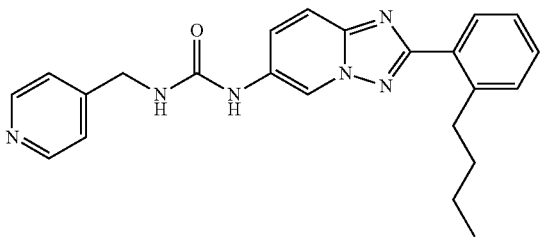 [SMILES: CCCCc1ccccc1-c1nc2ccc(NC(=O)NCc3ccncc3)cn2n1]

(Example 11-a) Methyl 2-(2-butylphenyl) [1,2,4]triazolo[1,5-a]pyridine-6-carboxylate 2-Butylbenzoic acid (0.26 g, 1.5 mmol), 3H-1,2,3-triazolo[4,5-b]pyridine-3-ol (0.20 g, 1.5 mmol), 1-ethyl-3-(3-dimethylaminopropyl)carbodiimide hydrochloride (0.28 g, 1.5 mmol), and triethylamine (0.27 mL, 1.9 mmol) were dissolved in dichloromethane (4 mL) and stirred at room temperature for 1 h. The solvent was distilled off under reduced pressure. Then, the obtained residue was dissolved in pyridine (3 mL). To the solution was added 1,2-diamino-5-(methoxycarbonyl)pyridin-1-ium 2,4,6-trimethylbenzene- 1-sulfonate (0.36 g, 0.97 mmol). The mixture was stirred at 80° C. for 5 h. After cooling to room temperature, the reaction solution was poured into water (30 mL), followed by partition operation using ethyl acetate. The organic phase was washed with a saturated aqueous solution of sodium bicarbonate and brine, then dried over magnesium sulfate, and filtered. Then, the solvent was distilled off under reduced pressure to give the crude title compound. The crude product was purified by silica gel column chromatography (EtOAc:hexane=10:90 to 45:55) to give the title compound (0.25 g, 84%) as a solid.

$^1$H NMR (400 MHz, CDCl$_3$) δ (ppm) 0.90 (t, J=7.3 Hz, 3H), 1.32-1.43 (m, 2H), 1.53-1.64 (m, 2H), 3.08-3.17 (m, 2H), 4.00 (s, 3H), 7.27-7.47 (m, 3H), 7.75-7.81 (m, 1H), 8.01-8.06 (m, 1H), 8.07-8.12 (m, 1H), 9.29-9.34 (m, 1H).

(Example 11-b) 2-(2-Butylphenyl) [1,2,4]triazolo[1,5-a]pyridine-6-carboxylic acid Methyl 2-(2-butylphenyl)-[1,2,4]triazolo[1,5-a]pyridine-6-carboxylate (0.25 g, 0.81 mmol) obtained in (Example 11-a) was dissolved in THF (4 mL) and MeOH (2 mL). To the solution was added a 2 M aqueous sodium hydroxide solution (0.81 mL, 1.6 mmol). The mixture was stirred at room temperature for 3 h. The reaction solution was neutralized by the addition of a 2 M aqueous hydrochloric acid solution (0.81 mL, 1.6 mmol). Then, the solvent was distilled off under reduced pressure. The obtained residue was diluted with ethyl acetate and then poured into water (30 mL), followed by partition operation using ethyl acetate. The organic phase was washed with brine, then dried over magnesium sulfate, and filtered. Then, the solvent was distilled off under reduced pressure to give the crude title compound. A small amount of a diethyl ether/hexane mixed solution (1:1) was added thereto. The precipitated solid was collected by filtration to give the title compound (0.19 g, 77%) as a solid.

$^1$H NMR (400 MHz, CDCl$_3$) δ (ppm) 0.90 (t, J=7.3 Hz, 3H), 1.33-1.44 (m, 2H), 1.54-1.65 (m, 2H), 3.09-3.17 (m, 2H), 7.29-7.47 (m, 2H), 7.84-7.89 (m, 1H), 8.02-8.07 (m, 1H), 8.13-8.17 (m, 1H), 9.40-9.43 (m, 1H) (one peak missing).

(Example 11-c) tert-Butyl [2-(2-butylphenyl) [1,2,4]triazolo[1,5-a]pyridin-6-yl]carbamate 2-(2-Butylphenyl) [1,2,4]triazolo[1,5-a]pyridine-6-carboxylic acid (0.19 g, 0.63 mmol) obtained in (Example 11-b) was suspended in dichloromethane (2 mL). To the suspension were added triethylamine (0.10 mL, 0.75 mmol) and diphenylphosphoryl azide (0.16 mL, 0.75 mmol). The mixture was stirred at room temperature for 15 min. The solvent was distilled off under reduced pressure. Then, the obtained residue was dissolved in toluene (4 mL). To the solution was added t-BuOH (0.30 mL, 3.1 mmol). The mixture was stirred at 100° C. for 4 h. After cooling to room temperature, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (EtOAc:hexane=5:95 to 45:55) to give the title compound (0.16 g, 68%) as an oil.

$^1$H NMR (400 MHz, CDCl$_3$) δ (ppm) 0.88 (t, J=7.3 Hz, 3H), 1.29-1.40 (m, 2H), 1.56 (s, 11H), 3.06-3.14 (m, 2H), 6.55 (br s, 1H), 7.24-7.39 (m, 5H), 7.64-7.68 (m, 1H), 7.95-7.99 (m, 1H).

(Example 11-d) 2-(2-Butylphenyl) [1,2,4]triazolo[1,5-a]pyridin-6-amine-hydrogen chloride (1/1)

tert-Butyl [2-(2-butylphenyl) [1,2,4]triazolo[1,5-a]pyridin-6-yl]carbamate (0.16 g, 0.43 mmol) obtained in (Example 11-c) was dissolved in dichloromethane (2 mL). To the solution was added a 4 M solution of hydrochloric acid in 1,4-dioxane (0.50 mL, 2.0 mmol). The mixture was stirred at room temperature for 1 h. The solvent was distilled off under reduced pressure. Then, a small amount of ethyl acetate was added to the obtained residue. The precipitated solid was collected by filtration to give the title compound (0.11 g, 81%) as a solid.

$^1$H NMR (400 MHz, CD$_3$OD) δ (ppm) 0.92 (dt, J=9.0, 7.4 Hz, 3H), 1.33-1.45 (m, 2H), 1.56-1.68 (m, 2H), 2.95-3.04 (m, 2H), 7.41-7.65 (m, 3H), 7.71-7.78 (m, 1H), 7.81-7.85 (m, 1H), 7.99-8.10 (m, 1H), 8.35-8.38 (m, 1H).

(Example 11-e) N-[2-(2-Butylphenyl) [1,2,4]triazolo[1,5-a]pyridin-6-yl]-N'-[(pyridin-4-yl)methyl]urea 2-(2-Butylphenyl) [1,2,4]triazolo[1,5-a]pyridin-6-amine-hydrogen chloride (1/1) (0.11 g, 0.35 mmol) obtained in (Example 11-d), and (4-nitrophenyl) N-(4-pyridylmethyl) carbamate (0.11 g, 0.42 mmol) obtained in (Reference Example 1) were suspended in 1,4-dioxane (2 mL). To the suspension was added N,N-diisopropylethylamine (0.24 mL, 1.4 mmol). The mixture was stirred at 100° C. for 3 h. After cooling to room temperature, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (MeOH:CH$_2$Cl$_2$=1:99 to 10:90) to give the title compound (89 mg, 64%) as a solid.

$^1$H NMR (500 MHz, DMSO-d$_6$) δ (ppm) 0.84 (t, J=7.1 Hz, 3 H), 1.26-1.34 (m, 2H), 1.47-1.54 (m, 2H), 3.05-3.11 (m, 2H), 4.37 (d, J=5.9 Hz, 2H), 7.02 (t, J=6.1 Hz, 1H), 7.29-7.40 (m, 5H), 7.52 (dd, J=9.5, 2.0 Hz, 1 H), 7.78 (dd, J=9.5, 0.73 Hz, 1H), 7.93-7.96 (m, 1 H), 8.50-8.53 (m, 2H), 9.10 (s, 1H), 9.22-9.24 (m, 1H).

LCMS (ES): m/z 401 [M+H]$^+$.

Example 12

N-[2-(1-Phenyl-1H-pyrrol-2-yl) [1,2,4]triazolo[1,5-a]pyridin-6-yl]-N'-[(pyridin-4-yl)methyl]urea

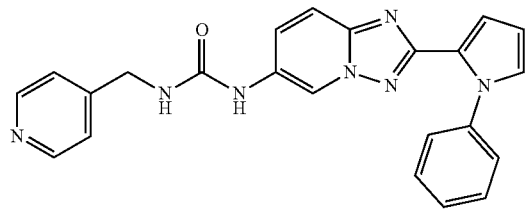 [SMILES: O=C(NCc1ccncc1)Nc1ccc2nc(-c3cccn3-c3ccccc3)nn2c1]

(Example 12-a) Methyl 2-(1-phenylpropyl-2-yl)-[1,2,4]triazolo[1,5-a]pyridine-6-carboxylate 1-Phenyl-1H-pyrrole-2-carboxylic acid (0.30 g, 1.6 mmol), 3H-1,2,3-triazolo[4,5-b]pyridine-3-ol (0.22 g, 1.6 mmol), 1-ethyl-3-(3-dimethylaminopropyl) carbodiimide hydrochloride (0.31 g, 1.6 mmol), and triethylamine (0.30 mL, 2.2 mmol) were dissolved in dichloromethane (4 mL) and stirred at room temperature for 30 min. The solvent was distilled off under reduced pressure. Then, the obtained residue was dissolved in pyridine (3 mL). To the solution was added 1,2-diamino-5-(methoxycarbonyl)pyridin-1-ium 2,4,6-trimethylbenzene-1-sulfonate (0.40 g, 1.1 mmol). The mixture was stirred at 80° C. for 2 h. After cooling to room temperature, the reaction solution was poured into water (30 mL), followed by partition operation using ethyl acetate. The organic phase was washed with a saturated aqueous solution of sodium bicarbonate and brine, then dried over magnesium sulfate, and filtered. Then, the solvent was distilled off under reduced pressure to give the crude title compound. The crude product was purified by silica gel column chromatography (EtOAc:hexane=10:90 to 50:50) to give the title compound (0.26 g, 76%) as an oil.

$^1$H NMR (400 MHz, CDCl$_3$) δ (ppm) 3.94 (s, 3H), 6.43 (dd, J=3.7, 2.7 Hz, 1H), 6.99-7.03 (m, 1H), 7.14-7.19 (m, 1H), 7.32-7.49 (m, 4H), 7.61 (d, J=9.2 Hz, 1H), 7.98 (dd, J=9.3, 1.7 Hz, 2H), 9.01-9.05 (m, 1H).

(Example 12-b) 2-(1-Phenylpropyl-2-yl)-triazolo[1,5-a]pyridine-6-carboxylic acid Methyl 2-(1-phenylpropyl-2-yl)-[1,2,4]triazolo[1,5-a]pyridine-6-carboxylate (0.26 g, 0.82 mmol) obtained in (Example 12-a) was dissolved in THF (2 mL) and MeOH (1 mL). To the solution was added a 2 M aqueous sodium hydroxide solution (0.82 mL, 1.6 mmol). The mixture was stirred at room temperature for 3 h. The reaction solution was neutralized by the addition of a 2 M aqueous hydrochloric acid solution (0.82 mL, 1.6 mmol). Then, the solvent was distilled off under reduced pressure. The obtained residue was diluted with ethyl acetate and then poured into water (30 mL), followed by partition operation using ethyl acetate. The organic phase was washed with brine, then dried over magnesium sulfate, and filtered. Then, the solvent was distilled off under reduced pressure to give the crude title compound. A small amount of diethyl ether was added thereto. The precipitated solid was collected by filtration to give the title compound (0.18 g, 71%) as a solid.

$^1$H NMR (400 MHz, CDCl$_3$) δ (ppm) 6.44 (dd, J=3.9, 2.7 Hz, 1H), 7.03 (dd, J=2.7, 1.8 Hz, 1H), 7.20 (dd, J=3.7, 1.8 Hz, 1H), 7.34-7.46 (m, 5H), 7.70 (dd, J=9.4, 1.0 Hz, 1H), 8.03 (d, J=9.2 Hz, 1H), 9.11-9.13 (m, 1H) (one peak missing).

(Example 12-c) t-Butyl N-[2-(1-phenylpyrrol-2-yl)-[1,2,4]triazolo[1,5-a]pyridine-6-yl]carbamate 2-(1-Phenylpropyl-2-yl)-[1,2,4]triazolo[1,5-a]pyridine-6-carboxylic acid (0.18 g, 0.59 mmol) obtained in (Example 12-b) was suspended in dichloromethane (2 mL). To the suspension were added triethylamine (0.10 mL, 0.71 mmol) and diphenylphosphoryl azide (0.15 mL, 0.71 mmol). The mixture was stirred at room temperature for 1 h. The solvent was distilled off under reduced pressure. Then, the obtained residue was dissolved in toluene (2 mL). To the solution was added t-BuOH (0.28 mL, 2.9 mmol). The mixture was stirred at 100° C. for 4 h. After cooling to room temperature, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. A small amount of a diethyl ether/dichloromethane mixed solution (2:1) was added thereto. The precipitated solid was collected by filtration to give the title compound (0.14 g, 62%) as a solid.

$^1$H NMR (400 MHz, DMSO-d$_6$) δ (ppm) 1.48 (s, 9H), 6.36 (dd, J=3.6, 2.8 Hz, 1H), 6.87 (dd, J=3.7, 1.8 Hz, 1H), 7.14 (dd, J=2.7, 2.0 Hz, 1H), 7.27-7.45 (m, 5H), 7.50 (dd, J=9.6, 2.0 Hz, 1H), 7.64 (dd, J=9.6, 0.8 Hz, 1H), 8.87 (br s, 1H), 9.66-9.77 (m, 1H).

(Example 12-d) 2-(1-Phenylpyrrol-2-yl)-triazolo[1,5-a]pyridine-6-amine hydrochloride t-Butyl N-[2-(1-phenylpyrrol-2-yl)-[1,2,4]triazolo[1,5-a]pyridine-6-yl]carbamate (0.14 g, 0.37 mmol) obtained in (Example 12-c) was dissolved in dichloromethane (2 mL). To the solution was added a 4 M solution of hydrochloric acid in 1,4-dioxane (0.50 mL, 2.0 mmol). The mixture was stirred at room temperature for 5 h. The solvent was distilled off under reduced pressure. Then, a small amount of ethyl acetate was added to the obtained residue. The precipitated solid was collected by filtration to give the title compound (0.10 g, 87%) as a solid.

$^1$H NMR (400 MHz, CD$_3$OD) δ (ppm) 6.51-6.53 (m, 1H), 7.17 (dd, J=3.9, 1.8 Hz, 1H), 7.23-7.27 (m, 1H), 7.35-7.55 (m, 5H), 7.60-7.70 (m, 2H), 7.94-7.99 (m, 1H).

(Example 12-e) N-[2-(1-Phenyl-1H-pyrrol-2-yl) [1,2,4]triazolo[1,5-a]pyridin-6-yl]-N'-[(pyridin-4-yl)methyl]urea 2-(1-Phenylpyrrol-2-yl)-[1,2,4]triazolo[1,5-a]pyridine-6-amine hydrochloride (96 mg, 0.31 mmol) obtained in (Example 12-d) and (4-nitrophenyl)N-(4-pyridylmethyl)carbamate (0.10 g, 0.37 mmol) obtained in (Reference Example 1) were suspended in 1,4-dioxane (2 mL). To the suspension was added N,N-diisopropylethylamine (0.21 mL, 1.2 mmol). The mixture was stirred at 80° C. for 6 h. After cooling to room temperature, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (NH silica gel, MeOH:CH$_2$Cl$_2$=1:99 to 10:90) to give the title compound (37 mg, 30%) as a solid.

$^1$H NMR (500 MHz, DMSO-d$_6$) δ (ppm) 4.33 (d, J=6.1 Hz, 2H), 6.35 (dd, J=3.7, 2.7 Hz, 1H), 6.84-6.86 (m, 1H), 6.94-6.99 (m, 1H), 7.13 (dd, J=2.7, 2.0 Hz, 1H), 7.26-7.31 (m, 4H), 7.33-7.43 (m, 4H), 7.58-7.62 (m, 1H), 8.49-8.51 (m, 2H), 8.97-8.98 (m, 1H), 9.00 (s, 1H).

LCMS (ES): m/z 410 [M+H]$^+$.

Example 13

N-[2-(1-Methyl-1H-pyrazol-5-yl) [1,2,4]triazolo[1,5-a]pyridin-6-yl]-N'-[(pyridin-4-yl)methyl]urea

(Example 13-a) Methyl 6-{[(ethoxycarbonyl)carbamothioyl]amino}pyridine-3-carboxylate Methyl 6-aminonicotinate (1.1 g, 7.2 mmol) was dissolved in 1,4-dioxane (14 mL). To the solution was added ethoxycarbonyl isothiocyanate (1.2 mL, 11 mmol). The mixture was stirred at room temperature for 30 min and then further stirred at 50° C. for 1 h. After cooling to room temperature, diethyl ether (15 mL) was added to the reaction solution. The precipitated solid was collected by filtration and washed with diethyl ether to give the title compound (1.4 g, 66%) as a solid.

$^1$H NMR (400 MHz, DMSO-d$_6$) δ (ppm) 1.27 (t, J=7.1 Hz, 3 H), 3.88 (s, 3H), 4.24 (q, J=7.0 Hz, 2H), 8.36 (dd, J=9.0, 2.2 Hz, 1H), 8.71-8.81 (m, 1H), 8.90 (d, J=2.4 Hz, 1H), 11.96 (br s, 1H), 12.38 (br s, 1H).

(Example 13-b) Methyl 2-amino[1,2,4]triazolo[1,5-a]pyridine-6-carboxylate

Methyl 6-(ethoxycarbonylcarbamothioylamino)pyridine-3-carboxylate (0.79 g, 2.8 mmol) obtained in (Example 13-a) and hydroxyammonium chloride (0.58 g, 8.4 mmol) were suspended in MeOH (10 mL) and EtOH (10 mL). To the suspension was added N,N-diisopropylethylamine (1.5 mL, 8.4 mmol). The mixture was stirred at 50° C. for 6 h. After cooling to room temperature, the precipitated solid was collected by filtration and washed with ethanol to give the title compound (0.47 g, 87%) as a solid.

$^1$H NMR (400 MHz, DMSO-d$_6$) δ (ppm) 3.87 (s, 3H), 6.39 (s, 2H), 7.39-7.43 (m, 1H), 7.83 (dd, J=9.2, 1.8 Hz, 1 H), 9.01-9.03 (m, 1H).

(Example 13-c) Methyl 2-bromo[1,2,4]triazolo[1,5-a]pyridine-6-carboxylate

Methyl 2-amino[1,2,4]triazolo[1,5-a]pyridine-6-carboxylate (0.47 g, 2.4 mmol) obtained in (Example 13-b), copper (II) bromide (0.60 g, 2.7 mmol), and t-butyl nitrite (0.28 g, 2.7 mmol) were dissolved in acetonitrile (7 mL) and stirred at 50° C. for 1 h. After cooling to room temperature, the reaction solution was poured into water (30 mL), followed by partition operation using dichloromethane. The organic phase was washed with brine, then dried over magnesium sulfate, and filtered through celite. Then, the solvent was distilled off under reduced pressure to give the crude title compound. A small amount of diethyl ether was added thereto. The precipitated solid was collected by filtration to give the title compound (0.36 g, 58%) as a solid.

$^1$H NMR (400 MHz, CDCl$_3$) δ (ppm) 4.01 (s, 3H), 7.73 (d, J=9.2 Hz, 1H), 8.14 (dd, J=9.0, 2.0 Hz, 1H), 8.15 (br s, 1H).

(Example 13-d) Methyl 2-(1-methyl-1H-pyrazol-5-yl) [1,2,4]triazolo[1,5-a]pyridine-6-carboxylate Methyl 2-bromo[1,2,4]triazolo[1,5-a]pyridine-6-carboxylate (0.15 g, 0.58 mmol) obtained in (Example 13-c), 1-methyl-1H-pyrazole-5-boronic acid pinacol ester (0.18 g, 0.87 mmol), [1,1'-bis(diphenylphosphino)ferrocene]palladium(II) dichloride dichloromethane adduct (24 mg, 0.029 mmol), and potassium carbonate (0.24 g, 1.7 mmol) were suspended in 1,4-dioxane (3 mL) and water (1 mL) and then stirred at 60° C. for 2 h. After cooling to room temperature, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (AcOEt:hexane=15:85 to 55:45) to give the title compound (0.14 g, 94%) as a solid.

$^1$H NMR (400 MHz, CDCl$_3$) δ (ppm) 4.01 (s, 3H), 4.37-4.39 (m, 3H), 7.04 (d, J=2.2 Hz, 1H), 7.58 (d, J=2.0 Hz, 1H), 7.78 (dd, J=9.3, 0.9 Hz, 1H), 8.13 (dd, J=9.3, 1.7 Hz, 1H), 9.32 (dd, J=1.7, 0.9 Hz, 1H).

(Example 13-e) 2-(1-Methyl-1H-pyrazol-5-yl) [1,2,4]triazolo[1,5-a]pyridine-6-carboxylic acid Methyl 2-(1-methyl-1H-pyrazol-5-yl) [1,2,4]triazolo[1,5-a]pyridine-6-carboxylate (0.20 g, 0.77 mmol) obtained in (Example 13-d) was dissolved in THF (3 mL) and MeOH (1 mL). To the solution was added a 2 M aqueous NaOH solution (0.77 mL, 1.5 mmol). The mixture was stirred at room temperature for 2 h. The reaction solution was neutralized by the addition of a 2 M aqueous hydrochloric acid solution (0.77 mL, 1.5 mmol). Then, the solvent was distilled off under reduced pressure. The obtained residue was suspended in water. Then, the solid was collected by filtration and washed with a small amount of acetonitrile to give the title compound (0.11 g, 60%) as a solid.

$^1$H NMR (400 MHz, DMSO-d$_6$) δ (ppm) 4.30 (s, 3H), 6.97 (d, J=2.0 Hz, 1H), 7.59 (d, J=2.2 Hz, 1H), 7.96 (dd, J=9.2, 0.8 Hz, 1H), 8.10 (dd, J=9.4, 2.0 Hz, 1H), 9.45 (dd, J=1.7, 0.9 Hz, 1H), 13.68 (br s, 1H).

(Example 13-f) tert-Butyl [2-(1-methyl-1H-pyrazol-5-yl) [1,2,4]triazolo[1,5-a]pyridin-6-yl]carbamate 2-(1-Methyl-1H-pyrazol-5-yl) [1,2,4]triazolo[1,5-a]pyridine-6-carboxylic acid obtained in (Example 13-e) was suspended in dichloromethane (2 mL). To the suspension were added triethylamine (0.076 mL, 0.55 mmol) and diphenylphosphoryl azide (0.12 mL, 0.55 mmol). The mixture was stirred at room temperature for 20 min. The solvent was distilled off under reduced pressure. Then, the obtained residue was dissolved in toluene (2 mL). To the solution was added t-BuOH (0.22 mL, 2.3 mmol). The mixture was stirred at 100° C. for 1 h. After cooling to room temperature, the precipitated solid was collected by filtration and washed with a small amount of toluene to give the title compound (67 mg, 46%) as a solid. The filtrate was concentrated under reduced pressure and then purified by silica gel column chromatography (AcOEt:hexane=10:90 to 30:70) to give the title compound (42 mg, 30%) as a solid.

$^1$H NMR (400 MHz, DMSO-d$_6$) δ (ppm) 1.51 (s, 9H), 4.26 (s, 3H), 6.88 (d, J=2.0 Hz, 1H), 7.54 (d, J=2.0 Hz, 1 H), 7.66 (dd, J=9.5, 2.1 Hz, 1H), 7.83-7.87 (m, 1H), 9.14 (br s, 1H) 9.85 (br s, 1H).

(Example 13-g) 2-(1-Methyl-1H-pyrazol-5-yl) [1,2,4]triazolo[1,5-a]pyridin-6-amine-hydrogen chloride (1/1)

tert-Butyl [2-(1-methyl-1H-pyrazol-5-yl) [1,2,4]triazolo[1,5-a]pyridin-6-yl]carbamate (0.11 g, 0.35 mmol) obtained in (Example 13-f) was dissolved in dichloromethane (2 mL). To the solution was added a 4 M solution of hydrochloric acid in 1,4-dioxane (1.0 mL, 4.0 mmol). The mixture was stirred at room temperature for 5 h. The solvent was distilled off under reduced pressure. Then, a small amount of ethyl acetate was added to the obtained residue. The precipitated solid was collected by filtration to give the title compound (0.087 g, 100%) as a solid.

¹H NMR (500 MHz, CDCl₃) δ (ppm) 4.00 (s, 3H), 4.05 (s, 3 H), 6.97 (d, J=2.2 Hz, 1H), 7.48 (d, J=2.2 Hz, 1H), 7.75 (dd, J=9.3, 1.0 Hz, 1H), 8.07 (dd, J=9.3, 1.7 Hz, 1H), 9.27-9.30 (m, 1H).

(Example 13-h)N-[2-(1-Methyl-1H-pyrazol-5-yl) [1,2,4]triazolo[1,5-a]pyridin-6-yl]-N'-[(pyridin-4-yl) methyl]urea 2-(1-Methyl-1H-pyrazol-5-yl) [1,2,4]triazolo[1,5-a]pyridin-6-amine-hydrogen chloride (1/1) (87 mg, 0.35 mmol) obtained in (Example 13-g) and (4-nitrophenyl) N-(4-pyridylmethyl)carbamate (0.11 g, 0.42 mmol) obtained in (Reference Example 1) were suspended in 1,4-dioxane (3 mL). To the suspension was added N,N-diisopropylethylamine (0.24 mL, 1.4 mmol). The mixture was stirred at 80° C. for 6 h. After cooling to room temperature, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (NH silica gel, MeOH:CH₂Cl₂=1:99 to 10:90) to give the title compound (35 mg, 29%) as a solid.

¹H NMR (400 MHz, DMSO-d₆) δ (ppm) 4.25 (s, 3H), 4.37 (d, J=6.1 Hz, 2H), 6.88 (d, J=2.0 Hz, 1H), 7.04 (t, J=6.0 Hz, 1H), 7.30-7.33 (m, 2H), 7.54 (d, J=2.0 Hz, 1H), 7.57 (dd, J=9.6, 2.2 Hz, 1H), 7.82 (d, J=9.6 Hz, 1H), 8.50-8.54 (m, 2H), 9.17 (s, 1H), 8.52 (d, J=1.4 Hz, 1H).

LCMS (ES): m/z 349 [M+H]⁺.

Example 14

N-[(Pyridin-4-yl)methyl]-N'-{2-[2-(trifluoromethyl) phenyl][1,2,4]triazolo[1,5-a]pyridin-6-yl}urea

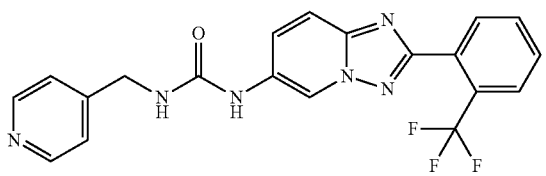 [SMILES: O=C(NCc1ccncc1)Nc1ccc2nc(-c3ccccc3C(F)(F)F)nn2c1]

(Example 14-a) Methyl 6-({imino[2-(trifluoromethyl)phenyl]methyl}amino)pyridine-3-carboxylate To a solution of methyl 6-aminopyridine-3-carboxylate (5.0 g, 33 mmol) in DMF (20 mL) was added NaH (2.6 g, 66 mmol, 60% purity). The mixture was stirred at 0° C. for 1 h. After that, 2-(trifluoromethyl)benzonitrile (6.8 g, 39 mmol) was added to the above solution, and the mixture was stirred at 25° C. for 11 h. The reaction mixture was partitioned between EA (100 mL) and H₂O (100 mL). The organic phase was separated, washed with brine (20 mL×3), dried over Na₂SO₄, filtered and concentrated under reduced pressure to give a residue. The crude product was purified by column chromatography (SiO₂, Petroleum ether/Ethyl acetate=10:1 to 2:1) to give the title compound (0.35 g, 0.87 mmol, 2.6% yield) as an oil.

¹H NMR: (400 MHz, DMSO-d₆) δ (ppm) 3.85 (s, 3H), 6.98 (d, J=8.4 Hz, 1H), 7.61-7.68 (m, 2H), 7.73-7.75 (m, 1H), 7.80-7.82 (m, 1H), 8.10-8.12 (m, 1H), 8.49 (s, 1H), 8.87 (s, 1H), 9.84 (s, 1H).

(Example 14-b) Methyl 2-[2-(trifluoromethyl)phenyl][1,2,4]triazolo[1,5-a]pyridine-6-carboxylate To a solution of methyl 6-({imino[2-(trifluoromethyl)phenyl]methyl}amino)pyridine-3-carboxylate (0.35 g, 0.87 mmol) in HFIP (8 mL) was added PIFA (0.70 g, 1.6 mmol). The mixture was stirred at 25° C. for 12 h. The reaction mixture was concentrated under reduced pressure to give a residue. The residue was partitioned between EA (20 mL) and H₂O (20 mL). The organic phase was separated, washed with brine (10 mL×3), dried over Na₂SO₄, filtered and concentrated under reduced pressure to give the crude title compound (0.25 g, crude) as an oil, which was used in the next step without further purification.

LCMS (ES): m/z 322 [M+H]⁺.

(Example 14-c) 2-[2-(Trifluoromethyl)phenyl][1,2,4]triazolo[1,5-a]pyridine-6-carboxylic acid To a solution of methyl 2-[2-(trifluoromethyl)phenyl][1,2,4]triazolo[1,5-a]pyridine-6-carboxylate (0.25 g, crude) in MeOH (2 mL), THF (2 mL) and H₂O (0.5 mL) was added LiOH·H₂O (0.13 g, 3.1 mmol). The mixture was stirred at 25° C. for 12 h. The reaction mixture was concentrated under reduced pressure to remove MeOH and THF. The reaction mixture was partitioned between EA (30 mL) and H₂O (30 mL). The organic phase was separated and discarded. The aqueous phase was adjusted to pH=5 with 1 M HCl (2 mL), and extracted with EA (10 mL×3). The organic phase was separated, washed with brine (10 mL×2), dried over Na₂SO₄, filtered and concentrated under reduced pressure to give the title compound (0.12 g, 0.35 mmol, 56% yield) as an oil, which was used in the next step without further purification.

¹H NMR: (400 MHz, CD₃OD) δ (ppm) 7.77-7.79 (m, 2H), 7.87-7.93 (m, 3H), 8.23-8.26 (m, 1H), 9.45 (s, 1H).

LCMS (ES): m/z 308 [M+H]⁺.

(Example 14-d)N-[(Pyridin-4-yl)methyl]-N'-{2-[2-(trifluoromethyl)phenyl][1,2,4]triazolo[1,5-a]pyridin-6-yl}urea To a solution of 2-[2-(trifluoromethyl)phenyl][1,2,4]triazolo[1,5-a]pyridine-6-carboxylic acid (30 mg, 0.098 mmol) in toluene (5 mL) were added DPPA (35 mg, 0.13 mmol) and TEA (0.027 ml, 0.20 mmol). The mixture was stirred at 25° C. for 1 h. Then the mixture was stirred at 90° C. for 1 h. After that, 4-pyridylmethanamine (13 mg, 0.12 mmol) was added the above solution. The mixture was stirred at 110° C. for 4 h. The reaction mixture was partitioned between EA (20 mL) and H₂O (15 mL). The organic phase was separated, washed with brine (10 mL×3), dried over Na₂SO₄, filtered and concentrated under reduced pressure to give a residue. The crude product was purified by prep-TLC and prep-HPLC (column: Gemini 150×25 5u; mobile phase: [water (0.04% NH₃H₂O)-ACN]; B %: 25%-55%) to give the title compound (3.7 mg, 0.0085 mmol, 8.7% yield) as a solid.

¹H NMR: (400 MHz, CD₃OD) δ (ppm) 4.50 (s, 2H), 7.43 (d, J=6.0 Hz, 2H), 7.59-7.62 (m, 1H), 7.72-7.76 (m, 3H), 7.80-7.81 (m, 1H), 7.89 (d, J=7.6 Hz, 1H), 8.48-8.50 (m, 2H), 9.27 (s, 1H).

LCMS (ES): m/z 413 [M+H]⁺.

Example 15

N-(2-Phenyl[1,2,4]triazolo[1,5-a]pyridin-7-yl)-N'-[(pyridin-4-yl)methyl]urea

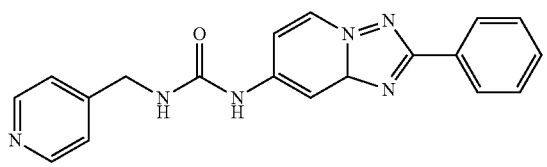

2-Phenyl-[1,2,4]triazolo[1,5-a]pyridine-7-carboxylic acid (62 mg, 0.26 mmol) was suspended in 1,4-dioxane (2 mL). To the suspension were added triethylamine (0.043 mL, 0.31 mmol) and diphenylphosphoryl azide (0.067 mL, 0.31 mmol). The mixture was stirred at 90° C. for 1 h. After cooling of the reaction solution to room temperature, 4-picolylamine (0.031 mL, 0.31 mmol) was added thereto, and the mixture was stirred at room temperature for 30 min. The reaction solution was concentrated under reduced pressure to give the crude title compound. The crude product was purified by silica gel column chromatography (NH silica gel, MeOH:CH$_2$Cl$_2$=1:99 to 10:90) to give the title compound (27 mg, 30%) as a solid.

$^1$H NMR (500 MHz, DMSO-d$_6$) δ (ppm) 4.38 (d, J=6.1 Hz, 2 H), 7.07 (t, J=6.0 Hz, 1H), 7.13 (dd, J=7.4, 2.3 Hz, 1 H), 7.30-7.34 (m, 2H), 7.45-7.54 (m, 3H), 7.89-7.92 (m, 1H), 8.13-8.19 (m, 2H), 8.50-8.54 (m, 2 H), 8.76-8.79 (m, 1H), 9.43 (s, 1H).

Example 16

N-(2-Phenylimidazo[1,2-a]pyridin-7-yl)-N'-[(pyridin-4-yl) methyl]urea

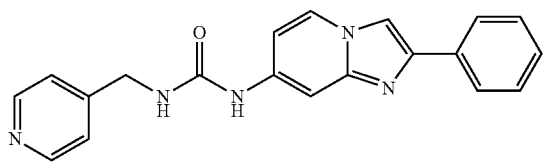 [SMILES: O=C(NCc1ccncc1)Nc1ccn2cc(-c3ccccc3)nc2c1]

2-Phenylimidazo[1,2-a]pyridine-7-carboxylic acid (90 mg, 0.38 mmol) was suspended in 1,4-dioxane (2 mL). To the suspension were added triethylamine (0.063 mL, 0.45 mmol) and diphenylphosphoryl azide (0.098 mL, 0.45 mmol). The mixture was stirred at 90° C. for 1 h. After cooling of the reaction solution to room temperature, 4-picolylamine (0.045 mL, 0.45 mmol) was added thereto, and the mixture was stirred at room temperature for 2 h. The reaction solution was poured into water (30 mL), followed by partition operation using dichloromethane. The organic phase was washed with brine, then dried over magnesium sulfate, and filtered. Then, the solvent was distilled off under reduced pressure to give the crude title compound. The crude product was purified by silica gel column chromatography (NH silica gel, methanol:dichloromethane=1:99 to 10:90) to give the title compound (43 mg, 33%) as a solid.

$^1$H NMR (500 MHz, DMSO-d$_6$) δ (ppm) 4.37 (d, J=6.1 Hz, 2 H), 6.88-6.93 (m, 2H), 7.26-7.33 (m, 3H), 7.38-7.43 (m, 2H), 7.66-7.68 (m, 1H), 7.89-7.93 (m, 2 H), 8.19 (d, J=0.7 Hz, 1H), 8.34-8.36 (m, 1H), 8.51-8.53 (m, 2H), 9.05 (br s, 1H).

LCMS (ES): m/z 344 [M+H]$^+$.

Example 17

N-[2-Phenyl-3-(pyrrolidine-1-carbonyl)-2H-indazol-6-yl]-N'-[(pyridin-4-yl)methyl]urea

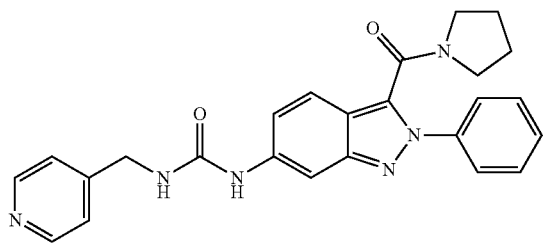 [SMILES: O=C(NCc1ccncc1)Nc1ccc2c(C(=O)N3CCCC3)n(-c3ccccc3)nc2c1]

(Example 17-a)
6-Nitro-2-phenyl-2H-indazole-3-carbonitrile

6-Nitro-1-oxo-2-phenyl-2H-1λ$^5$-indazole-3-carbonitrile (290 mg, 1.03 mmol) obtained by the manufacturing method described in J. Org. Chem. 1962, 27, 65-66 and triphenylphosphine (271 mg, 1.03 mmol) were dissolved in ethanol (25 mL) and then stirred at 80° C. for 4 h. The reaction solution was cooled to room temperature and then concentrated under reduced pressure to give the crude title compound. The crude product was purified by silica gel column chromatography (silica gel, ethyl acetate:hexane=0:100 to 10:90) to give the title compound (250 mg, 91%) as a solid.

$^1$H NMR (CDCl$_3$) δ (ppm): 7.61-7.71 (m, 3H), 7.89-7.95 (m, 2H), 7.99 (dd, J=9.2, 0.8 Hz, 1H), 8.22 (dd, J=9.2, 2.0 Hz, 1H), 8.92 (dd, J=2.0, 0.8 Hz, 1H).

(Example 17-b)
6-Amino-2-phenyl-2H-indazole-3-carbonitrile

6-Nitro-2-phenyl-2H-indazole-3-carbonitrile (250 mg, 0.95 mmol) obtained in (Example 17-a) and ammonium chloride (51 mg, 0.95 mmol) were dissolved in ethanol (14 mL) and water (7 mL) and then stirred at 80° C. for 1 min. Iron (530 mg, 9.5 mmol) was added to the reaction solution. The mixture was stirred at 80° C. for 2.5 h. The reaction solution was filtered through celite. Then, the filtrate was concentrated under reduced pressure. Water (20 mL) was added to the residue, followed by partition operation using ethyl acetate. The organic phase was washed with brine, then dried over magnesium sulfate, and filtered. Then, the solvent was distilled off under reduced pressure to give the title compound (209 mg, 94%) as a solid.

$^1$H NMR (CDCl$_3$) δ (ppm): 3.97 (br s, 2H), 6.88 (dd, J=9.0, 2.0 Hz, 1H) 6.93-6.95 (m, 1H), 7.48-7.53 (m, 1H), 7.55-7.61 (m, 2H), 7.63 (dd, J=9.0, 0.6 Hz, 1H), 7.82-7.87 (m, 2H).

(Example 17-c) (6-Amino-2-phenyl-2H-indazol-3-yl) (pyrrolidin-1-yl) methanone

To 6-amino-2-phenyl-2H-indazole-3-carbonitrile (136 mg, 0.58 mmol) obtained in (Example 17-b) was added a 5 N aqueous NaOH solution (10 mL). The mixture was stirred at 100° C. for 13.5 h. After cooling of the reaction solution to room temperature, 2N HCl solution (25 mL) and water (10 mL) were added thereto, followed by partition operation using ethyl acetate. The organic phase was washed with brine, then dried over magnesium sulfate, and filtered. Then, the solvent was distilled off under reduced pressure to give 6-amino-2-phenyl-2H-indazole-3-carboxylic acid (164 mg, <100%) as a crude product.

The obtained crude product (85 mg, <0.336 mmol), pyrrolidine (0.066 mL, 0.806 mmol), 1-ethyl-3-(3-dimethylaminopropyl)carbodiimide hydrochloride (77 mg, 0.403 mmol), 3H-1,2,3-triazolo[4,5-b]pyridin-3-ol (55 mg, 0.402 mmol), and triethylamine (0.168 mL, 1.20 mmol) were dissolved in DMF (2 mL) and stirred at room temperature for 10 h. The reaction solution was poured into water (10 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (silica gel, ethyl acetate:hexane=0:100 to 100:0) to give the title compound (30 mg, two steps 34%) as a solid.

$^1$H NMR (CDCl$_3$) δ (ppm): 1.65-1.73 (m, 2H), 1.84 (quin, J=6.9 Hz, 2H), 2.92-2.99 (m, 2H) 3.62 (t, J=7.0 Hz, 2H), 3.88 (s, 2H), 6.69 (dd, J=9.0, 2.0 Hz, 1H), 6.80-6.87 (m, 1H), 7.35-7.54 (m, 4H), 7.64-7.72 (m, 2H).

(Example 17-d) N-[2-Phenyl-3-(pyrrolidine-1-carbonyl)-2H-indazol-6-yl]-N'-[(pyridin-4-yl)methyl]urea (6-Amino-2-phenyl-2H-indazol-3-yl) (pyrrolidin-1-yl)methanone (30 mg, 0.097 mmol) obtained in (Example 17-c), triethylamine (0.041 mL, 0.29 mmol), and (4-nitrophenyl)N-(4-pyridylmethyl)carbamate (32 mg, 0.11 mmol) obtained in (Reference Example 1) were dissolved in 1,4-dioxane (2 mL) and then stirred at 80° C. for 3 h. The reaction solution was poured into water (10 mL), followed by partition operation using dichloromethane. The organic phase was washed with brine, then dried over magnesium sulfate, and filtered. Then, the solvent was distilled off under reduced pressure to give the crude title compound. The crude product was purified by silica gel column chromatography (NH silica gel+silica gel, methanol:dichloromethane=0:100 to 10:90) to give the title compound (28 mg, 64%) as a solid.

$^1$H NMR (CDCl$_3$) δ (ppm): 1.68-1.77 (m, 2H), 1.82-1.92 (m, 2H), 2.98 (t, J=7.0 Hz, 2H), 3.61 (t, J=7.0 Hz, 2H), 4.34-4.41 (m, 2H), 5.65-5.81 (m, 1H), 6.96-7.04 (m, 1H), 7.14-7.20 (m, 3H), 7.39-7.53 (m, 4H), 7.56-7.59 (m, 1H), 7.62-7.68 (m, 2H), 8.47-8.53 (m, 2H).
LCMS (ES): m/z 441 [M+H]$^+$.

Example 18

N,N-Diethyl-2-phenyl-6-({[(pyridin-4-yl)methyl]carbamoyl}amino)-2H-indazole-3-carboxamide

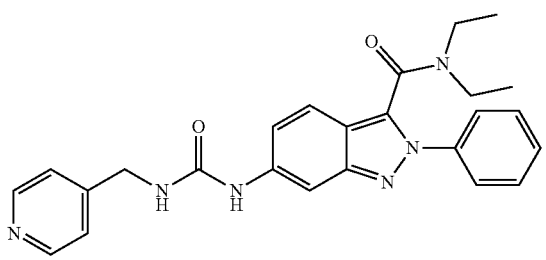 [SMILES: CCN(CC)C(=O)c1c2ccc(NC(=O)NCc3ccncc3)cc2nn1-c1ccccc1]

(Example 18-a) 6-Amino-N,N-diethyl-2-phenyl-2H-indazole-3-carboxamide

6-Amino-2-phenyl-2H-indazole-3-carboxylic acid (164 mg, <100%) was obtained as a crude product from 6-amino-2-phenyl-2H-indazole-3-carbonitrile (136 mg, 0.581 mmol), and the title compound (62 mg, two steps 81%) was then obtained as a solid from the obtained crude product (70 mg, <0.276 mmol), in the same way as in Example 17-C $^1$H NMR (CDCl$_3$) δ (ppm): 0.81 (t, J=7.1 Hz, 3H), 1.15 (t, J=7.1 Hz, 3H), 2.95-3.06 (m, 2H), 3.26-3.95 (m, 4H) 6.62-6.70 (m, 1H), 6.80-6.85 (m, 1H), 7.34-7.50 (m, 4H), 7.66-7.73 (m, 2H).

(Example 18-b) N,N-Diethyl-2-phenyl-6-({[(pyridin-4-yl)methyl]carbamoyl}amino)-2H-indazole-3-carboxamide The title compound (24 mg, 26%) was obtained as a solid from 6-amino-N,N-diethyl-2-phenyl-2H-indazole-3-carboxamide (62 mg, 0.201 mmol) in the same way as in (Example 17-d).

$^1$H NMR (CDCl$_3$) δ (ppm): 0.83 (t, J=7.1 Hz, 3H), 1.19 (t, J=6.8 Hz, 3H), 2.93-3.09 (m, 2H), 3.51-3.82 (m, 2H), 4.30 (d, J=5.9 Hz, 2H), 5.92-6.05 (m, 1H), 6.92-7.01 (m, 1H), 7.12 (d, J=5.9 Hz, 2H), 7.31-7.56 (m, 5H), 7.59-7.71 (m, 3H), 8.45 (d, J=5.9 Hz, 2H).
LCMS (ES): m/z 443 [M+H]$^+$.

Example 19

N-(3-Phenyl-5-propanoyl-2,3,4,5-tetrahydro-1,5-benzoxazepin-8-yl)-N'-[(pyridin-4-yl)methyl]urea

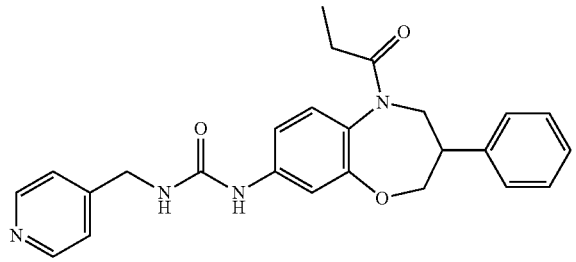 [SMILES: CCC(=O)N1CC(c2ccccc2)COc2cc(NC(=O)NCc3ccncc3)ccc21]

(Example 19-a) [3-(5-Bromo-2-nitrophenoxy)-2-phenylpropoxy] (tert-butyl)diphenylsilane 3-{[tert-Butyl(diphenyl)silyl]oxy}-2-phenylpropan-1-ol (1.07 g, 2.25 mmol) prepared by the manufacturing method described in Tetrahedron: Asymmetry 1995, 6, 1345-1356 and 5-bromo-2-nitrophenol (600 mg, 2.75 mmol) were dissolved in THF (27 mL) and then cooled to 0° C. Triphenylphosphine (1.44 g, 5.50 mmol) and bis(2-methoxyethyl)azodicarboxylate (1.29 g, 5.50 mmol) were added to the reaction solution. Then, the mixture was stirred at room temperature for 5.5 h. Diethyl ether (30 mL) was added to the reaction solution. The organic phase was washed with water and brine, then dried over magnesium sulfate, and filtered. Then, the solvent was distilled off under reduced pressure to give the crude title compound. The crude product was purified by silica gel column chromatography (silica gel, ethyl acetate:hexane=0:100 to 10:90) to give the title compound (1.16 g, 71%) as a solid.

¹H NMR (CDCl₃) δ (ppm): 1.02 (s, 9H), 3.23-3.36 (m, 1H), 3.99-4.21 (m, 2H), 4.33-4.47 (m, 2H), 7.10-7.21 (m, 2H), 7.22-7.34 (m, 9H), 7.34-7.42 (m, 2H), 7.50-7.61 (m, 4H), 7.76 (d, J=8.80 Hz, 1H).

(Example 19-b) 4-Bromo-2-(3-{[tert-butyl(diphenyl)silyl]oxy}-2-phenylpropoxy)aniline The title compound (852 mg, 77%) was obtained as an oil from [3-(5-bromo-2-nitrophenoxy)-2-phenylpropoxy] (tert-butyl)diphenylsilane (1.16 g, 1.96 mmol) obtained in (Example 19-a) in the same way as in (Example 17-b).
¹H NMR (CDCl₃) δ (ppm): 1.03 (s, 9H), 3.32 (quin, J=6.5 Hz, 1H). 3.50 (br s, 2H), 3.92-4.04 (m, 2H), 4.19 (dd, J=9.2, 6.5 Hz, 1H), 4.40 (dd, J=9.2, 6.5 Hz, 1H), 6.42-6.64 (m, 1H), 6.88 (d, J=8.8 Hz, 1H), 6.89 (s, 1H). 7.18-7.43 (m, 11H), 7.52-7.61 (m, 4H).

(Example 19-c) N-[4-Bromo-2-(3-hydroxy-2-phenylpropoxy)phenyl]-4-nitrobenzene-1-sulfonamide 4-Bromo-2-(3-{[tert-butyl(diphenyl)silyl]oxy}-2-phenylpropoxy)aniline (852 mg, 1.52 mmol) obtained in (Example 19-b) was dissolved in dichloromethane (5.6 mL) and then cooled to 0° C. Pyridine (0.14 mL, 1.82 mmol) and 4-nitrobenzenesulfonyl chloride (339 mg, 1.52 mmol) were added to the reaction solution. The mixture was stirred at room temperature for 3.5 h. The reaction solution was poured into 1 N hydrochloric acid (5 mL), followed by partition operation using ethyl acetate. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 25:75) to give N-[4-bromo-2-(3-{[tert-butyl(diphenyl)silyl]oxy}-2-phenylpropoxy)phenyl]-4-nitrobenzene-1-sulfonamide (1.13 g, <100%) as a crude product.

The obtained crude product (1.13 g, <1.52 mmol) was dissolved in THF (15 mL) and then stirred at room temperature. To the solution was added tetrabutylammonium fluoride (1 mol/L in tetrahydrofuran) (1.67 mL, 1.67 mmol). After stirring at room temperature for 12 h, the reaction solution was poured into water (15 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (silica gel, ethyl acetate:hexane=0:100 to 50:50) to give the title compound (535 mg, two steps 69%) as an oil.
¹H NMR (CDCl₃) δ (ppm): 1.75 (br t, J=5.0 Hz, 1H), 3.22 (quin, J=6.7 Hz, 1H), 3.85-3.99 (m, 2H), 4.05-4.23 (m, 2H), 6.95 (d, J=2.2 Hz, 1H), 7.07 (dd, J=8.5, 2.1 Hz, 1H), 7.20-7.26 (m, 2H), 7.33-7.46 (m, 4H), 7.67-7.74 (m, 2H), 8.12-8.17 (m, 2H).

(Example 19-d) 8-Bromo-5-(4-nitrobenzene-1-sulfonyl)-3-phenyl-2,3,4,5-tetrahydro-1,5-benzoxazepine N-[4-Bromo-2-(3-hydroxy-2-phenylpropoxy)phenyl]-4-nitrobenzene-1-sulfonamide (535 mg, 1.05 mmol) obtained in (Example 19-c) was dissolved in THF (21 mL) and then cooled to 0° C. Triphenylphosphine (1.10 g, 4.21 mmol) and bis(2-methoxyethyl) azodicarboxylate (987 mg, 4.21 mmol) were added to the reaction solution. Then, the mixture was stirred at room temperature for 4 h. Diethyl ether (20 mL) was added to the reaction solution. The organic phase was washed with water and brine, then dried over magnesium sulfate, and filtered. Then, the solvent was distilled off under reduced pressure to give the crude title compound. The crude product was purified by silica gel column chromatography (silica gel, ethyl acetate:hexane=0:100 to 20:80) to give the title compound (479 mg, 97%) as a solid.
¹H NMR (CDCl₃) δ (ppm): 3.09-3.28 (m, 1H), 3.30-3.43 (m, 1H), 3.64 (br t, J=11.3 Hz, 1H) 4.20 (ddd, J=12.1, 3.7, 1.8 Hz, 1H), 4.58 (br dd, J=14.7, 2.2 Hz, 1H), 7.01-7.13 (m, 2H), 7.24 (d, J=2.2 Hz, 1H), 7.28-7.37 (m, 4H), 7.37-7.45 (m, 1H), 7.77-7.91 (m, 2H), 8.29-8.38 (m, 2H).

(Example 19-e) tert-Butyl (3-phenyl-2,3,4,5-tetrahydro-1,5-benzoxazepin-8-yl)carbamate 8-Bromo-5-(4-nitrobenzene-1-sulfonyl)-3-phenyl-2,3,4,5-tetrahydro-1,5-benzoxazepine (479 mg, 0.979 mmol) obtained in (Example 19-d), tert-butyl carbamate (137 mg, 1.17 mmol), 2-di-tert-butylphosphino-2',4',6'-triisopropylbiphenyl (166 mg, 0.392 mmol), tris(dibenzylideneacetone)dipalladium(0) (89 mg, 0.0979 mmol), and sodium tert-butoxide (216 mg, 2.25 mmol) were dissolved in toluene (20 mL) and then stirred at room temperature for 11 h. The reaction solution was poured into water (20 mL), followed by partition operation using dichloromethane. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 25:75) to give tert-butyl [5-(4-nitrobenzene-1-sulfonyl)-3-phenyl-2,3,4,5-tetrahydro-1,5-benzoxazepin-8-yl] carbamate (246 mg, <47%) as a crude product.

The obtained crude product (246 mg, <0.468 mmol) was dissolved in DMF (2 mL) and then stirred at room temperature. To the solution were added lithium hydroxide monohydrate (79 mg, 1.87 mmol) and thioglycolic acid (0.065 mL, 0.936 mmol). Then, the mixture was stirred at room temperature for 2 h. The reaction solution was poured into a saturated aqueous solution of ammonium chloride (5 mL), followed by partition operation using ethyl acetate. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 40:60) to give the title compound (140 mg, two steps 41%) as an oil.
LCMS (ES): m/z 341.2 [M+H]⁺.

(Example 19-f) tert-Butyl (3-phenyl-5-propanoyl-2,3,4,5-tetrahydro-1,5-benzoxazepin-8-yl)carbamate tert-Butyl (3-phenyl-2,3,4,5-tetrahydro-1,5-benzoxazepin-8-yl)carbamate (49 mg, 0.144 mmol) obtained in (Example 19-e) was dissolved in dichloromethane (2 mL) and then cooled to 0° C. Pyridine (0.046 mL, 0.576 mmol) and propionyl chloride (0.053 mL, 0.576 mmol) were added to the reaction solution. The mixture was stirred at room temperature for 19.5 h. The reaction solution was poured into 1 N hydrochloric acid (5 mL), followed by partition operation using ethyl acetate. The organic phase was washed with brine, then dried over magnesium sulfate, and filtered. Then, the solvent was distilled off under reduced pressure to give the title compound (56 mg, 98%) as an oil.
LCMS (ES): m/z 397.2 [M+H]⁺.

(Example 19-g) 1-(8-Amino-3-phenyl-3,4-dihydro-1,5-benzoxazepin-5(2H)-yl)propan-1-one tert-Butyl (3-phenyl-5-propanoyl-2,3,4,5-tetrahydro-1,5-benzoxazepin-8-yl)carbamate (59 mg, 0.141 mmol)

obtained in (Example 19-f) was dissolved in dichloromethane (1 mL) and then stirred at room temperature. To the solution was added trifluoroacetic acid (0.2 mL). The mixture was stirred at room temperature for 2.5 h. Then, the reaction solution was poured into a saturated aqueous solution of sodium bicarbonate (5 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (silica gel, ethyl acetate:hexane=0:100 to 30:70) to give the title compound (19 mg, 45%) as an oil.

$^1$H NMR (CDCl$_3$) δ (ppm) 1.06 (t, J=7.43 Hz, 3H), 1.99-2.14 (m, 1H), 2.20-2.35 (m, 1H), 2.86 (dd, J=13.2, 11.3 Hz, 1H), 3.46 (tt, J=11.3, 3.7 Hz, 1H), 3.70-3.78 (m, 1H), 3.80 (br s, 2H), 4.36-4.44 (m, 1H), 4.87 (ddd, J=13.2, 3.7, 1.5 Hz, 1H), 6.44 (dd, J=8.3, 2.6 Hz, 1H), 6.49 (d, J=2.5 Hz, 1H), 6.99 (d, J=8.4 Hz, 1H), 7.14-7.22 (m, 2H), 7.22-7.29 (m, 1H), 7.29-7.37 (m, 2H).

(Example 19-h)N-(3-Phenyl-5-propanoyl-2,3,4,5-tetrahydro-1,5-benzoxazepin-8-yl)-N'-[(pyridin-4-yl)methyl]urea The title compound (12 mg, 43%) was obtained as a solid from 1-(8-amino-3-phenyl-3,4-dihydro-1,5-benzoxazepin-5(2H)-yl)propan-1-one (19 mg, 0.0641 mmol) in the same way as in (Example 17-d).

$^1$H NMR (CDCl$_3$) δ (ppm): 1.04 (t, J=7.4 Hz, 3H), 1.98-2.10 (m, 1H), 2.21-2.33 (m, 1H), 2.86 (t, J=12.2 Hz, 1H), 3.39-3.50 (m, 1H), 3.66-3.78 (m, 1H), 4.37-4.45 (m, 3H), 4.84 (br dd, J=13.4, 2.3 Hz, 1H), 5.72-5.81 (m, 1H), 7.07-7.37 (m, 11H), 8.52 (br d, J=5.5 Hz, 2H).

LCMS (ES): m/z 431.2 [M+H]$^+$.

Example 20

4-Fluoro-N,N-dimethyl-2-phenyl-6-({[(pyridin-4-yl)methyl]carbamoyl}amino)pyrazolo[1,5-a]pyridine-3-carboxamide

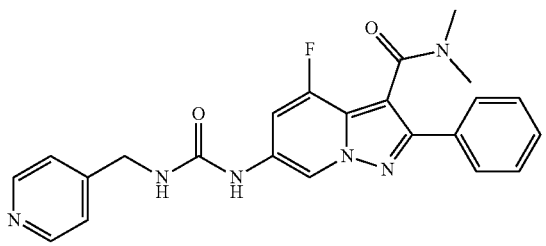 [SMILES: CN(C)C(=O)c1c(-c2ccccc2)nn2cc(NC(=O)NCc3ccncc3)cc(F)c12]

(Example 20-a) 1-Amino-3-bromo-5-fluoropyridin-1-ium 2,4,6-trimethylbenzene-1-sulfonate Ethyl O-mesitylsulfonylacetohydroxamate (1.11 g, 3.89 mmol) was dissolved in 1,4-dioxane (3 mL) and then cooled to 0° C. To the solution was added 70% perchloric acid (1.05 mL, 12.2 mmol). The mixture was stirred at 0° C. for 1 h. Water (5 mL) was added to the reaction solution. The precipitated solid was collected by filtration. The obtained solid was dissolved in dichloromethane (3 mL). This solution was added to a solution of 3-bromo-5-fluoropyridine (500 mg, 2.84 mmol) in dichloromethane (3 mL) in an ice bath. The reaction solution was stirred at 0° C. for 40 min. Then, diethyl ether (20 mL) was added thereto, and the mixture was stirred for 30 min. The precipitated solid was collected by filtration to give the title compound (953 mg, 86%) as a solid.

$^1$H NMR (DMSO-d$_6$) δ (ppm): 2.17 (s, 3H), 2.49 (s, 6H), 6.74 (s, 2H), 8.75-8.82 (m, 3H), 8.99-9.02 (m, 1H), 9.07-9.12 (m, 1H).

(Example 20-b) Methyl 6-[(tert-butoxycarbonyl)amino]-4-fluoro-2-phenylpyrazolo[1,5-a]pyridine-3-carboxylate 1-Amino-3-bromo-5-fluoropyridin-1-ium 2,4,6-trimethylbenzene-1-sulfonate (500 mg, 1.28 mmol) obtained in (Example 20-a) was suspended in DMF (3 mL). To the suspension were added potassium carbonate (264 mg, 1.92 mmol) and methyl phenylpropiolate (0.226 mL, 1.53 mmol). The mixture was stirred at room temperature for 92 h. The reaction solution was poured into water (10 mL), followed by partition operation using ethyl acetate. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 15:85) to give methyl 6-bromo-4-fluoro-2-phenylpyrazolo[1,5-a]pyridine-3-carboxylate (140 mg, <30%) as a crude product.

The obtained crude product (140 mg, <0.401 mmol), tert-butyl carbamate (56 mg, 0.481 mmol), 2-di-tert-butylphosphino-2',4',6'-triisopropylbiphenyl (68 mg, 0.160 mmol), tris(dibenzylideneacetone)dipalladium(0) (36 mg, 0.0401 mmol), and sodium tert-butoxide (88 mg, 0.922 mmol) were dissolved in toluene (10 mL) and stirred at room temperature for 24 h. The reaction solution was poured into water (10 mL), followed by partition operation using dichloromethane. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 20:80) to give the title compound (56 mg, two steps 11%) as a solid.

$^1$H NMR (CDCl$_3$) δ (ppm): 1.52 (s, 9H), 3.80 (s, 3H), 6.71-6.90 (m, 1H), 7.12 (br d, J=11.5 Hz, 1H), 7.40-7.49 (m, 3H), 7.66-7.75 (m, 2H), 8.82 (br s, 1H).

(Example 20-c) tert-Butyl [3-(dimethylcarbamoyl)-4-fluoro-2-phenylpyrazolo[1,5-a]pyridin-6-yl]carbamate Methyl 6-[(tert-butoxycarbonyl)amino]-4-fluoro-2-phenylpyrazolo[1,5-a]pyridine-3-carboxylate (56 mg, 0.145 mmol) obtained in (Example 20-b) was dissolved in methanol (1 mL) and THF (1 mL). To the solution was added a 5 N aqueous NaOH solution (1 mL). The mixture was stirred at room temperature for 4.5 h and at 50° C. for 2.5 h. After cooling of the reaction solution to room temperature, 2 N HCl (2.5 mL) and water (5 mL) were added thereto, followed by partition operation using dichloromethane. The organic phase was washed with brine, then dried over magnesium sulfate, and filtered. Then, the solvent was distilled off under reduced pressure to give 6-[(tert-butoxycarbonyl)amino]-4-fluoro-2-phenylpyrazolo[1,5-a]pyridine-3-carboxylic acid (34 mg, <63%) as a crude product.

The obtained crude product (34 mg, <0.0916 mmol), dimethylamine (2.0 M solution in tetrahydrofuran) (0.1 mL, 0.2 mmol), 1-ethyl-3-(3-dimethylaminopropyl)carbodiimide hydrochloride (21 mg, 0.110 mmol), 3H-1,2,3-triazolo [4,5-b]pyridin-3-ol (15 mg, 0.110 mmol), and triethylamine (0.03 mL, 0.220 mmol) were dissolved in DMF (2 mL) and stirred at room temperature for 20 h. The reaction solution was poured into water (10 mL), followed by partition operation using ethyl acetate. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 60:40) to give the title compound (14 mg, two steps 24%) as a solid.

$^1$H NMR (CDCl$_3$) δ (ppm): 1.50 (s, 9H), 2.76 (s, 3H), 3.16 (s, 3H), 6.88 (dd, J=11.3, 1.0 Hz, 1H), 6.96 (br s, 1H), 7.33-7.49 (m, 3H), 7.68-7.95 (m, 2H), 8.65 (br s, 1H).

(Example 20-d) 4-Fluoro-N,N-dimethyl-2-phenyl-6-({[(pyridin-4-yl)methyl]carbamoyl}amino)pyrazolo [1,5-a]pyridine-3-carboxamide 6-Amino-4-fluoro-N,N-dimethyl-2-phenylpyrazolo [1,5-a]pyridine-3-carboxamide (12 mg, <100%) was obtained as a crude product from tert-butyl [3-(dimethylcarbamoyl)-4-fluoro-2-phenylpyrazolo[1,5-a]pyridin-6-yl]carbamate (14 mg, 0.0351 mmol) obtained in (Example 20-c) in the same way as in (Example 19-g).

The title compound (8 mg, two steps 52%) was obtained as a solid from the obtained crude product (12 mg, <0.0402 mmol) in the same way as in (Example 17-d).

$^1$H NMR (CDCl$_3$) δ (ppm): 2.92 (s, 3H), 3.17 (s, 3H), 4.11 (dd, J=17.0, 5.8 Hz, 1H), 4.21 (dd, J=17.0, 5.8 Hz, 1H), 5.79 (t, J=5.8 Hz, 1H), 6.62 (d, J=6.6 Hz, 1H), 7.12 (d, J=5.9 Hz, 2H), 7.39-7.48 (m, 3H), 7.74-7.79 (m, 2H), 8.06 (s, 1H), 8.42 (s, 1H), 8.48-8.53 (m, 2H).

LCMS (ES): m/z 433.1 [M+H]$^+$, 865.4 [2M+H]$^+$.

Example 21

N-(3-Cyano-2-phenyl-2H-indazol-6-yl)-N'-[(pyridin-4-yl)methyl]urea

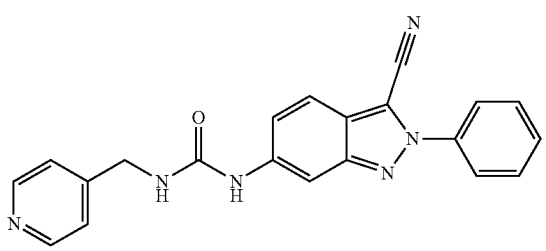 [SMILES: N#Cc1c2ccc(NC(=O)NCc3ccncc3)cc2nn1-c1ccccc1]

The title compound (26 mg, 71%) was obtained as a solid from 6-amino-2-phenyl-2H-indazole-3-carbonitrile (23 mg, 0.0982 mmol) obtained in (Example 17-b) in the same way as in (Example 17-d).

$^1$H NMR (DMSO-d$_6$) δ (ppm): 4.38 (d, J=6.0 Hz, 2H), 6.91 (br t, J=6.0 Hz, 1H), 7.27-7.38 (m, 3H), 7.59-7.73 (m, 3H) 7.82 (d, J=9.2 Hz, 1H), 7.86-7.95 (m, 2H), 8.18 (br d, J=4.3 Hz, 1H), 8.49-8.55 (m, 2H), 9.12 (s, 1H).

LCMS (ES): m/z 369.2 [M+H]$^+$.

Example 22

N-[3-(1-Methyl-1H-pyrazol-5-yl)-2-phenylpyrazolo [1,5-a]pyridin-6-yl]-N'-[(pyridin-4-yl)methyl]urea

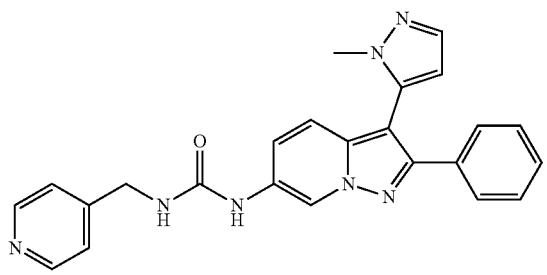 [SMILES: Cn1nccc1-c1c(-c2ccccc2)nn2cc(NC(=O)NCc3ccncc3)ccc12]

(Example 22-a) tert-Butyl (2-phenylpyrazolo[1,5-a] pyridin-6-yl)carbamate

6-Bromo-2-phenylpyrazolo[1,5-a]pyridine (400 mg, 1.46 mmol) obtained by the manufacturing method described in Bioorganic Med. Chem. Lett. 2017, 27, 4044-4050, tert-butyl carbamate (206 mg, 1.76 mmol), 2-di-tert-butylphosphino-2',4',6'-triisopropylbiphenyl (124 mg, 0.292 mmol), tris(dibenzylideneacetone)dipalladium(0) (67 mg, 0.0732 mmol), and sodium tert-butoxide (323 mg, 3.37 mmol) were dissolved in toluene (20 mL) and then stirred at room temperature for 41 h. The reaction solution was filtered through celite. Then, the filtrate was concentrated under reduced pressure to give the crude title compound. The residue was purified by silica gel column chromatography (silica gel, ethyl acetate:hexane=0:100 to 25:75) to give the title compound (308 mg, 68%) as a solid.

$^1$H NMR (CDCl$_3$) δ (ppm): 1.52 (s, 9H), 6.48-6.62 (m, 1H), 6.73 (s, 1H), 6.97 (dd, J=9.6, 1.2 Hz, 1H), 7.30-7.50 (m, 4H), 7.93 (d, J=7.2 Hz, 2H), 8.84 (br s, 1H).

(Example 22-b) tert-Butyl (3-bromo-2-phenylpyrazolo[1,5-a]pyridin-6-yl)carbamate tert-Butyl (2-phenylpyrazolo[1,5-a]pyridin-6-yl)carbamate (308 mg, 0.996 mmol) obtained in (Example 22-a) was dissolved in DMF (5 mL). To the solution was added N-bromosuccinimide (212 mg, 1.19 mmol). The mixture was stirred at room temperature for 21 h. The reaction solution was poured into a mixed solution of water (10 mL) and brine (5 mL), followed by partition operation using ethyl acetate. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 20:80) to give the title compound (204 mg, 52%) as an oil.

$^1$H NMR (CDCl$_3$) δ (ppm): 1.54 (s, 9H), 6.42 (br s, 1H), 7.04 (dd, J=9.4, 1.8 Hz, 1H), 7.35-7.52 (m, 4H), 7.99-8.07 (m, 2H), 8.93 (br s, 1H).

(Example 22-c)N-[3-(1-Methyl-1H-pyrazol-5-yl)-2-phenylpyrazolo[1,5-a]pyridin-6-yl]-N'-[(pyridin-4-yl)methyl]urea tert-Butyl (3-bromo-2-phenylpyrazolo[1,5-a]pyridin-6-yl)carbamate (45 mg, 0.116 mmol) obtained in (Example 22-b), 1-methyl-1H-pyrazole-5-boronic acid pinacol ester (31 mg, 0.151 mmol), tetrakis(triphenylphosphine)palladium(0) (13 mg, 0.0116 mmol), and potassium phosphate (74 mg, 0.348 mmol) were dissolved in DMF (2 mL) and then stirred at 90° C. for 7.5 h. The reaction solution was poured into a mixed solution of water (5 mL) and brine (2 mL), followed by partition operation using ethyl acetate. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 50:50) to give tert-butyl [3-(1-methyl-1H-pyrazol-5-yl)-2-phenylpyrazolo[1,5-a]pyridin-6-yl]carbamate (8 mg, <17%) as a crude product.

3-(1-Methyl-1H-pyrazol-5-yl)-2-phenylpyrazolo[1,5-a]pyridin-6-amine (6 mg, <100%) was obtained as a crude product from the obtained crude product (8 mg, <0.0205 mmol) in the same way as in (Example 19-g).

The title compound (4 mg, three steps 8%) was obtained as a solid from the obtained crude product (6 mg, <0.0207 mmol) in the same way as in (Example 17-d).

$^1$H NMR (DMSO-d$_6$) δ (ppm): 3.31 (s, 3H), 4.33 (d, J=5.6 Hz, 2H), 6.38 (d, J=1.8 Hz, 1H), 6.93 (t, J=5.6 Hz, 1H), 7.18 (dd, J=9.2, 1.8 Hz, 1H), 7.26-7.37 (m, 6H), 7.40-7.46 (m, 2H), 7.55 (d, J=1.8 Hz, 1H), 8.48 (d, J=4.8 Hz, 2H), 8.95 (s, 1H), 9.09 (s, 1H).

LCMS (ES): m/z 424.2 [M+H]$^+$.

Example 23

N,N-Dimethyl-2-phenyl-6-({[(pyridin-4-yl)methyl]carbamoyl}amino)pyrazolo[1,5-a]pyridine-3-carboxamide

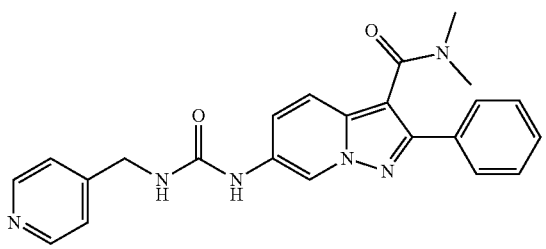 [SMILES: CN(C)C(=O)c1c(-c2ccccc2)nn2cc(NC(=O)NCc3ccncc3)ccc12]

(Example 23-a) Methyl 6-[(tert-butoxycarbonyl)amino]-2-phenylpyrazolo[1,5-a]pyridine-3-carboxylate Methyl 6-bromo-2-phenylpyrazolo[1,5-a]pyridine-3-carboxylate (572 mg, 1.73 mmol) obtained by the manufacturing method described in Bioorganic Med. Chem. Lett. 2017, 27, 4044-4050, tert-butyl carbamate (242 mg, 2.07 mmol), 2-di-tert-butylphosphino-2',4',6'-triisopropylbiphenyl (293 mg, 0.6910 mmol), tris(dibenzylideneacetone)dipalladium (0) (158 mg, 0.173 mmol), and sodium tert-Butoxide (381 mg, 3.97 mmol) were dissolved in toluene (10 mL) and stirred at room temperature for 23 h. The reaction solution was filtered through celite. Then, the filtrate was concentrated under reduced pressure to give the crude title compound. The residue was purified by silica gel column chromatography (silica gel, ethyl acetate:hexane=0:100 to 30:70) to give the title compound (541 mg, 85%) as a solid.

$^1$H NMR (CDCl$_3$) δ (ppm): 1.53 (s, 9H), 3.83 (s, 3H), 6.56-6.77 (m, 1H), 7.23 (dd, J=9.4, 2.0 Hz, 1H), 7.38-7.50 (m, 3H), 7.73-7.83 (m, 2H), 8.09 (dt, J=9.5, 0.9 Hz, 1H), 9.03 (br s, 1H).

(Example 23-b) 6-[(tert-Butoxycarbonyl)amino]-2-phenylpyrazolo[1,5-a]pyridine-3-carboxylic acid Methyl 6-[(tert-butoxycarbonyl)amino]-2-phenylpyrazolo[1,5-a]pyridine-3-carboxylate (346 mg, 0.942 mmol) obtained in (Example 23-a) was dissolved in methanol (2 mL) and THF (2 mL). To the solution was added a 5 N aqueous NaOH solution (0.904 mL, 4.52 mmol). The mixture was stirred at 50° C. for 18 h. After cooling of the reaction solution to room temperature, 1 N aqueous HCl solution (4.52 mL, 4.52 mmol) and water (10 mL) were added thereto, followed by partition operation using dichloromethane. The organic phase was washed with brine, then dried over magnesium sulfate, and filtered. Then, the solvent was distilled off under reduced pressure to give the title compound (233 mg, 63%) as a solid.

$^1$H NMR (DMSO-d$_6$) δ (ppm): 1.51 (s, 9H) 7.41-7.47 (m, 3H), 7.56 (dd, J=9.6, 2.0 Hz, 1H), 7.72-7.79 (m, 2H), 8.06 (dd, J=9.6, 0.7 Hz, 1H), 9.01 (br s, 1H), 9.78 (br s, 1H), 12.34 (br s, 1H).

(Example 23-c) tert-Butyl [3-(dimethylcarbamoyl)-2-phenylpyrazolo[1,5-a]pyridin-6-yl]carbamate 6-[(tert-Butoxycarbonyl)amino]-2-phenylpyrazolo[1,5-a]pyridine-3-carboxylic acid (50 mg, 0.141 mmol) obtained in (Example 23-b), dimethylamine (2.0 M solution in tetrahydrofuran) (0.084 mL, 0.170 mmol), 1-ethyl-3-(3-dimethylaminopropyl)carbodiimide hydrochloride (32 mg, 0.170 mmol), 3H-1,2,3-triazolo[4,5-b]pyridin-3-ol (23 mg, 0.170 mmol), and triethylamine (0.047 mL, 0.340 mmol) were dissolved in DMF (2 mL) and stirred at room temperature for 20 h. The reaction solution was poured into water (10 mL), followed by partition operation using ethyl acetate. The organic phase was washed with brine, then dried over magnesium sulfate, and filtered. Then, the solvent was distilled off under reduced pressure. The residue was purified by silica gel column chromatography (silica gel, ethyl acetate:hexane=0:100 to 80:20) to give the title compound (44 mg, 82%) as an oil.

$^1$H NMR (CDCl$_3$) δ (ppm): 1.52 (s, 9H), 2.61 (br s, 3H), 3.10 (br s, 3H), 6.75-6.94 (m, 1H), 7.05 (dd, J=9.4, 1.8 Hz, 1H), 7.34-7.46 (m, 3H), 7.47-7.57 (m, 1H), 7.69-7.80 (m, 2H), 8.89 (br s, 1H).

(Example 23-d) N,N-Dimethyl-2-phenyl-6-({[(pyridin-4-yl)methyl]carbamoyl}amino)pyrazolo[1,5-a]pyridine-3-carboxamide The deprotected amino compound (32 mg, <100%) was obtained as a crude product from tert-butyl [3-(dimethylcarbamoyl)-2-phenylpyrazolo[1,5-a]pyridin-6-yl]carbamate (44 mg, 0.116 mmol) obtained in (Example 23-d) in the same way as in (Example 19-g).

The title compound (25 mg, two steps 52%) was obtained as a solid from the obtained crude product (32 mg, <0.116 mmol) in the same way as in (Example 17-d).

$^1$H NMR (DMSO-d$_6$) δ (ppm): 2.69 (br s, 3H), 3.02 (br s, 3H), 4.37 (d, J=6.1 Hz, 2H), 6.97 (br t, J=6.1 Hz, 1H), 7.25 (dd, J=9.5, 1.9 Hz, 1H), 7.30-7.33 (m, 2H), 7.37-7.53 (m, 4H), 7.68-7.73 (m, 2H), 8.50-8.53 (m, 2H), 8.97 (br s, 1H), 9.08-9.10 (m, 1H).

LCMS (ES): m/z 415.2 [M+H]$^+$, 829.4 [2M+H]$^+$.

Example 24

N-(3-Cyano-2-phenylpyrazolo[1,5-a]pyridin-6-yl)-N'-[(pyridin-4-yl)methyl]urea

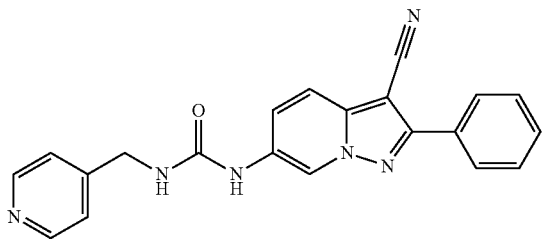 [SMILES: N#Cc1c(-c2ccccc2)nn2cc(NC(=O)NCc3ccncc3)ccc12]

(Example 24-a) tert-Butyl (3-cyano-2-phenylpyrazolo[1,5-a]pyridin-6-yl)carbamate tert-Butyl (3-bromo-2-phenylpyrazolo[1,5-a]pyridin-6-yl)carbamate (76 mg, 0.196 mmol) obtained in (Example 22-b), zinc cyanide (48 mg, 0.411 mmol), and tetrakis(triphenylphosphine)palladium(0) (22 mg, 0.0196 mmol) were dissolved in DMF (2 mL) and then heated at 100° C. for 6 h. Water (10 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 20:80) to give the title compound (38 mg, 58%) as a solid.

$^1$H NMR (CDCl$_3$) δ (ppm): 1.54 (s, 9H), 6.55-6.67 (m, 1H), 7.23 (dd, J=9.4, 2.0 Hz, 1H), 7.39-7.55 (m, 3H), 7.64 (dd, J=9.4, 0.8 Hz, 1H), 8.06-8.20 (m, 2H), 9.14 (br s, 1H).

(Example 24-b) N-(3-Cyano-2-phenylpyrazolo[1,5-a]pyridin-6-yl)-N'-[(pyridin-4-yl)methyl]urea The deprotcted amino compound (27 mg, <100%) was obtained as a crude product from tert-butyl (3-cyano-2-phenylpyrazolo[1,5-a]pyridin-6-yl)carbamate (38 mg, 0.114 mmol) in the same way as in (Example 19-g).

The title compound (10 mg, two steps 24%) was obtained as a solid from the obtained crude product (27 mg, <0.119 mmol) in the same way as in (Example 17-d).

$^1$H NMR (DMSO-d$_6$) δ (ppm): 4.37 (d, J=6.0 Hz, 2H), 7.08 (t, J=6.0 Hz, 1H), 7.29-7.34 (m, 2H), 7.49-7.62 (m, 4H), 7.85 (d, J=9.4 Hz, 1H), 8.00-8.05 (m, 2H), 8.50-8.54 (m, 2H), 9.21 (s, 1H), 9.24-9.29 (m, 1H).

LCMS (ES): m/z 369.2 [M+H]$^+$.

Example 25

N-(3-Methyl-2-phenylpyrazolo[1,5-a]pyridin-6-yl)-N'-[(pyridin-4-yl)methyl]urea

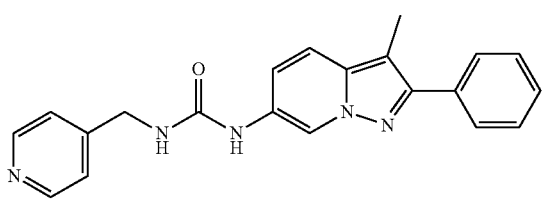 [SMILES: Cc1c(-c2ccccc2)nn2cc(NC(=O)NCc3ccncc3)ccc12]

(Example 25-a) 6-Bromo-2-phenylpyrazolo[1,5-a]pyridine-3-carbaldehyde

6-Bromo-2-phenylpyrazolo[1,5-a]pyridine (150 mg, 0.549 mmol) was suspended in acetonitrile (2 mL). To the suspension was added (chloromethylene)dimethylimium chloride (84 mg, 0.659 mmol). The mixture was stirred at room temperature for 1 h. A saturated aqueous solution of ammonium chloride (4 mL) was added thereto, and the mixture was stirred at room temperature for 1 h. A saturated aqueous solution of ammonium chloride (10 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 15:85) to give the title compound (96 mg, 58%) as a solid.

$^1$H NMR (CDCl$_3$) δ (ppm): 7.50-7.56 (m, 3H), 7.57-7.65 (m, 1H), 7.71-7.82 (m, 2H), 8.26-8.39 (m, 1H), 8.74 (s, 1H), 10.09 (s, 1H).

(Example 25-b) tert-Butyl (3-methyl-2-phenylpyrazolo[1,5-a]pyridin-6-yl)carbamate 6-Bromo-2-phenylpyrazolo[1,5-a]pyridine-3-carbaldehyde (96 mg, 0.319 mmol) obtained in (Example 25-a) was dissolved in TFA (3 mL). To the solution was added triethylsilane (1.02 mL, 6.38 mmol). The mixture was stirred at room temperature for 19 h. A saturated aqueous solution of sodium bicarbonate (10 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 10:90) to give 6-bromo-3-methyl-2-phenylpyrazolo[1,5-a]pyridine (98 mg, <100%) as a crude product.

The title compound (64 mg, two steps 62%) was obtained as an oil from the obtained crude product (98 mg, <0.341 mmol) in the same way as in (Example 23-a).

$^1$H NMR (CDCl$_3$) δ (ppm): 1.53 (s, 9H), 2.42 (s, 3H), 6.43 (br d, J=5.3 Hz, 1H), 6.97 (br d, J=9.4 Hz, 1H), 7.27-7.38 (m, 2H), 7.40-7.52 (m, 2H), 7.73-7.83 (m, 2H), 8.78 (br s, 1H).

(Example 25-c) N-(3-Methyl-2-phenylpyrazolo[1,5-a]pyridin-6-yl)-N'-[(pyridin-4-yl)methyl]urea The deprotected amino compound (45 mg, <100%) was obtained as a crude product from tert-butyl (3-methyl-2-phenylpyrazolo[1,5-a]pyridin-6-yl)carbamate (64 mg, 0.198 mmol) in the same way as in (Example 19-g).

The title compound (6 mg, two steps 8%) was obtained as a solid from 3-methyl-2-phenylpyrazolo[1,5-a]pyridin-6-amine (45 mg, <0.202 mmol) in the same way as in (Example 17-d).

$^1$H NMR (DMSO-d$_6$) δ (ppm): 2.40 (s, 3H), 4.36 (d, J=6.1 Hz, 2H), 6.87-6.93 (m, 1H), 7.06 (dd, J=9.6, 1.8 Hz, 1H), 7.29-7.33 (m, 2H), 7.36-7.41 (m, 1H), 7.44-7.51 (m, 2H), 7.60 (d, J=9.4 Hz, 1H), 7.75-7.80 (m, 2H), 8.50-8.53 (m, 2H), 8.81 (s, 1H), 8.96-8.99 (m, 1H).

LCMS (ES): m/z 358.2 [M+H]$^+$.

Example 26

N-(2-Phenyl-2H-indazol-6-yl)-N'-[(pyridin-4-yl)methyl]urea

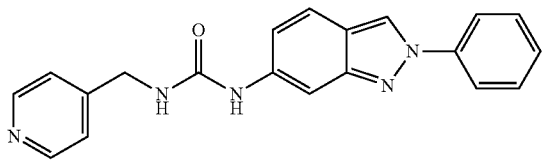 [SMILES: O=C(NCc1ccncc1)Nc1ccc2cn(-c3ccccc3)nc2c1]

The title compound (6 mg, 8%) was obtained as a solid from 3-methyl-2-phenylpyrazolo[1,5-a]pyridin-6-amine (45 mg, 0.202 mmol) obtained by the manufacturing method described in Taiho Pharmaceutical Co., Ltd. EP2762476, 2014, A1 in the same way as in (Example 17-d).

$^1$H NMR (DMSO-d$_6$) δ (ppm): 4.37 (d, J=6.1 Hz, 2H), 6.80 (t, J=6.1 Hz, 1H), 6.99 (dd, J=9.0, 2.0 Hz, 1H), 7.30-7.34 (m, 2H), 7.37-7.43 (m, 1H), 7.53-7.59 (m, 2H), 7.64 (dd, J=9.0, 0.7 Hz, 1H), 7.89-7.91 (m, 1H), 8.02-8.07 (m, 2H), 8.50-8.54 (m, 2H), 8.84 (s, 1H), 8.96 (d, J=1.0 Hz, 1H).

LCMS (ES): m/z 344.2 [M+H]$^+$.

Example 27

N-{2-[3-(Methanesulfonyl)phenyl]-2H-indazol-6-yl}-N'-[(pyridin-4-yl)methyl]urea

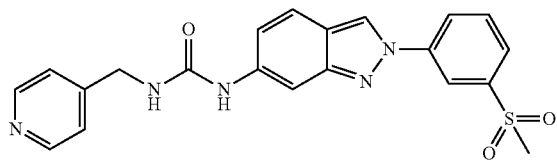 [SMILES: CS(=O)(=O)c1cccc(-n2cc3ccc(NC(=O)NCc4ccncc4)cc3n2)c1]

(Example 27-a) 6-Bromo-2-[3-(methanesulfonyl)phenyl]-2H-indazole

4-Bromo-2-nitrobenzaldehyde (300 mg, 1.30 mmol) and 3-(methylsulfonyl)aniline (246 mg, 1.43 mmol) were dissolved in 2-propanol (4 mL) and then stirred at 80° C. for 6 h. tri-n-Butylphosphine (0.975 mL, 3.92 mmol) was added to the reaction solution. The mixture was stirred at 80° C. for 6 h. A saturated aqueous solution of ammonium chloride (20 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 60:40) to give the title compound (226 mg, 49%) as a solid.

$^1$H NMR (CDCl$_3$) δ (ppm): 3.16 (s, 3H), 7.23 (dd, J=8.9, 1.7 Hz, 1H), 7.61 (dd, J=8.9, 0.7 Hz, 1H), 7.73-7.80 (m, 1H), 7.93-8.02 (m, 2H), 8.22-8.30 (m, 1H), 8.46-8.52 (m, 2H).

(Example 27-b) tert-Butyl {2-[3-(methanesulfonyl)phenyl]-2H-indazol-6-yl}carbamate The title compound (95 mg, 74%) was obtained as a solid from 6-bromo-2-[3-(methanesulfonyl)phenyl]-2H-indazole (116 mg, 0.330 mmol) obtained in (Example 27-a) in the same way as in (Example 23-a).

$^1$H NMR (CDCl$_3$) δ (ppm): 1.56 (s, 9H), 3.14 (s, 3H), 6.61 (s, 1H), 7.13 (br d, J=9.0 Hz, 1H), 7.63 (d, J=9.2 Hz, 1H), 7.74 (t, J=7.9 Hz, 1H), 7.79 (s, 1H), 7.92-7.96 (m, 1H), 8.22-8.29 (m, 1H), 8.42 (s, 1H), 8.44-8.46 (m, 1H).

(Example 27-c) 2-[3-(Methanesulfonyl)phenyl]-2H-indazol-6-amine

The title compound (68 mg, 97%) was obtained as a solid from tert-butyl {2-[3-(methanesulfonyl)phenyl]-2H-indazol-6-yl}carbamate (95 mg, 0.245 mmol) obtained in (Example 27-b) in the same way as in (Example 19-g).

$^1$H NMR (CDCl$_3$) δ (ppm): 3.14 (s, 3H), 3.90 (br s, 2H), 6.66 (dd, J=8.9, 1.7 Hz, 1H), 6.78-6.85 (m, 1H), 7.53 (dd, J=8.9, 0.7 Hz, 1H), 7.68-7.74 (m, 1H), 7.87-7.92 (m, 1H), 8.20 (ddd, J=8.2, 2.2, 1.0 Hz, 1H), 8.34 (s, 1H), 8.40-8.46 (m, 1H).

(Example 27-d) N-{2-[3-(Methanesulfonyl)phenyl]-2H-indazol-6-yl}-N'-[(pyridin-4-yl)methyl]urea The title compound (14 mg, 14%) was obtained as a solid from 2-[3-(methanesulfonyl)phenyl]-2H-indazol-6-amine (68 mg, 0.237 mmol) obtained in (Example 27-c) in the same way as in (Example 17-d).

$^1$H NMR (DMSO-d$_6$) δ (ppm): 3.34 (s, 3H), 4.37 (d, J=5.9 Hz, 2H), 6.79-6.86 (m, 1H), 7.03 (dd, J=9.1, 1.7 Hz, 1H), 7.29-7.36 (m, 2H), 7.67 (d, J=9.0 Hz, 1H), 7.80-7.88 (m, 1H), 7.89-7.96 (m, 2H), 8.38-8.45 (m, 1H), 8.49-8.54 (m, 2H), 8.54-8.58 (m, 1H), 8.91 (s, 1H), 9.15 (d, J=1.0 Hz, 1H).

LCMS (ES): m/z 422.1 [M+H]$^+$, 843.2 [2M+H]$^+$.

Example 28

N-(3-Methyl-2-phenyl-2H-indazol-6-yl)-N'-[(pyridin-4-yl)methyl]urea

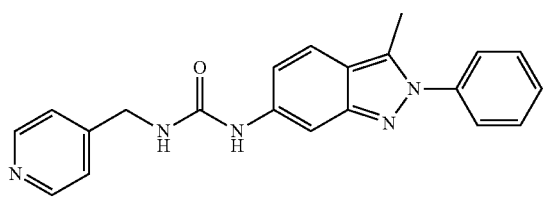 [SMILES: Cc1c2ccc(NC(=O)NCc3ccncc3)cc2nn1-c1ccccc1]

(Example 28-a) 6-Bromo-3-methyl-2-phenyl-2H-indazole

6-Bromo-2-phenyl-2H-indazole (100 mg, 0.366 mmol) obtained by the manufacturing method described in RSC Adv. 2014, 4, 34232-34236 was dissolved in THF (3 mL) and then cooled to −78° C. Lithium diisopropylamide (in n-hexane-tetrahydrofuran) (0.48 mL, 0.549 mmol) was added dropwise to the reaction solution. The mixture was stirred at 0° C. for 30 min. After cooling to −78° C. again, iodomethane (0.068 mL, 1.10 mmol) was added to the reaction solution. The mixture was stirred at room temperature for 1 h. A saturated aqueous solution of ammonium chloride (10 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 20:80) to give the title compound (58 mg, 55%) as a solid.

$^1$H NMR (CDCl$_3$) δ (ppm): 2.64 (s, 3H), 7.15 (dd, J=8.9, 1.7 Hz, 1H), 7.41-7.61 (m, 6H), 7.84-7.92 (m, 1H).

(Example 28-b) 3-Methyl-2-phenyl-2H-indazol-6-amine

6-Bromo-3-methyl-2-phenyl-2H-indazole (58 mg, 0.202 mmol) obtained in (Example 28-a), benzophenone imine (0.051 mL, 0.303 mmol), cesium carbonate (132 mg, 0.404 mmol), palladium(II) acetate (4 mg, 0.0202 mmol), and 4,5-bis(diphenylphosphino)-9,9-dimethylxanthene (17 mg, 0.0303 mmol) were dissolved in 1,4-dioxane (1 mL) and then heated at 100° C. for 10 h. After cooling of the reaction solution to room temperature, dichloromethane (5 mL) was added thereto, and the mixture was filtered. The filtrate was concentrated under reduced pressure. THF (0.5 mL) and 2N HCl solution (0.5 mL) were added to the residue. The mixture was stirred at room temperature for 6.5 h. A saturated aqueous solution of sodium bicarbonate (10 mL) was added to the reaction solution, followed by partition operation using dichloromethane. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 90:10) to give the title compound (10 mg, 22%) as a solid.

$^1$H NMR (CDCl$_3$) δ (ppm): 2.59 (s, 3H), 3.82 (br s, 2H), 6.60 (dd, J=8.8, 2.0 Hz, 1H), 6.79 (d, J=2.0 Hz, 1H), 7.38-7.46 (m, 2H), 7.47-7.59 (m, 4H).

(Example 28-c)N-(3-Methyl-2-phenyl-2H-indazol-6-yl)-N'-[(pyridin-4-yl)methyl]urea The title compound (14 mg, 87%) was obtained as a solid from 3-methyl-2-phenyl-2H-indazol-6-amine (10 mg, 0.0448 mmol) in the same way as in (Example 17-d).

$^1$H NMR (CDCl$_3$) δ (ppm): 2.59 (s, 3H), 4.37 (m, 2H), 5.94 (m, 1H), 7.06-7.16 (m, 3H), 7.44-7.55 (m, 8H), 8.45 (br s, 2H).

LCMS (ES): m/z 358.2 [M+H]$^+$.

Example 29

N-{2-[2-(2-Methoxyethoxy)phenyl]-2H-indazol-6-yl}-N'-[(pyridin-4-yl)methyl]urea

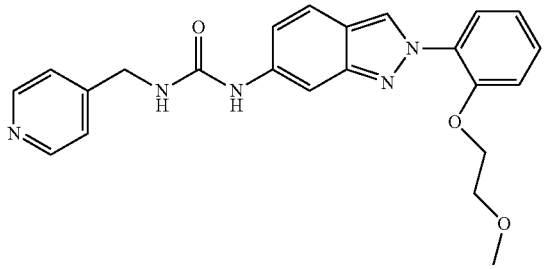 [SMILES: COCCOc1ccccc1-n1cc2ccc(NC(=O)NCc3ccncc3)cc2n1]

(Example 29-a) 6-Bromo-2-[2-(2-methoxyethoxy)phenyl]-2H-indazole

The title compound (313 mg, 62%) was obtained as a solid from 2-(2-methoxyethoxy)aniline (239 mg, 1.43 mmol) in the same way as in (Example 27-a).

$^1$H NMR (CDCl$_3$) δ (ppm): 3.40 (s, 3H), 3.68-3.75 (m, 2H), 4.18-4.26 (m, 2H), 7.09-7.20 (m, 3H), 7.35-7.41 (m, 1H), 7.60 (d, J=9.0 Hz, 1H), 7.93 (dd, J=7.9, 1.7 Hz, 1H), 7.95-7.97 (m, 1H), 8.70 (d, J=1.0 Hz,1H).

(Example 29-b) 2-[2-(2-Methoxyethoxy)phenyl]-2H-indazol-6-amine

The title compound (139 mg, 54%) was obtained as a solid from 6-bromo-2-[2-(2-methoxyethoxy)phenyl]-2H-indazole (313 mg, 0.901 mmol) obtained in (Example 29-a) in the same way as in (Example 28-b).

$^1$H NMR (CDCl$_3$) δ (ppm): 3.40 (s, 3H), 3.71 (td, J=4.7, 0.8 Hz, 2H), 3.82 (br s, 2H), 4.19 (td, J=4.7, 1.0 Hz, 2H), 6.60 (dd, J=8.8, 2.0 Hz, 1H), 6.85 (s, 1H), 7.05-7.16 (m, 2H), 7.27-7.34 (m, 1H), 7.53 (d, J=8.8 Hz, 1H), 7.94 (dd, J=8.0, 1.6 Hz, 1H), 8.56 (d, J=1.0 Hz, 1H).

(Example 29-c)N-{2-[2-(2-Methoxyethoxy)phenyl]-2H-indazol-6-yl}-N'-[(pyridin-4-yl)methyl]urea The title compound (120 mg, 75%) was obtained as a solid from 2-[2-(2-methoxyethoxy)phenyl]-2H-indazol-6-amine (109 mg, 0.384 mmol) obtained in (Example 29-b) in the same way as in (Example 17-d).

$^1$H NMR (CDCl$_3$) δ (ppm): 3.40 (s, 3H), 3.69-3.75 (m, 2H), 4.20-4.27 (m, 2H), 4.48 (d, J=6.1 Hz, 2H), 5.43 (br t, J=6.1 Hz, 1H), 6.57 (s, 1H), 7.04 (dd, J=8.9, 1.7 Hz, 1H), 7.09-7.17 (m, 2H), 7.19-7.25 (m, 2H), 7.34-7.40 (m, 1H), 7.61-7.64 (m, 1H), 7.71 (d, J=8.8 Hz, 1H), 7.92 (dd, J=8.0, 1.8 Hz, 1H), 8.53-8.56 (m, 2H), 8.70 (d, J=1.0 Hz, 1H).

LCMS (ES): m/z 418.2 [M+H]$^+$.

Example 30

N-[2-(3-Methoxyphenyl)-2H-indazol-6-yl]-N'-[(pyridin-4-yl)methyl]urea

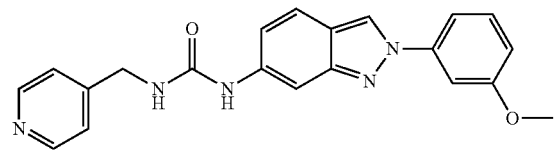 [SMILES: COc1cccc(-n2cc3ccc(NC(=O)NCc4ccncc4)cc3n2)c1]

(Example 30-a) 6-Bromo-2-(3-methoxyphenyl)-2H-indazole

The title compound (332 mg, 76%) was obtained as a solid from m-anisidine (0.161 mL, 1.43 mmol) in the same way as in (Example 27-a).

$^1$H NMR (CDCl$_3$) δ (ppm): 3.92 (s, 3H), 6.94-6.99 (m, 1H), 7.19 (dd, J=9.0, 1.6 Hz, 1H),7.40-7.44 (m, 2H), 7.47-7.51 (m, 1H), 7.59 (d, J=8.8 Hz, 1H), 7.93-8.00 (m, 1H), 8.39 (d, J=1.0 Hz, 1H).

(Example 30-b) 2-(3-Methoxyphenyl)-2H-indazol-6-amine

The title compound (170 mg, 65%) was obtained as an oil from 6-bromo-2-(3-methoxyphenyl)-2H-indazole (332 mg, 1.09 mmol) obtained in (Example 30-a) in the same way as in (Example 28-b).

$^1$H NMR (CDCl$_3$) δ (ppm): 3.79-3.85 (br s, 2H) 3.89 (s, 3H) 6.59-6.66 (m, 1H), 6.83-6.92 (m, 2H), 7.33-7.40 (m, 2H), 7.44-7.48 (m, 1H), 7.48-7.54 (m, 1H), 8.22-8.27 (m, 1H).

(Example 30-c) N-[2-(3-Methoxyphenyl)-2H-indazol-6-yl]-N'-[(pyridin-4-yl)methyl]urea The title compound (33 mg, 12%) was obtained as a solid from 2-(3-methoxyphenyl)-2H-indazol-6-amine (170 mg, 0.710 mmol) obtained in (Example 30-b) in the same way as in (Example 17-d).

$^1$H NMR (CDCl$_3$) δ (ppm): 3.86 (s, 3H), 4.37 (br d, J=5.9 Hz, 2H), 5.94 (br s, 1H), 6.89-6.94 (m, 1H), 7.07-7.15 (m, 3H), 7.31-7.44 (m, 3H), 7.50-7.63 (m, 3H), 8.28 (s, 1H), 8.45 (d, J=4.7 Hz, 2H).

LCMS (ES): m/z 374.2 [M+H]$^+$.

Example 31

N-(2-Phenylpyrazolo[1,5-a]pyrimidin-6-yl)-N'-[(pyridin-4-yl)methyl]urea

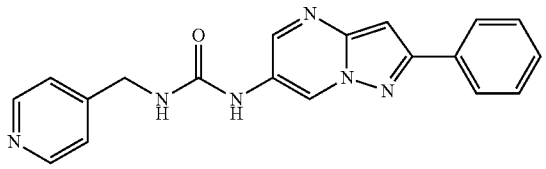 [SMILES: O=C(NCc1ccncc1)Nc1cnc2cc(-c3ccccc3)nn2c1]

The title compound (50 mg, 43%) was obtained as a solid from 2-phenylpyrazolo[1,5-a]pyrimidin-6-amine (72 mg, 0.342 mmol) obtained by the manufacturing method described in Bioorganic and Medicinal Chemistry Letters, 2012, vol. 22, 2, p. 1165-1168 in the same way as in (Example 17-d).

$^1$H NMR (DMSO-d$_6$) δ (ppm): 4.37 (d, J=6.1 Hz, 2H), 7.13 (t, J=6.1 Hz, 1H), 7.17 (d, J=0.8 Hz, 1H), 7.30-7.34 (m, 2H), 7.37-7.42 (m, 1H), 7.45-7.51 (m, 2H), 7.98-8.02 (m, 2H), 8.48 (d, J=2.4 Hz, 1H), 8.51-8.53 (m, 2H), 9.08 (br s, 1H), 9.25 (dd, J=2.4, 0.6 Hz, 1H).

LCMS (ES): m/z 345.2 [M+H]$^+$.

Example 32

N-(2-Phenyl-1H-indol-5-yl)-N'-[(pyridin-4-yl)methyl]urea

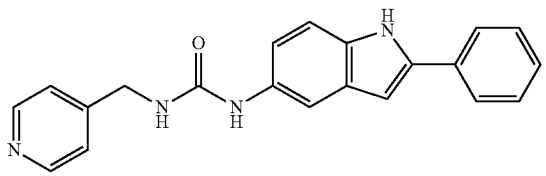 [SMILES: O=C(NCc1ccncc1)Nc1ccc2[nH]c(-c3ccccc3)cc2c1]

The title compound (157 mg, 95%) was obtained as a solid from 2-phenyl-1H-indol-5-amine (100 mg, 0.480 mmol) in the same way as in (Example 17-d).

$^1$H NMR (DMSO-d$_6$) δ (ppm): 4.34 (d, J=6.1 Hz, 2H), 6.61 (t, J=6.1 Hz, 1H), 6.81 (d, J=1.6 Hz, 1H), 7.05 (dd, J=8.6, 2.0 Hz, 1H), 7.25-7.33 (m, 4H), 7.44 (t, J=7.7 Hz, 2H), 7.64 (d, J=2.0 Hz, 1H), 7.83 (d, J=7.6 Hz, 2H), 8.43 (s, 1H), 8.51 (d, J=4.9 Hz, 2H), 11.35 (s, 1H).

LCMS (ES): m/z 343.2 [M+H]$^+$.

Example 33

N-[3-Cyano-2-(2-methoxypyridin-4-yl)-2H-indazol-6-yl]-N'-[(pyridin-4-yl)methyl]urea

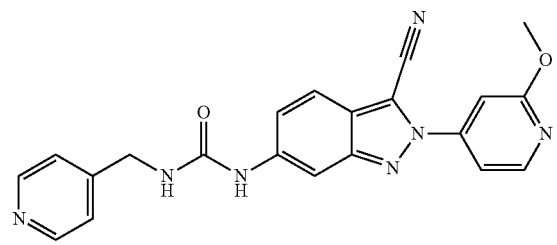 [SMILES: COc1cc(-n2nc3cc(NC(=O)NCc4ccncc4)ccc3c2C#N)ccn1]

(Example 33-a) 6-Bromo-2-(2-methoxypyridin-4-yl)-2H-indazole

4-Bromo-2-nitrobenzaldehyde (1.00 g, 4.35 mmol), 4-amino-2-methoxypyridine (593 mg, 4.78 mmol), and acetic acid (1.24 mL, 21.7 mmol) were dissolved in 1,2-dichloroethane (15 ml) and then stirred at 90° C. for 15 h. A saturated aqueous solution of ammonium chloride (30 mL) was added to the reaction solution, followed by partition operation using ethyl acetate. The organic phase was washed with brine, then dried over magnesium sulfate, and filtered. Then, the solvent was distilled off under reduced pressure to give the crude compound. The residue was purified by silica gel column chromatography (silica gel, ethyl acetate:hexane=0:100 to 25:75) to give 1-(4-bromo-2-nitrophenyl)-N-(2-methoxypyridin-4-yl)methanimine (468 mg, <32%) as a crude product.

The obtained crude product (468 mg, <1.39 mmol) and tri-n-butylphosphine (1.04 mL, 4.18 mmol) were dissolved in 2-propanol (10 mL) and then stirred at 80° C. for 5 h. A saturated aqueous solution of ammonium chloride (30 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 30:70) to give the title compound (329 mg, two steps 25%) as a solid.

$^1$H NMR (CDCl$_3$) δ (ppm): 4.02 (s, 3H), 7.20 (dd, J=9.0, 1.6 Hz, 1H), 7.25-7.29 (m, 1H), 7.46 (dd, J=5.7, 2.0 Hz, 1H), 7.57 (dd, J=9.0, 0.8 Hz, 1H), 7.95 (dt, J=1.6, 0.8 Hz, 1H), 8.29 (d, J=5.7 Hz, 1H), 8.45 (d, J=1.0 Hz, 1H).

(Example 33-b) 6-Bromo-3-chloro-2-(2-methoxypyridin-4-yl)-2H-indazole

6-Bromo-2-(2-methoxypyridin-4-yl)-2H-indazole (329 mg, 1.08 mmol) obtained in (Example 33-a) and N-Chlorosuccinimide (158 mg, 1.19 mmol) were dissolved in DMF (8 mL) and then stirred at 80° C. for 4 h. A saturated aqueous solution of ammonium chloride (30 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 20:80) to give the title compound (307 mg, 84%) as a solid.

$^1$H NMR (CDCl$_3$) δ (ppm): 4.03 (s, 3H), 7.19 (dd, J=1.9, 0.7 Hz, 1H), 7.21-7.26 (m, 1H), 7.35 (dd, J=5.7, 2.0 Hz, 1H), 7.50 (dd, J=9.0, 0.8 Hz, 1H), 7.90 (dd, J=1.5, 0.7 Hz, 1H), 8.35 (dd, J=5.7, 0.6 Hz, 1H).

(Example 33-c) tert-Butyl [3-chloro-2-(2-methoxy-pyridin-4-yl)-2H-indazol-6-yl]carbamate The title compound (152 mg, 45%) was obtained as a solid from 6-bromo-3-chloro-2-(2-methoxypyridin-4-yl)-2H-indazole (307 mg, 0.906 mmol) obtained in (Example 33-b) in the same way as in (Example 23-a).

$^1$H NMR (CDCl$_3$) δ (ppm): 1.55 (s, 9H), 4.02 (s, 3H), 6.70 (br d, J=3.3 Hz, 1H), 7.13 (dd, J=9.1, 1.3 Hz, 1H), 7.20 (d, J=1.8 Hz, 1H), 7.37 (dd, J=5.7, 1.8 Hz, 1H), 7.51 (dd, J=9.2, 0.8 Hz, 1H), 7.74 (s, 1H), 8.32 (dd, J=5.7, 0.6 Hz, 1H).

(Example 33-d) tert-Butyl [3-cyano-2-(2-methoxy-pyridin-4-yl)-2H-indazol-6-yl]carbamate tert-Butyl [3-chloro-2-(2-methoxypyridin-4-yl)-2H-indazol-6-yl]carbamate (97 mg, 0.259 mmol) obtained in (Example 33-c) and sodium cyanide (199 mg, 3.88 mmol) were dissolved in DMF (5 mL) and then stirred at 120° C. for 3 h. A saturated aqueous solution of ammonium chloride (20 mL) was added to the reaction solution, followed by partition operation using ethyl acetate. The organic phase was washed with brine, then dried over magnesium sulfate, and filtered. Then, the solvent was distilled off under reduced pressure to give the crude title compound. The residue was purified by silica gel column chromatography (silica gel, ethyl acetate:hexane=0:100 to 20:80) to give the title compound (67 mg, 71%) as a solid.

$^1$H NMR (CDCl$_3$) δ (ppm): 1.55 (s, 9H), 4.03 (s, 3H), 6.85 (s, 1H), 7.27 (dd, J=9.2, 1.8 Hz, 1H), 7.35 (d, J=2.0 Hz, 1H), 7.50-7.56 (m, 1H), 7.70 (dd, J=9.0, 0.8 Hz, 1H), 8.04 (s, 1H), 8.36 (dd, J=5.7, 0.6 Hz, 1H).

(Example 33-e)N-[3-Cyano-2-(2-methoxypyridin-4-yl)-2H-indazol-6-yl]-N'-[(pyridin-4-yl)methyl]urea 6-Amino-2-(2-methoxypyridin-4-yl)-2H-indazole-3-carbonitrile (53 mg, <100%) was obtained as a crude product from tert-butyl [3-cyano-2-(2-methoxypyridin-4-yl)-2H-indazol-6-yl]carbamate (67 mg, 0.183 mmol) obtained in (Example 33-d) in the same way as in (Example 19-g).

The title compound (37 mg, two steps 50%) was obtained as a solid from the obtained crude product (53 mg, <0.200 mmol) in the same way as in (Example 17-d).

$^1$H NMR (DMSO-d$_6$) δ (ppm): 3.97 (s, 3H), 4.37 (d, J=6.1 Hz, 2H), 6.94 (t, J=6.1 Hz, 1H), 7.27-7.37 (m, 3H), 7.41 (d, J=2.0 Hz, 1H), 7.59 (dd, J=5.7, 2.0 Hz, 1H),7.82 (d, J=9.0, 0.8 Hz, 1H), 8.16 (dd, J=1.6, 0.8 Hz, 1H), 8.45 (dd, J=5.5, 0.4 Hz, 1H), 8.48-8.55 (m, 2H), 9.18 (s, 1H).

LCMS (ES): m/z 400.2 [M+H]$^+$.

Example 34

N-(1-Acetyl-2-phenyl-2,3-dihydro-1H-indol-5-yl)-N'-[(pyridin-4-yl)methyl]urea

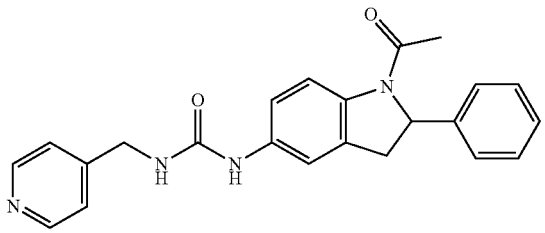 [SMILES: CC(=O)N1c2ccc(NC(=O)NCc3ccncc3)cc2CC1c1ccccc1]

(Example 34-a) 2-Bromo-5-nitro-1H-indole

To a mixture of 5-nitroindolin-2-one (15 g, 84 mmol) in 1,2-dichloroethane (300 mL) was added POBr$_3$ (23 g, 80 mmol). The mixture was heated to 90° C. and stirred for 0.5 h. Then the reaction was cooled just below 90° C. and imidazole (6.9 g, 101 mmol) was added in one portion. The mixture was stirred at 90° C. for 2 h. The reaction was quenched by ice water (200 mL) and then extracted with DCM (200 mL×3). The combined organic phase was washed with brine (300 mL×2), dried over anhydrous Na$_2$SO$_4$, filtered and concentrated in vacuo. The residue was purified by column chromatography (SiO$_2$, Petroleum ether/Ethyl acetate=10:1 to 5:1 to 3:1) to give the title compound (11 g, 46 mmol, 54% yield) as a solid.

$^1$H NMR (400 MHz, DMSO-d$_6$) δ (ppm) 6.86 (s, 1H), 7.49 (d, J=9.2 Hz, 1H), 7.91-8.07 (m, 1H), 8.50 (s, 1H), 12.63 (br s, 1H).

(Example 34-b) 5-Nitro-2-phenyl-1H-indole

To a solution of 2-bromo-5-nitro-1H-indole (6.0 g, mmol), phenylboronic acid (6.1 g, 50 mmol) and K$_2$CO$_3$ (6.9 g, 50 mmol) in dioxane (100 mL) and H$_2$O (10 mL) was added Pd(dppf)Cl$_2$ (1.8 g, 2.5 mmol). The mixture was degassed under vacuum and purged with nitrogen three times. The mixture was stirred at 100° C. for 12 h. The reaction mixture was concentrated under reduced pressure to remove dioxane. The residue was diluted with H$_2$O (100 mL) and extracted with EA(100 mL×3). The combined organic phase was dried over anhydrous Na$_2$SO$_4$, filtered and concentrated under reduced pressure to give a residue. The residue was purified by column chromatography (SiO$_2$, Petroleum ether/Ethyl acetate=10:1 to 3:1) to give the title compound (6.0 g, 14 mmol, 56% yield) as a solid.

$^1$H NMR (400 MHz, DMSO-d$_6$) δ (ppm) 7.20 (s, 1H), 7.32-7.34 (m, 1H), 7.40-7.42 (m, 1H), 7.53 (t, J=7.2 Hz, 2H), 7.76-7.78 (m, 1H), 7.76-7.80 (m, 1H), 7.91 (s, 1H), 8.55 (d, J=2.4 Hz, 1H), 12.30 (br s, 1H).

LCMS (ES): m/z 239 [M+H]$^+$.

(Example 34-c) tert-Butyl 5-nitro-2-phenyl-1H-indole-1-carboxylate

To a solution of 5-nitro-2-phenyl-1H-indole (500 mg, 2.1 mmol) and DMAP (26 mg, 0.21 mmol) in THF (10 mL) was added BoC$_2$O (0.92 g, 4.2 mmol). The mixture was stirred at 25° C. for 2 h. The reaction was concentrated in vacuo. The residue was purified by column chromatography (SiO₂, Petroleum ether/Ethyl acetate=0:1 to 10:1) to give the title compound (500 mg, 1.5 mmol, 70% yield) as a solid.

$^1$H NMR (400 MHz, CDCl₃) δ (ppm) 1.23 (s, 9H), 6.60 (s, 1H), 7.24-7.46 (m, 5H), 8.06-8.18 (m, 1H), 8.20-8.29 (m, 1H), 8.40 (d, J=2.4 Hz, 1H).

(Example 34-d) tert-Butyl 5-amino-2-phenyl-2,3-dihydro-1H-indole-1-carboxylate

To a solution of tert-butyl 5-nitro-2-phenyl-1H-indole-1-carboxylate (300 mg, 0.89 mmol) in toluene (10 mL) was added Pd/C (50 mg). The suspension was degassed under vacuum and purged with H₂ several times. The mixture was stirred under H₂ (50 psi) at 40° C. for 12 h. The reaction mixture was filtered and the filtrate was concentrated. The crude product was purified by column chromatography (SiO₂, Petroleum ether/Ethyl acetate=10:1 to 5:1) to give the title compound (160 mg, 0.52 mmol, 58% yield) as an oil.

$^1$H NMR (400 MHz, CDCl₃) δ (ppm) 1.19 (br s, 9H), 2.79 (br d, J=16.0 Hz, 1H), 3.42 (br s, 2H,), 3.40-3.59 (m, 1H), 5.23 (s, 1H), 6.44 (s, 1H), 6.50 (br d, J=8.0 Hz, 1H), 7.04-7.18 (m, 4H), 7.19-7.24 (m, 1H), 7.67 (br s, 1H).

LCMS (ES): m/z 311 [M+H]⁺.

(Example 34-e) tert-Butyl 2-phenyl-5-({[(pyridin-4-yl)methyl]carbamoyl}amino)-2,3-dihydro-1H-indole-1-carboxylate To a solution of tert-butyl 5-amino-2-phenyl-2,3-dihydro-1H-indole-1-carboxylate (1.0 g, 3.2 mmol) and (4-nitrophenyl)N-(4-pyridylmethyl)carbamate (1.1 g, 3.2 mmol) in dioxane (20 mL) was added DIPEA (1.7 g, 13 mmol). The mixture was stirred at 60° C. for 1 h. The reaction mixture was concentrated under reduced pressure to remove solvent. The residue was diluted with NaOH (2M, 50 mL) and then extracted with DCM (50 mL×3). The combined organic phase was dried over anhydrous Na₂SO₄, filtered and concentrated under reduced pressure to give a residue. The crude title product (2.0 g, crude) was obtained as an oil, which was used in the next step without further purification.

LCMS (ES): m/z 445 [M+H]⁺.

(Example 34-f) N-(2-Phenyl-2,3-dihydro-1H-indol-5-yl)-N'-[(pyridin-4-yl)methyl]urea hydrogen chloride salt (1/1)

To a solution of tert-butyl 2-phenyl-5-({[(pyridin-4-yl)methyl]carbamoyl}amino)-2,3-dihydro-1H-indole-1-carboxylate (1.5 g, 3.4 mmol) in EtOAc (10 mL) was added HCl/EtOAc (4 M, 10 mL). The mixture was stirred at 20° C. for 1 h. The reaction was concentrated under reduced pressure to give a product. The crude title product (1.1 g, crude) was obtained as a solid, which was used in the next step without further purification.

$^1$H NMR (400 MHz, DMSO-d₆) δ (ppm) 3.32-3.38 (m, 1H), 3.51-3.56 (m, 1H), 4.61 (br d, J=5.6 Hz, 2H), 5.23 (t, J=8.6 Hz, 1H), 7.16-7.23 (m, 1H), 7.32-7.37 (m, 1H), 7.41-7.51 (m, 4H), 7.53-7.58 (m, 2H), 7.61 (s, 1H), 7.96 (d, J=6.8 Hz, 2H), 8.87 (d, J=6.8 Hz, 2H), 9.75 (s, 1H).

LCMS (ES): m/z 345 [M+H]⁺ (as free).

(Example 34-g) N-(1-Acetyl-2-phenyl-2,3-dihydro-1H-indol-5-yl)-N'-[(pyridin-4-yl)methyl]urea To a solution of N-(2-phenyl-2,3-dihydro-1H-indol-5-yl)-N'-[(pyridin-4-yl)methyl]urea hydrogen chloride salt (1/1) (100 mg, 0.26 mmol) and DIPEA (135 mg, 1.1 mmol) and AcOH (32 mg, 0.53 mmol) in DMF (2 mL) was added HATU (200 mg, 0.53 mmol). The mixture was stirred at 20° C. for 1.5 h. The reaction was filtered and concentrated under reduced pressure to give a residue. The residue was purified by prep-HPLC (water (0.05% ammonia hydroxide v/v)-ACN) to give the title compound (62 mg, 0.16 mmol, 61% yield) as a solid.

$^1$H NMR (400 MHz, DMSO-d₆) δ (ppm) 1.91 (s, 3H), 2.74-2.87 (m, 1H), 3.62-3.84 (m, 1H), 4.31 (d, J=6.0 Hz, 2H), 5.61 (br d, J=9.6 Hz, 1H), 6.69 (br t, J=6.0 Hz, 1H), 7.12-7.42 (m, 9H), 8.00 (d, J=8.8 Hz, 1H), 8.42-8.52 (m, 2H), 8.65 (s, 1H).

LCMS (ES): m/z 387 [M+H]⁺.

Example 35

Methyl [2-phenyl-5-({[(pyridin-4-yl)methyl]carbamoyl}amino)-1H-indol-1-yl]acetate

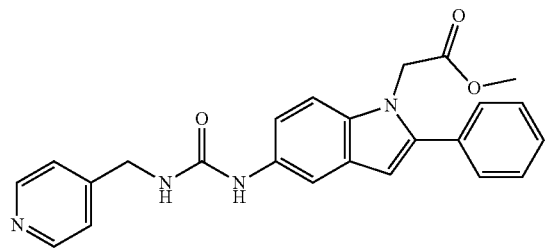 [SMILES: COC(=O)Cn1c(-c2ccccc2)cc2cc(NC(=O)NCc3ccncc3)ccc21]

(Example 35-a) Methyl (5-amino-2-phenyl-1H-indol-1-yl) acetate

2-Phenyl-1H-indol-5-amine (300 mg, 1.4 mmol) was dissolved in N,N-dimethylformamide (10 mL) and cooled to 0° C. To the solution was added sodium hydride (63 wt % dispersion in paraffin liquid) (75 mg, 1.7 mmol). The mixture was stirred for 30 min. Then, bromoacetic acid methyl ester (0.16 ml, 1.7 mmol) was added thereto, and the mixture was stirred at room temperature for 20 h. A saturated aqueous solution of ammonium chloride was added to the reaction solution, followed by extraction with ethyl acetate. Then, the extract was washed with brine. The organic phase was concentrated. The obtained residue was purified by silica gel column chromatography (ethyl acetate:hexane=20:80 to 100:0) to give the title compound (270 mg, 0.96 mmol, 67%) as an oil.

LCMS (ES): m/z 281 [M+H]⁺.

(Example 35-b) Methyl [2-phenyl-5-({[(pyridin-4-yl)methyl]carbamoyl}amino)-1H-indol-1-yl]acetate The title compound (64 mg, 0.15 mmol, 21%) was obtained as a solid in the same way as in (Example 17-d) using methyl (5-amino-2-phenyl-1H-indol-1-yl)acetate (210 mg, 0.75 mmol) obtained in Example 35-a.

$^1$H NMR (500 MHz, DMSO-d₆) δ (ppm) 3.63 (s, 3H), 4.34 (d, J=5.9 Hz, 2H), 4.98 (s, 2H), 6.51 (s, 1H), 6.67 (t, J=6.1 Hz, 1H), 7.13 (dd, J=8.8, 2.2 Hz, 1H), 7.30 (dd, J=7.2, 2.5 Hz, 3H), 7.41-7.52 (m, 5H), 7.69 (d, J=2.0 Hz, 1H), 8.50-8.54 (m, 3H).

LCMS (ES): m/z 415[M+H]⁺.

Example 36

N-[1-(2-Methoxyethyl)-2-phenyl-1H-indol-5-yl]-N'-[(pyridin-4-yl)methyl]urea

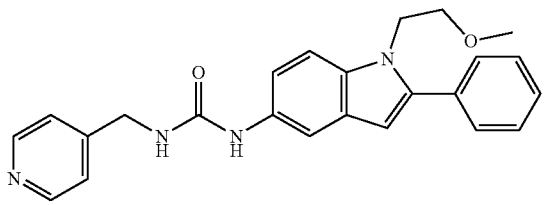 [SMILES: COCCn1c(-c2ccccc2)cc2cc(NC(=O)NCc3ccncc3)ccc21]

(Example 36-a) 2-Bromo-1-(2-methoxyethyl)-5-nitro-1H-indole

To a solution of 2-bromo-5-nitro-1H-indole (500 mg, 2.07 mmol) in DMF (10 mL) was added NaH (124 mg, 3.11 mmol, 60% purity) at 0° C. The mixture was stirred at 0° C. for 0.5 h. Then 1-bromo-2-methoxy-ethane (432 mg, 3.11 mmol) was added at 0° C. The mixture was stirred at 60° C. for 3 h. The reaction was quenched by $H_2O$ (20 mL) slowly and extracted with EA (30 mL×3). The combined organic phase was dried over $Na_2SO_4$, filtered and the filtrate was concentrated under vacuum to give the residue. The residue was purified by column chromatography ($SiO_2$, Petroleum ether/Ethyl acetate=20:1 to 10:1 to 5:1) to give the title compound (550 mg, 1.84 mmol, 88.6% yield) as a solid.

$^1$H NMR (400 MHz, $CDCl_3$) δ (ppm) 3.30 (s, 3H), 3.71 (t, J=5.6 Hz, 2H), 4.43 (t, J=5.6 Hz, 2H), 6.79 (s, 1H), 7.44 (d, J=8.8 Hz, 1H), 8.11 (dd, J=9.2, 2.0 Hz, 1H), 8.49 (d, J=2.4 Hz, 1H).

LCMS (ES): m/z 298 [M+H]$^+$.

(Example 36-b) 1-(2-Methoxyethyl)-5-nitro-2-phenyl-1H-indole

To a mixture was 2-bromo-1-(2-methoxyethyl)-5-nitro-1H-indole (530 mg, 1.77 mmol), phenylboronic acid (324 mg, 2.66 mmol) and $K_2CO_3$ (490 mg, 3.54 mmol) in dioxane (10 mL) and $H_2O$ (2 mL) was added Pd(dppf)Cl$_2$ (130 mg, 0.177 mmol). The mixture was degassed under vacuum and purged with $N_2$ three times. The mixture was stirred at 80° C. for 12 h. The reaction was removed the organic solvent under vacuum, then diluted with $H_2O$ (30 mL) and extracted with EA (30 mL×3). The combined organic phase was dried over anhydrous $Na_2SO_4$, filtered and concentrated under reduced pressure to give a residue. The residue was purified by column chromatography ($SiO_2$, Petroleum ether/Ethyl acetate=10:1 to 5:1) to give the title compound (350 mg, 1.18 mmol, 66.7% yield) as a solid.

$^1$H NMR (400 MHz, $CDCl_3$) δ (ppm) 3.23 (s, 3H), 3.63 (t, J=6.0 Hz, 2H), 4.38 (t, J=6.0 Hz, 2H), 6.72 (d, J=0.4 Hz, 1H), 7.49-7.57 (m, 6H), 8.11-8.22 (m, 1H), 8.60 (d, J=2.4 Hz, 1H).

LCMS (ES): m/z 297 [M+H]$^+$.

(Example 36-c) 1-(2-Methoxyethyl)-2-phenyl-1H-indol-5-amine

To a solution of 1-(2-methoxyethyl)-5-nitro-2-phenyl-1H-indole (100 mg, 0.337 mmol) in THF (5 mL) was added Pd/C (20 mg, 0.337 mmol). The suspension was degassed under vacuum and purged with $H_2$ several times. The mixture was stirred under $H_2$ (15 psi) at 25° C. for 2 h. The reaction was filtered and concentrated under vacuum. The crude title product (100 mg, crude) was obtained as a solid, which was used in the next step without further purification.

LCMS (ES): m/z 267 [M+H]$^+$.

(Example 36-d) N-[1-(2-Methoxyethyl)-2-phenyl-1H-indol-5-yl]-N'-[(pyridin-4-yl)methyl]urea To a solution of 1-(2-methoxyethyl)-2-phenyl-1H-indol-5-amine (100 mg, 0.375 mmol) and (4-nitrophenyl) N-(4-pyridylmethyl)carbamate (154 mg, 0.563 mmol) in dioxane (5 mL) was added DIPEA (0.261 ml, 1.50 mmol). The mixture was stirred at 60° C. for 1 h. The reaction was concentrated under vacuum. The residue was purified by prep-HPLC (water (0.05% ammonia hydroxide v/v)-ACN) to give the title compound (32.0 mg, 0.794 mmol, 21.1% yield) as a solid.

$^1$H NMR (400 MHz, DMSO-$d_6$) δ (ppm) 3.07 (s, 3H), 3.53 (t, J=5.6 Hz, 2H), 4.26-4.40 (m, 4H), 6.43 (s, 1H), 6.64 (t, J=6.0 Hz, 1H), 7.06-7.18 (m, 1H), 7.32 (d, J=5.6 Hz, 2H), 7.40-7.47 (m, 2H), 7.47-7.54 (m, 2H), 7.56-7.62 (m, 2H), 7.67 (d, J=1.6 Hz, 1H), 8.45-8.58 (m, 3H).

LCMS (ES): m/z 401 [M+H]$^+$.

Example 37

N-{2-[3-(2-Methoxyethoxy)phenyl]-1-methyl-1H-indol-5-yl}-N'-[(pyridin-4-yl)methyl]urea

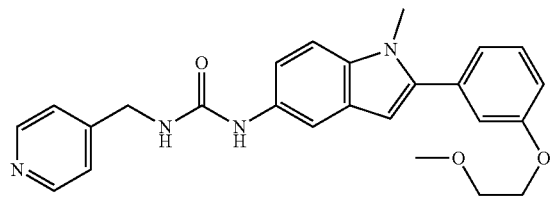 [SMILES: COCCOc1cccc(-c2cc3cc(NC(=O)NCc4ccncc4)ccc3n2C)c1]

(Example 37-a) 2-Bromo-1-methyl-5-nitro-1H-indole

To a mixture of sodium hydride (60 wt % dispersion in paraffin liquid) (3.3 g, 83 mmol) in DMF (50 mL) at 0° C. was added a solution of 2-bromo-5-nitro-1H-indole (10 g, 41 mmol) in DMF (50 mL) under $N_2$ atmosphere. The mixture was stirred at 0° C. for 30 mins. Then MeI (3.1 ml, 50 mmol) was added. The mixture was stirred at 25° C. for 3 h. The mixture was diluted with $H_2O$ (500 mL), extracted with EtOAc (500 mL×3). The combined EtOAc phase was washed with brine (500 mL×1), dried over anhydrous $Na_2SO_4$, filtered and concentrated in vacuo to give a residue. The residue was purified by column chromatography ($SiO_2$, PE/EtOAc=3:1) to give 2-bromo-1-methyl-5-nitro-indole (10 g, 40 mmol, 97% yield) as a solid.

1HNMR (400 MHz, $CDCl_3$) δ (ppm) 3.84 (s, 3H), 6.80 (d, J=0.8 Hz, 1H), 7.33 (d, J=8.8 Hz, 1H), 8.11-8.14 (m, 1H), 8.50 (d, J=2.4 Hz, 1H).

(Example 37-b) 3-(1-Methyl-5-nitro-1H-indol-2-yl)phenol

To a solution of 2-bromo-1-methyl-5-nitro-1H-indole (500 mg, 1.96 mmol), 3-(4,4,5,5-tetramethyl-1,3,2-dioxaborolan-2-yl)phenol (431 mg, 1.96 mmol) and K₂CO₃ (542 mg, 3.92 mmol) in dioxane (10 mL) and H₂O (1 mL) was added Pd(dppf)Cl₂ (143 mg, 0.196 mmol). The mixture was degassed in vacuo and purged with N₂ for three times and stirred at 100° C. for 12 h. The reaction was cooled to room temperature. EtOAc (30 mL) and H₂O (30 mL) were added and phases were separated. The aqueous phase was extracted with EtOAc (30 mL×3). The combined organic phase was washed with brine (60 mL), dried over Na₂SO₄, filtered and concentrated under vacuum to give the residue. The residue was purified by column chromatography (SiO₂, Petroleum ether/Ethyl acetate=10:1 to 5:1 to 3:1) to give the title compound (400 mg, 1.30 mmol, 66.2% yield) as a solid.

¹H NMR (400 MHz, DMSO-d₆) δ (ppm) 3.83 (s, 3H), 6.84 (s, 1H), 6.87-6.93 (m, 1H), 6.96-7.01 (m, 1H), 7.04 (d, J=7.6 Hz, 1H), 7.35 (t, J=8.0 Hz, 1H), 7.72 (d, J=9.2 Hz, 1H), 8.01-8.13 (m, 1H), 8.58 (d, J=2.0 Hz, 1H), 9.76 (s, 1H).

LCMS (ES): m/z 269 [M+H]⁺.

(Example 37-c) 2-[3-(2-Methoxyethoxy)phenyl]-1-methyl-5-nitro-1H-indole

To a solution of 3-(1-methyl-5-nitro-1H-indol-2-yl)phenol (380 mg, 1.23 mmol) in DMF (10 mL) was added NaH (73.9 mg, 1.85 mmol, 60% purity) at 0° C. The mixture was stirred at 0° C. for 0.5 h. Then 1-bromo-2-methoxy-ethane (257 mg, 1.85 mmol) was added at 0° C. The mixture was stirred at 0° C. for 1.5 h. The reaction was quenched with H₂O (30 mL) and extracted with EA (30 mL×3). The combined organic phase was dried over Na₂SO₄, filtered and the filtrate concentrated under vacuum to give the residue. The residue was purified by column chromatography (SiO₂, PE/EA=20:1 to 10:1 to 5:1) to give the title compound (350 mg, 1.07 mmol, 87.0% yield) as a solid.

¹H NMR (400 MHz, CDCl₃) δ (ppm) 3.49 (s, 3H), 3.78-3.83 (m, 5H), 4.17-4.23 (m, 2H), 6.72 (s, 1H), 7.00-7.13 (m, 3H), 7.36-7.46 (m, 2H), 8.16 (dd, J=9.2, 2.4 Hz, 1H), 8.59 (d, J=2.4 Hz, 1H).

(Example 37-d) 2-[3-(2-Methoxyethoxy)phenyl]-1-methyl-1H-indol-5-amine

To a solution of 2-[3-(2-methoxyethoxy)phenyl]-1-methyl-5-nitro-1H-indole (350 mg, 1.07 mmol) in THF (10 mL) was added Pd/C (100 mg) under N₂. The suspension was degassed under vacuum and purged with H₂ several times. The mixture was stirred under H₂ (15 psi) at 25° C. for 2 h. The reaction was filtered and concentrated under vacuum. The crude title compound (350 mg, crude) was obtained as an oil, which was used in the next step without further purification.

¹H NMR (400 MHz, CDCl₃) δ (ppm) 3.49 (s, 3H), 3.71 (s, 3H), 3.79-3.84 (m, 2H), 4.18-4.22 (m, 2H), 6.40 (s, 1H), 6.71-6.76 (m, 1H), 6.94-7.00 (m, 2H), 7.06-7.13 (m, 2H), 7.19 (d, J=8.4 Hz, 1H), 7.34-7.42 (m, 1H).

(Example 37-e) N-{2-[3-(2-Methoxyethoxy)phenyl]-1-methyl-1H-indol-5-yl}-N'-[(pyridin-4-yl)methyl]urea The title compound (205 mg, 0.470 mmol, 39.8% yield) was obtained as a solid in the same way as in (Example 17-d) using 2-[3-(2-methoxyethoxy)phenyl]-1-methyl-indol-5-amine (350 mg, 1.18 mmol) obtained in (Example 37-d).

¹H NMR (400 MHz, DMSO-d₆) δ (ppm) 3.33 (s, 3H), 3.67-3.71 (m, 2H), 3.72 (s, 3H), 4.15-4.21 (m, 2H), 4.34 (d, J=6.0 Hz, 2H), 6.50 (s, 1H), 6.59-6.69 (m, 1H), 6.97-7.05 (m, 1H), 7.09-7.17 (m, 3H), 7.32 (d, J=6.0 Hz, 2H), 7.35-7.45 (m, 2H), 7.68 (d, J=1.6 Hz, 1H), 8.49-8.55 (m, 3H).

LCMS (ES): m/z 431 [M+H]⁺.

Example 38

N-{2-[3-(Methanesulfonyl)phenyl]-1-methyl-1H-indol-5-yl}-N'-[(pyridin-4-yl)methyl]urea

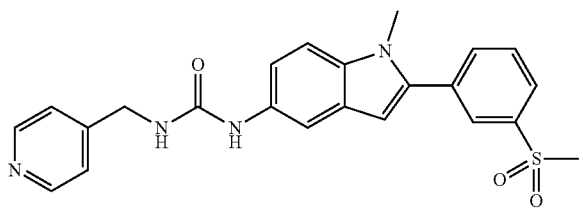 [SMILES: Cn1c(-c2cccc(S(C)(=O)=O)c2)cc2cc(NC(=O)NCc3ccncc3)ccc21]

(Example 38-a) 2-[3-(Methanesulfonyl)phenyl]-1-methyl-5-nitro-1H-indole

To a solution of 2-bromo-1-methyl-5-nitro-indole (500 mg, 1.96 mmol) and (3-methylsulfonylphenyl)boronic acid (784 mg, 3.92 mmol) in dioxane (20 mL) and H₂O (5 mL) were added Pd(PPh₃)₄ (453 mg, 0.392 mmol) and K₂CO₃ (1.22 g, 8.82 mmol). The mixture was stirred at 100° C. for 12 h under N₂. The reaction mixture was filtered and concentrated under reduced pressure to remove solvent. The residue was diluted with H₂O (30 mL) and extracted with EtOAc (20 mL×3). The combined organic phase was washed with brine (15 mL×3), dried over Na₂SO₄, filtered and concentrated under reduced pressure to give a residue. The residue was purified by column chromatography (SiO₂, Petroleum ether/Ethyl acetate=10:1 to 1:1) to give the title compound (800 mg, crude) as yellow solid, which was used in the next step without further purification.

LCMS (ES): m/z 332 [M+H]⁺.

(Example 38-b) 2-[3-(Methanesulfonyl)phenyl]-1-methyl-1H-indol-5-amine

To a solution of 2-[3-(methanesulfonyl)phenyl]-1-methyl-5-nitro-1H-indole (500 mg, 1.51 mmol) in THF (12 mL) and MeOH (12 mL) was added Pd/C (50 mg). The mixture was stirred at 25° C. for 10 h under H₂ (15 psi). The reaction mixture was filtered and concentrated under reduced pressure to give a residue. The residue was purified by prep-HPLC (basic condition) to give the title compound (150 mg, 0.499 mmol, 33.0% yield) as a solid.

¹H NMR (400 MHz, CDCl₃) δ (ppm) 3.04 (3H, s), 3.64 (3H, s), 6.41 (1H, s), 6.69 (1H, dd, J=8.4, 2.0 Hz), 6.87 (1H, d, J=2.0 Hz), 7.12 (1H, d, J=8.4 Hz), 7.55-7.63 (1H, m), 7.68-7.75 (1H, m), 7.82-7.91 (1H, m), 8.01 (1H, t, J=1.6 Hz).

(Example 38-c) N-{2-[3-(Methanesulfonyl)phenyl]-1-methyl-1H-indol-5-yl}-N'-[(pyridin-4-yl)methyl]urea The title compound (192 mg, 0.441 mmol, 88.4% yield) was obtained as a solid in the same way as in (Example 17-d) using 2-[3-(methanesulfonyl)phenyl]-1-methyl-1H-indol-5-amine (150 mg, 0.499 mmol) obtained in (Example 38-b).

$^1$H NMR (400 MHz, DMSO-d$_6$) δ (ppm) 3.33 (s, 3H), 3.75 (s, 3H), 4.35 (d, J=6.0 Hz, 2H), 6.61-6.69 (m, 2H), 7.20 (dd, J=8.8, 2.0 Hz, 1H), 7.32 (d, J=6.0 Hz, 2H), 7.42 (d, J=8.8 Hz, 1H), 7.69-7.84 (m, 2H), 7.92-8.01 (m, 2H), 8.05-8.13 (m, 1H), 8.48-8.57 (m, 3H).
LCMS (ES): m/z 435 [M+H]$^+$.

Example 39

N-[1-Methyl-2-(pyridin-2-yl)-1H-indol-5-yl]-N'-[(pyridin-4-yl) methyl]urea

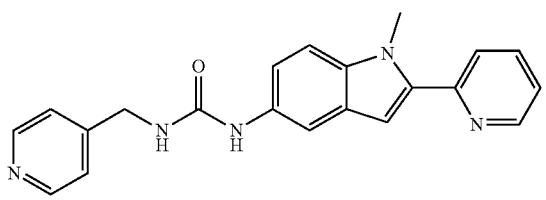 [SMILES: Cn1c(-c2ccccn2)cc2cc(NC(=O)NCc3ccncc3)ccc21]

(Example 39-a) Methyl-5-nitro-2-(pyridin-2-yl)-1H-indole

To an oven dried schlenck flask were added 2-bromo-1-methyl-5-nitro-1H-indole (300 mg, 1.18 mmol), 2-(tributylstannyl)pyridine (563 mg, 1.53 mmol), Pd(PPh$_3$)$_4$ (68.0 mg, 0.588 mmol), LiCl (100 mg, 2.35 mmol), CuI (22.4 mg, 0.118 mmol) and PPh$_3$ (308 mg, 1.18 mmol). And then DMF (5 mL) was added and degassed under an atmosphere of nitrogen then heated at 100° C. for 12 h 10 mL of THF was added to the reaction mixture which was stirred at 25° C. for 10 min. Then the mixture was filtered and concentrated in vacuo. The residue was purified by trituration with H$_2$O (10 mL), Ethyl acetate (20 mL) and MeOH (20 mL) to give the title compound (120 mg, 0.332 mmol, 28.2% yield) as a solid.
$^1$H NMR (400 MHz, DMSO-d$_6$) δ (ppm) 4.13 (s, 3H), 7.27 (s, 1H), 7.46 (t, J=5.2 Hz, 1H), 7.78 (d, J=9.2 Hz, 1H), 7.92-8.01 (m, 2H), 8.12 (dd, J=9.2, 2.4 Hz, 1H), 8.64 (d, J=2.0 Hz, 1H), 8.75 (d, J=5.2 Hz, 1H).
LCMS (ES): m/z 254 [M+H]$^+$.

(Example 39-b) Methyl-2-(pyridin-2-yl)-1H-indol-5-amine

To a mixture of methyl-5-nitro-2-(pyridin-2-yl)-1H-indole (120 mg, 0.332 mmol) in THF (30 mL) was added Pd/C (25 mg). The mixture was stirred at 30° C. for 2 h under H$_2$ (50 psi). The mixture was filtered and concentrated in vacuo. The residue was purified by prep-TLC (DCM/EtOAc=5:1) to give the title compound (50.0 mg, 0.201 mmol, 60.8% yield) as a solid.
LCMS (ES): m/z 224 [M+H]$^+$.

(Example 39-c) N-[1-Methyl-2-(pyridin-2-yl)-1H-indol-5-yl]-N'-[(pyridin-4-yl)methyl]urea To a solution of methyl-2-(pyridin-2-yl)-1H-indol-5-amine (50.0 mg, 0.201 mmol) in dioxane (5 mL) were added 4-nitrophenyl (pyridin-4-ylmethyl)carbamate (102 mg, 0.302 mmol) and DIPEA (0.140 ml, 0.806 mmol). The mixture was stirred at 60° C. for 2 h. A large quantity of precipitate was formed. The mixture was concentrated. The mixture was purified by prep-HPLC (TFA). After purification, the desired product (TFA salt) was neutralized by aq. NaHCO$_3$ to give the title compound (33.3 mg, 0.0910 mmol, 45.1% yield) as a solid.
$^1$H NMR (400 MHz, DMSO-d$_6$) δ (ppm) 4.02 (s, 3H), 4.35 (d, J=6.0 Hz, 2H), 6.66 (t, J=6.0 Hz, 1H), 6.88 (s, 1H), 7.18 (dd, J=8.8, 2.0 Hz, 1H), 7.29-7.38 (m, 3H), 7.41 (d, J=8.8 Hz, 1H), 7.74 (d, J=2.0 Hz, 1H), 7.83-7.93 (m, 2H), 8.49-8.56 (m, 3H), 8.69 (dt, J=4.4, 1.6 Hz, 1H).
LCMS (ES): m/z 358 [M+H]$^+$.

Example 40

N-{1-[(1,4-Dioxan-2-yl)methyl]-2-phenyl-1H-indol-5-yl}-N'-[(pyridin-4-yl)methyl]urea

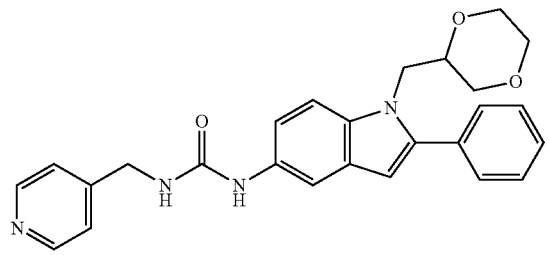 [SMILES: O=C(NCc1ccncc1)Nc1ccc2c(c1)cc(-c1ccccc1)n2CC1COCCO1]

(Example 40-a) 1-[(1,4-Dioxan-2-yl)methyl]-5-nitro-2-phenyl-1H-indole

To a solution of 5-nitro-2-phenyl-1H-indole (300 mg, 1.26 mmol) in DMF (5 mL) were added NaI (18.9 mg, 0.126 mmol), NaH (50.4 mg, 1.26 mmol, 60% purity) and 2-(chloromethyl)-1,4-dioxane (172 mg, 1.26 mmol) at 0° C. The mixture was stirred at 90° C. for 12 h. The reaction mixture was partitioned between H$_2$O (20 mL) and AcOEt (20 mL). The organic phase was separated, washed with brine (15 mL×2), dried over Na$_2$SO$_4$, filtered and concentrated under reduced pressure to give a residue. The residue was purified by column chromatography (SiO$_2$, Petroleum ether/Ethyl acetate=10:1 to 3:1) to give the title compound (30.0 mg, 0.0887 mmol, 7.04% yield) as an oil.
$^1$H NMR (400 MHz, CD$_3$OD) δ (ppm) 3.11-3.19 (m, 1H), 3.42-3.50 (m, 3H), 3.54-3.69 (m, 2H), 3.72-3.83 (m, 1H), 4.24-4.41 (m, 2H), 6.75 (s, 1H), 7.49-7.61 (m, 5H), 7.68 (d, J=9.2 Hz, 1H), 8.12 (dd, J=9.2, 2.4 Hz, 1H), 8.56 (d, J=2.0 Hz, 1H).

(Example 40-b) 1-[(1,4-Dioxan-2-yl)methyl]-2-phenyl-1H-indol-5-amine

To a solution of 1-[(1,4-dioxan-2-yl)methyl]-5-nitro-2-phenyl-1H-indole (30 mg, 0.89 mmol) in EtOAc (3 mL) was added Pd/C (20 mg). The mixture was degassed and recharged with H$_2$ for 3 times. The mixture was stirred at 25° C. for 10 h. The reaction mixture was filtered and concentrated under reduced pressure to give the title compound (23 mg, 0.075 mmol, 84% yield) as a solid.
LCMS (ES): m/z 309 [M+H]$^+$.

(Example 40-c) N-{1-[(1,4-Dioxan-2-yl)methyl]-2-phenyl-1H-indol-5-yl}-N'-[(pyridin-4-yl)methyl]urea The title compound (13 mg, 0.028 mmol, 37% yield) was obtained as a solid in the same way as in (Example 17-d)

using a solution of 1-[(1,4-dioxan-2-yl)methyl]-2-phenyl-1H-indol-5-amine (23 mg, 0.075 mmol).

$^1$H NMR (400 MHz, CDCl$_3$) δ (ppm) 3.03-3.13 (m, 1H), 3.35-3.42 (m, 1H), 3.46-3.65 (m, 3H), 3.67-3.75 (m, 1H), 3.79-3.89 (m, 1H), 4.07-4.17 (m, 1H), 4.21-4.30 (m, 1H), 4.43-4.49 (m, 2H), 5.08-5.17 (m, 1H), 6.27 (s, 1H), 6.54 (s, 1H), 7.14 (dd, J=8.8, 2.0 Hz, 1H), 7.21 (d, J=6.0 Hz, 2H), 7.43-7.55 (m, 7H), 8.51-8.58 (m, 2H).

LCMS (ES): m/z 443 [M+H]$^+$.

Example 41

N,N-Dimethyl-2-phenyl-5-({[(pyridin-4-yl)methyl] carbamoyl}amino)-1H-indole-1-carboxamide

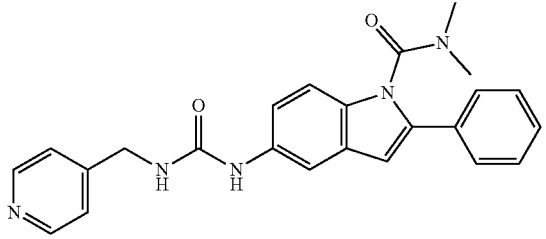 [SMILES: CN(C)C(=O)n1c(-c2ccccc2)cc2cc(NC(=O)NCc3ccncc3)ccc21]

(Example 41-a) N,N-Dimethyl-5-nitro-2-phenyl-1H-indole-1-carboxamide

To a solution of 5-nitro-2-phenyl-1H-indole (300 mg, 1.26 mmol) in DMF (2 mL) was added NaH (60 mg, 1.50 mmol, 60% purity) and N,N-dimethylcarbamoyl chloride (140 mg, 1.30 mmol) at 0° C. The mixture was stirred at 60° C. for 16 h. The reaction mixture was partitioned between H$_2$O (20 mL) and EtOAc (20 mL). The organic phase was separated, washed with brine (15 mL×2), dried over Na$_2$SO$_4$, filtered and concentrated under reduced pressure to give a residue. The residue was purified by column chromatography (SiO$_2$, Petroleum ether/Ethyl acetate=10:1 to 1:1) to give the title compound (50 mg, 0.162 mmol, 12.8% yield) as an oil.

$^1$H NMR (400 MHz, CD$_3$OD) δ (ppm) 2.61 (s, 3H), 3.11 (s, 3H), 7.06 (s, 1H), 7.49-7.56 (m, 3H), 7.59-7.63 (m, 3H), 8.21 (dd, J=8.8, 2.0 Hz, 1H), 8.65 (d, J=2.4 Hz, 1H).

(Example 41-b) 5-Amino-N,N-dimethyl-2-phenyl-1H-indole-1-carboxamide

To a solution of N,N-dimethyl-5-nitro-2-phenyl-1H-indole-1-carboxamide (50 mg, 0.16 mmol) in THF (3 mL) was added Pd/C (20 mg). The mixture was degassed and recharged with H$_2$ for 3 times. The mixture was stirred at 25° C. for 6 h under H$_2$ (15 psi). The reaction mixture was filtered and concentrated under reduced pressure to give the title compound (40 mg, 0.14 mmol, 89% yield) as an oil.

LCMS (ES): m/z 280 [M+H]$^+$.

(Example 41-c) N,N-Dimethyl-2-phenyl-5-({[(pyridin-4-yl)methyl]carbamoyl}amino)-1H-indole-1-carboxamide The title compound (11 mg, 0.027 mmol, 19% yield) was obtained as a solid in the same way as in (Example 17-d) using 5-amino-N,N-dimethyl-2-phenyl-1H-indole-1-carboxamide (40 mg, 0.14 mmol) obtained in (Example 41-b).

$^1$H NMR (400 MHz, CD$_3$OD) δ (ppm) 2.64 (s, 3H), 3.07 (s, 3H), 4.49 (s, 2H), 6.78 (s, 1H), 7.24 (dd, J=8.8, 2.0 Hz, 1H), 7.35-7.50 (m, 6H), 7.53-7.59 (m, 2H), 7.71 (d, J=1.6 Hz, 1H), 8.46-8.53 (m, 2H).

LCMS (ES): m/z 414 [M+H]$^+$.

Example 42

N-(1-Methyl-2-phenyl-1H-indol-5-yl)-N'-[(pyridin-4-yl)methyl]urea

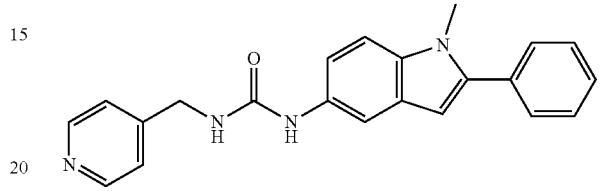

(Example 42-a) Methyl-5-nitro-2-phenyl-1H-indole

To a solution of 5-nitro-2-phenyl-1H-indole (300 mg, 1.26 mmol) in DMF (5 mL) was added NaH (75.6 mg, 1.89 mmol, 60% purity) at 0° C. The mixture was stirred at 0° C. for 0.5 h. Then iodomethane (357 mg, 2.52 mmol) was added. The mixture was stirred at 20° C. for 1.5 h. The reaction was quenched by H$_2$O (20 mL) and then extracted with EA (30 mL×3). The combined organic phase was dried over anhydrous Na$_2$SO$_4$, filtered and concentrated in vacuo. The crude product was suspended in EA (10 mL) and collected by filtration to give the title compound (270 mg, 1.07 mmol, 85.0% yield) as a solid.

$^1$H NMR (400 MHz, DMSO-d$_6$) δ (ppm) 3.84 (s, 3H), 6.89 (s, 1H), 7.47-7.60 (m, 3H), 7.62-7.68 (m, 2H), 7.74 (d, J=9.2 Hz, 1H), 8.05-8.12 (m, 1H), 8.59 (d, J=2.0 Hz, 1H).

(Example 42-b) Methyl-5-nitro-2-phenyl-1H-indole

To a solution of methyl-5-nitro-2-phenyl-1H-indole (100 mg, 0.396 mmol) in EtOAc (5 mL) was added Pd/C (20 mg, 10% purity) under N$_2$. The suspension was degassed under vacuum and purged with H$_2$ several times. The mixture was stirred under H$_2$ (15 psi) at 20° C. for 2 h. The reaction was filtered and concentrated in vacuo to give the crude title compound (80 mg, crude) as an oil, which was used in the next step without further purification.

LCMS (ES): m/z 223 [M+H]$^+$.

(Example 42-c) N-(1-Methyl-2-phenyl-1H-indol-5-yl)-N'-[(pyridin-4-yl)methyl]urea To a solution of methyl-5-nitro-2-phenyl-1H-indole (80 mg, 0.36 mmol) and (4-nitrophenyl)N-(4-pyridylmethyl)carbamate (0.12 g, 0.36 mmol) in dioxane (5 mL) was added DIPEA (0.25 ml, 1.4 mmol). The mixture was stirred at 60° C. for 1 h. The reaction was concentrated under reduced pressure to give a residue. The crude product was suspended in EA (10 mL) and collected by filtration to give the title compound (99 mg, 0.28 mmol, 77% yield) as a solid.

$^1$H NMR (400 MHz, DMSO-d$_6$) δ (ppm) 3.72 (s, 3H), 4.34 (d, J=6.0 Hz, 2H), 6.48 (s, 1H), 6.69 (br t, J=5.6 Hz, 1H), 7.08-7.20 (m, 1H), 7.32 (d, J=6.0 Hz, 2H), 7.35-7.40

(m, 1H), 7.41-7.47 (m, 1H), 7.52 (t, J=7.2 Hz, 2H), 7.56-7.61 (m, 2H), 7.69 (d, J=1.6 Hz, 1H), 8.47-8.57 (m, 3H).
LCMS (ES): m/z 357 [M+H]⁺.

Example 43

N-[(1,3-Oxazol-5-yl)methyl]-N'-(2-phenyl-2H-indazol-6-yl) urea

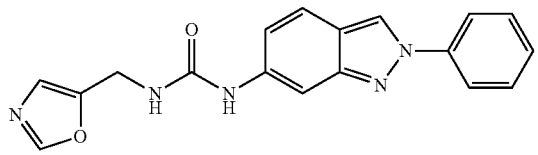 [SMILES: O=C(NCc1cnco1)Nc1ccc2cn(-c3ccccc3)nc2c1]

The title compound (22 mg, 35%) was obtained as a solid from 3-methyl-2-phenylpyrazolo[1,5-a]pyridin-6-amine (40 mg, 0.191 mmol) in the same way as in (Example 1-d).
¹H NMR (DMSO-d₆) δ (ppm): 4.41 (d, J=5.7 Hz, 2H), 6.68 (t, J=5.7 Hz, 1H), 6.95 (dd, J=9.0, 1.8 Hz, 1H), 7.02-7.06 (m, 1H), 7.36-7.43 (m, 1H), 7.53-7.59 (m, 2H), 7.63 (dd, J=9.0, 0.6 Hz, 1H), 7.89-7.91 (m, 1H), 8.03-8.04 (m, 1H), 8.04-8.06 (m, 1H), 8.31 (s, 1H), 8.71 (s, 1H), 8.96 (d, J=1.0 Hz, 1H).
LCMS (ES): m/z 334.2 [M+H]⁺.

Example 44

N-{2-[3-(Difluoromethoxy)phenyl]-2H-indazol-6-yl}-N'-[(pyridin-4-yl)methyl]urea

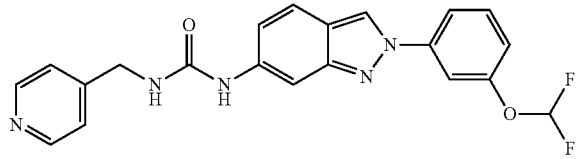 [SMILES: O=C(NCc1ccncc1)Nc1ccc2cn(-c3cccc(OC(F)F)c3)nc2c1]

The title compound (50 mg, four steps 20%) was obtained as a solid from 3-(difluoromethoxy)aniline (0.177 mL, 1.43 mmol) in the same way as in (Example 27-a), (Example 23-a), (Example 19-g), and (Example 17-d)
¹H NMR (DMSO-d₆) δ (ppm) 4.30-4.41 (m, 2H), 6.82 (t, J=6.1 Hz, 1H), 7.00 (dd, J=9.2, 1.8 Hz, 1H), 7.14-7.43 (m, 4H), 7.56-7.72 (m, 2H), 7.84-7.91 (m, 2 H), 7.94 (ddd, J=8.2, 2.2, 0.8 Hz, 1H), 8.48-8.56 (m, 2H), 8.88 (s, 1H), 9.00-9.06 (m, 1H).
LCMS (ES): m/z 410 [M+H]⁺.

Example 45

N-[2-(3-Methoxyphenyl)pyrazolo[1,5-a]pyridin-6-yl]-N'-[(pyridin-4-yl)methyl]urea

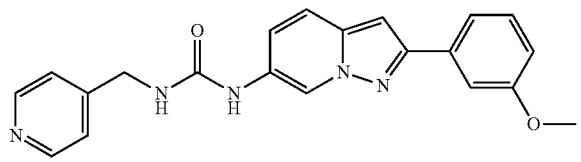 [SMILES: COc1cccc(-c2cc3ccc(NC(=O)NCc4ccncc4)cn3n2)c1]

(Example 45-a) 2-(5-Bromopyridin-2-yl)-1-(3-methoxyphenyl)ethan-1-one

To a solution of methyl 3-methoxybenzoate (1.93 g, 11.6 mmol) and 5-bromo-2-methyl-pyridine (2.0 g, 11.6 mmol) in THF (20 mL) was added LiHMDS (1 M, 11.6 ml, 11.6 mmol) at 0° C. The mixture was stirred at 25° C. for 16 h. The reaction mixture was quenched by addition saturate NH₄Cl solution (30 mL) and extracted with EtOAc (20 mL×3). The combined organic phase was washed with brine (30 mL), dried over Na₂SO₄, filtered and concentrated under reduced pressure to give a residue. The residue was purified by column chromatography on silica gel (PE/EtOAc=0 to 20:1) to give the title compound (1.35 g, 4.19 mmol, yield: 36.0%) as an oil.
LCMS (ES): m/z 305 [M+H]⁺.

(Example 45-b) N-[(1Z)-2-(5-bromopyridin-2-yl)-1-(3-methoxyphenyl)ethylidene]hydroxylamine To a solution of 2-(5-bromopyridin-2-yl)-1-(3-methoxyphenyl)ethan-1-one (1.35 g, 4.19 mmol) in MeOH (15 mL) at 25° C. was added NaOH (6.70 g, 16.76 mmol, 4.41 mL, 10% purity aqueous). The resulting solution was stirred vigorously as solid hydroxylamine hydrochloride (1.46 g, 20.95 mmol) was added. The mixture was heated to 80° C. for 2 h. The mixture was concentrated. The resulting solids were dissolved in 30 mL of EtOAc, washed with water (20 mL×2), dried and concentrated under vacuum. The residue was purified by column chromatography on silica gel (1000 mesh silica gel, PE/EtOAc=3:1) to give the title compound (1.0 g, 3.11 mmol, yield: 74.3%) as a solid.
¹HNMR: (400 MHz, CD₃OD) δ (ppm) 3.79 (s, 3H), 4.33 (s, 2H), 6.90-6.91 (m, 1H), 7.23-7.28 (m, 4H), 7.87 (dd, J=8.4, 2.4 Hz, 1H), 8.53 (d, J=2.4 Hz, 1H).

(Example 45-c) N-[1-(5-Bromopyridin-2-yl)-2-(3-methoxyphenyl)ethyl]methanimine

To a solution of N-[(1Z)-2-(5-bromopyridin-2-yl)-1-(3-methoxyphenyl)ethylidene]hydroxylamine (1.0 g, 3.11 mmol) in DCM (15 mL) at 25° C. was added TEA (1.26 g, 12.5 mmol, 1.73 ml). The resulting solution was stirred vigorously as TFAA (0.78 g, 3.74 mmol, 0.52 ml) was added at 0° C. The mixture was stirred at 30° C. for 1 h. The mixture was poured into water (20 mL) and stirred for 10 min. The aqueous phase was extracted with ethyl acetate (20 mL×2). The combined organic phase was washed with brine (20 mL), dried over anhydrous Na₂SO₄, filtered and concentrated in vacuo. The residue was purified by column chromatography on silica gel (1000 mesh silica gel, PE/EtOAc=3:1) to give the title compound (0.80 g, 2.64 mmol, yield: 84.8%) as a solid.
¹HNMR: (400 MHz, CDCl₃) δ (ppm) 3.47 (s, 1H), 3.89 (s, 3H), 6.98 (d, J=8.4 Hz, 1H), 7.18-7.20 (m, 1H), 7.45-7.49 (m, 3H), 7.73 (dd, J=8.4, 2.4 Hz, 1H), 8.59 (d, J=2.4 Hz, 1H).

(Example 45-d) 6-Bromo-2-(3-methoxyphenyl)pyrazolo[1,5-a]pyridine

To a solution of N-[1-(5-bromopyridin-2-yl)-2-(3-methoxyphenyl)ethyl]methanimine (0.75 g, 2.47 mmol) in DME (20 mL) was added FeCl₂·4H₂O (39.0 mg, 0.247 mmol). The resulting solution was stirred 75° C. for 2 h. The mixture was filtered and concentrated in vacuo. The residue was purified by column chromatography on silica gel (100 mesh silica gel, PE/EtOAc=10:1) to give the title compound (0.50 g, 1.65 mmol, yield: 66.7%) as a solid.

$^1$H NMR: (400 MHz, CDCl$_3$) δ (ppm) 3.83 (s, 3H), 6.73 (s, 1H), 6.85-6.88 (m, 1H), 7.08-7.10 (m, 1H), 7.29-7.35 (m, 2H), 7.43-7.45 (m, 2H), 8.55-8.56 (m, 1H).

LCMS (ES): m/z 302 [M+H]$^+$.

(Example 45-e) N-[2-(3-Methoxyphenyl)pyrazolo[1,5-a]pyridin-6-yl]-1,1-diphenylmethanimine To an oven dried schlenck flask were added 6-bromo-2-(3-methoxyphenyl)pyrazolo[1,5-a]pyridine (0.30 g, 0.99 mmol), diphenylmethanimine (0.219 g, 1.19 mmol), Pd(OAc)$_2$ (22.2 mg, 0.0990 mmol), BINAP (92.4 mg, 0.148 mmol) and Cs$_2$CO$_3$ (0.967 g, 2.97 mmol). And then toluene (3 mL) was added and degassed under an atmosphere of nitrogen and then heated at 110° C. for 8 h. The mixture was filtered and concentrated in vacuo to give the title compound (0.30 g, crude) as an oil, which was used in the next step directly.

LCMS (ES): m/z 404 [M+H]$^+$.

(Example 45-f) 2-(3-Methoxyphenyl)pyrazolo[1,5-a]pyridin-6-amine

To mixture of N-[2-(3-methoxyphenyl)pyrazolo[1,5-a]pyridin-6-yl]-1,1-diphenylmethanimine (0.30 g, 0.74 mmol) in THF (5 mL) was added HCl (2 M, 1.20 ml). And then the mixture was stirred at 30° C. for 1 h. The mixture was filtered and concentrated in vacuo. The residue was purified by prep-TLC on silica gel plate (PE/EtOAc=1:1) to give the title compound (0.10 g, 0.42 mmol, 56% yield) as a solid.

LCMS (ES): m/z 240 [M+H]$^+$.

(Example 45-g) N-[2-(3-Methoxyphenyl)pyrazolo[1,5-a]pyridin-6-yl]-N'-[(pyridin-4-yl)methyl]urea To a solution of 2-(3-methoxyphenyl)pyrazolo[1,5-a]pyridin-6-amine (0.10 g, 0.42 mmol) in dioxane (5 mL) were added 4-nitrophenyl (pyridin-4-ylmethyl)carbamate (0.15 g, 0.54 mmol) and DIPEA (0.29 ml, 1.7 mmol,). The mixture was stirred at 60° C. for 12 h. The mixture was concentrated in vacuo. The residue was purified by prep-HPLC (FA) to give the title compound (53 mg, 0.13 mmol, yield: 32%) as a solid.

$^1$H NMR: (400 MHz, CD$_3$OD) δ (ppm) 3.74 (s, 3H), 4.35 (s, 2H), 6.71 (s, 1H), 6.78-6.80 (m, 1H), 6.95 (d, J=9.2 Hz, 1H), 7.20-7.22 (m, 1H), 7.28 (d, J=5.6 Hz, 2H), 7.34-7.40 (m, 3H), 8.35 (d, J=5.2 Hz, 2H), 8.86 (s, 1H).

LCMS (ES): m/z 374 [M+H]$^+$.

Example 46

N-[1-(2-Methylpropyl)-1H-indazol-5-yl]-N'-[(pyridin-4-yl)methyl]urea

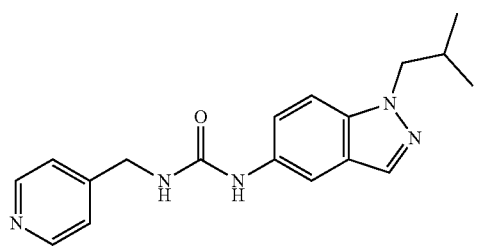 [SMILES: CC(C)Cn1ncc2cc(NC(=O)NCc3ccncc3)ccc21]

(Example 46-a) 1-Isobutyl-5-nitro-indazole

5-Nitroindazole (0.50 g, 3.1 mmol), isobutyl iodide (0.68 g, 3.7 mmol) was dissolved in N,N-dimethylformamide (5 mL) and cooled to 0° C. To the solution was added sodium hydride (63 wt % dispersion in paraffin liquid) (0.14 g, 3.7 mmol). The mixture was stirred at 0° C. for 4 h. A saturated aqueous solution of ammonium chloride (3 mL) was added thereto. Then, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. The crude product was purified by silica gel column chromatography (AcOEt:hexane=5:95 to 35:65) to give the title compound (0.41 g, 61%) as a solid.

$^1$H NMR (400 MHz, CDCl$_3$) δ (ppm) 0.95 (d, J=6.7 Hz, 6H), 2.37 (dt, J=13.7, 7.1 Hz, 1H), 4.23 (d, J=7.4 Hz, 2H), 7.46 (dt, J=9.2, 0.8 Hz, 1H), 8.22 (d, J=1.0 Hz, 1H), 8.24-8.29 (m, 1H), 8.73-8.75 (m, 1H).

(Example 46-b) 1-Isobutylindazol-5-amine

1-Isobutyl-5-nitro-indazole (0.41 g, 1.9 mmol) obtained in (Example 46-a) was dissolved in ethanol (3 mL) and ethyl acetate (3 mL). To the solution was added 10% Pd/C (50% wet) (50 mg). After purging of the reaction container with hydrogen, the mixture was stirred at room temperature for 4 h. The reaction solution was filtered through celite. Then, the filtrate was concentrated under reduced pressure to give the crude title compound. The crude product was purified by silica gel column chromatography (ethyl acetate:hexane=30:70 to 75:25) to give the title compound (0.35 g, 100%) as a solid.

$^1$H NMR (500 MHz, CDCl$_3$) δ (ppm) 0.91 (d, J=6.6 Hz, 6H), 2.25-2.37 (m, 1H), 3.59 (br s, 2H), 4.10 (d, J=7.3 Hz, 2H), 6.85 (dd, J=8.8, 2.0 Hz, 1H), 6.91-6.94 (m, 1H), 7.20-7.24 (m, 1H), 7.78 (d, J=1.0 Hz, 1H).

(Example 46-c) N-[1-(2-Methylpropyl)-1H-indazol-5-yl]-N'-[(pyridin-4-yl)methyl]urea 1-Isobutylindazol-5-amine (80 mg, 0.42 mmol) obtained in (Example 46-b) and (4-nitrophenyl)-N-(4-pyridylmethyl)carbamate (0.14 g, 0.50 mmol) obtained in (Reference Example 1) were suspended in 1,4-dioxane (2 mL). To the suspension was added N,N-diisopropylamine (0.11 mL, 0.85 mmol). The mixture was stirred at 60° C. for 2 h. After cooling to room temperature, the reaction solution was poured into water (30 mL), followed by partition operation using ethyl acetate. The organic phase was washed with brine, then dried over magnesium sulfate, and filtered. Then, the solvent was distilled off under reduced pressure to give the crude title compound. A small amount of ethyl acetate was added thereto. Then, the precipitated solid was collected by filtration and washed with diethyl ether to give the title compound (98 mg, 72%) as a solid.

$^1$H NMR (500 MHz, DMSO-d$_6$) δ (ppm) 0.83 (d, J=6.8 Hz, 6 H), 2.14-2.24 (m, 1H), 4.15 (d, J=7.1 Hz, 2H), 4.34 (d, J=6.1 Hz, 2H), 6.69 (t, J=5.6 Hz, 1H), 7.27-7.33 (m, 3H), 7.52-7.57 (m, 1H), 7.81-7.85 (m, 1H), 7.92 (d, J=1.0 Hz, 1H), 8.48-8.53 (m, 2H), 8.64 (br s, 1H).

LCMS (ES): m/z 324 [M+H]$^+$.

Example 47

N-(2-Phenyl-3,4-dihydro-2H-1,4-benzoxazin-7-yl)-N'-[(pyridin-4-yl)methyl]urea

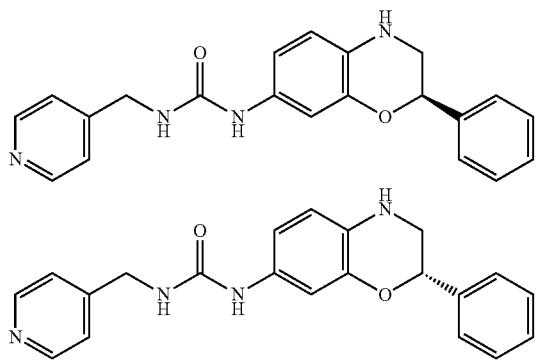

(Example 47-a) 7-Nitro-2-phenyl-2H-1,4-benzoxazin-3(4H)-one

To a solution of methyl 2-bromo-2-phenyl-acetate (2.0 g, 8.73 mmol) and 2-amino-5-nitro-phenol (1.35 g, 8.73 mmol) in DMF (20 mL) was added $K_2CO_3$ (2.41 g, 17.5 mmol). The mixture was stirred at 80° C. for 2 h. The reaction mixture was diluted with $H_2O$ (100 mL) and then extracted with AcOEt (100 mL×3). The combined organic phase was dried over anhydrous $Na_2SO_4$, filtered and concentrated under reduced pressure to give a residue. The residue was purified by column chromatography ($SiO_2$, Petroleum ether/Ethyl acetate=10:1 to 5:1) to give the title compound (0.80 g, 2.96 mmol, 34% yield) as a solid.

$^1$H NMR (400 MHz, DMSO-$d_6$) δ (ppm) 5.96 (s, 1H), 7.12 (d, J=8.8 Hz, 1H), 7.39-7.43 (m, 5H), 7.86 (d, J=2.4 Hz, 1H), 7.91-7.95 (m, 1H), 11.60 (s, 1H).

LCMS (ES): m/z 269 [M−H]$^-$.

(Example 47-b) 7-Amino-2-phenyl-2H-1,4-benzoxazin-3(4H)-one

To a solution of 7-nitro-2-phenyl-2H-1,4-benzoxazin-3(4H)-one (800 mg, 2.96 mmol) in EtOAc (10 mL) was added Pd/C (100 mg) under $N_2$. The suspension was degassed under vacuum and purged with $H_2$ several times. The mixture was stirred under $H_2$ (15 psi) at 25° C. for 1 h. The reaction was filtered and concentrated in vacuo. The residue was purified by column chromatography ($SiO_2$, Petroleum ether/Ethyl acetate=5:1 to 3:1) to give the title compound (500 mg, 2.08 mmol, 70.3% yield) as a solid.

$^1$H NMR (400 MHz, DMSO-$d_6$) δ (ppm) 4.89 (s, 2H), 5.61 (s, 1H), 6.12-6.18 (m, 1H), 6.23 (d, J=2.4 Hz, 1H), 6.58 (d, J=8.0 Hz, 1H), 7.28-7.44 (m, 5H), 10.51 (s, 1H).

(Example 47-c) N-(3-Oxo-2-phenyl-3,4-dihydro-2H-1,4-benzoxazin-7-yl)-N'-[(pyridin-4-yl)methyl]urea To a solution of 7-amino-2-phenyl-2H-1,4-benzoxazin-3(4H)-one (0.50 g, 2.1 mmol) and (4-nitrophenyl)N-(4-pyridylmethyl)carbamate (0.84 g, 2.5 mmol) in dioxane (10 mL) was added DIPEA (0.81 g, 6.2 mmol). The mixture was stirred at 60° C. for 2 h. The reaction was filtrated to give the solid and washed with ethyl acetate (10 mL×2). The title racemic product (0.50 g, 1.3 mmol, 64% yield) was obtained. The obtained racemic compound was separated by Supercritical Fluid Chromatography (SFC) to afford the more polar title compound (1$^{st}$ peak, 0.21 g, 0.56 mmol, 27% yield) and the less polar title compound (2$^{nd}$ peak, 0.24 g, 0.64 mmol, 31%) as solids, respectively.

Supercritical Fluid Chromatography (SFC) conditions are as follows "AD-3S_3_40_3ML Column: Chiralpak AD-3 50×4.6 mm I.D., 3 um Mobile phase: 40% methanol (0.05% DEA) in $CO_2$ Flow rate: 3 mL/min Wavelength: 220 nm" $^1$H NMR (400 MHz, DMSO-$d_6$) δ (ppm) 4.30 (d, J=6.4 Hz, 2H), 5.72 (s, 1H), 6.65-6.72 (m, 1H), 6.74-6.79 (m, 1H), 6.85-6.90 (m, 1H), 7.23 (d, J=2.0 Hz, 1H), 7.27 (d, J=6.0 Hz, 2H), 7.34-7.39 (m, 4H), 8.41-8.55 (m, 2H), 8.67 (s, 1H), 10.81 (s, 1H).

(Example 47-d) N-(2-Phenyl-3,4-dihydro-2H-1,4-benzoxazin-7-yl)-N'-[(pyridin-4-yl)methyl]urea <1$^{st}$ peak>

To a solution of N-(3-oxo-2-phenyl-3,4-dihydro-2H-1,4-benzoxazin-7-yl)-N'-[(pyridin-4-yl)methyl]urea (first peak, 100 mg, 0.27 mmol) in THF (5 mL) was added $BH_3$-$Me_2S$ (10 M, 0.27 ml, 2.7 mmol) at 0° C. The mixture was stirred at 25° C. for 12 h under $N_2$. The reaction was quenched by saturated $NH_4Cl$ (30 mL) and then extracted with AcOEt (30 mL×3). The combined organic phase was dried over anhydrous $Na_2SO_4$, filtered and concentrated in vacuo. The residue was purified by prep-HPLC (water (0.04% $NH_3H_2O$)-ACN) to give the title compound (41 mg, 0.11 mmol, 39% yield) as a solid.

$^1$H NMR (400 MHz, DMSO-$d_6$) δ (ppm) 3.07-3.22 (m, 1H), 3.38-3.46 (m, 1H), 4.41 (d, J=5.6 Hz, 2H), 4.89-5.10 (m, 1H), 5.63 (br s, 1H), 6.53 (d, J=8.4 Hz, 1H), 6.63-6.75 (m, 1H), 6.94 (d, J=2.4 Hz, 1H), 7.24-7.47 (m, 5H), 7.56 (d, J=6.0 Hz, 2H), 8.40 (s, 1H), 8.50 (d, J=6.8 Hz, 2H).

(Example 47-e) N-(2-Phenyl-3,4-dihydro-2H-1,4-benzoxazin-7-yl)-N'-[(pyridin-4-yl)methyl]urea <2$^{nd}$ peak>

To a solution of N-(3-oxo-2-phenyl-3,4-dihydro-2H-1,4-benzoxazin-7-yl)-N'-[(pyridin-4-yl)methyl]urea second peak, 100 mg, 0.27 mmol) in THF (5 mL) was added $BH_3$-$Me_2S$ (10 M, 0.27 ml, 2.7 mmol) at 0° C. The mixture was stirred at 25° C. for 12 h under $N_2$. The reaction was quenched by saturated $NH_4Cl$ (30 mL) and then extracted with AcOEt (30 mL×3). The combined organic phase was dried over anhydrous $Na_2SO_4$, filtered and concentrated in vacuo. The residue was purified by prep-HPLC (water (0.04% $NH_3H_2O$)-ACN) to give the title compound (52 mg, 0.13 mmol, 49% yield) as a solid.

$^1$H NMR (400 MHz, DMSO-$d_6$) δ (ppm) 3.06-3.19 (m, 1H), 3.37-3.45 (m, 1H), 4.41 (d, J=6.4 Hz, 2H), 4.93-5.05 (m, 1H), 5.63 (br s, 1H), 6.53 (d, J=8.4 Hz, 1H), 6.62-6.73 (m, 1H), 6.93 (d, J=2.0 Hz, 1H), 7.30-7.46 (m, 5H), 7.56 (d, J=6.4 Hz, 2H), 8.39 (s, 1H), 8.50 (d, J=6.8 Hz, 2H).

Example 48

N-[4-(2-Methoxyethyl)-2-phenyl-3,4-dihydro-2H-1,4-benzoxazin-7-yl]⁻N'-[(pyridin-4-yl)methyl]urea

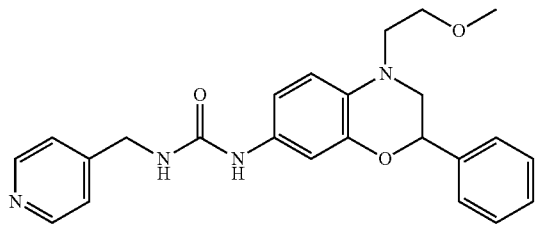 [SMILES: COCCN1CC(c2ccccc2)Oc2cc(NC(=O)NCc3ccncc3)ccc21]

(Example 48-a) 4-(2-Methoxyethyl)-7-nitro-2-phenyl-2H-1,4-benzoxazin-3(4H)-one

7-Nitro-2-phenyl-2H-1,4-benzoxazin-3(4H)-one (0.35 g, 1.3 mmol) obtained in Example 47-a and cesium carbonate (0.92 mg, 2.6 mmol) were dissolved in N,N-dimethylformamide (2 mL). To the solution was added 2-bromoethyl methyl ether (0.18 ml, 1.9 mmol). The mixture was stirred at room temperature for 12 h. Water was added to the reaction solution, followed by extraction with ethyl acetate. The organic phase was concentrated. The obtained residue was purified by silica gel column chromatography (ethyl acetate:hexane=20:80 to 50:50) to give the title compound (0.20 g, 0.61 mmol, 47%) as an oil.

(Example 48-b) 4-(2-Methoxyethyl)-7-nitro-2-phenyl-3,4-dihydro-2H-1,4-benzoxazine 4-(2-Methoxyethyl)-7-nitro-2-phenyl-2H-1,4-benzoxazin-3(4H)-one (0.10 g, 0.30 mmol) obtained in Example 48-a was dissolved in THF (8 mL). To the solution was added a 1.0 M solution of a borane-tetrahydrofuran complex in THF (0.50 ml, 0.50 mmol). The mixture was stirred at room temperature for 10 h. A small amount of methanol and water were added to the reaction solution, followed by extraction with ethyl acetate. The organic phase was concentrated. The obtained residue was purified by silica gel column chromatography (ethyl acetate:hexane=20:80 to 50:50) to give the title compound (0.061 g, 0.19 mmol, 64%) as an oil.

LCMS (ES): m/z 315 [M+H]⁺.

(Example 48-c) 4-(2-Methoxyethyl)-2-phenyl-3,4-dihydro-2H-1,4-benzoxazin-7-amine 4-(2-Methoxyethyl)-7-nitro-2-phenyl-3,4-dihydro-2H-1,4-benzoxazine (61 mg, 0.19 mmol) obtained in Example 48-b was dissolved in methanol (5 mL) and ethyl acetate (5 mL). To the solution added was 10% palladium carbon (M), wet (60 mg). The mixture was stirred at room temperature for 5 h under the hydrogen atmosphere. The reaction solution was filtered through celite. The filtrate was concentrated under reduced pressure. The obtained residue was purified by silica gel column chromatography (ethyl acetate:methanol=100:0 to 75:25) to give the title compound (51 mg, 0.18 mmol, 92%) as an oil.

LCMS (ES): m/z 285 [M+H]⁺.

(Example 48-d)N-[4-(2-Methoxyethyl)-2-phenyl-3,4-dihydro-2H-1,4-benzoxazin-7-yl]⁻N'-[(pyridin-4-yl)methyl]urea The title compound (0.035 g, 0.47 mmol, 47%) was obtained as a solid in the same way as in Example 17-d using 4-(2-methoxyethyl)-2-phenyl-3,4-dihydro-2H-1,4-benzoxazin-7-amine (0.051 g, 0.18 mmol) obtained in Example 48-c.

$^1$H NMR (400 MHz, CDCl$_3$) δ (ppm) 3.32 (s, 3H), 3.38-3.57 (m, 6H), 4.42 (d, J=6.3 Hz, 2H), 5.00 (dd, J=8.8, 2.4 Hz, 1H), 5.07 (t, J=5.9 Hz, 1H), 5.99 (s, 1H), 6.67 (d, J=8.8 Hz, 1H), 6.76 (dd, J=8.5, 2.2 Hz, 1H), 6.80 (d, J=2.4 Hz, 1H), 7.16 (d, J=5.9 Hz, 2H), 7.32-7.41 (m, 5H), 8.51 (t, J=2.9 Hz, 2H).

LCMS (ES): m/z 419 [M+H]⁺.

Example 49

2-(2-Chlorophenyl)-N-ethyl-7-({[(pyridin-4-yl)methyl]carbamoyl}amino)-2,3-dihydro-4H-1,4-benzoxazine-4-carboxamide

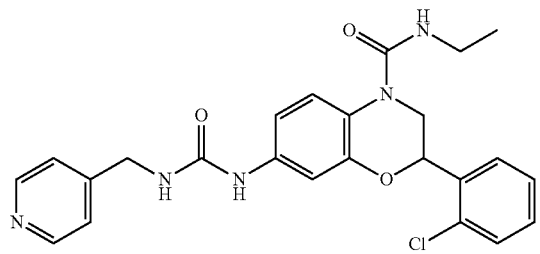 [SMILES: CCNC(=O)N1CC(c2ccccc2Cl)Oc2cc(NC(=O)NCc3ccncc3)ccc21]

(Example 49-a) 2-(2-Chlorophenyl)-7-nitro-3,4-dihydro-2H-1,4-benzoxazine

The title compound (1.43 g, 4.9 mmol) was obtained in the same way as in Example 47-a and Example 47-d using methyl bromo(2-chlorophenyl)acetate (1.8 ml, 11 mmol).

(Example 49-b) 2-(2-Chlorophenyl)-N-ethyl-7-nitro-2,3-dihydro-4H-1,4-benzoxazine-4-carboxamide 2-(2-Chlorophenyl)-7-nitro-3,4-dihydro-2H-1,4-benzoxazine (100 mg, 0.344 mmol) obtained in Example 49-a was suspended in acetone (10 mL). To the suspension was added cesium carbonate (400 mg, 1.2 mmol). The mixture was heated at 50° C. to prepare a homogeneous solution. Then, ethyl isocyanate (100 mg, 1.4 mmol) was added thereto, and the mixture was stirred at 50° C. for 2 h. The reaction solution was concentrated. The obtained residue was purified by silica gel column chromatography (ethyl acetate:hexane=20:80 to 50:50) to give the title compound (130 mg, 0.36 mmol, 100%) as an oil.

$^1$H NMR (500 MHz, CDCl$_3$) δ (ppm) 1.11 (t, J=7.6 Hz, 3H), 3.24-3.39 (m, 3H), 4.50 (dd, J=13.4, 2.7 Hz, 1H), 5.07 (brs, 1H), 5.54 (dd, J=8.1, 2.7 Hz, 1H), 7.28-7.33 (m, 3H), 7.38-7.44 (m, 2H), 7.62 (d, J=9.3 Hz, 1H), 7.84 (dd, J=9.0, 2.7 Hz, 1H).

(Example 49-c) 7-Amino-2-(2-chlorophenyl)-N-ethyl-2,3-dihydro-4H-1,4-benzoxazine-4-carboxamide To 2-(2-chlorophenyl)-N-ethyl-7-nitro-2,3-dihydro-4H-1,4-benzoxazine-4-carboxamide (130 mg, 0.36 mmol) obtained in Example 49-b were added water (1 mL), THF (8 mL), ammonium chloride (60 mg, 1.0 mmol), and zinc (110 mg, 1.7 mmol). The mixture was stirred at 90° C. for 2 h. Insoluble matter was filtered off. Then, the reaction solution was concentrated. The obtained residue was purified by silica gel column chromatography (ethyl acetate:hexane=50:50 to 100:0) to give the title compound (65 mg, 0.20 mmol, 56%) as an oil.
$^1$H NMR (500 MHz, CDCl$_3$) δ (ppm) 1.04 (t, J=7.3 Hz, 3H), 3.10-3.36 (m, 3H), 4.51 (dd, J=13.7, 2.9 Hz, 1H), 5.19 (brs, 1H), 5.50 (dd, J=7.8, 2.9 Hz, 1H), 6.30 (dd, J=8.3, 2.4 Hz, 1H), 6.40 (d, J=2.4 Hz, 1H), 7.03 (d, J=8.8 Hz, 1H), 7.33-7.43 (m, 4H).
LCMS (ES): m/z 332 [M+H]$^+$.

(Example 49-d) 2-(2-Chlorophenyl)-N-ethyl-7-({[(pyridin-4-yl)methyl]carbamoyl}amino)-2,3-dihydro-4H-1,4-benzoxazine-4-carboxamide The title compound (30 mg, 0.064 mmol, 33%) was obtained as a solid in the same way as in Example 17-d using 7-amino-2-(2-chlorophenyl)-N-ethyl-2,3-dihydro-4H-1,4-benzoxazine-4-carboxamide (65 mg, 0.20 mmol) obtained in Example 49-c.
$^1$H NMR (500 MHz, DMSO-d$_6$) δ (ppm) 0.92 (t, J=7.3 Hz, 3H), 2.99-3.07 (m, 2H), 3.49 (dd, J=13.7, 7.3 Hz, 1H), 4.13 (dd, J=13.7, 2.4 Hz, 1H), 4.32 (d, J=5.9 Hz, 2H), 5.40 (dd, J=7.3, 2.4 Hz, 1H), 6.71 (t, J=5.9 Hz, 2H), 6.87 (dd, J=8.8, 2.4 Hz, 1H), 7.27-7.31 (m, 4H), 7.37-7.44 (m, 3H), 7.50-7.52 (m, 1H), 8.50 (d, J=5.9 Hz, 2H), 8.69 (s, 1H).
LCMS (ES): m/z 466 [M+H]$^+$.

Example 50

N,N-Diethyl-6-({[(pyridin-4-yl)methyl]carbamoyl}amino)-1,2-benzoxazole-3-carboxamide

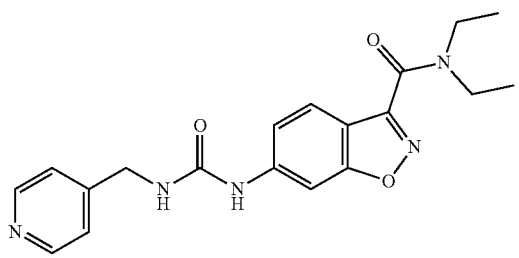 [SMILES: CCN(CC)C(=O)c1noc2cc(NC(=O)NCc3ccncc3)ccc12]

(Example 50-a) Methyl 6-[(diphenylmethylidene)amino]-1,2-benzoxazole-3-carboxylate To a solution of methyl 6-bromo-1,2-benzoxazole-3-carboxylate (0.50 g, 2.0 mmol) in toluene (20 mL) were added benzophenone imine (0.50 ml, 2.9 mmol), cesium carbonate (1.1 g, 2.9 mmol), 9,9-dimethyl-4,5-bis(diphenylphosphino)xanthene, (0.24 g, 0.39 mmol), and palladium(II) acetate (53 mg, 0.20 mmol). The mixture was stirred at 100° C. for 12 h. The reaction solution was concentrated. The obtained residue was purified by silica gel column chromatography (ethyl acetate:hexane=0:100 to 70:30) to give the title compound (0.59 g, 1.7 mmol, 85%) as a solid.
$^1$H NMR (500 MHz, CDCl$_3$) δ (ppm) 4.04 (s, 3H), 6.85 (dd, J=8.8, 1.5 Hz, 1H), 6.92 (d, J=1.0 Hz, 1H), 7.08-7.17 (m, 2H), 7.22-7.32 (m, 3H), 7.41-7.55 (m, 3H), 7.77-7.87 (m, 3H).
LCMS (ES): m/z 357 [M+H]$^+$.

(Example 50-b) Methyl 6-amino-1,2-benzoxazole-3-carboxylate-hydrogen chloride (1/1)

Methyl 6-[(diphenylmethylidene)amino]-1,2-benzoxazole-3-carboxylate (0.59 g, 1.7 mmol) obtained in Example 50-a was dissolved in dichloromethane (10 mL). To the solution was added 4 M hydrogen chloride in dioxane (1.0 ml, 4.0 mmol). The mixture was stirred at room temperature for 12 h. The reaction solution was concentrated. The obtained residue was diluted by the addition of ethyl acetate. Then, the precipitated solid was collected by filtration. The solid was washed with ethyl acetate and hexane to give the title compound (0.25 g, 1.1 mmol, 66%) as a solid.
$^1$H NMR (500 MHz, DMSO-d$_6$) δ (ppm) 3.96 (s, 3H), 6.74 (d, J=1.5 Hz, 1H), 6.80 (dd, J=8.8, 2.0 Hz, 1H), 7.65 (d, J=8.8 Hz, 1H).
LCMS (ES): m/z 193 [M+H]$^+$ (as free).

(Example 50-c) Methyl 6-({[(pyridin-4-yl)methyl]carbamoyl}amino)-1,2-benzoxazole-3-carboxylate The title compound (180 mg, 0.55 mmol, 70%) was obtained as a solid in the same way as in Example 17-d using methyl 6-amino-1,2-benzoxazole-3-carboxylate-hydrogen chloride (1/1) (180 mg, 0.79 mmol) obtained in Example 50-b.
$^1$H NMR (500 MHz, CD$_3$OD) δ (ppm) 4.05 (s, 3H), 4.49 (s, 2H), 7.29 (dd, J=8.5, 1.7 Hz, 1H), 7.42 (d, J=6.3 Hz, 2H), 7.94 (d, J=8.8 Hz, 1H), 8.11 (s, 1H), 8.48 (d, J=5.9 Hz, 2H).
LCMS (ES): m/z 327 [M+H]$^+$.

(Example 50-d) 6-({[(Pyridin-4-yl)methyl]carbamoyl}amino)-1,2-benzoxazole-3-carboxylic acid Methyl 6-({[(pyridin-4-yl)methyl]carbamoyl}amino)-1,2-benzoxazole-3-carboxylate (155 mg, 0.48 mmol) obtained in Example 50-c was dissolved in methanol (10 mL) and THF (3 mL). To the solution was added a 1 mol/l sodium hydroxide solution (2 mL). The mixture was stirred at room temperature for 15 h. The reaction solution was neutralized by the addition of 1 N hydrochloric acid and then concentrated under reduced pressure. The precipitated solid was collected by filtration using water to give the title compound (139 mg, 0.15 mmol, 94%) as a solid.
$^1$H NMR (500 MHz, DMSO-d$_6$) δ (ppm) 4.33 (d, J=5.9 Hz, 2H), 6.83 (dd, J=8.3, 2.0 Hz, 1H), 6.88 (t, J=6.1 Hz, 1H), 7.28 (d, J=5.9 Hz, 2H), 7.35 (d, J=2.0 Hz, 1H), 7.40 (d, J=8.8 Hz, 1H), 8.50 (dd, J=4.4, 1.5 Hz, 2H), 9.14 (s, 1H), 10.85 (s, 1H).

(Example 50-e) N,N-Diethyl-6-({[(pyridin-4-yl)methyl]carbamoyl}amino)-1,2-benzoxazole-3-carboxamide 6-({[(Pyridin-4-yl)methyl]carbamoyl}amino)-1,2-benzoxazole-3-carboxylic acid (19 mg, 0.061 mmol) obtained in Example 50-d was dissolved in N,N-dimethylformamide (1 mL). To the solution were added diethylamine (0.015 ml, 0.12 mmol), DIPEA (0.035 ml, 0.24 mmol), and HATU (37 mg, 0.12 mmol). The mixture was stirred at room temperature for 12 h. The reaction solution was concentrated. The obtained residue was purified by silica gel column chromatography (NH+SiO$_2$ silica, ethyl acetate:methanol=100:0 to 75:25) to give the title compound (4.6 mg, 0.022 mmol, 21%) as a solid.

$^1$H NMR (500 MHz, CD$_3$OD) δ (ppm) 1.24 (t, J=7.3 Hz, 3H), 1.30 (t, J=7.2 Hz, 3H), 3.58 (q, J=7.0 Hz, 2H), 3.64 (q, J=7.2 Hz, 2H), 4.49 (s, 2H), 7.23 (dd, J=8.8, 1.5 Hz, 1H), 7.41 (d, J=6.3 Hz, 2H), 7.69 (d, J=8.8 Hz, 1H), 8.07 (d, J=1.5 Hz, 1H), 8.48 (d, J=5.9 Hz, 2H).

LCMS (ES): m/z 368 [M+H]$^+$.

Example 51

N-(2-Phenyl-2,3-dihydro-1-benzofuran-6-yl)-N'-[(pyridin-4-yl)methyl]urea

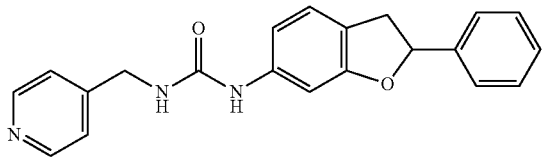 [SMILES: O=C(NCc1ccncc1)Nc1ccc2c(c1)OC(c1ccccc1)C2]

(Example 51-a) 2-iodo-5-nitrophenol

To a solution of 2-amino-5-nitro-phenol (3.0 g, 19.5 mmol) in a mixture of 30% H$_2$SO$_4$ (60 mL) and DMSO (60 mL) was added a solution of NaNO$_2$ (2 g, 29.5 mmol) in H$_2$O (10 mL) dropwise under 5° C. After stirring at 5° C. for 0.5 h, to the reaction mixture was added a solution of potassium iodide (9.7 g, 58.5 mmol) in H$_2$O (10 mL) dropwise at room temperature. After stirring at room temperature overnight, the reaction mixture was partitioned between EA (100 mL) and 10% NaHSO$_3$ (100 mL). The aqueous phase was then extracted with ether (200 mL). The organic phase was combined, dried over anhydrous Na$_2$SO$_4$, filtered and evaporated in vacuo. The residue was purified by silica gel column chromatography (DCM) to afford the title compound (3.75 g, yield 72%) as a solid.

$^1$H NMR (400 MHz, DMSO-d$_6$) δ (ppm) 11.36 (s, 1H), 7.99 (d, J=8.4 Hz, 1H), 7.62 (d, J=2.4 Hz, 1H), 7.43 (dd, J=8.4, 2.0 Hz, 1H).

(Example 51-b) 6-Nitro-2-phenyl-1-benzofuran

To a solution of 2-iodo-5-nitrophenol (2.76 g, 10.4 mmol) in ACN (100 mL) was added ethynyl-benzene (3.18 g, 31.2 mmol), Pd(PPh$_3$)$_2$Cl$_2$ (702 mg, 1 mmol), CuI (198 mg, 1 mmol) and TEA (10.5 g, 104 mmol). After stirring at 60° C. overnight under N$_2$ atmosphere, the reaction mixture was concentrated in vacuo. The residue was purified by column chromatography (ACN in water, 10% to 95%, 60 min) to give the title compound (2.17 g, yield 87%) as a solid.

$^1$H NMR (400 MHz, DMSO-d$_6$) δ (ppm) 8.57 (s, 1H), 8.19 (dd, J=8.4, 2.0 Hz, 1H), 8.01 (d, J=8.0 Hz, 2H), 7.90 (d, J=8.8 Hz, 1H), 7.69 (s, 1H), 7.60-7.52 (m, 3H).

(Example 51-c) 2-Phenyl-2,3-dihydro-1-benzofuran-6-amine

To a solution of 6-nitro-2-phenyl-1-benzofuran (1 g, 4.2 mmol) in EA (100 mL) was added 10% Pd/C (444 mg, 0.4 mmol). After stirring at room temperature overnight under balloon H$_2$ atmosphere, the reaction mixture was filtered. The filtrate was concentrated in vacuo. The residue was purified by column chromatography (ACN in water, 5% to 95%, 60 min) to give the title compound (70 mg, yield 8%) as a solid.

$^1$H NMR (400 MHz, DMSO-d$_6$) δ (ppm) 7.39-7.29 (m, 5H), 6.82 (dd, J=7.2, 1.2 Hz, 1H), 6.09-6.07 (m, 2H), 5.69 (dd, J=9.2, 7.6 Hz, 1H), 5.01 (s, 2H), 3.46 (dd, J=15.2, 8.8 Hz, 1H), 2.89 (dd, J=15.2, 7.6 Hz, 1H).

(Example 51-d) Phenyl (2-phenyl-2,3-dihydro-1-benzofuran-6-yl)carbamate

To a solution of 2-phenyl-2,3-dihydro-1-benzofuran-6-amine (130 mg, 0.61 mmol) in DCM (5 mL) was added phenyl chloroformate (233 mg, 1.2 mmol) and TEA (185 mg, 1.8 mmol). After stirring at room temperature overnight, the reaction mixture was concentrated in vacuo. The residue was purified by silica gel column chromatography (PE/EA=3:1) to give the crude title compound, which was used in the next step without further purification.

(Example 51-e) N-(2-Phenyl-2,3-dihydro-1-benzofuran-6-yl)-N'-[(pyridin-4-yl)methyl]urea To a solution of phenyl (2-phenyl-2,3-dihydro-1-benzofuran-6-yl)carbamate (66 mg, 0.2 mmol) in ACN (10 mL) was added 4-picolylamine (65 mg, 0.6 mmol) and TEA (61 mg, 0.6 mmol). The reaction mixture was stirred at 80° C. overnight. The reaction mixture was concentrated in vacuo. The residue was diluted in H$_2$O (10 mL) and extracted with EA (10 mL×3). The combined organic phase was washed with brine, dried over anhydrous Na$_2$SO$_4$, filtered and concentrated in vacuo. The residue was purified by pre-HPLC to give the title compound (31 mg, yield 45%) as a solid.

$^1$H NMR (400 MHz, DMSO-d$_6$) δ (ppm) 8.65 (s, 1H), 8.50 (d, J=5.6 Hz, 2H), 7.38-7.28 (m, 7H), 7.10 (d, J=2.0 Hz, 1H), 7.05 (d, J=8.4 Hz, 1H), 6.78 (dd, J=8.4, 2.0 Hz, 1H), 6.69 (t, J=6.0 Hz, 1H), 5.78 (dd, J=9.6, 7.6 Hz, 1H), 4.32 (d, J=6.0 Hz, 2H), 3.57 (dd, J=15.2, 9.2 Hz, 1H), 3.00 (dd, J=15.2, 7.6 Hz, 1H). MS: m/z 346.1 (M+H)+.

Example 52

N-[2-(3-Methoxyphenyl)-2,3-dihydro-1-benzofuran-6-yl]-N'-[(pyridin-4-yl)methyl]urea

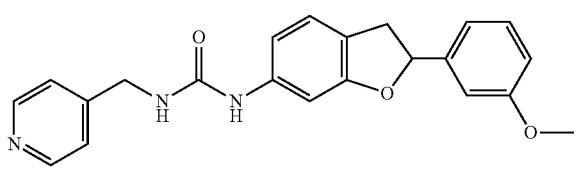 [SMILES: COc1cccc(C2Cc3ccc(NC(=O)NCc4ccncc4)cc3O2)c1]

(Example 52-a) 5-Bromo-2-[(E)-2-(3-methoxyphenyl)ethenyl]phenol

Diethyl [(3-methoxyphenyl)methyl]phosphonate (771 mg, 3.0 mmol) and 4-bromo-2-hydroxy-benzaldehyde (500 mg, 2.5 mmol) were dissolved in THF (13 mL). To the solution was added potassium tert-butoxide (586 mg, 5.2 mmol). The mixture was stirred at room temperature for 4 h.

The pH of the reaction solution was adjusted to approximately 4 by the addition of 1 N HCl, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=0:100 to 15:85) to give the title compound (514 mg, 68%).

$^1$H NMR (CDCl$_3$) δ (ppm): 3.85 (s, 3H), 6.83 (dd, J=8.50, 1.70 Hz, 1H), 6.99 (d, J=1.95 Hz, 1H), 7.04-7.13 (m, 4H), 7.23-7.29 (m, 2H), 7.37 (d, J=8.30 Hz, 1H).

(Example 52-b) 6-Bromo-2-(3-methoxyphenyl)-2,3-dihydro-1-benzofuran

5-Bromo-2-[(E)-2-(3-methoxyphenyl)ethenyl]phenol (200 mg, 0.66 mmol) obtained in (Example 52-a) was dissolved in THF (4 mL). To the solution was added an approximately 0.9 mol/L solution of a borane-tetrahydrofuran complex in THF (1.6 mL, 1.4 mmol) under ice cooling. The mixture was stirred at room temperature for 2 h. A 30% aqueous hydrogen peroxide solution (372 µL, 3.3 mmol) and a 5 N sodium hydroxide solution (655 µL, 3.3 mmol) were added to the reaction solution under ice cooling. The mixture was stirred at 40° C. for 1 h. A saturated aqueous solution of sodium thiosulfate and water were added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=0:100 to 15:85) to give a crude product (191 mg).

The obtained crude product (190 mg) was dissolved in THF (12 mL). To the solution were added triphenylphosphine (231 mg, 0.88 mmol) and bis(2-methoxyethyl) azodicarboxylate (207 mg, 0.88 mmol) under ice cooling. The mixture was stirred at room temperature for 1 h. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=1:99 to 15:85) to give the title compound (46 mg, 26%).

$^1$H NMR (CDCl$_3$) δ (ppm): 3.14 (dd, J=15.86, 8.05 Hz, 1H), 3.57 (dd, J=15.86, 9.52 Hz, 1H), 3.81 (s, 3H), 5.76 (t, J=8.79 Hz, 1H), 6.82-7.07 (m, 6H), 7.26-7.32 (m, 1H).

(Example 52-c) tert-Butyl [2-(3-methoxyphenyl)-2,3-dihydro-1-benzofuran-6-yl]carbamate 6-Bromo-2-(3-methoxyphenyl)-2,3-dihydro-1-benzofuran (46 mg, 0.151 mmol) obtained in (Example 52-b) was dissolved in toluene (2 mL). To the solution were added tert-butyl carbamate (31 mg, 0.26 mmol), 2-di-tert-butylphosphino-2',4',6'-triisopropylbiphenyl (37 mg, 0.087 mmol), tris(dibenzylideneacetone)dipalladium (20 mg, 0.022 mmol), and sodium tert-butoxide (48 mg, 0.50 mmol). The mixture was stirred at room temperature for 3 h. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=1:99 to 15:85) to give the title compound (46 mg, 90%).

$^1$H NMR (CDCl$_3$) δ (ppm): 1.52 (s, 9H), 3.12 (dd, J=15.50, 7.93 Hz, 1H), 3.56 (dd, J=15.38, 9.27 Hz, 1H), 3.80 (s, 3H), 5.73 (t, J=8.66 Hz, 1H), 6.42 (br s, 1H), 6.78-7.11 (m, 6H), 7.19-7.34 (m, 1H).

LCMS (ES): m/z 286 [M+H-tBu]$^+$.

(Example 52-d) 2-(3-Methoxyphenyl)-2,3-dihydro-1-benzofuran-6-amine tert-Butyl [2-(3-methoxyphenyl)-2,3-dihydro-1-benzofuran-6-yl]carbamate (43 mg, 0.13 mmol) obtained in (Example 52-c) was dissolved in dichloromethane (1 mL). To the solution was added TFA (0.5 mL). The mixture was stirred at room temperature for 1 h. The solvent was distilled off under reduced pressure to give the crude title compound. The crude product was purified by silica gel column chromatography (NH silica gel, ethyl acetate:hexane=0:100 to 5:95) to give the crude title compound.

(Example 52-e) N-[2-(3-Methoxyphenyl)-2,3-dihydro-1-benzofuran-6-yl]-N'-[(pyridin-4-yl)methyl]urea The crude product of 2-(3-methoxyphenyl)-2,3-dihydro-1-benzofuran-6-amine (0.13 mmol) obtained in (Example 52-d) was dissolved in 1,4-dioxane (1.5 mL). To the solution were added triethylamine (53 µL, 0.38 mmol) and 4-nitrophenyl [(pyridin-4-yl)methyl]carbamate (38 mg, 0.14 mmol). The mixture was stirred at 90° C. for 2 h. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (NH silica gel, methanol:dichloromethane=2:98 to 3:97) to give the title compound (35 mg, 77%).

$^1$H NMR (CDCl$_3$) δ (ppm): 3.16 (dd, J=15.90, 8.10 Hz, 1H), 3.58 (dd, J=15.62, 9.27 Hz, 1H), 3.80 (s, 3H), 4.45 (d, J=6.10 Hz, 2H), 5.22-5.33 (m, 1H), 5.75 (t, J=8.66 Hz, 1H), 6.45 (br s, 1H), 6.78 (dd, J=7.93, 1.83 Hz, 1 H), 6.81-6.88 (m, 2H), 6.91-6.98 (m, 2H), 7.11 (d, J=7.81 Hz, 1H), 7.21 (d, J=5.86 Hz, 2H), 7.24-7.32 (m, 1H), 8.27-8.74 (m, 2H).

LCMS (ES): m/z 376 [M+H]$^+$

Example 53

N-[(2S*,3S*)-2-(3-Methoxyphenyl)-3-methyl-2,3-dihydro-1-benzofuran-6-yl]-N'-[(pyridin-4-yl)methyl]urea

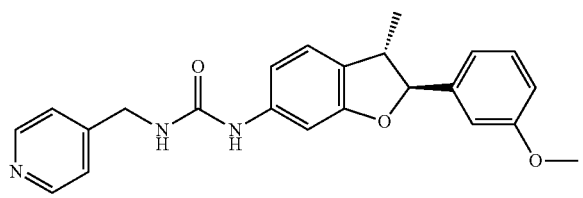 [SMILES: COc1cccc([C@H]2Oc3cc(NC(=O)NCc4ccncc4)ccc3[C@@H]2C)c1]

(Example 53-a) 1-[4-Bromo-2-(methoxymethoxy)phenyl]ethan-1-one 1-(4-Bromo-2-hydroxy-phenyl)ethanone (500 mg, 2.3 mmol) was dissolved in dichloromethane (12 mL). To the solution were added N,N-diisopropylethylamine (1.2 mL, 7.0 mmol) and chloromethyl methyl ether (210 µL, 2.8 mmol) under ice cooling. The mixture was stirred at room temperature for 2 h. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=0:100 to 15:85) to give the title compound (484 mg, 80%).

$^1$H NMR (CDCl$_3$) δ (ppm): 2.61 (s, 3H), 3.52 (s, 3H), 5.28 (s, 2H), 7.20 (dd, J=8.30, 1.71 Hz, 1H), 7.38 (d, J=1.71 Hz, 1H), 7.60 (d, J=8.30 Hz, 1H).

(Example 53-b) 4-Bromo-2-(methoxymethoxy)-1-[1-(3-methoxyphenyl)prop-1-en-2-yl]benzene Diethyl [(3-methoxyphenyl)methyl]phosphonate (425 mg, 1.6 mmol) was dissolved in DMF (4 mL). To the solution was added sodium hydride (63 wt % dispersion in paraffin liquid) (63 mg, 1.6 mmol). The mixture was stirred for 10 min. A solution of 1-[4-bromo-2-(methoxymethoxy)phenyl]ethan-1-one (284 mg, 1.1 mmol) obtained in (Example 53-a) in DMF (2 mL) was added thereto, and the mixture was stirred overnight at room temperature. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=5:95 to 20:80) to give the title isomeric mixture (285 mg, 72%).

(Example 53-c) 5-Bromo-2-[1-(3-methoxyphenyl)prop-1-en-2-yl]phenol

4-Bromo-2-(methoxymethoxy)-1-[1-(3-methoxyphenyl)prop-1-en-2-yl]benzene (280 mg, 0.77 mmol) obtained in (Example 53-b) was dissolved in MeOH (1 mL). To the solution was added 4 N HCl in 1,4-dioxane (0.5 mL). The mixture was stirred at room temperature for 2 h. The pH of the reaction solution was adjusted to approximately 4 by the addition of an aqueous sodium bicarbonate solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=0:100 to 15:85) to give the title isomeric mixture (233 mg, 95%).

(Example 53-d) 5-Bromo-2-[(1R*,2S*)-1-hydroxy-1-(3-methoxyphenyl)propan-2-yl]phenol 5-Bromo-2-[1-(3-methoxyphenyl)prop-1-en-2-yl]phenol (200 mg, 0.6 mmol) obtained in (Example 53-c) was dissolved in THF (3.6 mL). To the solution was added an approximately 0.9 mol/L borane-THF complex in THF (1.7 mL, 1.6 mmol) under ice cooling. The mixture was stirred at room temperature for 2 h. 5 N NaOH and a 30% aqueous hydrogen peroxide solution were added thereto under ice cooling, and the mixture was stirred at 40° C. for 1 h. Water and a saturated aqueous solution of sodium thiosulfate were added thereto, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=5:95 to 15:85) to give an isomeric mixture containing the title compound (226 mg, 93%).

(Example 53-e) (2S*,3S*)-6-Bromo-2-(3-methoxyphenyl)-3-methyl-2,3-dihydro-1-benzofuran The isomeric mixture of 5-bromo-2-[(1R*,2S*)-1-hydroxy-1-(3-methoxyphenyl)propan-2-yl]phenol (222 mg, 0.6 mmol) obtained in (Example 53-d) was dissolved in THF (13 mL). To the solution were added triphenyl phosphine (173 mg, 0.66 mmol) and bis(2-methoxyethyl) azodicarboxylate (154 mg, 0.66 mmol) under ice cooling. The mixture was stirred at room temperature for 1 h. Water, a phosphate buffer solution of pH=7, a saturated aqueous solution of sodium bicarbonate, and 1 N HCl were added thereto, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=5:95 to 15:85) to give the title compound (125 mg, 60%).

$^1$H NMR (CDCl$_3$) δ (ppm): 1.41 (d, J=6.83 Hz, 3H), 3.33-3.41 (m, 1H), 3.81 (s, 3H), 5.16 (d, J=8.54 Hz, 1H), 6.85-7.06 (m, 6H), 7.27-7.36 (m, 1H).

(Example 53-f) tert-Butyl [(2S*,3S*)-2-(3-methoxyphenyl)-3-methyl-2,3-dihydro-1-benzofuran-6-yl]carbamate (2S*,3S*)-6-Bromo-2-(3-methoxyphenyl)-3-methyl-2,3-dihydro-1-benzofuran (115 mg, 0.36 mmol) obtained in (Example 53-e) was dissolved in toluene (4 mL). To the solution were added tert-butyl carbamate (51 mg, 0.43 mmol), 2-di-tert-butylphosphino-2',4',6'-triisopropylbiphenyl (62 mg, 0.14 mmol), tris(dibenzylideneacetone)dipalladium (33 mg, 0.036 mmol), and sodium tert-butoxide (80 mg, 0.83 mmol). The mixture was stirred at room temperature for 3 h. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=1:99 to 15:85) to give the title compound (92 mg, 72%).

$^1$H NMR (CDCl$_3$) δ (ppm): 1.40 (d, J=6.59 Hz, 3H), 1.52 (s, 9H), 3.32-3.41 (m, 1H), 3.81 (s, 3H), 5.13 (d, J=8.30 Hz, 1H), 6.43 (br s, 1H), 6.83-7.05 (m, 6H), 7.26 (s, 1H).

LCMS (ES): m/z 286 [M+H-tBu]$^+$.

(Example 53-g) (2S*,3S*)-2-(3-Methoxyphenyl)-3-methyl-2,3-dihydro-1-benzofuran-6-amine tert-Butyl [(2S*,3S*)-2-(3-methoxyphenyl)-3-methyl-2,3-dihydro-1-benzofuran-6-yl]carbamate (90 mg, 0.25 mmol) obtained in (Example 53-f) was dissolved in dichloromethane (1 mL). To the solution was added TFA (0.5 mL).

The mixture was stirred at room temperature for 1 h. The solvent was distilled off under reduced pressure to give the crude title compound.

(Example 53-h)N-[(2S*,3S*)-2-(3-Methoxyphenyl)-3-methyl-2,3-dihydro-1-benzofuran-6-yl]-N'-[(pyridin-4-yl)methyl]urea The crude product of (2S*,3S*)-2-(3-methoxyphenyl)-3-methyl-2,3-dihydro-1-benzofuran-6-amine (0.13 mmol) obtained in (Example 53-g) was dissolved in 1,4-dioxane (1.5 mL). To the solution were added triethylamine (53 µL, 0.38 mmol) and 4-nitrophenyl [(pyridin-4-yl)methyl]carbamate (39 mg, 0.14 mmol). The mixture was stirred at 90° C. for 2 h. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (NH silica gel, methanol:dichloromethane=1:99 to 3:97) to give the title compound (35 mg, 70%).

$^1$H NMR (CDCl$_3$) δ (ppm): 1.41 (d, J=6.83 Hz, 3H), 3.40 (quin, J=7.08 Hz, 1H), 3.81 (s, 3H), 4.47 (d, J=6.10 Hz, 2H), 5.16 (d, J=8.54 Hz, 1H), 5.23-5.30 (m, 1H), 6.41 (br s, 1H), 6.78-6.90 (m, 3H), 6.93-7.00 (m, 2H), 7.07 (d, J=7.57 Hz, 1H), 7.19-7.32 (m, 3H), 8.53-8.57 (m, 2H).
LCMS (ES): m/z 390 [M+H]$^+$ Example 54

N-(3-Phenyl-2,3-dihydro-1-benzofuran-6-yl)-N'-[(pyridin-4-yl)methyl]urea

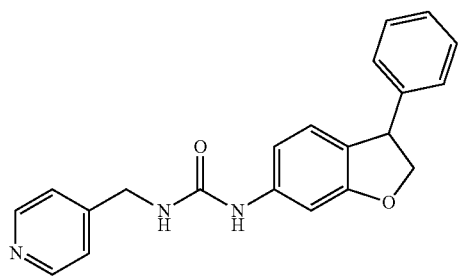 [SMILES: O=C(NCc1ccncc1)Nc1ccc2c(c1)OCC2c1ccccc1]

(Example 54-a) [4-Bromo-2-(methoxymethoxy)phenyl] (phenyl)methanol

4-Bromo-2-(methoxymethoxy)benzaldehyde (1000 mg, 4.1 mmol) obtained in the same way as in (Example 53-a) was dissolved in THF (21 mL). To the solution was added 1 mol/L phenyl magnesium bromide in THF (4.5 mL, 4.5 mmol) under ice cooling. The mixture was stirred at room temperature for 1 h. Water was added to the reaction solution, followed by partition operation using ethyl acetate. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=0:100 to 15:85) to give the title compound (1259 mg, 96%).

$^1$H NMR (CDCl$_3$) δ (ppm): 2.62 (d, J=5.37 Hz, 1H), 3.27 (s, 3H), 5.05-5.16 (m, 2H), 6.02 (d, J=5.13 Hz, 1H), 7.09-7.42 (m, 8H).

(Example 54-b) [4-Bromo-2-(methoxymethoxy)phenyl] (phenyl)methanone

[4-Bromo-2-(methoxymethoxy)phenyl] (phenyl)methanol (1256 mg, 3.9 mmol) obtained in (Example 54-a) was dissolved in dichloromethane (20 mL). To the solution was added manganese (IV) oxide (3768 mg, 43 mmol). The mixture was stirred at room temperature for 2 h. The reaction solution was filtered through celite. Then, the solvent was distilled off under reduced pressure to give the crude title compound. The crude product was purified by silica gel column chromatography (silica gel, ethyl acetate:hexane=0:100 to 10:90) to give the title compound (785 mg, 63%).

$^1$H NMR (CDCl$_3$) δ (ppm): 3.31 (s, 3H), 5.04 (s, 2H), 7.23-7.29 (m, 2H), 7.38-7.60 (m, 4H), 7.77-7.83 (m, 2H).
LCMS (ES): m/z 321 [M+H]$^+$.

(Example 54-c) 4-Bromo-2-(methoxymethoxy)-1-(1-phenylethenyl)benzene

Methyltriphenylphosphonium bromide was dissolved in THF (5 mL). To the solution was added 1.6 mol/l n-butyllithium in hexane (0.88 mL, 1.4 mmol) at −78° C. The mixture was stirred at room temperature for 1 h. After cooling to −78° C. again, a solution of [4-bromo-2-(methoxymethoxy)phenyl] (phenyl)methanone (300 mg, 0.9 mmol) obtained in (Example 54-b) in THF (1 mL) was added thereto, and the mixture was stirred for 3 h under ice cooling. Water was added to the reaction solution, followed by partition operation using diethyl ether. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=0:100 to 10:90) to give the title compound (272 mg, 91%).

$^1$H NMR (CDCl$_3$) δ (ppm): 3.15 (s, 3H), 4.92 (s, 2H), 5.30 (d, J=0.98 Hz, 1H), 5.70 (d, J=0.98 Hz, 1H), 7.09-7.33 (m, 8H).

(Example 54-d)
5-Bromo-2-(1-phenylethenyl)phenol

The crude title compound was obtained in the same way as in Example 53-c using 4-bromo-2-(methoxymethoxy)-1-(1-phenylethenyl)benzene (100 mg, 0.32 mmol) obtained in (Example 54-c), and used in the next reaction without further purification.

(Example 54-e) 5-Bromo-2-(2-hydroxy-1-phenylethyl)phenol

The crude title compound was obtained in the same way as in (Example 53-d) using the crude product of 5-bromo-2-(1-phenylethenyl)phenol obtained in (Example 54-d). The crude product was purified by silica gel column chromatography (silica gel, ethyl acetate:hexane=15:85 to 40:60) to give the title compound (27 mg, 28%).

$^1$H NMR (CDCl$_3$) δ (ppm): 4.22-4.44 (m, 3H), 6.85 (d, J=8.30 Hz, 1H), 6.97 (dd, J=8.05, 1.95 Hz, 1H), 7.09 (d, J=1.95 Hz, 1H), 7.18-7.38 (m, 5H), 7.58 (s, 1H).
LCMS (ES): m/z 291 [M−H]$^+$.

(Example 54-f)
6-Bromo-3-phenyl-2,3-dihydro-1-benzofuran

The crude title compound was obtained in the same way as in (Example 53-e) using 5-bromo-2-(2-hydroxy-1-phenylethyl)phenol (30 mg, 0.1 mmol) obtained in (Example 54-e). The crude product was purified by silica gel column chromatography (silica gel, ethyl acetate:hexane=0:100 to 15:85) to give the title compound (16 mg, 58%).

$^1$H NMR (CDCl$_3$) δ (ppm): 4.44 (dd, J=8.91, 7.44 Hz, 1H), 4.54-4.67 (m, 1H), 4.86-5.02 (m, 1H), 6.86 (dd, J=7.93, 0.85 Hz, 1H), 6.98 (dd, J=8.05, 1.71 Hz, 1H), 7.03 (d, J=1.71 Hz, 1H), 7.15-7.36 (m, 5H).

(Example 54-g) tert-Butyl (3-phenyl-2,3-dihydro-1-benzofuran-6-yl)carbamate

The crude title compound was obtained in the same way as in (Example 53-f) using 6-bromo-3-phenyl-2,3-dihydro-1-benzofuran (87 mg, 0.3 mmol) obtained in (Example 54-f). The crude product was purified by silica gel column chromatography (silica gel, ethyl acetate:hexane=0:100 to 10:90) to give the title compound (35 mg, 36%).

$^1$H NMR (CDCl$_3$) δ (ppm) 1.52 (s, 9H), 4.41 (dd, J=8.79, 7.08 Hz, 1H), 4.54-4.65 (m, 1H), 4.90 (t, J=9.15 Hz, 1H), 6.43 (br s, 1H), 6.78 (br d, J=7.81 Hz, 1H), 6.89 (d, J=8.05 Hz, 1H), 6.98-7.06 (m, 1H), 7.14-7.68 (m, 5H).

(Example 54-h) N-(3-Phenyl-2,3-dihydro-1-benzofuran-6-yl)-N'-[(pyridin-4-yl)methyl]urea The crude title compound was obtained in the same way as in (Example 53-g) and (Example 53-h) using tert-butyl (3-phenyl-2,3-dihydro-1-benzofuran-6-yl)carbamate (34 mg, 0.1 mmol) obtained in (Example 54-g). The crude product was purified by silica gel column chromatography (NH silica gel+silica gel, methanol:dichloromethane=2:98 to 7:93) to give the title compound (31 mg, 82%).

$^1$H NMR (CDCl$_3$) δ (ppm): 4.42-4.48 (m, 3H), 4.58-4.67 (m, 1H), 4.93 (t, J=9.27 Hz, 1H), 5.20-5.30 (m, 1H), 6.44 (br s, 1H), 6.73 (dd, J=7.93, 1.83 Hz, 1H), 6.88 (d, J=1.71 Hz, 1H), 6.94 (d, J=8.05 Hz, 1H), 7.16-7.36 (m, 7H), 8.54 (d, J=5.86 Hz, 2H).

LCMS (ES): m/z 346 [M+H]$^+$

Example 55

N,N-Diethyl-6-({[(pyridin-4-yl)methyl]carbamoyl}amino)-1-benzofuran-3-carboxamide

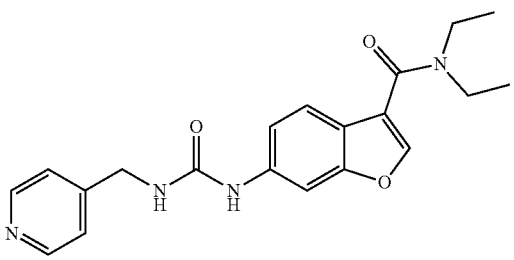 [SMILES: CCN(CC)C(=O)c1coc2cc(NC(=O)NCc3ccncc3)ccc12]

(Example 55-a) Ethyl 6-bromo-1-benzofuran-3-carboxylate

4-Bromo-2-hydroxy-benzaldehyde (1500 mg, 7.5 mmol) was dissolved in dichloromethane (19 mL). To the solution were added ethyl diazoacetate (1393 μL, 13.4 mmol) and hydrofluoboric acid (47 μL, 0.75 mmol). The mixture was stirred at room temperature for 40 min. A most part of the solvent was distilled off under reduced pressure. Then, concentrated sulfuric acid (0.75 mL) was added to the residue. The mixture was stirred at room temperature for 15 min. Dichloromethane and an aqueous sodium bicarbonate solution were added to the reaction solution, followed by partition operation using dichloromethane. The organic phase was washed with brine, then dried over sodium sulfate, and filtered. Then, the solvent was distilled off under reduced pressure to give the crude title compound. The crude product was purified by silica gel column chromatography (silica gel, ethyl acetate:hexane=0:100 to 8:92) to give the title compound (1664 mg, 83%).

$^1$H NMR (CDCl$_3$) δ (ppm): 1.42 (t, J=7.20 Hz, 3H), 4.41 (q, J=7.08 Hz, 2H), 7.48 (dd, J=8.42, 1.59 Hz, 1H), 7.72 (d, J=1.22 Hz, 1H), 7.93 (d, J=8.54 Hz, 1H), 8.22 (s, 1 H).

(Example 55-b) 6-Bromo-1-benzofuran-3-carboxylic acid

Ethyl 6-bromo-1-benzofuran-3-carboxylate (1261 mg, 4.7 mmol) obtained in (Example 55-a) was dissolved in THF (10 mL) and MeOH (10 mL). To the solution was added 5 N NaOH (2.9 mL, 14 mmol). The mixture was stirred at room temperature for 1 h. The reaction solution was rendered acidic by the addition of 1 N HCl and water. The precipitated solid was collected by filtration, washed with water, and then dried under reduced pressure to give a crude product (1076 mg, 95%), which was used in the next reaction without further purification.

$^1$H NMR (DMSO-d$_6$) δ (ppm): 7.56 (dd, J=8.42, 1.59 Hz, 1H), 7.90 (d, J=8.30 Hz, 1H), 8.05 (d, J=1.46 Hz, 1H), 8.70 (s, 1H), 13.11 (br s, 1H).

LCMS (ES): m/z 239 [M–H]$^+$.

(Example 55-c) 6-Bromo-N,N-diethyl-1-benzofuran-3-carboxamide

6-Bromo-1-benzofuran-3-carboxylic acid (400 mg, 1.7 mmol) obtained in (Example 55-b) was dissolved in DMF (6 mL). To the solution were added diethylamine (260 μL, 2.5 mmol), N,N-diisopropylethylamine (280 μL, 1.7 mmol), and DMT-MM·H$_2$O (636 mg, 2.2 mmol). The mixture was stirred overnight at room temperature. Water was added to the reaction solution, followed by partition operation using ethyl acetate. The organic phase was washed with brine, then dried over sodium sulfate, and filtered. Then, the solvent was distilled off under reduced pressure to give the crude title compound (442 mg, 90%), which was used in the next reaction without further purification.

$^1$H NMR (CDCl$_3$) δ (ppm): 1.24 (br s, 6H), 3.52 (br s, 4 H), 7.43 (dd, J=8.41, 1.76 Hz, 1H), 7.61 (d, J=8.41 Hz, 1H), 7.70 (d, J=1.56 Hz, 1H), 7.76 (s, 1H).

(Example 55-d) tert-Butyl [3-(diethylcarbamoyl)-1-benzofuran-6-yl]carbamate

The crude title compound was obtained in the same way as in (Example 53-f) using 6-bromo-N,N-diethyl-1-benzofuran-3-carboxamide (440 mg, 1.5 mmol) obtained in (Example 55-c). The crude product was purified by silica gel column chromatography (silica gel, ethyl acetate: hexane=20:80 to 50:50) to give the title compound (481 mg, 97%).

$^1$H NMR (CDCl$_3$) δ (ppm): 1.25 (br s, 6H), 1.54 (s, 9H), 3.53 (br s, 4H), 6.56-6.63 (m, 1H), 7.04 (d, J=8.50 Hz, 1H), 7.59 (d, J=8.30 Hz, 1H), 7.73 (s, 1H), 7.91 (br s, 1H).

LCMS (ES): m/z 333 [M+H]$^+$.

(Example 55-e) N,N-Diethyl-6-({[(pyridin-4-yl) methyl]carbamoyl}amino)-1-benzofuran-3-carboxamide The crude title compound was obtained in the same way as in (Example 53-g) and (Example 53-h) using tert-butyl [3-(diethylcarbamoyl)-1-benzofuran-6-yl]carbamate (30 mg, 0.09 mmol) obtained in (Example 55-d). The crude product was purified by silica gel column chromatography (NH silica gel+silica gel, methanol:dichloromethane=2:98 to 7:93) to give the title compound (18 mg, 56%).

$^1$H NMR (CDCl$_3$) δ (ppm): 1.13-1.33 (m, 6H), 3.49 (br s, 4H), 4.35 (d, J=5.86 Hz, 2H), 6.21-6.34 (m, 1H), 6.73 (dd, J=8.54, 1.46 Hz, 1H), 7.17 (br d, J=5.13 Hz, 2H), 7.38 (d, J=8.30 Hz, 1H), 7.62-7.76 (m, 2H), 7.85 (br s, 1H), 8.47 (d, J=5.10 Hz, 2H).

LCMS (ES): m/z 367 [M+H]$^+$

Example 56

N-Benzyl-N-ethyl-6-({[(pyridin-4-yl)methyl] carbamoyl}amino)-1,2-benzoxazole-3-carboxamide

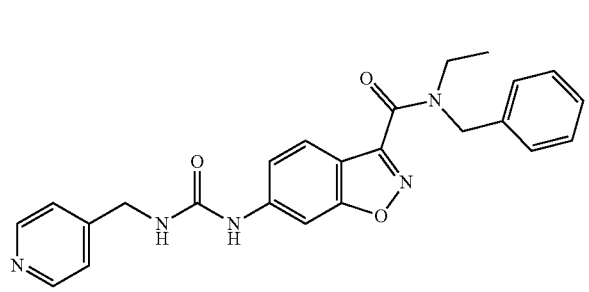 [SMILES: CCN(Cc1ccccc1)C(=O)c1noc2cc(NC(=O)NCc3ccncc3)ccc12]

The title compound (11 mg, 0.034 mmol, 32%) was obtained as a solid in the same way as in Example 50-e using 6-({[(pyridin-4-yl)methyl]carbamoyl}amino)-1,2-benzoxazole-3-carboxylic acid (25 mg, 0.080 mmol) and n-ethyl-benzylamine (0.024 ml, 0.16 mmol).

$^1$H NMR (CD$_3$OD) δ (ppm): 1.18-1.26 (m, 3H), 3.55-3.58 (m, 2H), 4.49 (s, 2H), 4.86 (s, 2H), 7.21-7.33 (m, 4H), 7.36-7.44 (m, 4H), 7.72 (d, J=8.8 Hz, 1H), 8.07 (d, J=18.5 Hz, 1H), 8.48 (d, J=4.4 Hz, 2H).

LCMS (ES): m/z 430 [M+H]$^+$.

Example 57

N-[3-(8-Oxa-3-azabicyclo[3.2.1]octane-3-carbonyl)-1,2-benzoxazol-6-yl]-N'-[(pyridin-4-yl)methyl]urea

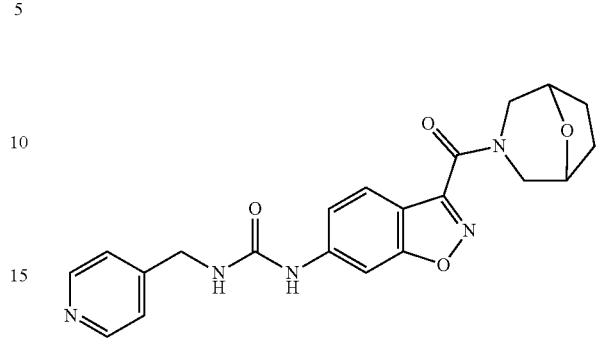

The title compound (14 mg, 0.033 mmol, 41%) was obtained as a solid in the same way as in Example 50-e using 6-({[(pyridin-4-yl)methyl]carbamoyl}amino)-1,2-benzoxazole-3-carboxylic acid (25 mg, 0.080 mmol) and 8-oxa-3-aza-bicyclo[3.2.1]octane (18 mg, 0.16 mmol).

$^1$H NMR (CD$_3$OD) δ: 1.86-2.02 (m, 4H), 3.21 (dd, J=13.1, 2.2 Hz, 1H), 3.25-3.31 (m, 1H), 3.51 (dd, J=13.1, 2.2 Hz, 1H), 4.01 (d, J=13.3 Hz, 1H), 4.41-4.32 (m, 2H), 4.50 (s, 2H), 7.24 (dd, J=8.6, 2.0 Hz, 1H), 7.43-7.41 (m, 2H), 7.71 (d, J=8.2 Hz, 1H), 8.09 (d, J=1.2 Hz, 1H), 8.49 (dd, J=4.3, 1.6 Hz, 2H).

LCMS (ES): m/z 408 [M+H]$^+$.

Reference Example 1

4-Nitrophenyl [(pyridin-4-yl)methyl]carbamate

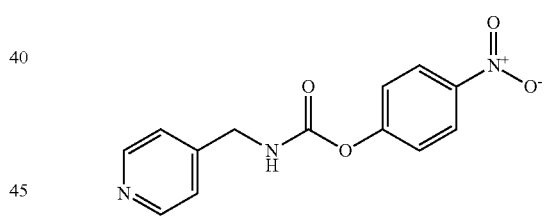

Bis(4-nitrophenyl) carbonate (6.8 g, 22 mmol) was dissolved in dichloromethane (40 mL) and cooled to 0° C. To the solution were added pyridine (2.3 ml, 29 mmol) and 4-picolylamine (2.4 g, 22 mmol). The mixture was stirred for 3 h. The precipitated solid was collected by filtration and washed with a mixed solution of diethyl ether/dichloromethane (1/1) to give the title compound (3.4 g, 12 mmol, 56%) as a solid.

$^1$H NMR (500 MHz, CDCl$_3$) δ (ppm) 4.51 (d, J=6.3 Hz, 2H), 5.74 (s, 1H), 7.28 (dd, J=5.9, 3.1 Hz, 2H), 7.36 (dd, J=7.0, 2.0 Hz, 2H), 8.27 (dd, J=7.0, 2.0 Hz, 2H), 8.62 (d, J=5.9 Hz, 2H).

(Experimental Example 1) Study on NAMPT Enzyme Activating Effect (In Vitro Cell-Free Enzyme Assay)

The NAMPT enzyme assay was conducted in accordance with the method of Formentini et al. (Formentini L. et al., Biochemical Pharmacology 77 (2009) 1612-20) by chemically converting nicotinamide mononucleotide (NMN) produced by the NAMPT enzyme to a fluorescent substance and using the fluorescence intensity of this fluorescent substance as an index for the amount of NMN produced. Hereinafter, the procedures will be briefly described. The NAMPT enzyme reaction was carried out using polypropylene 384 well V shaped black plate (Greiner Bio One International GmbH). The NAMPT activity was measured in assay buffer containing 50 mM HEPES, 50 mM NaCl, 5 mM $MgCl_2$, 1 mM TCEP, 0.1% Prionex, 0.005% Tween 20, 0.12 mM adenosine triphosphate (ATP), 5 µM nicotinamide (NAM), 6.25 µM phospho-ribosyl pyro-phosphate (PRPP), 0.04 U/mL pyrophosphatase and 2 ng/mL human NAMPT enzyme in the presence or absence of test compounds. After the 1-h incubation at 25° C., the enzyme reaction was terminated by the addition of 5 µL of 2 M KOH and 5 µL of a 20% acetophenone solution. Then, 22 µL of 88% formic acid was added and the mixture was further incubated for 30 min in the dark. The NAMPT enzyme activity was calculated as the difference between fluorescence intensity (Ex 380 nm/Em 450 nm) from the reaction of a test compound treatment group and fluorescence intensity from control reaction free from the NAMPT enzyme.

[NAMPT enzyme activity]=[Fluorescence intensity of the test substance treatment group]−[Mean fluorescence intensity of the control reaction free from the NAMPT enzyme]

$EC_{50}$ value of each compound was calculated from the enzyme activities of the compound at various concentrations by using GraphPad Prism software (GraphPad Software) (Table 1.)

TABLE 1

| compounds | $EC_{50}$ (µM) |
|---|---|
| 1 | 0.11 |
| 2 | 0.05 |
| 3 | 0.15 |
| 4 | 0.98 |
| 5 | 0.11 |
| 6 | 0.01 |
| 7 | 0.41 |
| 8 | 0.08 |
| 9 | 0.02 |
| 10 | 0.14 |
| 11 | 0.02 |
| 12 | 0.23 |
| 13 | 0.18 |
| 14 | 0.18 |
| 15 | 0.23 |
| 17 | 0.11 |
| 18 | 0.05 |
| 19 | 0.38 |
| 20 | 0.16 |
| 21 | 0.11 |
| 22 | 0.08 |
| 23 | 0.11 |
| 24 | 0.05 |
| 25 | 0.07 |
| 26 | 0.04 |
| 27 | 0.13 |
| 28 | 1.00 |
| 29 | 0.06 |
| 30 | 0.01 |
| 31 | 0.43 |
| 32 | 0.51 |
| 33 | 0.13 |
| 34 | 0.18 |
| 35 | 0.56 |
| 36 | 0.13 |
| 37 | 0.16 |
| 38 | 0.62 |
| 39 | 0.53 |

TABLE 1-continued

| compounds | $EC_{50}$ (µM) |
|---|---|
| 40 | 0.19 |
| 41 | 0.29 |
| 42 | 0.10 |
| 43 | 0.14 |
| 44 | 0.11 |
| 45 | 0.06 |
| 46 | 0.79 |
| 48 | 0.65 |
| 49 | 0.13 |
| 50 | 0.24 |
| 51 | 0.12 |
| 52 | 0.08 |
| 53 | 0.08 |
| 54 | 0.27 |
| 55 | 0.49 |
| 56 | 0.03 |
| 57 | 0.19 |

(Experimental Example 2) Study on Effect of NAMVPT Activator on the Intracellular $NAD^+$ Level (In Vitro Cell-Based Assay)

HEK293A cells were cultured in Dulbecco's Modified Eagle Medium (DMEM (high glucose)) containing 10% fetal bovine serum (FBS), non-essential amino acid (NEAA), and antibiotic-antimycotic [reaction medium]. On the day before the test, HEK293A cells were inoculated at a ratio of $3.0 \times 10^4$ cells/80 µL to 96 well poly-D-lysine coated plate and cultured overnight in a $CO_2$ incubator.

On the day of the test, each test compound diluted with reaction medium to a concentration of 5 times the final concentration was added at a ratio of 20 µL/well, and the cells were further cultured for 3 h. After removal of the medium, the cells were lysed in 50 µL/well of Bicarbonate Base Buffer (100 mM sodium carbonate, 20 mM sodium bicarbonate, 100 mM nicotinamide, 20 mM Triton X-100) containing 1% dodecyl trimethyl-ammonium bromide (DTAB). The $NAD^+$ content in the cell extract was measured using $NAD^+$/NADH-Glo assay kit according to the manufacturer's instructions. Hereinafter, the procedures will be briefly described. 20 µL of the lysate was separated, and 10 µL of 0.4 N HCL was added thereto, followed by incubation at 60° C. for 15 min and subsequently at 25° C. for 10 min. The mixture was neutralized by the addition of 10 µL of 0.5 M Trizma base solution and then diluted 10-fold with distilled water. 15 µL of the diluted sample was mixed with an equal amount (15 µL) of $NAD^+$/NADH-Glo reagent in 384 well black plate, and the mixture was incubated for 30 min in the dark. Then, chemiluminescence intensity was measured.

For calculation of $EC_{50}$ values of compounds, the average of vehicle control group was subtracted from each value as background. $EC_{50}$ value of each compound was calculated from the calculated values of the compound at various concentrations using GraphPad Prism software (Table 2.).

TABLE 2

| compounds | $EC_{50}$ (µM) |
|---|---|
| 1 | 0.43 |
| 2 | 0.19 |
| 7 | 0.54 |
| 8 | 0.21 |
| 21 | 0.23 |
| 22 | 0.12 |

TABLE 2-continued

| compounds | EC$_{50}$ (µM) |
|---|---|
| 50 | 0.45 |
| 52 | 1.24 |

(Test Example 1) Evaluation of NAMPT Activator on Tissue NAD$^+$ Level in Normal Mice 0.5% MC or the compound of Example 2 prepared with 0.5% MC was orally administered at 30 or 100 mg/kg to 7-week-old male C57BL/6N mice. 24 h after the administration, each mouse was sacrificed by exsanguination. The liver, gastrocnemius, soleus, and brown adipose tissues were harvested. Each tissue was homogenized with a 10- or 100-fold amount of 2 M perchloric acid per its weight. Then, the samples were centrifuged and the supernatant was neutralized with 5 M sodium hydroxide. After removal of potassium perchlorate, the NAD$^+$ concentration in the supernatant of sample was measured using LC/MS. The NAD$^+$ concentration in each tissue is shown in FIG. 1.

The results of FIG. 1 indicated that the treatment with the compound of Example 2 increased NAD$^+$ levels in the mouse liver, gastrocnemius, soleus, and brown adipose tissues.

(Test Example 2) Evaluation of NAMPT activator on tissue NAD$^+$ level in diet-induced obese (DIO) mice The compound of Example 2 prepared with 0.5% MC was orally administered at 30 or 100 mg/kg to 47-week-old male C57BL/6N DIO mice (high-fat loading obesity mouse models) having a pathological obese condition induced by purified high-fat diet (D12451) from 7 weeks of age. 24 h after the administration, each mouse was sacrificed by exsanguination. The liver, gastrocnemius, soleus, and brown adipose tissues were harvested. Each tissue was homogenized with a 10- or 100-fold amount of 2 M perchloric acid per its weight. Then, the samples were centrifuged and the supernatant was neutralized with 5 M sodium hydroxide. After removal of potassium perchlorate, the NAD$^+$ concentration in the supernatant of sample was measured using LC/MS. The NAD$^+$ concentration in each tissue is shown in FIG. 2.

Figure 2:
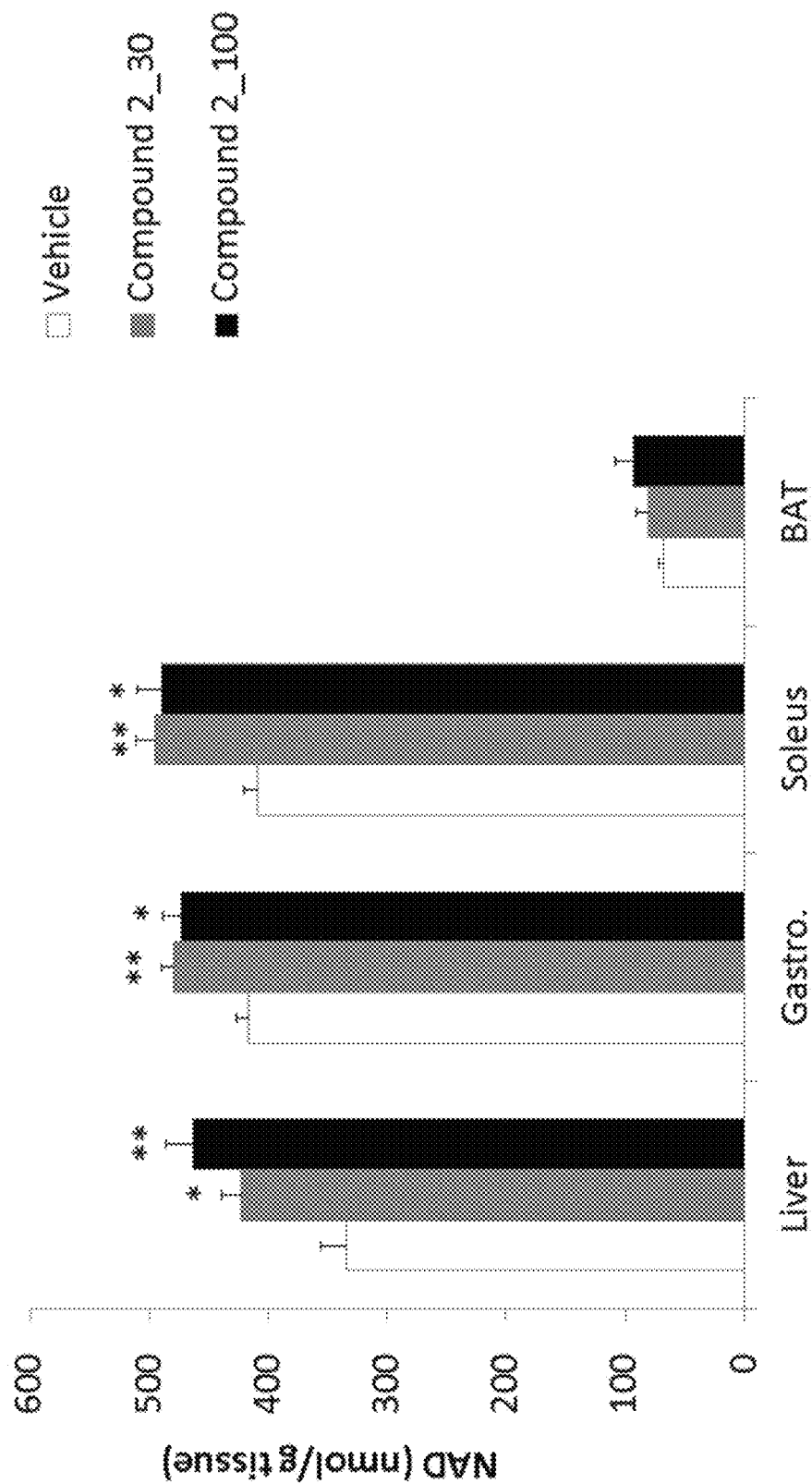
FIG. 2 Effect of NAMPT activator on tissue $NAD^+$ levels in DIO mouse

The results of FIG. 2 indicated that the treatment with the compound of Example 2 increased NAD$^+$ levels in the liver, gastrocnemius, soleus, and brown adipose tissues of the DIO mice in which NAD$^+$ levels in the tissues were reduced.

(Test Example 3) Evaluation of NAMPT activator on energy expenditure in DIO mouse 48-week-old male C57BL/6N DIO mice were divided into 2 groups each involving 4 mice. Each mouse was acclimatized for 3 d under individual housing and then fasted overnight. The next morning, the compound of Example 2 prepared with 0.5% MC was orally administered at 100 mg/kg once a day (a vehicle group was treated with 0.5% MC in the same way as above). Oxygen consumptions (VO$_2$) and carbon dioxide outputs (VCO$_2$) were measured for approximately 73 h (approximately 9 h under fasting (on the order of 9:00 to 18:00) and approximately 64 h under feeding (on the order of 18:00 to 10:00 of two days later)) using Comprehensive Lab Animal Monitoring System (Columbus Instruments International Corp.).

Figure 3:
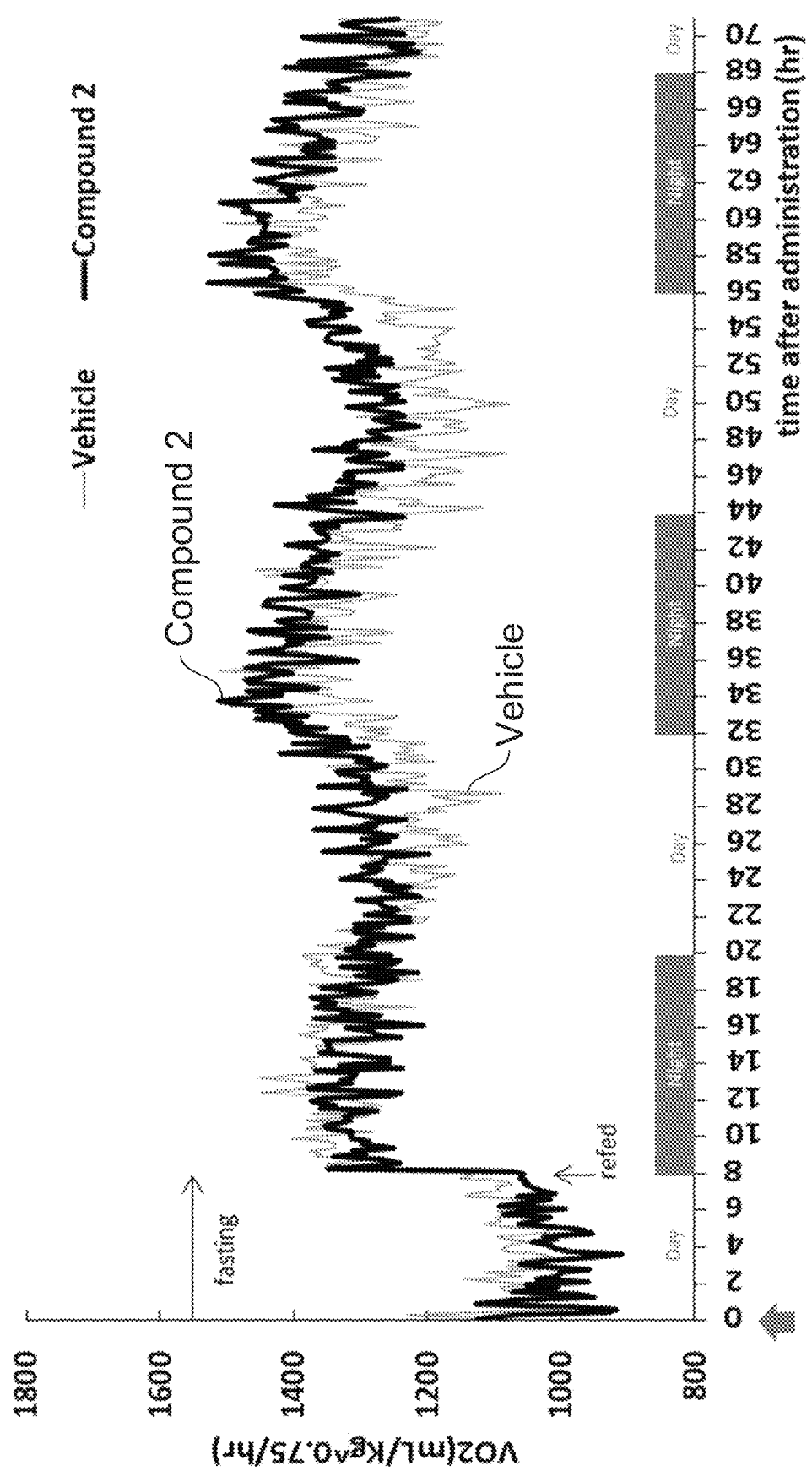
FIG. 3 Promotion of energy expenditure by NAMPT activator in DIO mice

The results are shown in FIG. 3. The results of FIG. 3 indicated that the treatment with the compound of Example 2 increased an oxygen consumption per weight as compared to the vehicle group.

(Test Example 4) Evaluation of anti-obesity effect of NAMPT activator (DIO mouse, free feeding)

45-week-old male C57BL/6N DIO mice were each acclimatized for 1 wk under individual housing. Then, the mice were divided into 2 groups each involving 6 mice with their weights, amounts of weight change, and food intakes during the acclimatization period as indexes. Each mouse was freely fed a purified high-fat diet (D12451) for 3 wk under individual rearing. The compound of Example 2 prepared with 0.5% MC was orally administered at 30 mg/kg once a day for 3 wk from the start day of the test (a vehicle group was treated with 0.5% MC in the same way as above). The weight was compared between the test groups.

Figure 4:
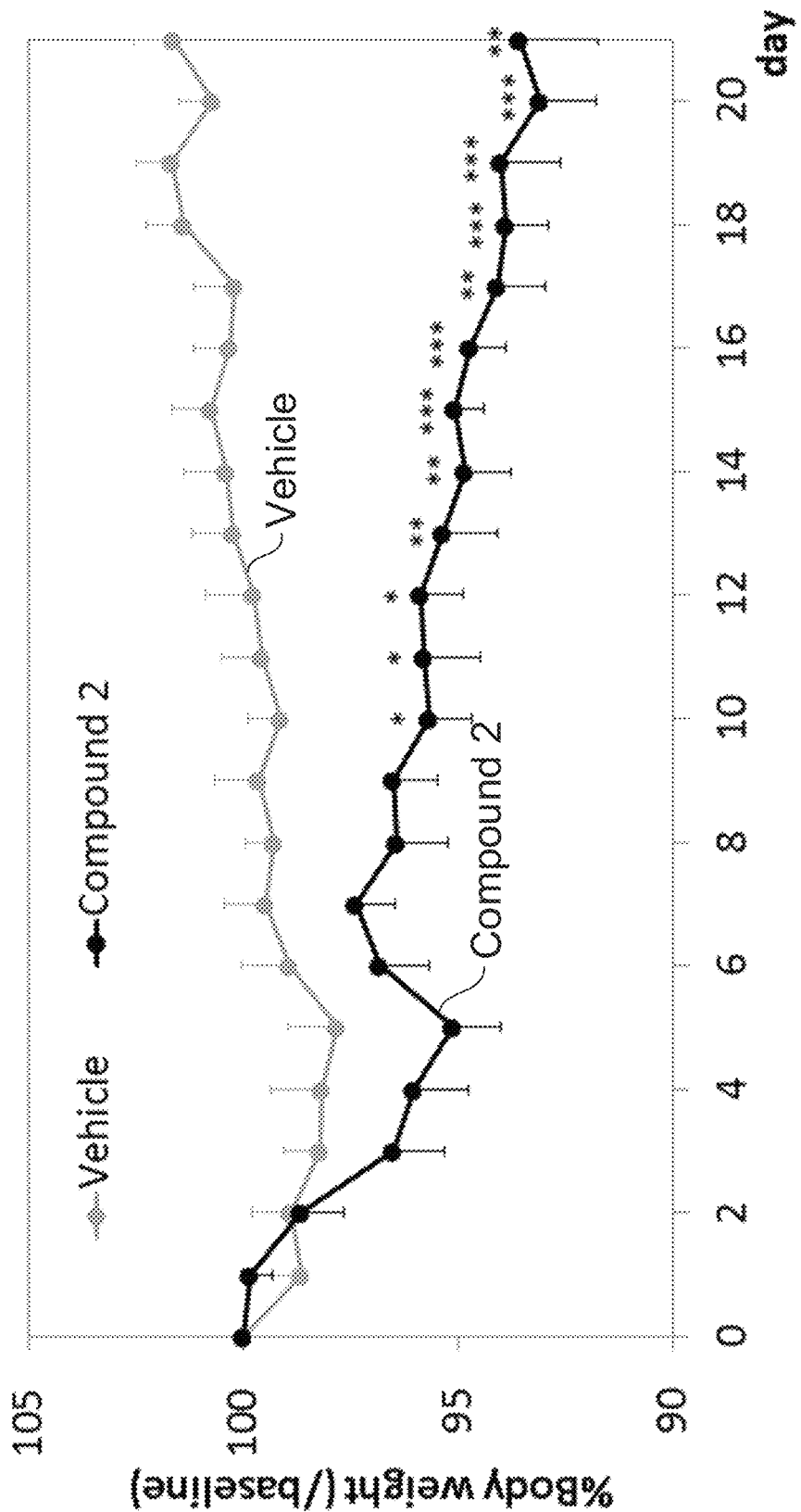
FIG. 4 Anti-obesity effect of NAMPT activator in DIO mice

From the results of FIG. 4, the treatment with the compound of Example 2 was confirmed to have a weight lowering effect in obese mice as compared to the vehicle group.

(Test Example 5) Effect of NAMPT Activator on Tissue NAD$^+$ Level in DIO Mouse—2

The compound of Example 2 prepared with 0.5% MC was orally administered at 30 mg/kg to 47-week-old male C57BL/6N DIO mice (a vehicle group was treated with 0.5% MC in the same way as above). 24 h after the administration, each mouse was sacrificed by exanguination. The heart, kidney, spleen, lung, and white adipose tissues were harvested. For a control, the same organs as above were harvested from 8-week-old male C57BL/6N mice. Each tissue was homogenized with a 10- or 100-fold amount of 2 M perchloric acid per its weight. Then, the samples were centrifuged and the supernatant was neutralized with 5 M sodium hydroxide. After removal of potassium perchlorate, the NAD$^+$ concentration in the supernatant of sample was measured using LC/MS. The NAD$^+$ concentration in each tissue is shown in FIG. 5.

Figure 5:
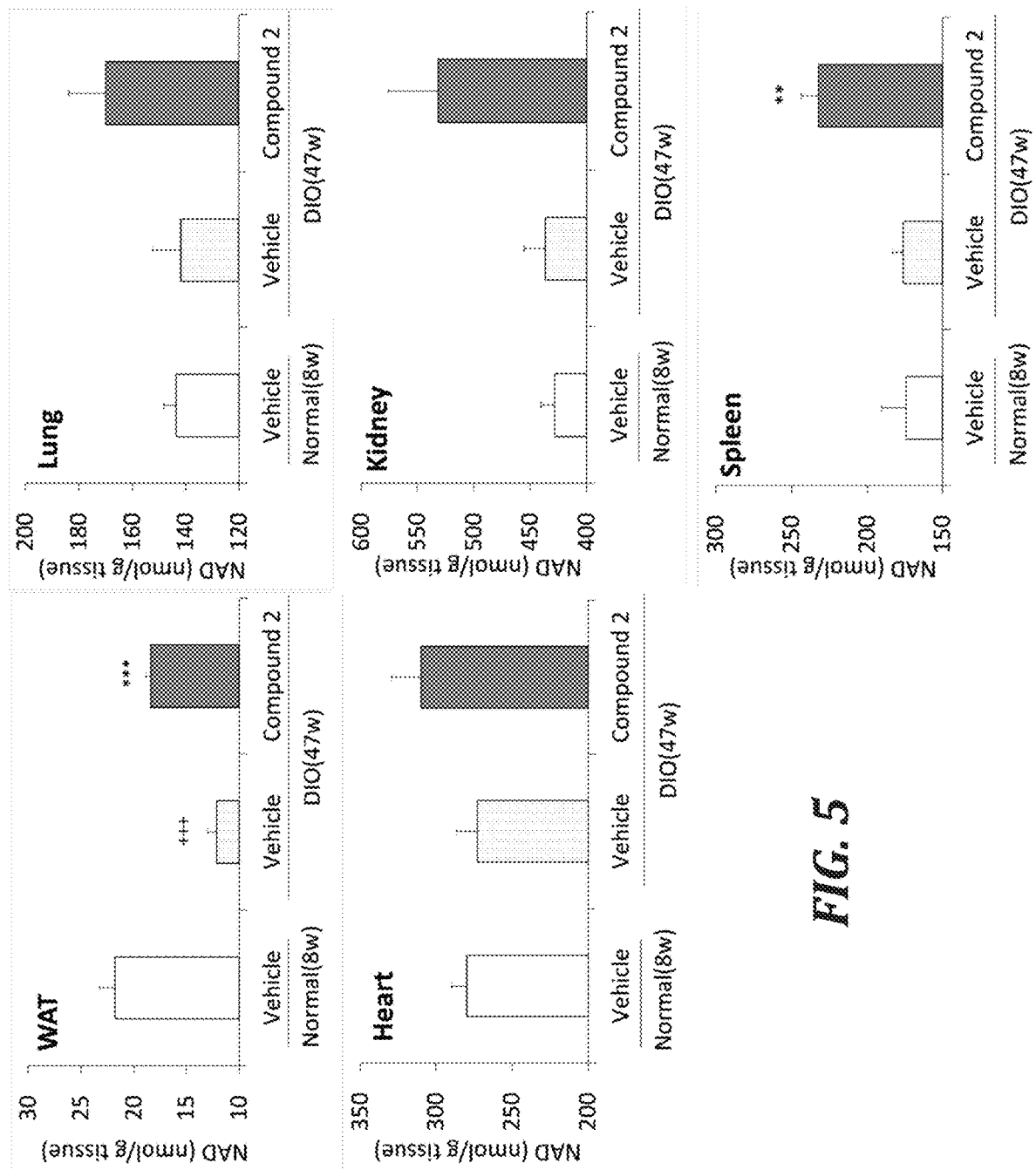
FIG. 5 Effect of NAMPT activator on $NAD^+$ levels in major tissues of DIO mice

The results of FIG. 5 indicated that NAD$^+$ levels tend to be decreased in the white adipose tissue due to obesity and aging, whereas NAD$^+$ levels were increased in the major tissues of the DIO mice 24 h after the administration of the compound of Example 2.

(Test Example 6) Effect of NAMPT Activator on NAD$^+$ Level in Retina (Normal Mouse)

The compound of Example 2 prepared with 0.5% MC was orally administered at 30 mg/kg to 8-week-old male C57BL/6N mice (a vehicle group was treated with 0.5% MC in the same way as above). 4 h after the administration, each mouse was sacrificed by exanguination. The retina was harvested from both eyes. The retina (4 eye pools per sample) was homogenized with a 100-fold amount of 2 M perchloric acid per retinal tissue weight. Then, the samples were centrifuged and the supernatant was neutralized with 5 M sodium hydroxide. After removal of potassium perchlorate, the NAD$^+$ concentration in the supernatant sample was measured using LC/MS. The NAD$^+$ concentrations in the retinal tissues of each group are shown in FIG. 6.

Figure 6:
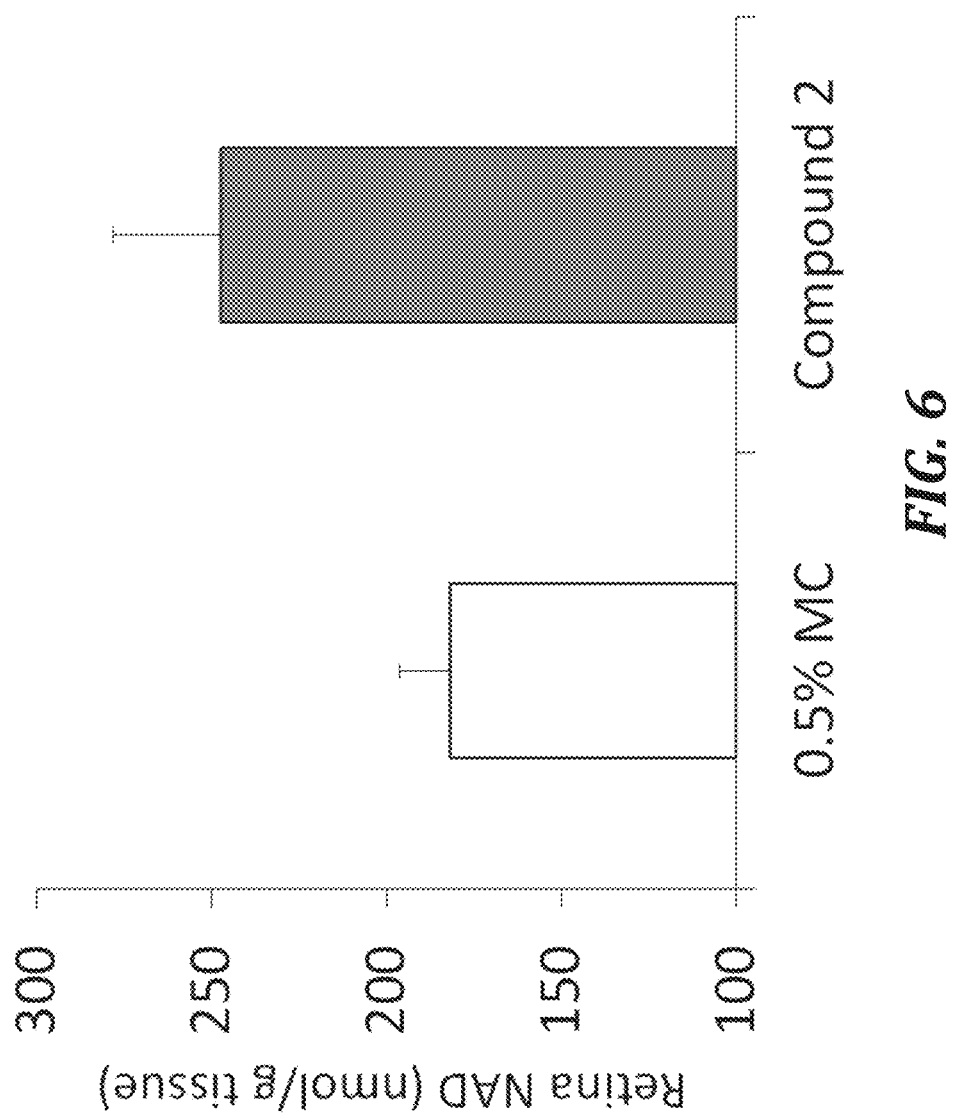
FIG. 6 Effect of NAMPT activator on retina $NAD^+$ level in normal mice

The results of FIG. 6 indicated that NAD$^+$ levels were increased in the retina 4 h after the administration of the compound of Example 2.

(Test Example 7) Evaluation of NAMPT Activator on the Immobility Time in the Forced Swimming Test of WKY Rats The Wistar Kyoto (WKY) rat strain demonstrates an endogenous depressive-like phenotype, which has been proposed as an experimental treatment-resistant depression model in which selective serotonin reuptake inhibitors did not produce an antidepressant-like effect. In this model, ketamine produced a rapid and long-lasting antidepressant-like effect.

Pre forced swimming test (FST) was performed a day before Main FST. The 6-week-old male WKY rats were individually placed in a water-containing acrylic cylinder (diameter: 180 mm, height: 400 mm, water depth: 250 mm, water temperature: 23±1° C.) for 15 min.

Next day, Main FST for 6 min was performed in the same manner as in Pre FST. Compound 2 of Example 2 suspension prepared with 0.5% MC was orally administered at 30, 100, or 300 mg/kg 2 h before Main FST. Ketamine prepared with saline was intraperitoneally administered at 5 mg/kg 0.5 h before Main FST.

Figure 7:
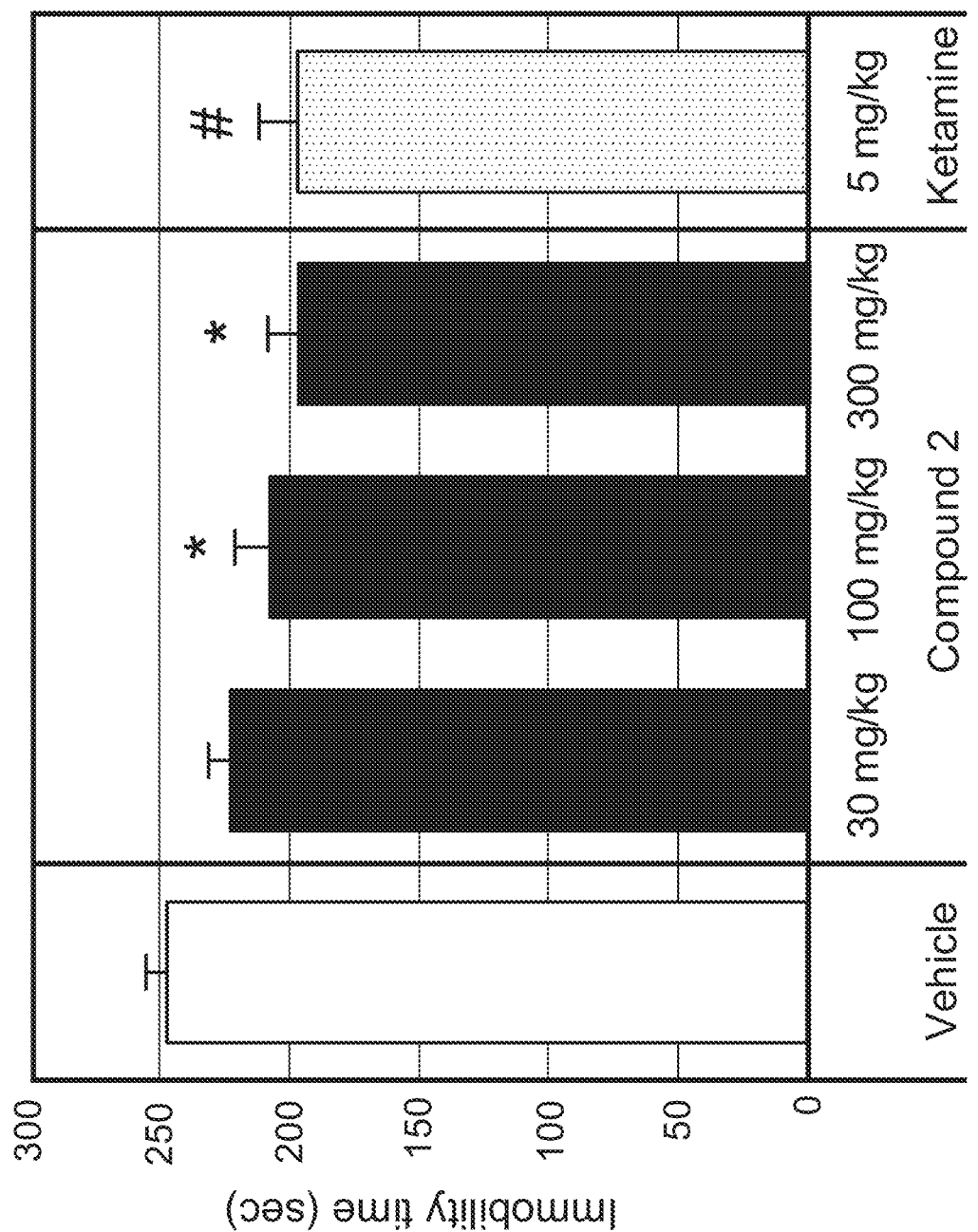
FIG. 7 Effects of compound 2 and ketamine on the Immobility Time in the Forced Swimming Test of WKY Rats

The behavior of Main FST in the water was filmed with a video camera. The rats were visually evaluated for an immobile posture, and the total immobility time was measured. The immobility time in each group is shown in FIG. 7. FIG. 7 compares the effects of compound 2 and ketamine on the Immobility Time in the Forced Swimming Test of WKY Rats. Ketamine group was compared to vehicle control by t-test (mean±SEM, n=16). Each compound 2 group was compared to vehicle control by Dunnett's test (mean±SEM, n=16).

The result of FIG. 7 indicated that the treatment with compound 2 at 100 and 300 mg/kg, similar to ketamine at 5 mg/kg, significantly shortened the immobility time compared to vehicle control, which reflects the anti-depressant-like effect.

INDUSTRIAL APPLICABILITY

The present invention provides a drug capable of ameliorating diseases and conditions associated with reduced $NAD^+$ levels by increasing $NAD^+$ levels in tissues. The present invention provides a novel safe and effective approach for suppressing weight gain, ameliorating obesity by increase in energy consumption in the body, and ameliorating other diseases and conditions and dysfunctions associated with reduce $NAD^+$ level in major organs such as liver, heart, kidney, skeletal muscle, retina.

The invention claimed is:

1. A compound of formula (I), or a pharmaceutically acceptable salt thereof:

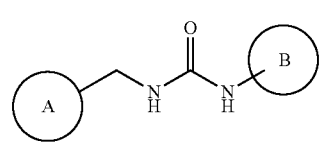
(I)

wherein:

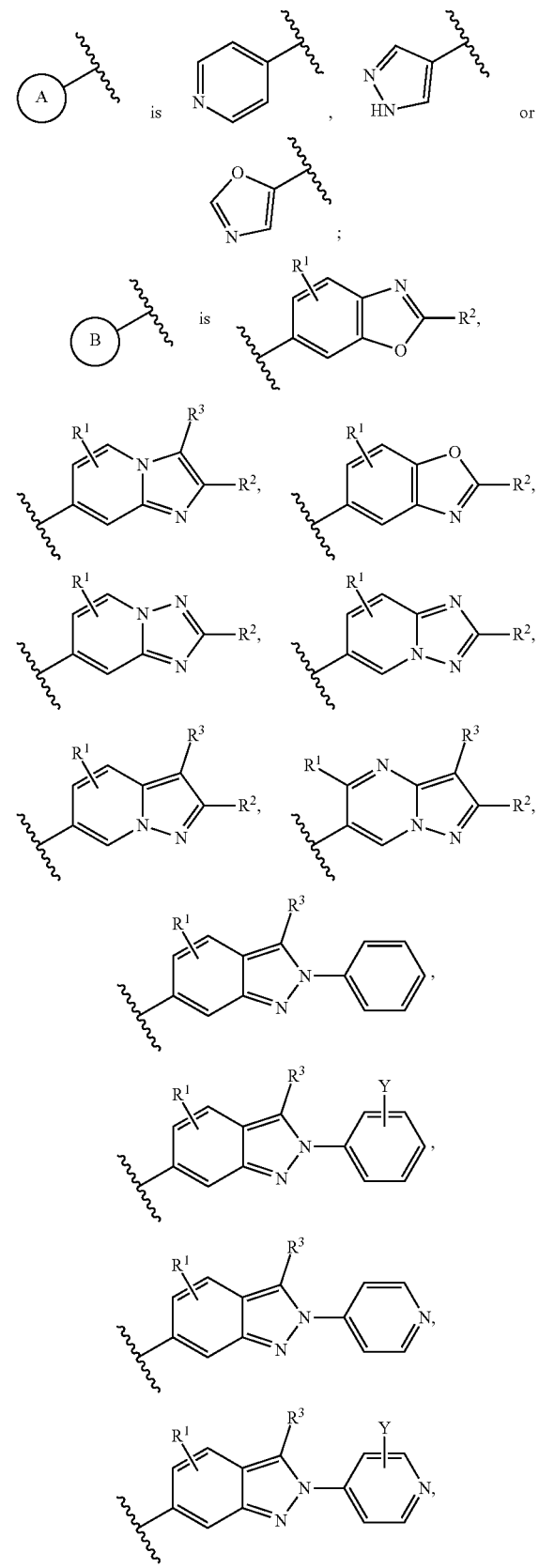

-continued

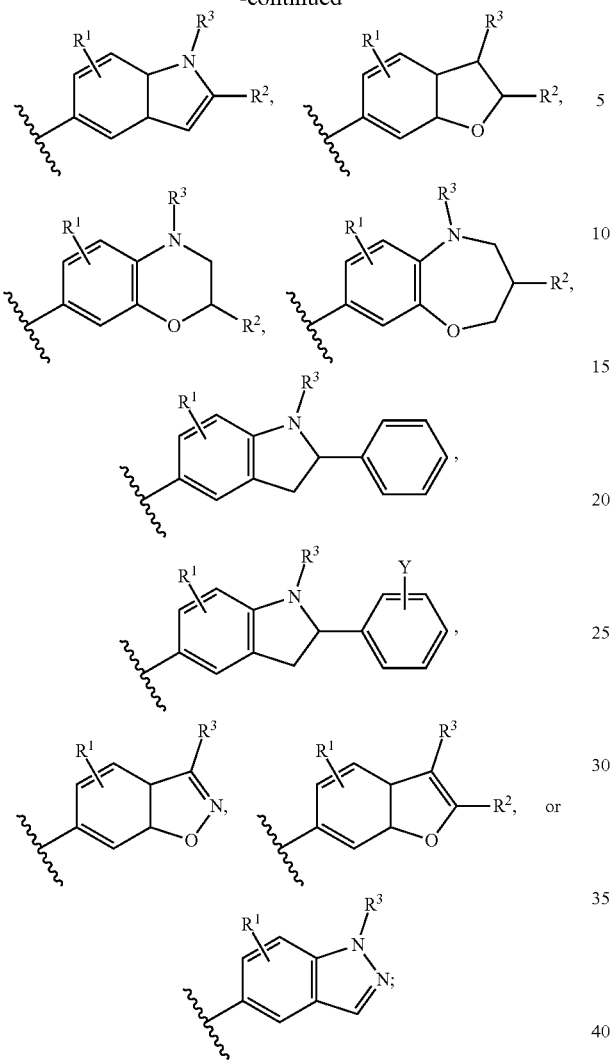

R¹ is a hydrogen atom or a halogen atom;
R² is a hydrogen atom; a phenyl group or a heteroaryl group optionally substituted with one or more Y; or a C₁-C₆ alkyl group optionally substituted with a C₃-C₆ cycloalkyl group;
R³ is a hydrogen atom; a cyano group; a phenyl group or a heteroaryl group each optionally substituted with one or more Y; a C₁-C₄ alkylcarbonyl group or a C₁-C₄ alkyl group, each optionally substituted with one or more Z; or —C(=O)—Z;
each Y is independently selected from a C₁-C₄ alkyl group, a C₁-C₄ alkoxy group, a phenyl group, a C₁-C₃ alkylsulfonyl group, a C₁-C₃ haloalkyl group, a halogen atom, and a C₁-C₃ alkyl group or a C₁-C₃ alkoxy group substituted with a C₁-C₃ alkoxy group;
each Z is independently selected from a C₁-C₃ alkoxy group, a dioxanyl group, an 8-oxa-3-azabicyclo [3.2.1] octyl group, a C₁-C₄ alkoxycarbonyl group, and an amino group or a C₃-C₆ cycloalkylamino group each optionally substituted with one or more W; and
each W is independently selected from a phenyl group, a heteroaryl group, a C₁-C₃ alkyl group, a C₁-C₃ alkyl group substituted with phenyl, and a C₁-C₃ alkyl group substituted with a heteroaryl group.

2. The compound of claim 1, wherein A is

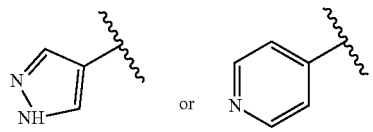

3. The compound of claim 1, wherein A is

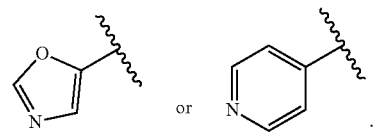 [SMILES: *c1cnco1 ; *c1ccncc1]

4. The compound of claim 1, wherein A is

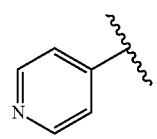

5. The compound of claim 1, wherein B is

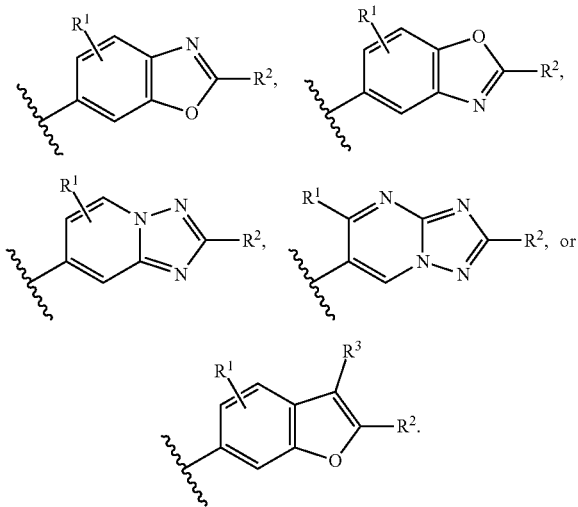

6. The compound of claim 1, wherein ring B is

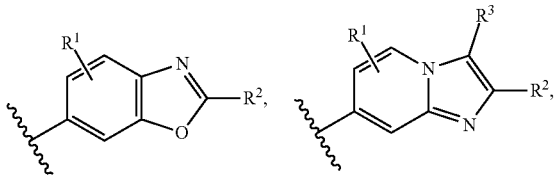

-continued

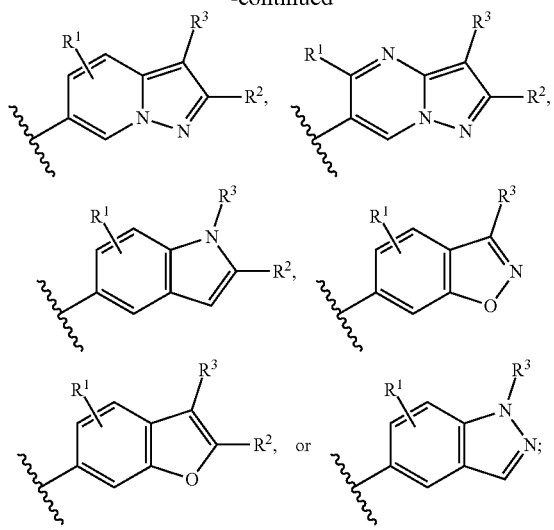

R³ is a hydrogen atom; a cyano group; a C₁-C₄ alkyl group;
a phenyl group or a heteroaryl group each optionally substituted with one or more Y; an ethylcarbonyl group or a methyl group each optionally substituted with one or more Z; or —C(=O)—Z; wherein each Y is independently selected from a $C_1$-$C_3$ alkyl group, a $C_1$-$C_3$ alkoxy group, a phenyl group, a halogen atom, a $C_1$-$C_3$ alkylsulfonyl group, a $C_1$-$C_3$ haloalkyl group, and a $C_1$-$C_3$ alkyl group or a $C_1$-$C_3$ alkoxy group each substituted with a $C_1$-$C_3$ alkoxy group; wherein each Z is independently selected from a $C_1$-$C_2$ alkoxy group, a dioxanyl group, an 8-oxa-3-azabicyclo [3.2.1] octyl group, and an amino group or a $C_3$-$C_6$ cycloalkylamino group each optionally substituted with one or more W; and wherein each W is independently selected from a phenyl group, a heteroaryl group, a $C_1$-$C_3$ alkyl group, a $C_1$-$C_3$ alkyl group substituted with phenyl, and a $C_1$-$C_3$ alkyl group substituted with a heteroaryl group.

7. The compound of claim 1, wherein ring B is

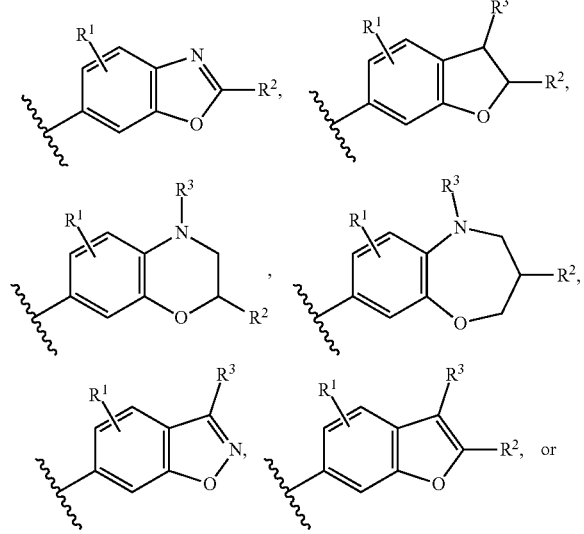

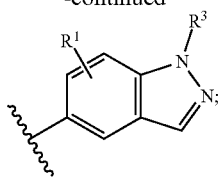

R³ is a hydrogen atom, a cyano group, a N-methylpyrazolyl group, a phenyl group, a methyl group, a 2-methoxyethyl group, a dioxanylmethyl group, or —C(=O)—Z; wherein Z is selected from an 8-oxa-3-azabicyclo [3.2.1] octyl group and an amino group optionally substituted with one or more W; and wherein each W is independently selected from a $C_1$-$C_3$ alkyl group, a methylphenyl group, and a $C_1$-$C_3$ alkyl group substituted with a heteroaryl group.

8. The compound of claim 1, wherein R¹ is a hydrogen atom or a fluorine atom.

9. The compound of claim 1, wherein R² is a hydrogen atom; a phenyl group, a pyrazolyl group, a pyridinyl group, or a pyrrole group each optionally substituted with one Y; or a $C_1$-$C_3$ alkyl group optionally substituted with a $C_3$-$C_6$ cycloalkyl group; wherein Y is selected from a phenyl group, a halogen atom, a $C_1$-$C_4$ alkyl group, a $C_1$-$C_3$ haloalkyl group, a $C_1$-$C_3$ alkylsulfonyl group, a $C_1$-$C_3$ alkoxy group, and a $C_1$-$C_3$ alkyl group or a $C_1$-$C_3$ alkoxy group substituted with a $C_1$-$C_3$ alkoxy group.

10. The compound of claim 1, wherein R² is a hydrogen atom; a phenyl group, a pyrazolyl group, or a pyridinyl group each optionally substituted with one Y; or a $C_1$-$C_3$ alkyl group; wherein Y is selected from a $C_1$-$C_4$ alkyl group, a methanesulfonyl group, an ethanesulfonyl group, a methoxy group, an ethoxy group, a 2-methoxyethoxy group, a phenyl group, a trifluoromethyl group, a difluoromethyl group, a 2-methoxyethyl group, and a chlorine atom.

11. The compound of claim 1, wherein the compound is selected from the group consisting of:

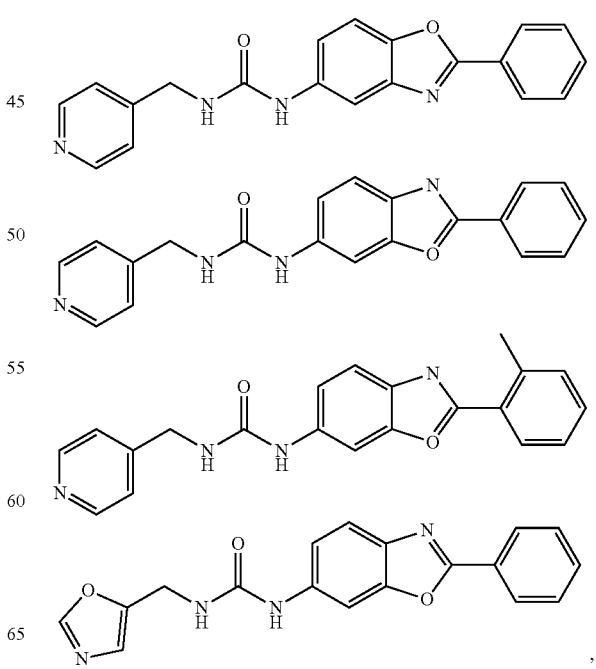

129
-continued

130
-continued

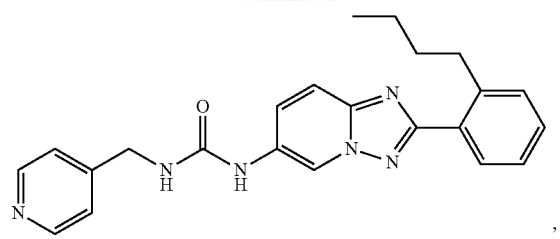
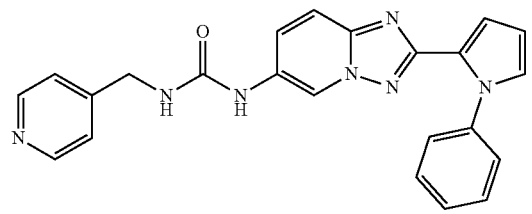
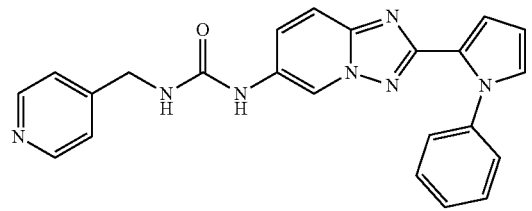
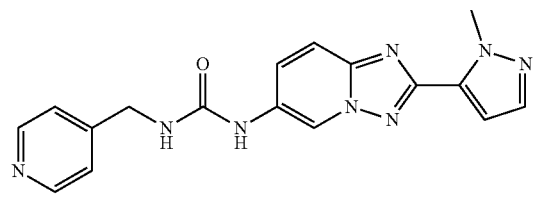
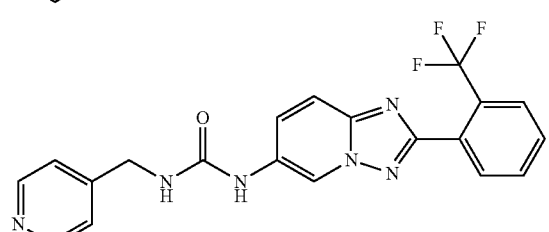
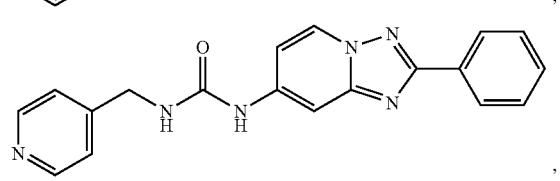
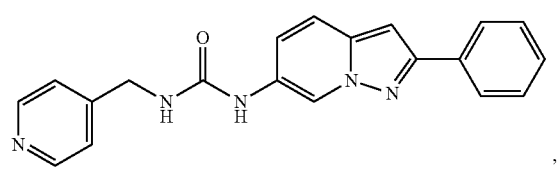
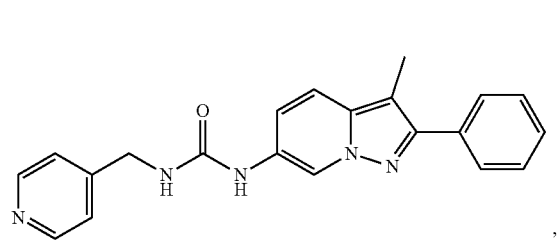
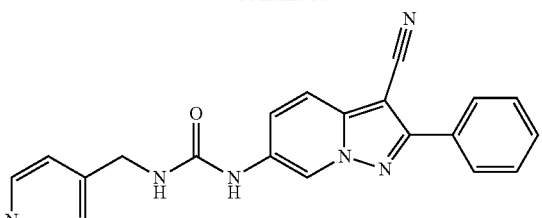
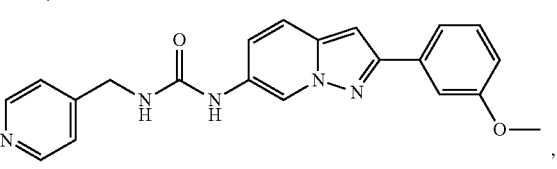
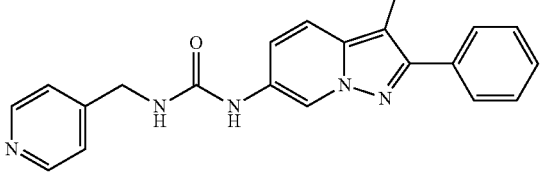
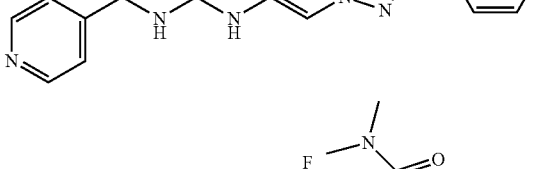
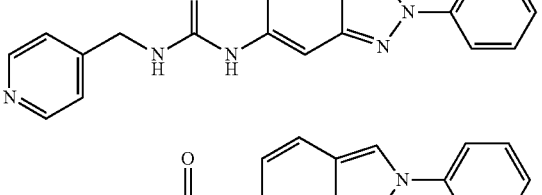
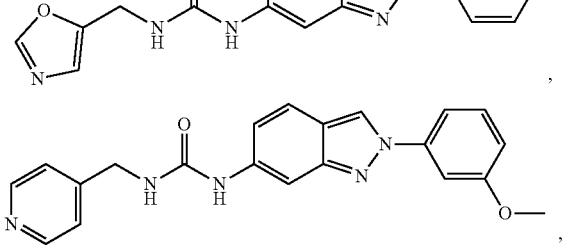

133
-continued
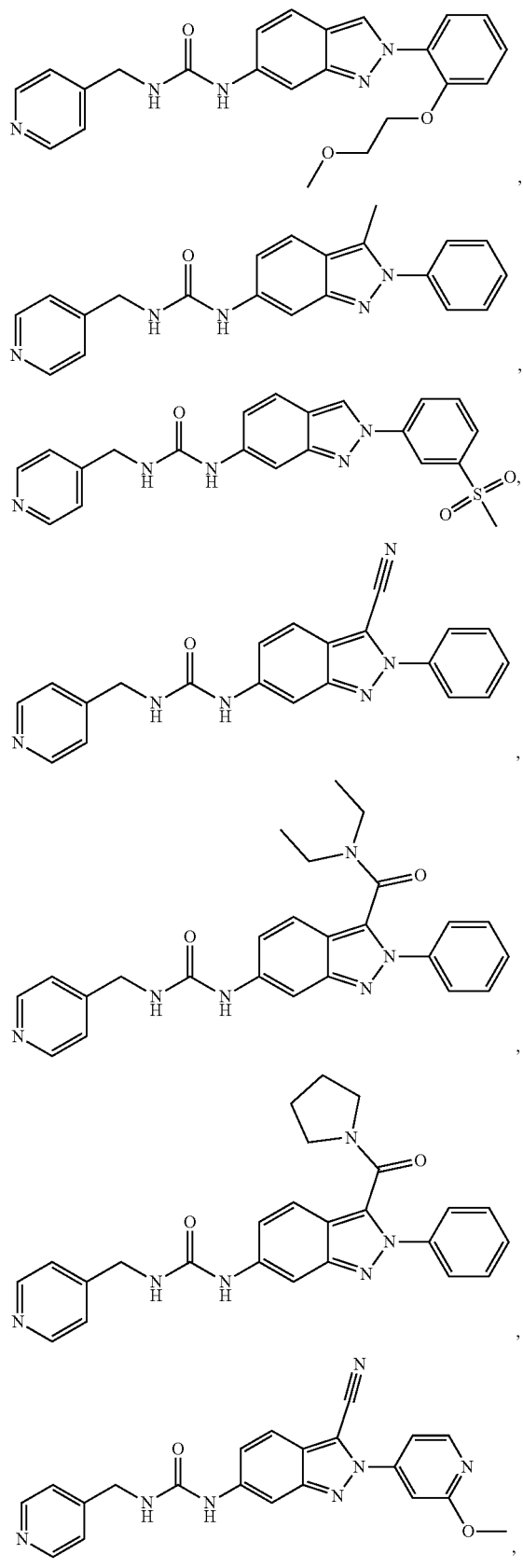
134
-continued
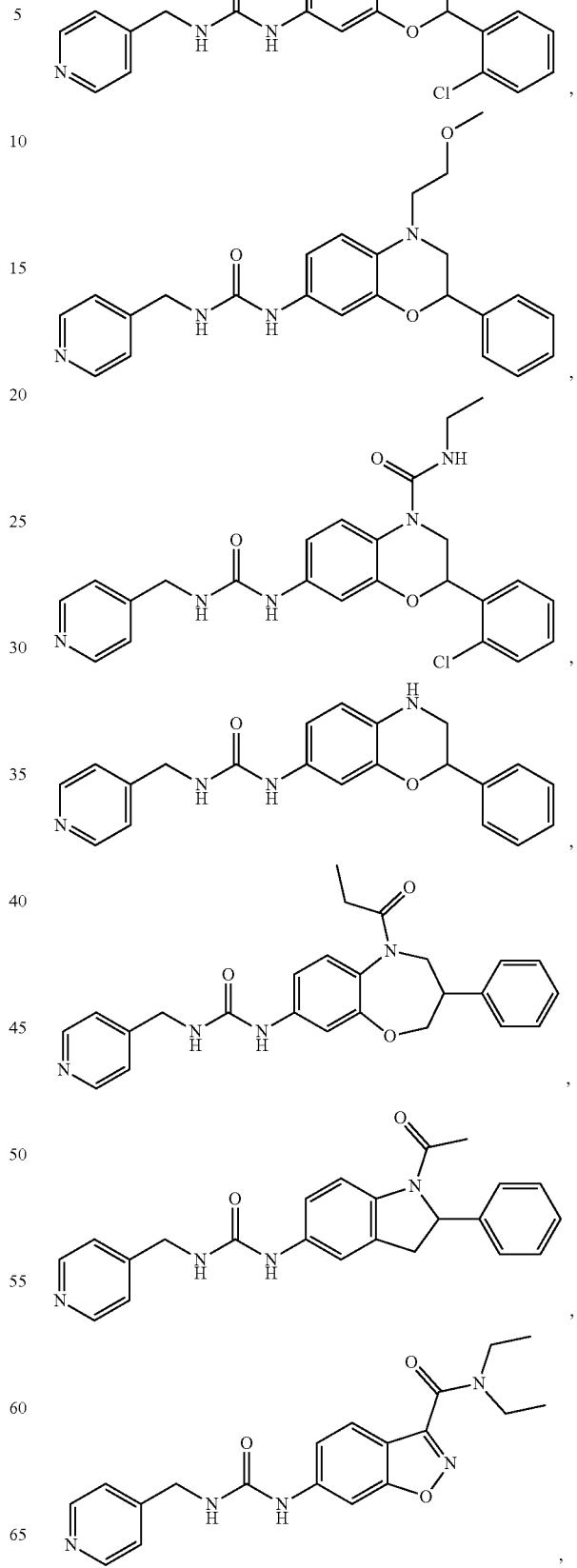

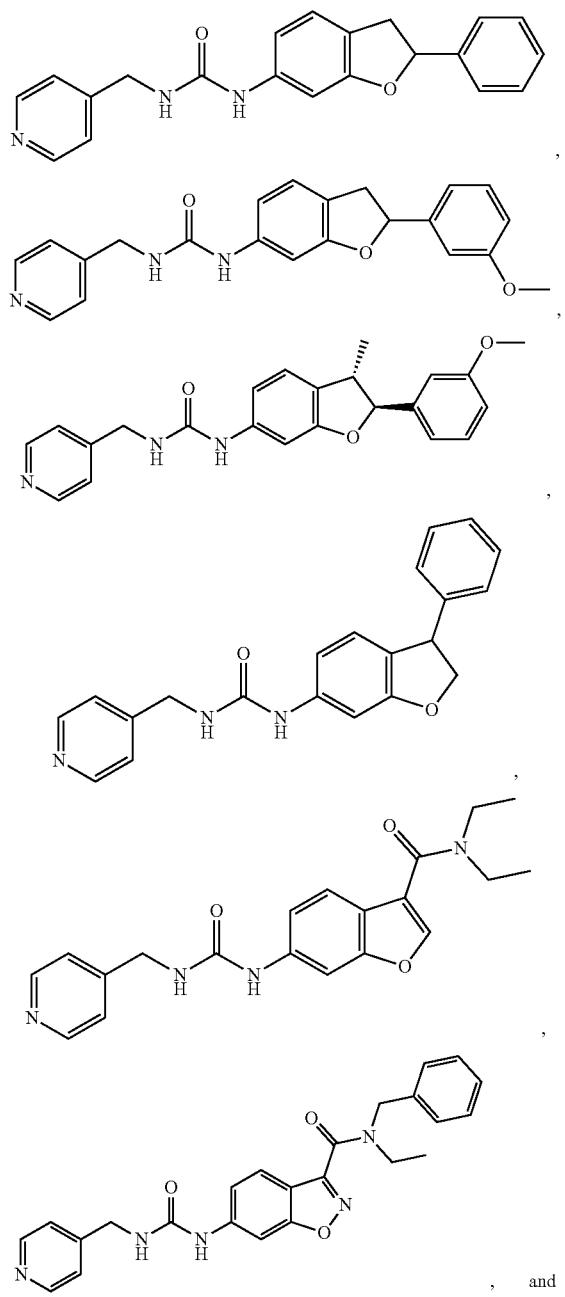
or a pharmaceutically acceptable salt thereof.
12. The compound of claim 1, wherein the compound is selected from the group consisting of:
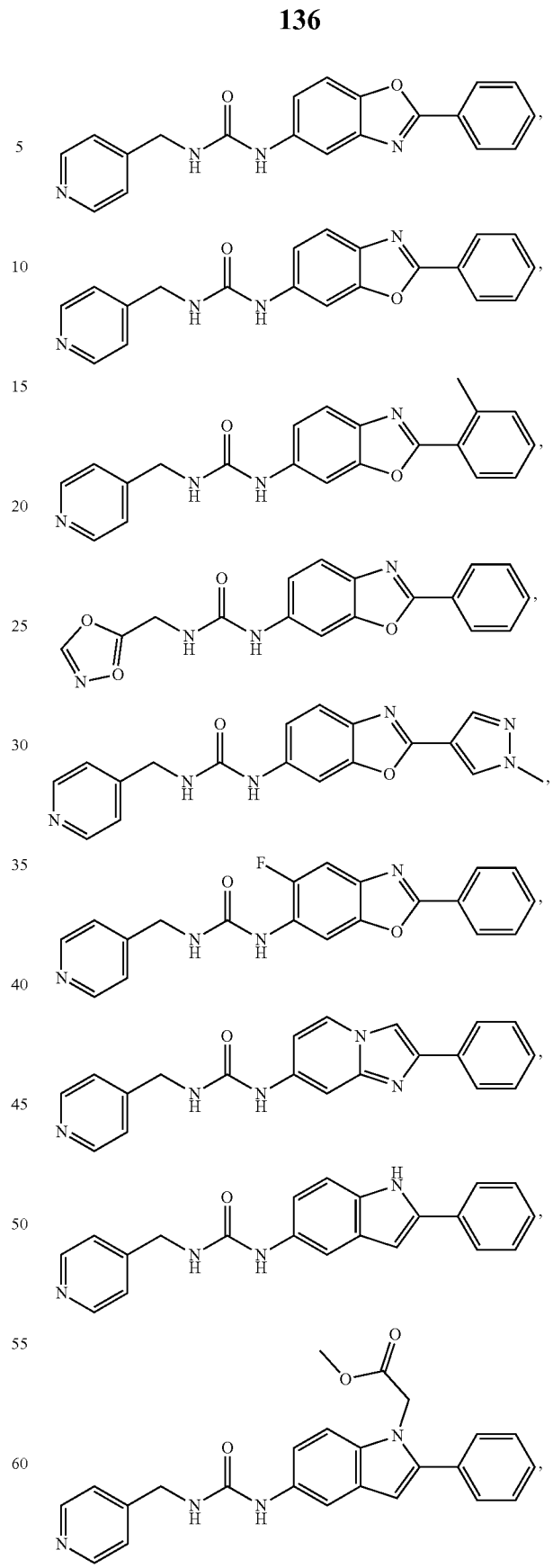

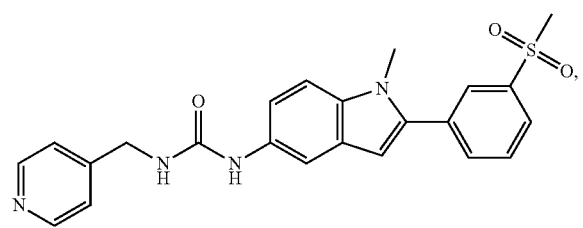
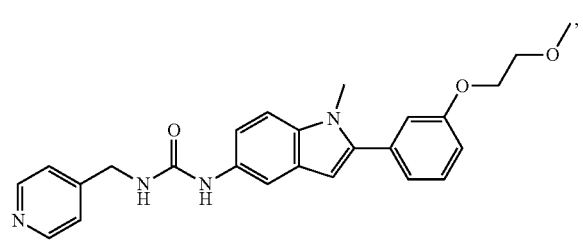
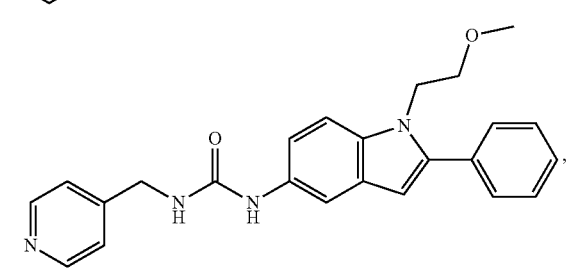
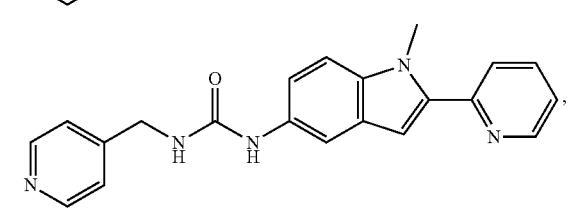
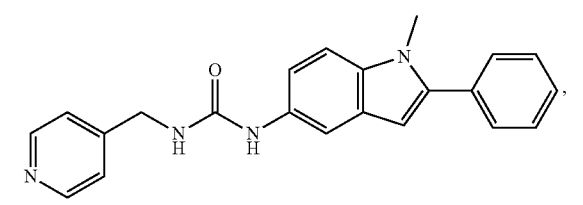
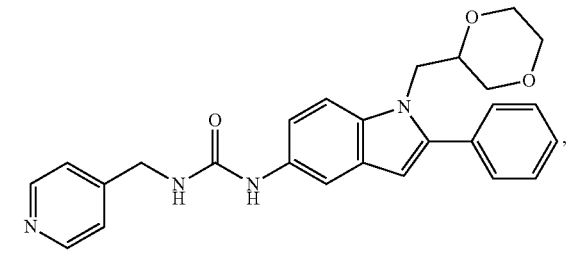
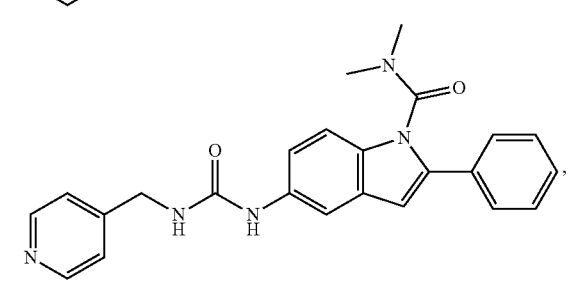
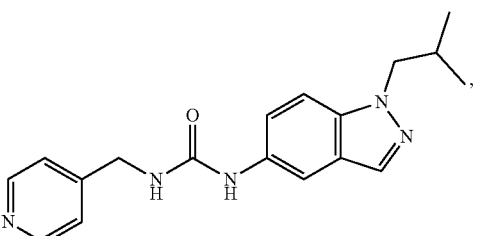
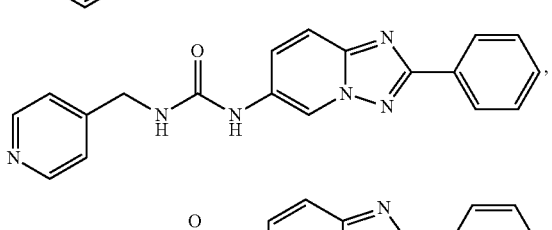
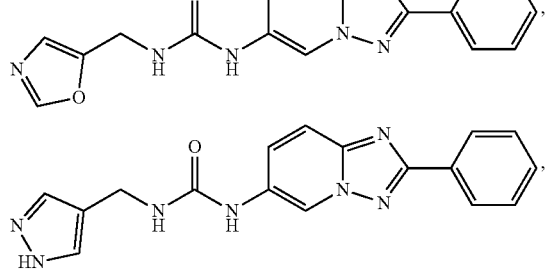
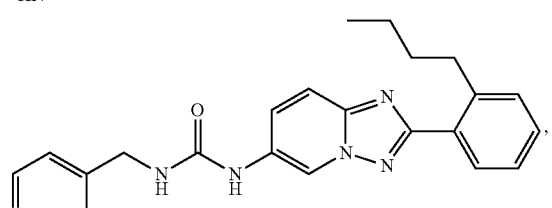
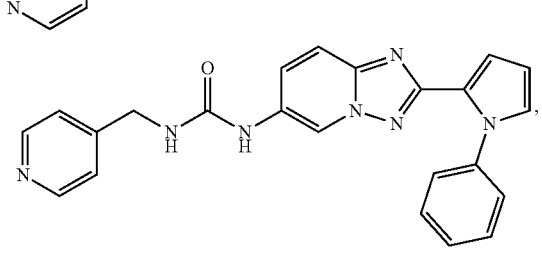
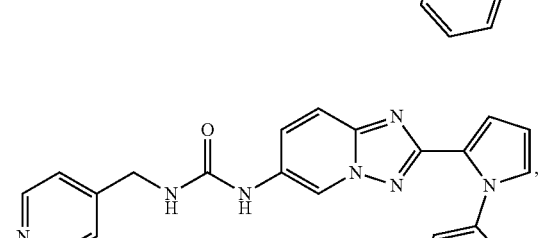

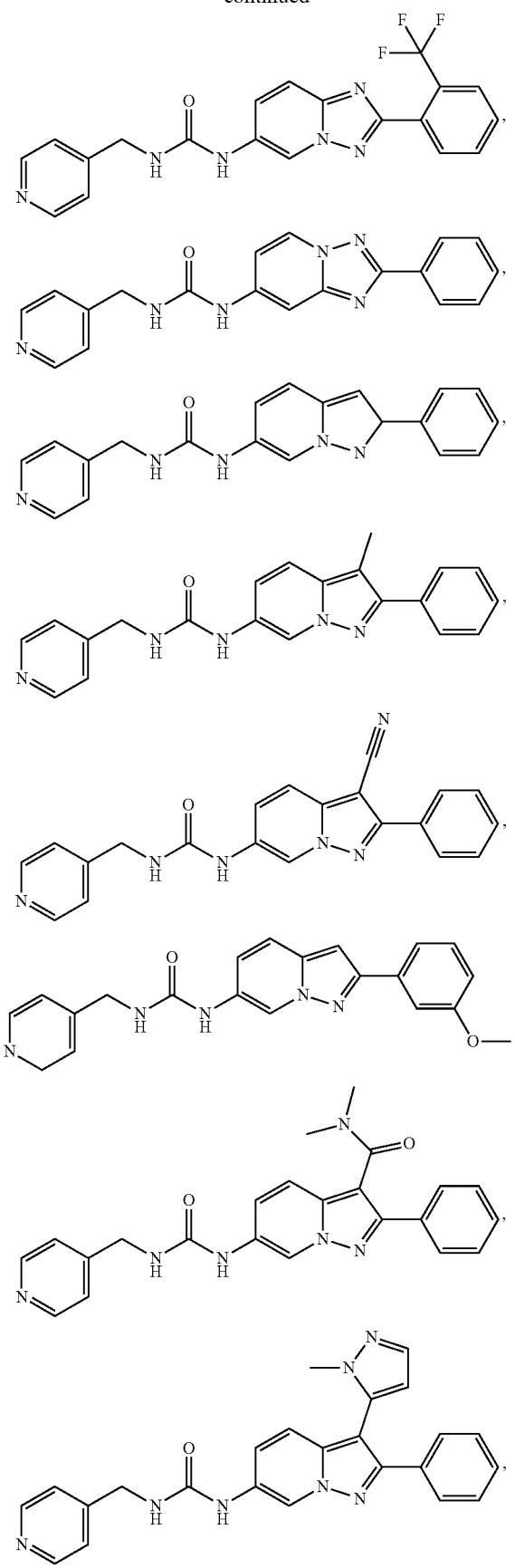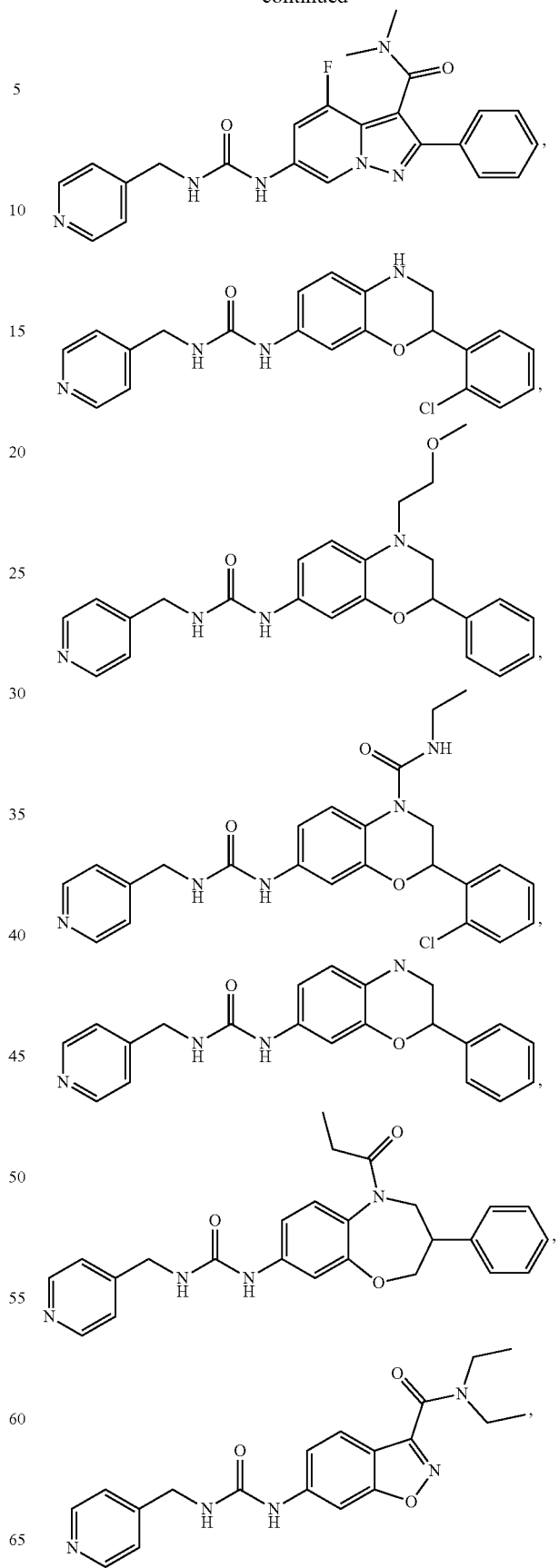

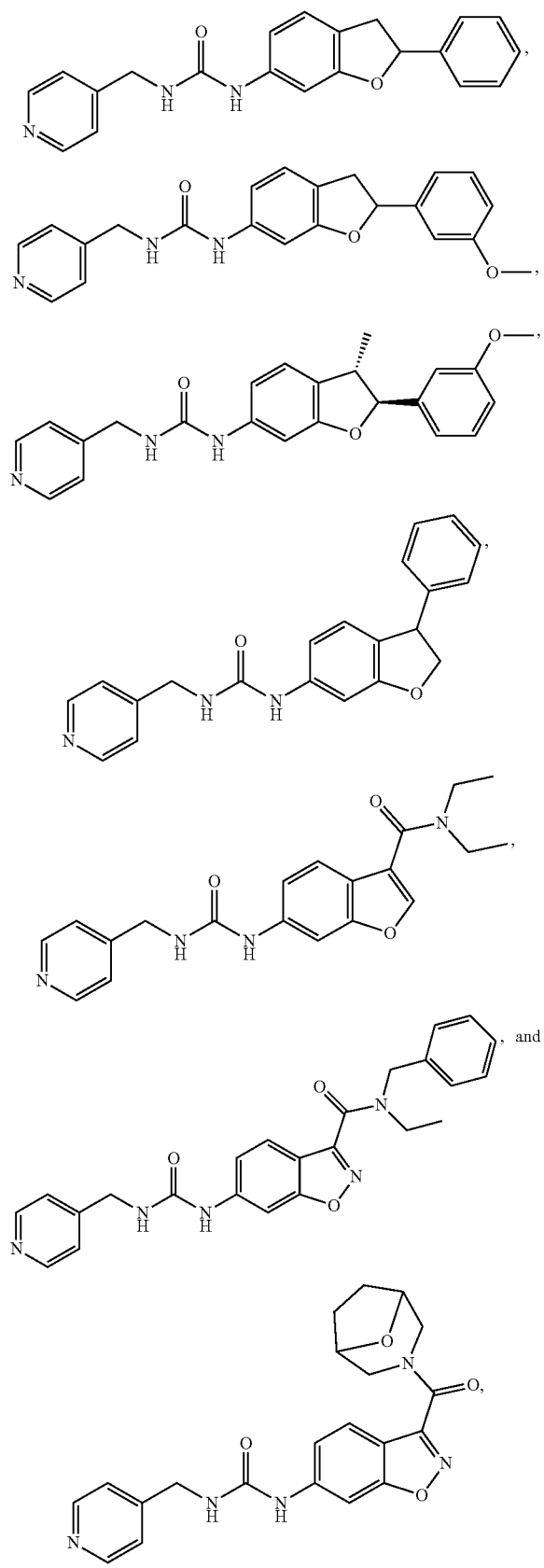

or a pharmaceutically acceptable salt thereof.

13. The compound of claim 1, wherein the compound is selected from the group consisting of:

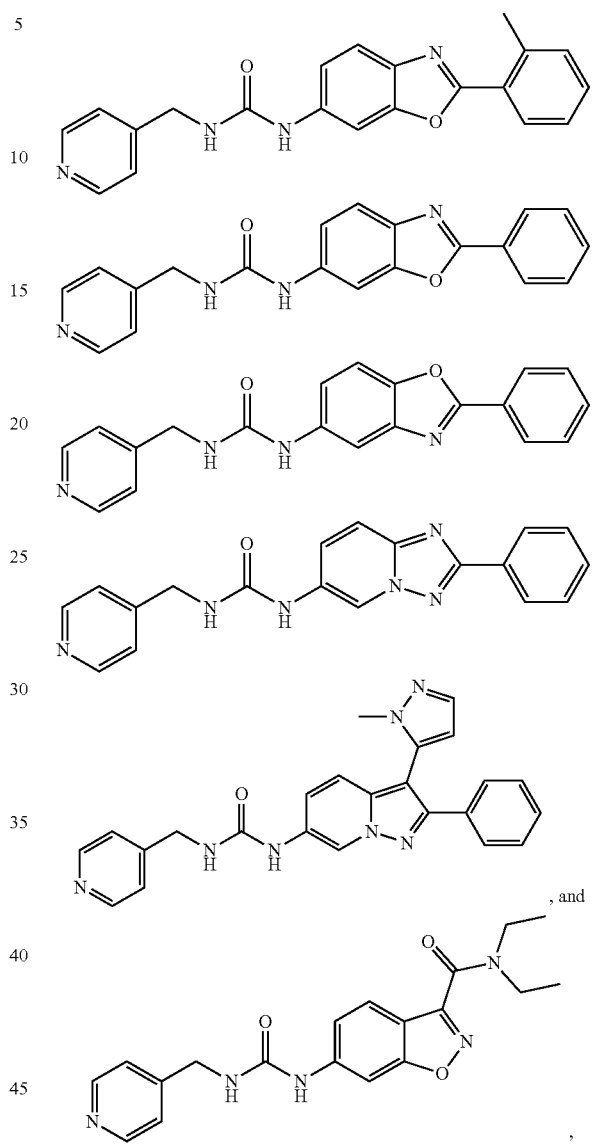

or a pharmaceutically acceptable salt thereof.

14. A pharmaceutical composition comprising a compound of claim 1, or a pharmaceutically acceptable salt thereof, and at least one pharmaceutically acceptable excipient.

15. The pharmaceutical composition of claim 14, wherein the pharmaceutical composition is formulated for oral administration, intravenous injection, subcutaneous injection, inhalation, nasal administration, dermal administration, or ophthalmic administration.

16. The pharmaceutical composition of claim 14, wherein the pharmaceutical composition is in a tablet, or a capsule.

17. A method of treating a disease or condition mediated by nicotinamide phosphoribosyltransferase (NAMPT) activity in a mammal comprising administering a compound of claim 1, or a pharmaceutically acceptable salt thereof, to the mammal.

18. The method of claim 17, wherein the disease or condition is a metabolic disorder, a cardiovascular disease, a kidney disease, a mitochondrial disease, a neurodegenerative disease, an ocular disease, or a muscle wasting disorder.

19. The method of claim 17, wherein the mammal is a human.

* * * * *